United States Patent [19]
Inouye et al.

[11] Patent Number: 6,077,682
[45] Date of Patent: Jun. 20, 2000

[54] METHODS OF IDENTIFYING INHIBITORS OF SENSOR HISTIDINE KINASES THROUGH RATIONAL DRUG DESIGN

[75] Inventors: Masayori Inouye, Piscataway, N.J.; Heiyoung Park, Cambridge, Mass.; Mitsuhiko Ikura, North York, Canada

[73] Assignees: University of Medicine and Dentistry of New Jersey, New Brunswick, N.J.; Ontario Cancer Institute, Ontario, Canada

[21] Appl. No.: 09/045,631

[22] Filed: Mar. 19, 1998

[51] Int. Cl.[7] .............................. C12Q 1/48; G01N 33/00
[52] U.S. Cl. .............................. 435/15; 435/194; 436/86; 530/300; 530/350
[58] Field of Search ..................... 435/15, 194; 436/86; 530/350, 300; 536/23.2, 23.7

[56] References Cited

PUBLICATIONS

Tanaka et al. "NMR structure of the histidine kinase domain of the *E. coli* osmosensor EnvZ" Nature 395, 88–92, Nov. 5, 1998.
Tomomori et al. "Solution structure of the homodimeric core domain of *Escherichia coli* histidine kinase EnvZ" Nature Struc. Biol. 6, 729–734, Aug. 1999.
Alex et al, 1996, Proc Natl Acad Sci USA, 93:3416–21.
Alexandrov et al., 1992, J Mol Biol 225:5–9.
Altschul et al., 1997, Nucleic Acids Res, 25:3389–402.
Altschul et al., 1990, J Mol Biol, 215:403–10.
Appleby et al., 1996, Cell. 86:845–8.
Bagby et al, 1995, Cell, 82:857–67.
Bagby et al., 1994, Biochem, 33:2409–21.
Barrett et al., 1998, Proc Natl Acad Sci USA, 95:5317–22.
Baumgartner et al., 1994, J Bacteriol, 176:1157–63.
Chang et al., 1993, Science, 262:539–44.
Delgado et al., Mol Microbiol, 10:1037–47.
Dutta et al, 1996, J Biol Chem, 271:1424–9.
Egger et al., 1997, Gen Cell, 2:167–84.
Gardina et al., 1996, Science, 274:425–6.
Gill et al., 1989, Analytical Biochem, 182:319–26.
Hidaka et al., 1997, FEBS Lett, 400:238–42.
Holdgate et al., 1997, Biochemistry, 36:9663–73.
Igo et al., 1989, Gen Dev, 3:1725–34.
Inouye, 1996. Cell, 85:13–4.
Jin et al., 1993, J Mol Biol, 232:484–92.
Kraulis, 1991, J. Appl. Cryst. 24:946–959.
Levy, 1998, Scientific American, Mar:46–53.
Milburn et al., 1991, Science, 254:1342–7.
Munoz–Dorado et al., 1993, J Cell Biochem, 51:29–33.
Ota et al., 1993, Science, 262:566–9.
Pan et al., 1993, Proc Natl Acad Sci USA, 90:9939–43.
Park et al., 1997, J Bacteriol, 179:4382–90.
Parkinson et al., 1992, Ann Rev Gen, 26:71–112.
Prodromou et al., 1997, Cell, 90:65–76.
Roberts et al., 1994, J Biol Chem. 269:8728–33.
Shuker et al, 1996, Science, 274:1531–4.
Sicheri et al., 1997, Nature, 385:602–9.
Soncini et al., 1996, J Bacteriol, 178:6796–801.
Stock et al., 1989, Microbiol Rev, 53:450–90.
Swanson et al., 1993, Mol Microbiol, 8:435–41.
Swanson et al., 1993, Biochem, 32:7623–9.
Surette et al., 1996, J Biol Chem, 271:939–45.
Tatsuno et al., 1996, Science, 274:423–5.
Tokishita et al., 1990, J Biochem, 108:488–93.

(List continued on next page.)

*Primary Examiner*—Nashaat Nashed
*Attorney, Agent, or Firm*—Klauber & Jackson

[57] ABSTRACT

The present invention provides N-terminal truncated transmembrane sensor histidine kinases that retain their ability to be autophophorylated and/or their related histidine kinase activity. The N-terminal truncated transmembrane sensor histidine kinases are useful for obtaining detailed three-dimensional structural data of the catalytic portion of the protein. The three-dimensional structural data is included as part of the invention. In addition, the present invention provides methodology for related structure based rational drug design using the three-dimensional data. Nucleotide and amino acid sequences of the N-terminal truncated transmembrane sensor histidine kinases are also provided.

18 Claims, 89 Drawing Sheets

OTHER PUBLICATIONS

Uhl et al., 1996, EMBO J, 15:1028–36.
Utsumi et al., 1989, Science, 245:1246–9.
Wigley et al., 1991, Nature, 351:624–9.
Yang et al., 1993, J Mol Biol, 232, 493–498.
Yang et al., 1991, Proc Natl Acad Sci USA, 88:11057–61.
Yang et al., 1993, J Mol Biol, 231:335–42.
Yoshida et al., 1993, Biochemistry 32:2162–66.

FIG. 6A

```
             290        300        310        320        330       340*        * 350
ENVZ_ECOLI   TGQEMP-----MEMADLN-AVLGEVIAAESGYEREIETATALYPGS-----IEVKMHPLSIKRAVANMVVNAARYG-N-G
CPXA_ECOLI   NQQKNALVSETIKANQLWSEVLDNAAFEAEQMGKSLTVNFPPGP-----WPLYGNPNALESALENIVRNALRYS---H
PHOR_KLEPN   IEAAPAL--AMNDRIDVP-MMLRVVEREAQTLSQEKQTLIFTVD-EQLKVLGNEEQLRSAISNLVYNAVNHTPP-G
KDPD_ECOLI   IQSGGFN--LKKEWLTLEEVVGSALQMLEPGLSSPINLSLPEPL-----TLIHVDGPLFERVLINLLENAVKYAGA-Q
PHOQ_ECOLI   MRGGTLLSRELHPVAPLLDNLTSALNKVYQRKGVNISLDISPEI-----SFVGEQNDFVEVMGNVLDNACKYC---L
BASS_SALTY   VGQSFSSG-NYQEVKLLEDVILPSYDELNTMLETRQQTLLLPESAADVVVRGDATLIRMLLRNLVENAHRYSPE-G
CREC_ECOLI   LENRQEV--VLTAVDVAALFRRVSEARTVQLAEKKITLHVTPTE---VNVAAEPALLEQALGNLLDNAIDFTPE-S
ARCB_ECOLI   MERRKVQL-DNQPVDFTSFLADLENLSALQAQQKGLRFNLEPTLPLPHQVITDGTRLRQILWNLISNAVKFTQQ-G
CHEA_ECOLI   DLAGKLG--KQVELTLVGSSTELDKSLIERIIDPLTHLVRNSLD----HGIELPEKRLAAGKNSVGNLILSAEHQG
                     A                              α1                  B                    C                 α2

360        370        *  380        390        400*        *   410
ENVZ_ECOLI   -WIKVSSGTEP-----NRAWFQVEDDGPGIAPEQRK-----HLFQPFVRGDSART--ISGTGLGLAIVQRIVDNH
CPXA_ECOLI   TKIEVGFAVDK-----DGITITVDDDGPGVSPEDRE-----QIFRPFYRTDEARDRESGGTGLGLAIVETAIQQH
PHOR_KLEPN   TEIRVSWQRTP-----QGALFSVEDNGPGIAPEHIP-----LLTERFYRGDKARSRQTGGSGLGLAIVKHAVNHH
KDPD_ECOLI   AEIGIDAHVEG-----ENLQLDVWDNGPGLPPGQEQ---VPGVGLGLAICRAIVDVH
PHOQ_ECOLI   EFVEISARQTD-----EHLYIVVEDDGPGIPLSKRE-----VIFDRGQRVDTLR----PGQGVGLAVAREITEQY
BASS_SALTY   THITIHISADP-----D-AIMAVEDEGPGIDESKCG-----KLSEAFVRMDSR----YGGIGLGLSIVSRITQLH
CREC_ECOLI   GCITLSAEVDQ-----EHVTLKVLDTGSGIPDYALS-----RIFERFYSLPRANG--QKSSGLGLAFVSEVARLF
ARCB_ECOLI   -QVTVRVRYDEG----DMLHFEVEDSGIGIPQDELD-----KIFAMYYQVKDSHGG-KPATGIGLAVSRRLAKNM
CHEA_ECOLI   GNICIEVTDDGAGLNRERILAKAASQGLTVSENMSDDEVAMLIFAPGFSTAEQVTD-VSGRGVGMDVVKRNIQKM
                     D                           E                α3                               α4
```

FIG. 6B

```
                    420           *430          440              450
ENVZ_ECOLI    NGMLELGT-SERGGLSIRAWLPVPVTRAQ--GTTKEG
CPXA_ECOLI    RGWVKAED-SPLGGLRLVIWLPLYKRS------
PHOR_KLEPN    DSRLEIDS-TVGKGTRFSFLLPERLIARN--DA----
KDPD_ECOLI    GGTITAFNRPE-GGACFRVTLPQQTAPEL--EEFHEDM
PHOQ_ECOLI    EGKIVAGE-SMLGGARMEVIFGRQHSAPK---DE----
BASS_SALTY    QGQFFLQNRTERTGT--RAWVLLKKA-----
CREC_ECOLI    NGEVTLRNVQE-GGVLASLRHFT------
ARCB_ECOLI    GGDITVTS-EQGKGSTFTLTIHAPSVAEEVDDAFDED
CHEA_ECOLI    GGHVEIQS-KQGTGTTIRILPLTLAILDGMSVRVAD
                    F                     G
```

Figure 8-1

Coordinates determined by NMR for sub-domain A [EnvZ(C)(223-289), SEQ ID NO:12]

```
REMARK envZ   final structure, seed 726891 ,noe 1084.93 ,tot 2773.89 REMARK
DATE:10-Feb-98  13:57:38       created by user:
ATOM     1  CA   MET   223     14.751  -8.953 -18.178  1.00  0.00      A
ATOM     2  HA   MET   223     14.048  -9.180 -18.962  1.00  0.00      A
ATOM     3  CB   MET   223     14.254  -9.526 -16.849  1.00  0.00      A
ATOM     4  HB1  MET   223     13.304  -9.081 -16.597  1.00  0.00      A
ATOM     5  HB2  MET   223     14.973  -9.307 -16.072  1.00  0.00      A
ATOM     6  CG   MET   223     14.088 -11.040 -16.979  1.00  0.00      A
ATOM     7  HG1  MET   223     15.038 -11.484 -17.234  1.00  0.00      A
ATOM     8  HG2  MET   223     13.370 -11.257 -17.755  1.00  0.00      A
ATOM     9  SD   MET   223     13.505 -11.724 -15.408  1.00  0.00      A
ATOM    10  CE   MET   223     15.048 -11.521 -14.485  1.00  0.00      A
ATOM    11  HE1  MET   223     15.435 -10.523 -14.648  1.00  0.00      A
ATOM    12  HE2  MET   223     15.769 -12.243 -14.826  1.00  0.00      A
ATOM    13  HE3  MET   223     14.859 -11.672 -13.431  1.00  0.00      A
ATOM    14  C    MET   223     14.961  -7.440 -18.068  1.00  0.00      A
ATOM    15  O    MET   223     16.076  -6.960 -18.026  1.00  0.00      A
ATOM    16  N    MET   223     16.058  -9.638 -18.434  1.00  0.00      A
ATOM    17  HT1  MET   223     15.892 -10.504 -18.985  1.00  0.00      A
ATOM    18  HT2  MET   223     16.507  -9.884 -17.528  1.00  0.00      A
ATOM    19  HT3  MET   223     16.683  -9.002 -18.969  1.00  0.00      A
ATOM    20  N    ALA   224     13.896  -6.684 -18.021  1.00  0.00      A
ATOM    21  HN   ALA   224     13.004  -7.090 -18.058  1.00  0.00      A
ATOM    22  CA   ALA   224     14.037  -5.204 -17.912  1.00  0.00      A
ATOM    23  HA   ALA   224     14.617  -4.943 -17.044  1.00  0.00      A
ATOM    24  CB   ALA   224     14.783  -4.786 -19.180  1.00  0.00      A
ATOM    25  HB1  ALA   224     15.598  -4.128 -18.918  1.00  0.00      A
ATOM    26  HB2  ALA   224     14.104  -4.271 -19.845  1.00  0.00      A
ATOM    27  HB3  ALA   224     15.173  -5.663 -19.674  1.00  0.00      A
ATOM    28  C    ALA   224     12.658  -4.540 -17.854  1.00  0.00      A
ATOM    29  O    ALA   224     11.661  -5.115 -18.245  1.00  0.00      A
ATOM    30  N    ALA   225     12.597  -3.332 -17.369  1.00  0.00      A
ATOM    31  HN   ALA   225     13.413  -2.890 -17.058  1.00  0.00      A
ATOM    32  CA   ALA   225     11.289  -2.622 -17.281  1.00  0.00      A
ATOM    33  HA   ALA   225     10.817  -2.576 -18.248  1.00  0.00      A
ATOM    34  CB   ALA   225     10.445  -3.461 -16.325  1.00  0.00      A
ATOM    35  HB1  ALA   225      9.424  -3.490 -16.677  1.00  0.00      A
ATOM    36  HB2  ALA   225     10.474  -3.021 -15.339  1.00  0.00      A
ATOM    37  HB3  ALA   225     10.840  -4.466 -16.283  1.00  0.00      A
ATOM    38  C    ALA   225     11.502  -1.219 -16.719  1.00  0.00      A
ATOM    39  O    ALA   225     10.955  -0.858 -15.697  1.00  0.00      A
ATOM    40  N    GLY   226     12.297  -0.425 -17.381  1.00  0.00      A
ATOM    41  HN   GLY   226     12.724  -0.738 -18.206  1.00  0.00      A
ATOM    42  CA   GLY   226     12.553   0.957 -16.891  1.00  0.00      A
ATOM    43  HA1  GLY   226     13.373   1.386 -17.443  1.00  0.00      A
ATOM    44  HA2  GLY   226     12.807   0.924 -15.840  1.00  0.00      A
ATOM    45  C    GLY   226     11.306   1.821 -17.085  1.00  0.00      A
ATOM    46  O    GLY   226     10.941   2.592 -16.225  1.00  0.00      A
ATOM    47  N    VAL   227     10.658   1.707 -18.215  1.00  0.00      A
ATOM    48  HN   VAL   227     10.974   1.081 -18.899  1.00  0.00      A
ATOM    49  CA   VAL   227      9.432   2.527 -18.463  1.00  0.00      A
ATOM    50  HA   VAL   227      9.616   3.561 -18.223  1.00  0.00      A
ATOM    51  CB   VAL   227      9.154   2.382 -19.957  1.00  0.00      A
ATOM    52  HB   VAL   227      9.009   1.339 -20.196  1.00  0.00      A
ATOM    53  CG1  VAL   227      7.894   3.169 -20.322  1.00  0.00      A
ATOM    54  HG11 VAL   227      7.345   2.636 -21.083  1.00  0.00      A
```

Figure 8-2

| | | | | | | | | | |
|---|---|---|---|---|---|---|---|---|---|
| ATOM | 55 | HG12 | VAL | 227 | 8.172 | 4.144 | -20.695 | 1.00 | 0.00 | A |
| ATOM | 56 | HG13 | VAL | 227 | 7.274 | 3.283 | -19.444 | 1.00 | 0.00 | A |
| ATOM | 57 | CG2 | VAL | 227 | 10.343 | 2.930 | -20.751 | 1.00 | 0.00 | A |
| ATOM | 58 | HG21 | VAL | 227 | 10.331 | 4.010 | -20.720 | 1.00 | 0.00 | A |
| ATOM | 59 | HG22 | VAL | 227 | 10.274 | 2.598 | -21.775 | 1.00 | 0.00 | A |
| ATOM | 60 | HG23 | VAL | 227 | 11.263 | 2.567 | -20.316 | 1.00 | 0.00 | A |
| ATOM | 61 | C | VAL | 227 | 8.254 | 1.992 | -17.644 | 1.00 | 0.00 | A |
| ATOM | 62 | O | VAL | 227 | 7.407 | 1.281 | -18.148 | 1.00 | 0.00 | A |
| ATOM | 63 | N | LYS | 228 | 8.191 | 2.331 | -16.387 | 1.00 | 0.00 | A |
| ATOM | 64 | HN | LYS | 228 | 8.869 | 2.918 | -16.003 | 1.00 | 0.00 | A |
| ATOM | 65 | CA | LYS | 228 | 7.069 | 1.841 | -15.540 | 1.00 | 0.00 | A |
| ATOM | 66 | HA | LYS | 228 | 6.902 | 0.793 | -15.706 | 1.00 | 0.00 | A |
| ATOM | 67 | CB | LYS | 228 | 7.535 | 2.081 | -14.102 | 1.00 | 0.00 | A |
| ATOM | 68 | HB1 | LYS | 228 | 6.827 | 1.643 | -13.419 | 1.00 | 0.00 | A |
| ATOM | 69 | HB2 | LYS | 228 | 7.610 | 3.143 | -13.917 | 1.00 | 0.00 | A |
| ATOM | 70 | CG | LYS | 228 | 8.903 | 1.422 | -13.894 | 1.00 | 0.00 | A |
| ATOM | 71 | HG1 | LYS | 228 | 9.613 | 1.836 | -14.593 | 1.00 | 0.00 | A |
| ATOM | 72 | HG2 | LYS | 228 | 8.818 | 0.357 | -14.054 | 1.00 | 0.00 | A |
| ATOM | 73 | CD | LYS | 228 | 9.387 | 1.684 | -12.464 | 1.00 | 0.00 | A |
| ATOM | 74 | HD1 | LYS | 228 | 8.685 | 1.261 | -11.762 | 1.00 | 0.00 | A |
| ATOM | 75 | HD2 | LYS | 228 | 9.464 | 2.751 | -12.300 | 1.00 | 0.00 | A |
| ATOM | 76 | CE | LYS | 228 | 10.761 | 1.036 | -12.261 | 1.00 | 0.00 | A |
| ATOM | 77 | HE1 | LYS | 228 | 10.706 | -0.025 | -12.441 | 1.00 | 0.00 | A |
| ATOM | 78 | HE2 | LYS | 228 | 11.124 | 1.233 | -11.261 | 1.00 | 0.00 | A |
| ATOM | 79 | NZ | LYS | 228 | 11.643 | 1.682 | -13.274 | 1.00 | 0.00 | A |
| ATOM | 80 | HZ1 | LYS | 228 | 11.510 | 1.220 | -14.194 | 1.00 | 0.00 | A |
| ATOM | 81 | HZ2 | LYS | 228 | 12.637 | 1.587 | -12.977 | 1.00 | 0.00 | A |
| ATOM | 82 | HZ3 | LYS | 228 | 11.399 | 2.689 | -13.355 | 1.00 | 0.00 | A |
| ATOM | 83 | C | LYS | 228 | 5.800 | 2.646 | -15.862 | 1.00 | 0.00 | A |
| ATOM | 84 | O | LYS | 228 | 4.777 | 2.097 | -16.217 | 1.00 | 0.00 | A |
| ATOM | 85 | N | GLN | 229 | 5.867 | 3.942 | -15.737 | 1.00 | 0.00 | A |
| ATOM | 86 | HN | GLN | 229 | 6.697 | 4.352 | -15.447 | 1.00 | 0.00 | A |
| ATOM | 87 | CA | GLN | 229 | 4.671 | 4.794 | -16.037 | 1.00 | 0.00 | A |
| ATOM | 88 | HA | GLN | 229 | 4.211 | 4.466 | -16.956 | 1.00 | 0.00 | A |
| ATOM | 89 | CB | GLN | 229 | 3.682 | 4.596 | -14.866 | 1.00 | 0.00 | A |
| ATOM | 90 | HB1 | GLN | 229 | 3.470 | 3.542 | -14.756 | 1.00 | 0.00 | A |
| ATOM | 91 | HB2 | GLN | 229 | 2.762 | 5.121 | -15.086 | 1.00 | 0.00 | A |
| ATOM | 92 | CG | GLN | 229 | 4.267 | 5.134 | -13.544 | 1.00 | 0.00 | A |
| ATOM | 93 | HG1 | GLN | 229 | 3.488 | 5.164 | -12.791 | 1.00 | 0.00 | A |
| ATOM | 94 | HG2 | GLN | 229 | 4.652 | 6.130 | -13.700 | 1.00 | 0.00 | A |
| ATOM | 95 | CD | GLN | 229 | 5.393 | 4.228 | -13.065 | 1.00 | 0.00 | A |
| ATOM | 96 | OE1 | GLN | 229 | 5.274 | 3.025 | -13.122 | 1.00 | 0.00 | A |
| ATOM | 97 | NE2 | GLN | 229 | 6.481 | 4.756 | -12.570 | 1.00 | 0.00 | A |
| ATOM | 98 | HE21 | GLN | 229 | 6.568 | 5.729 | -12.507 | 1.00 | 0.00 | A |
| ATOM | 99 | HE22 | GLN | 229 | 7.209 | 4.180 | -12.263 | 1.00 | 0.00 | A |
| ATOM | 100 | C | GLN | 229 | 5.077 | 6.278 | -16.157 | 1.00 | 0.00 | A |
| ATOM | 101 | O | GLN | 229 | 4.438 | 7.149 | -15.599 | 1.00 | 0.00 | A |
| ATOM | 102 | N | LEU | 230 | 6.140 | 6.574 | -16.883 | 1.00 | 0.00 | A |
| ATOM | 103 | HN | LEU | 230 | 6.643 | 5.866 | -17.325 | 1.00 | 0.00 | A |
| ATOM | 104 | CA | LEU | 230 | 6.570 | 8.004 | -17.029 | 1.00 | 0.00 | A |
| ATOM | 105 | HA | LEU | 230 | 5.867 | 8.649 | -16.541 | 1.00 | 0.00 | A |
| ATOM | 106 | CB | LEU | 230 | 7.948 | 8.124 | -16.347 | 1.00 | 0.00 | A |
| ATOM | 107 | HB1 | LEU | 230 | 8.338 | 9.119 | -16.504 | 1.00 | 0.00 | A |
| ATOM | 108 | HB2 | LEU | 230 | 8.625 | 7.404 | -16.785 | 1.00 | 0.00 | A |
| ATOM | 109 | CG | LEU | 230 | 7.836 | 7.857 | -14.842 | 1.00 | 0.00 | A |
| ATOM | 110 | HG | LEU | 230 | 7.001 | 8.413 | -14.440 | 1.00 | 0.00 | A |
| ATOM | 111 | CD1 | LEU | 230 | 7.620 | 6.372 | -14.597 | 1.00 | 0.00 | A |
| ATOM | 112 | HD11 | LEU | 230 | 8.252 | 6.045 | -13.785 | 1.00 | 0.00 | A |

Figure 8-3

| | | | | | | | | | |
|---|---|---|---|---|---|---|---|---|---|
| ATOM | 113 | HD12 | LEU | 230 | 7.873 | 5.824 | -15.492 | 1.00 | 0.00 | A |
| ATOM | 114 | HD13 | LEU | 230 | 6.590 | 6.196 | -14.344 | 1.00 | 0.00 | A |
| ATOM | 115 | CD2 | LEU | 230 | 9.126 | 8.301 | -14.149 | 1.00 | 0.00 | A |
| ATOM | 116 | HD21 | LEU | 230 | 9.899 | 7.567 | -14.324 | 1.00 | 0.00 | A |
| ATOM | 117 | HD22 | LEU | 230 | 8.952 | 8.392 | -13.088 | 1.00 | 0.00 | A |
| ATOM | 118 | HD23 | LEU | 230 | 9.438 | 9.255 | -14.547 | 1.00 | 0.00 | A |
| ATOM | 119 | C | LEU | 230 | 6.702 | 8.392 | -18.512 | 1.00 | 0.00 | A |
| ATOM | 120 | O | LEU | 230 | 7.579 | 9.150 | -18.881 | 1.00 | 0.00 | A |
| ATOM | 121 | N | ALA | 231 | 5.849 | 7.891 | -19.365 | 1.00 | 0.00 | A |
| ATOM | 122 | HN | ALA | 231 | 5.155 | 7.278 | -19.062 | 1.00 | 0.00 | A |
| ATOM | 123 | CA | ALA | 231 | 5.966 | 8.263 | -20.818 | 1.00 | 0.00 | A |
| ATOM | 124 | HA | ALA | 231 | 6.172 | 9.303 | -20.910 | 1.00 | 0.00 | A |
| ATOM | 125 | CB | ALA | 231 | 7.154 | 7.452 | -21.336 | 1.00 | 0.00 | A |
| ATOM | 126 | HB1 | ALA | 231 | 7.875 | 8.117 | -21.788 | 1.00 | 0.00 | A |
| ATOM | 127 | HB2 | ALA | 231 | 6.809 | 6.740 | -22.072 | 1.00 | 0.00 | A |
| ATOM | 128 | HB3 | ALA | 231 | 7.615 | 6.923 | -20.514 | 1.00 | 0.00 | A |
| ATOM | 129 | C | ALA | 231 | 4.696 | 7.910 | -21.607 | 1.00 | 0.00 | A |
| ATOM | 130 | O | ALA | 231 | 4.703 | 7.894 | -22.820 | 1.00 | 0.00 | A |
| ATOM | 131 | N | ASP | 232 | 3.613 | 7.671 | -20.931 | 1.00 | 0.00 | A |
| ATOM | 132 | HN | ASP | 232 | 3.630 | 7.745 | -19.963 | 1.00 | 0.00 | A |
| ATOM | 133 | CA | ASP | 232 | 2.328 | 7.319 | -21.634 | 1.00 | 0.00 | A |
| ATOM | 134 | HA | ASP | 232 | 2.211 | 7.904 | -22.500 | 1.00 | 0.00 | A |
| ATOM | 135 | CB | ASP | 232 | 2.427 | 5.824 | -22.000 | 1.00 | 0.00 | A |
| ATOM | 136 | HB1 | ASP | 232 | 1.498 | 5.505 | -22.447 | 1.00 | 0.00 | A |
| ATOM | 137 | HB2 | ASP | 232 | 2.606 | 5.250 | -21.103 | 1.00 | 0.00 | A |
| ATOM | 138 | CG | ASP | 232 | 3.570 | 5.586 | -22.987 | 1.00 | 0.00 | A |
| ATOM | 139 | OD1 | ASP | 232 | 4.695 | 5.446 | -22.538 | 1.00 | 0.00 | A |
| ATOM | 140 | OD2 | ASP | 232 | 3.301 | 5.553 | -24.177 | 1.00 | 0.00 | A |
| ATOM | 141 | C | ASP | 232 | 1.158 | 7.535 | -20.705 | 1.00 | 0.00 | A |
| ATOM | 142 | O | ASP | 232 | 0.117 | 8.022 | -21.088 | 1.00 | 0.00 | A |
| ATOM | 143 | N | ASP | 233 | 1.323 | 7.162 | -19.499 | 1.00 | 0.00 | A |
| ATOM | 144 | HN | ASP | 233 | 2.170 | 6.774 | -19.242 | 1.00 | 0.00 | A |
| ATOM | 145 | CA | ASP | 233 | 0.233 | 7.329 | -18.498 | 1.00 | 0.00 | A |
| ATOM | 146 | HA | ASP | 233 | -0.686 | 6.906 | -18.867 | 1.00 | 0.00 | A |
| ATOM | 147 | CB | ASP | 233 | 0.705 | 6.558 | -17.262 | 1.00 | 0.00 | A |
| ATOM | 148 | HB1 | ASP | 233 | -0.038 | 6.637 | -16.483 | 1.00 | 0.00 | A |
| ATOM | 149 | HB2 | ASP | 233 | 1.640 | 6.972 | -16.913 | 1.00 | 0.00 | A |
| ATOM | 150 | CG | ASP | 233 | 0.902 | 5.084 | -17.625 | 1.00 | 0.00 | A |
| ATOM | 151 | OD1 | ASP | 233 | 1.742 | 4.808 | -18.466 | 1.00 | 0.00 | A |
| ATOM | 152 | OD2 | ASP | 233 | 0.210 | 4.255 | -17.055 | 1.00 | 0.00 | A |
| ATOM | 153 | C | ASP | 233 | 0.045 | 8.811 | -18.170 | 1.00 | 0.00 | A |
| ATOM | 154 | O | ASP | 233 | -0.995 | 9.228 | -17.712 | 1.00 | 0.00 | A |
| ATOM | 155 | N | ARG | 234 | 1.042 | 9.612 | -18.406 | 1.00 | 0.00 | A |
| ATOM | 156 | HN | ARG | 234 | 1.871 | 9.262 | -18.783 | 1.00 | 0.00 | A |
| ATOM | 157 | CA | ARG | 234 | 0.905 | 11.068 | -18.101 | 1.00 | 0.00 | A |
| ATOM | 158 | HA | ARG | 234 | 0.487 | 11.193 | -17.115 | 1.00 | 0.00 | A |
| ATOM | 159 | CB | ARG | 234 | 2.330 | 11.639 | -18.128 | 1.00 | 0.00 | A |
| ATOM | 160 | HB1 | ARG | 234 | 2.933 | 11.117 | -17.405 | 1.00 | 0.00 | A |
| ATOM | 161 | HB2 | ARG | 234 | 2.296 | 12.687 | -17.872 | 1.00 | 0.00 | A |
| ATOM | 162 | CG | ARG | 234 | 2.956 | 11.480 | -19.515 | 1.00 | 0.00 | A |
| ATOM | 163 | HG1 | ARG | 234 | 2.406 | 12.073 | -20.229 | 1.00 | 0.00 | A |
| ATOM | 164 | HG2 | ARG | 234 | 2.930 | 10.440 | -19.812 | 1.00 | 0.00 | A |
| ATOM | 165 | CD | ARG | 234 | 4.407 | 11.970 | -19.465 | 1.00 | 0.00 | A |
| ATOM | 166 | HD1 | ARG | 234 | 4.974 | 11.392 | -18.754 | 1.00 | 0.00 | A |
| ATOM | 167 | HD2 | ARG | 234 | 4.437 | 13.020 | -19.208 | 1.00 | 0.00 | A |
| ATOM | 168 | NE | ARG | 234 | 4.940 | 11.756 | -20.837 | 1.00 | 0.00 | A |
| ATOM | 169 | HE | ARG | 234 | 4.375 | 11.346 | -21.524 | 1.00 | 0.00 | A |
| ATOM | 170 | CZ | ARG | 234 | 6.165 | 12.114 | -21.124 | 1.00 | 0.00 | A |

Figure 8-4

| | | | | | | | | | |
|---|---|---|---|---|---|---|---|---|---|
| ATOM | 171 | NH1 | ARG | 234 | 6.801 | 11.536 | -22.106 | 1.00 | 0.00 | A |
| ATOM | 172 | HH11 | ARG | 234 | 6.353 | 10.818 | -22.638 | 1.00 | 0.00 | A |
| ATOM | 173 | HH12 | ARG | 234 | 7.737 | 11.811 | -22.327 | 1.00 | 0.00 | A |
| ATOM | 174 | NH2 | ARG | 234 | 6.753 | 13.051 | -20.428 | 1.00 | 0.00 | A |
| ATOM | 175 | HH21 | ARG | 234 | 6.267 | 13.494 | -19.675 | 1.00 | 0.00 | A |
| ATOM | 176 | HH22 | ARG | 234 | 7.689 | 13.325 | -20.649 | 1.00 | 0.00 | A |
| ATOM | 177 | C | ARG | 234 | 0.002 | 11.753 | -19.136 | 1.00 | 0.00 | A |
| ATOM | 178 | O | ARG | 234 | -0.910 | 12.451 | -18.788 | 1.00 | 0.00 | A |
| ATOM | 179 | N | THR | 235 | 0.240 | 11.548 | -20.399 | 1.00 | 0.00 | A |
| ATOM | 180 | HN | THR | 235 | 0.963 | 10.952 | -20.672 | 1.00 | 0.00 | A |
| ATOM | 181 | CA | THR | 235 | -0.619 | 12.199 | -21.437 | 1.00 | 0.00 | A |
| ATOM | 182 | HA | THR | 235 | -0.842 | 13.214 | -21.169 | 1.00 | 0.00 | A |
| ATOM | 183 | CB | THR | 235 | 0.217 | 12.146 | -22.720 | 1.00 | 0.00 | A |
| ATOM | 184 | HB | THR | 235 | 0.490 | 11.115 | -22.930 | 1.00 | 0.00 | A |
| ATOM | 185 | OG1 | THR | 235 | 1.396 | 12.918 | -22.544 | 1.00 | 0.00 | A |
| ATOM | 186 | HG1 | THR | 235 | 2.086 | 12.336 | -22.219 | 1.00 | 0.00 | A |
| ATOM | 187 | CG2 | THR | 235 | -0.593 | 12.700 | -23.893 | 1.00 | 0.00 | A |
| ATOM | 188 | HG21 | THR | 235 | 0.037 | 13.339 | -24.495 | 1.00 | 0.00 | A |
| ATOM | 189 | HG22 | THR | 235 | -1.430 | 13.270 | -23.518 | 1.00 | 0.00 | A |
| ATOM | 190 | HG23 | THR | 235 | -0.957 | 11.882 | -24.497 | 1.00 | 0.00 | A |
| ATOM | 191 | C | THR | 235 | -1.902 | 11.414 | -21.595 | 1.00 | 0.00 | A |
| ATOM | 192 | O | THR | 235 | -2.913 | 11.922 | -22.036 | 1.00 | 0.00 | A |
| ATOM | 193 | N | LEU | 236 | -1.864 | 10.182 | -21.238 | 1.00 | 0.00 | A |
| ATOM | 194 | HN | LEU | 236 | -1.031 | 9.803 | -20.885 | 1.00 | 0.00 | A |
| ATOM | 195 | CA | LEU | 236 | -3.065 | 9.338 | -21.354 | 1.00 | 0.00 | A |
| ATOM | 196 | HA | LEU | 236 | -3.460 | 9.366 | -22.323 | 1.00 | 0.00 | A |
| ATOM | 197 | CB | LEU | 236 | -2.582 | 7.948 | -21.039 | 1.00 | 0.00 | A |
| ATOM | 198 | HB1 | LEU | 236 | -2.095 | 7.941 | -20.076 | 1.00 | 0.00 | A |
| ATOM | 199 | HB2 | LEU | 236 | -1.890 | 7.621 | -21.802 | 1.00 | 0.00 | A |
| ATOM | 200 | CG | LEU | 236 | -3.774 | 7.036 | -21.006 | 1.00 | 0.00 | A |
| ATOM | 201 | HG | LEU | 236 | -4.529 | 7.491 | -20.365 | 1.00 | 0.00 | A |
| ATOM | 202 | CD1 | LEU | 236 | -4.342 | 6.876 | -22.421 | 1.00 | 0.00 | A |
| ATOM | 203 | HD11 | LEU | 236 | -5.259 | 6.306 | -22.379 | 1.00 | 0.00 | A |
| ATOM | 204 | HD12 | LEU | 236 | -3.625 | 6.358 | -23.041 | 1.00 | 0.00 | A |
| ATOM | 205 | HD13 | LEU | 236 | -4.542 | 7.850 | -22.841 | 1.00 | 0.00 | A |
| ATOM | 206 | CD2 | LEU | 236 | -3.356 | 5.684 | -20.449 | 1.00 | 0.00 | A |
| ATOM | 207 | HD21 | LEU | 236 | -2.510 | 5.311 | -21.012 | 1.00 | 0.00 | A |
| ATOM | 208 | HD22 | LEU | 236 | -4.177 | 4.992 | -20.531 | 1.00 | 0.00 | A |
| ATOM | 209 | HD23 | LEU | 236 | -3.076 | 5.794 | -19.413 | 1.00 | 0.00 | A |
| ATOM | 210 | C | LEU | 236 | -4.124 | 9.753 | -20.366 | 1.00 | 0.00 | A |
| ATOM | 211 | O | LEU | 236 | -5.280 | 9.907 | -20.710 | 1.00 | 0.00 | A |
| ATOM | 212 | N | LEU | 237 | -3.763 | 9.938 | -19.148 | 1.00 | 0.00 | A |
| ATOM | 213 | HN | LEU | 237 | -2.829 | 9.814 | -18.882 | 1.00 | 0.00 | A |
| ATOM | 214 | CA | LEU | 237 | -4.777 | 10.340 | -18.152 | 1.00 | 0.00 | A |
| ATOM | 215 | HA | LEU | 237 | -5.699 | 9.852 | -18.376 | 1.00 | 0.00 | A |
| ATOM | 216 | CB | LEU | 237 | -4.237 | 9.816 | -16.840 | 1.00 | 0.00 | A |
| ATOM | 217 | HB1 | LEU | 237 | -4.991 | 9.883 | -16.079 | 1.00 | 0.00 | A |
| ATOM | 218 | HB2 | LEU | 237 | -3.370 | 10.396 | -16.547 | 1.00 | 0.00 | A |
| ATOM | 219 | CG | LEU | 237 | -3.831 | 8.329 | -17.036 | 1.00 | 0.00 | A |
| ATOM | 220 | HG | LEU | 237 | -2.899 | 8.292 | -17.578 | 1.00 | 0.00 | A |
| ATOM | 221 | CD1 | LEU | 237 | -3.629 | 7.689 | -15.695 | 1.00 | 0.00 | A |
| ATOM | 222 | HD11 | LEU | 237 | -4.544 | 7.749 | -15.133 | 1.00 | 0.00 | A |
| ATOM | 223 | HD12 | LEU | 237 | -2.845 | 8.207 | -15.172 | 1.00 | 0.00 | A |
| ATOM | 224 | HD13 | LEU | 237 | -3.355 | 6.658 | -15.832 | 1.00 | 0.00 | A |
| ATOM | 225 | CD2 | LEU | 237 | -4.916 | 7.551 | -17.840 | 1.00 | 0.00 | A |
| ATOM | 226 | HD21 | LEU | 237 | -4.529 | 6.585 | -18.124 | 1.00 | 0.00 | A |
| ATOM | 227 | HD22 | LEU | 237 | -5.173 | 8.100 | -18.733 | 1.00 | 0.00 | A |
| ATOM | 228 | HD23 | LEU | 237 | -5.795 | 7.423 | -17.237 | 1.00 | 0.00 | A |

Figure 8-5

| | | | | | | | | | |
|---|---|---|---|---|---|---|---|---|---|
| ATOM | 229 | C    | LEU | 237 | -4.999  | 11.838 | -18.181 | 1.00 | 0.00 | A |
| ATOM | 230 | O    | LEU | 237 | -5.506  | 12.438 | -17.264 | 1.00 | 0.00 | A |
| ATOM | 231 | N    | MET | 238 | -4.571  | 12.430 | -19.211 | 1.00 | 0.00 | A |
| ATOM | 232 | HN   | MET | 238 | -4.251  | 11.912 | -19.935 | 1.00 | 0.00 | A |
| ATOM | 233 | CA   | MET | 238 | -4.732  | 13.873 | -19.368 | 1.00 | 0.00 | A |
| ATOM | 234 | HA   | MET | 238 | -4.947  | 14.314 | -18.418 | 1.00 | 0.00 | A |
| ATOM | 235 | CB   | MET | 238 | -3.435  | 14.420 | -19.954 | 1.00 | 0.00 | A |
| ATOM | 236 | HB1  | MET | 238 | -3.634  | 15.339 | -20.481 | 1.00 | 0.00 | A |
| ATOM | 237 | HB2  | MET | 238 | -3.011  | 13.694 | -20.635 | 1.00 | 0.00 | A |
| ATOM | 238 | CG   | MET | 238 | -2.452  | 14.691 | -18.815 | 1.00 | 0.00 | A |
| ATOM | 239 | HG1  | MET | 238 | -2.346  | 13.809 | -18.212 | 1.00 | 0.00 | A |
| ATOM | 240 | HG2  | MET | 238 | -2.834  | 15.495 | -18.203 | 1.00 | 0.00 | A |
| ATOM | 241 | SD   | MET | 238 | -0.846  | 15.171 | -19.497 | 1.00 | 0.00 | A |
| ATOM | 242 | CE   | MET | 238 | -0.091  | 15.713 | -17.944 | 1.00 | 0.00 | A |
| ATOM | 243 | HE1  | MET | 238 | -0.170  | 14.921 | -17.211 | 1.00 | 0.00 | A |
| ATOM | 244 | HE2  | MET | 238 | -0.603  | 16.588 | -17.581 | 1.00 | 0.00 | A |
| ATOM | 245 | HE3  | MET | 238 |  0.951  | 15.951 | -18.115 | 1.00 | 0.00 | A |
| ATOM | 246 | C    | MET | 238 | -5.890  | 14.022 | -20.292 | 1.00 | 0.00 | A |
| ATOM | 247 | O    | MET | 238 | -6.738  | 14.851 | -20.136 | 1.00 | 0.00 | A |
| ATOM | 248 | N    | ALA | 239 | -5.842  | 13.245 | -21.340 | 1.00 | 0.00 | A |
| ATOM | 249 | HN   | ALA | 239 | -5.075  | 12.653 | -21.457 | 1.00 | 0.00 | A |
| ATOM | 250 | CA   | ALA | 239 | -6.897  | 13.242 | -22.354 | 1.00 | 0.00 | A |
| ATOM | 251 | HA   | ALA | 239 | -7.398  | 14.192 | -22.399 | 1.00 | 0.00 | A |
| ATOM | 252 | CB   | ALA | 239 | -6.172  | 12.942 | -23.667 | 1.00 | 0.00 | A |
| ATOM | 253 | HB1  | ALA | 239 | -6.206  | 11.878 | -23.860 | 1.00 | 0.00 | A |
| ATOM | 254 | HB2  | ALA | 239 | -5.141  | 13.259 | -23.590 | 1.00 | 0.00 | A |
| ATOM | 255 | HB3  | ALA | 239 | -6.652  | 13.470 | -24.474 | 1.00 | 0.00 | A |
| ATOM | 256 | C    | ALA | 239 | -7.869  | 12.109 | -22.006 | 1.00 | 0.00 | A |
| ATOM | 257 | O    | ALA | 239 | -8.592  | 11.615 | -22.850 | 1.00 | 0.00 | A |
| ATOM | 258 | N    | GLY | 240 | -7.888  | 11.685 | -20.752 | 1.00 | 0.00 | A |
| ATOM | 259 | HN   | GLY | 240 | -7.332  | 12.118 | -20.063 | 1.00 | 0.00 | A |
| ATOM | 260 | CA   | GLY | 240 | -8.784  | 10.603 | -20.349 | 1.00 | 0.00 | A |
| ATOM | 261 | HA1  | GLY | 240 | -8.276  |  9.652 | -20.454 | 1.00 | 0.00 | A |
| ATOM | 262 | HA2  | GLY | 240 | -9.673  | 10.614 | -20.951 | 1.00 | 0.00 | A |
| ATOM | 263 | C    | GLY | 240 | -9.132  | 10.811 | -18.909 | 1.00 | 0.00 | A |
| ATOM | 264 | O    | GLY | 240 | -10.263 | 10.672 | -18.503 | 1.00 | 0.00 | A |
| ATOM | 265 | N    | VAL | 241 | -8.163  | 11.088 | -18.099 | 1.00 | 0.00 | A |
| ATOM | 266 | HN   | VAL | 241 | -7.243  | 11.192 | -18.425 | 1.00 | 0.00 | A |
| ATOM | 267 | CA   | VAL | 241 | -8.479  | 11.294 | -16.704 | 1.00 | 0.00 | A |
| ATOM | 268 | HA   | VAL | 241 | -9.389  | 10.821 | -16.523 | 1.00 | 0.00 | A |
| ATOM | 269 | CB   | VAL | 241 | -7.368  | 10.580 | -15.915 | 1.00 | 0.00 | A |
| ATOM | 270 | HB   | VAL | 241 | -6.440  | 11.081 | -16.057 | 1.00 | 0.00 | A |
| ATOM | 271 | CG1  | VAL | 241 | -7.709  | 10.549 | -14.436 | 1.00 | 0.00 | A |
| ATOM | 272 | HG11 | VAL | 241 | -7.103  |  9.793 | -13.948 | 1.00 | 0.00 | A |
| ATOM | 273 | HG12 | VAL | 241 | -8.753  | 10.302 | -14.315 | 1.00 | 0.00 | A |
| ATOM | 274 | HG13 | VAL | 241 | -7.509  | 11.507 | -14.001 | 1.00 | 0.00 | A |
| ATOM | 275 | CG2  | VAL | 241 | -7.260  |  9.133 | -16.408 | 1.00 | 0.00 | A |
| ATOM | 276 | HG21 | VAL | 241 | -6.419  |  8.653 | -15.933 | 1.00 | 0.00 | A |
| ATOM | 277 | HG22 | VAL | 241 | -7.130  |  9.121 | -17.475 | 1.00 | 0.00 | A |
| ATOM | 278 | HG23 | VAL | 241 | -8.165  |  8.599 | -16.153 | 1.00 | 0.00 | A |
| ATOM | 279 | C    | VAL | 241 | -8.619  | 12.823 | -16.402 | 1.00 | 0.00 | A |
| ATOM | 280 | O    | VAL | 241 | -9.328  | 13.229 | -15.502 | 1.00 | 0.00 | A |
| ATOM | 281 | N    | SER | 242 | -7.906  | 13.661 | -17.126 | 1.00 | 0.00 | A |
| ATOM | 282 | HN   | SER | 242 | -7.329  | 13.321 | -17.836 | 1.00 | 0.00 | A |
| ATOM | 283 | CA   | SER | 242 | -8.000  | 15.149 | -16.883 | 1.00 | 0.00 | A |
| ATOM | 284 | HA   | SER | 242 | -8.303  | 15.337 | -15.866 | 1.00 | 0.00 | A |
| ATOM | 285 | CB   | SER | 242 | -6.589  | 15.678 | -17.100 | 1.00 | 0.00 | A |
| ATOM | 286 | HB1  | SER | 242 | -6.304  | 15.516 | -18.128 | 1.00 | 0.00 | A |

Figure 8-6

```
ATOM    287  HB2  SER   242      -5.903   15.164  -16.453   1.00   0.00      A
ATOM    288  OG   SER   242      -6.559   17.070  -16.807   1.00   0.00      A
ATOM    289  HG   SER   242      -6.529   17.547  -17.640   1.00   0.00      A
ATOM    290  C    SER   242      -8.984   15.849  -17.872   1.00   0.00      A
ATOM    291  O    SER   242      -9.673   16.775  -17.525   1.00   0.00      A
ATOM    292  N    HIS   243      -9.019   15.418  -19.106   1.00   0.00      A
ATOM    293  HN   HIS   243      -8.497   14.648  -19.358   1.00   0.00      A
ATOM    294  CA   HIS   243      -9.942   16.057  -20.115   1.00   0.00      A
ATOM    295  HA   HIS   243     -10.092   17.088  -19.868   1.00   0.00      A
ATOM    296  CB   HIS   243      -9.188   15.954  -21.447   1.00   0.00      A
ATOM    297  HB1  HIS   243      -9.033   14.913  -21.691   1.00   0.00      A
ATOM    298  HB2  HIS   243      -8.231   16.447  -21.356   1.00   0.00      A
ATOM    299  CG   HIS   243      -9.986   16.612  -22.546   1.00   0.00      A
ATOM    300  ND1  HIS   243     -11.262   16.191  -22.902   1.00   0.00      A
ATOM    301  HD1  HIS   243     -11.751   15.438  -22.517   1.00   0.00      A
ATOM    302  CD2  HIS   243      -9.705   17.678  -23.365   1.00   0.00      A
ATOM    303  HD2  HIS   243      -8.789   18.249  -23.348   1.00   0.00      A
ATOM    304  CE1  HIS   243     -11.692   16.995  -23.893   1.00   0.00      A
ATOM    305  HE1  HIS   243     -12.654   16.901  -24.375   1.00   0.00      A
ATOM    306  NE2  HIS   243     -10.781   17.917  -24.212   1.00   0.00      A
ATOM    307  C    HIS   243     -11.278   15.319  -20.180   1.00   0.00      A
ATOM    308  O    HIS   243     -12.308   15.866  -20.506   1.00   0.00      A
ATOM    309  N    ASP   244     -11.256   14.084  -19.927   1.00   0.00      A
ATOM    310  HN   ASP   244     -10.464   13.687  -19.609   1.00   0.00      A
ATOM    311  CA   ASP   244     -12.484   13.310  -19.968   1.00   0.00      A
ATOM    312  HA   ASP   244     -13.209   13.797  -20.600   1.00   0.00      A
ATOM    313  CB   ASP   244     -12.110   11.951  -20.552   1.00   0.00      A
ATOM    314  HB1  ASP   244     -11.375   11.493  -19.943   1.00   0.00      A
ATOM    315  HB2  ASP   244     -11.717   12.084  -21.548   1.00   0.00      A
ATOM    316  CG   ASP   244     -13.348   11.057  -20.612   1.00   0.00      A
ATOM    317  OD1  ASP   244     -14.342   11.488  -21.174   1.00   0.00      A
ATOM    318  OD2  ASP   244     -13.277    9.953  -20.099   1.00   0.00      A
ATOM    319  C    ASP   244     -13.000   13.210  -18.564   1.00   0.00      A
ATOM    320  O    ASP   244     -14.182   13.274  -18.329   1.00   0.00      A
ATOM    321  N    LEU   245     -12.104   13.028  -17.599   1.00   0.00      A
ATOM    322  HN   LEU   245     -11.081   12.942  -17.830   1.00   0.00      A
ATOM    323  CA   LEU   245     -12.586   12.923  -16.167   1.00   0.00      A
ATOM    324  HA   LEU   245     -13.587   12.520  -16.163   1.00   0.00      A
ATOM    325  CB   LEU   245     -11.657   11.921  -15.505   1.00   0.00      A
ATOM    326  HB1  LEU   245     -11.443   12.230  -14.496   1.00   0.00      A
ATOM    327  HB2  LEU   245     -10.759   11.871  -16.063   1.00   0.00      A
ATOM    328  CG   LEU   245     -12.311   10.537  -15.489   1.00   0.00      A
ATOM    329  HG   LEU   245     -11.638    9.828  -15.026   1.00   0.00      A
ATOM    330  CD1  LEU   245     -13.610   10.602  -14.685   1.00   0.00      A
ATOM    331  HD11 LEU   245     -14.445   10.368  -15.328   1.00   0.00      A
ATOM    332  HD12 LEU   245     -13.734   11.596  -14.282   1.00   0.00      A
ATOM    333  HD13 LEU   245     -13.568    9.889  -13.875   1.00   0.00      A
ATOM    334  CD2  LEU   245     -12.620   10.090  -16.923   1.00   0.00      A
ATOM    335  HD21 LEU   245     -12.209   10.799  -17.618   1.00   0.00      A
ATOM    336  HD22 LEU   245     -13.688   10.032  -17.060   1.00   0.00      A
ATOM    337  HD23 LEU   245     -12.182    9.118  -17.098   1.00   0.00      A
ATOM    338  C    LEU   245     -12.589   14.290  -15.405   1.00   0.00      A
ATOM    339  O    LEU   245     -13.467   14.539  -14.604   1.00   0.00      A
ATOM    340  N    ARG   246     -11.632   15.172  -15.633   1.00   0.00      A
ATOM    341  HN   ARG   246     -10.959   15.003  -16.315   1.00   0.00      A
ATOM    342  CA   ARG   246     -11.651   16.497  -14.875   1.00   0.00      A
ATOM    343  HA   ARG   246     -12.190   16.368  -13.961   1.00   0.00      A
ATOM    344  CB   ARG   246     -10.189   16.856  -14.573   1.00   0.00      A
```

Figure 8-7

| ATOM | 345 | HB1 | ARG | 246 | -9.640 | 16.934 | -15.483 | 1.00 | 0.00 | A |
| --- | --- | --- | --- | --- | --- | --- | --- | --- | --- | --- |
| ATOM | 346 | HB2 | ARG | 246 | -9.751 | 16.088 | -13.953 | 1.00 | 0.00 | A |
| ATOM | 347 | CG | ARG | 246 | -10.141 | 18.198 | -13.831 | 1.00 | 0.00 | A |
| ATOM | 348 | HG1 | ARG | 246 | -10.676 | 18.111 | -12.899 | 1.00 | 0.00 | A |
| ATOM | 349 | HG2 | ARG | 246 | -10.603 | 18.960 | -14.442 | 1.00 | 0.00 | A |
| ATOM | 350 | CD | ARG | 246 | -8.684 | 18.585 | -13.546 | 1.00 | 0.00 | A |
| ATOM | 351 | HD1 | ARG | 246 | -8.182 | 17.793 | -13.017 | 1.00 | 0.00 | A |
| ATOM | 352 | HD2 | ARG | 246 | -8.646 | 19.504 | -12.975 | 1.00 | 0.00 | A |
| ATOM | 353 | NE | ARG | 246 | -8.058 | 18.780 | -14.886 | 1.00 | 0.00 | A |
| ATOM | 354 | HE | ARG | 246 | -8.503 | 18.442 | -15.689 | 1.00 | 0.00 | A |
| ATOM | 355 | CZ | ARG | 246 | -6.914 | 19.407 | -14.988 | 1.00 | 0.00 | A |
| ATOM | 356 | NH1 | ARG | 246 | -6.111 | 19.475 | -13.960 | 1.00 | 0.00 | A |
| ATOM | 357 | HH11 | ARG | 246 | -6.368 | 19.047 | -13.094 | 1.00 | 0.00 | A |
| ATOM | 358 | HH12 | ARG | 246 | -5.238 | 19.959 | -14.039 | 1.00 | 0.00 | A |
| ATOM | 359 | NH2 | ARG | 246 | -6.572 | 19.961 | -16.120 | 1.00 | 0.00 | A |
| ATOM | 360 | HH21 | ARG | 246 | -7.183 | 19.905 | -16.908 | 1.00 | 0.00 | A |
| ATOM | 361 | HH22 | ARG | 246 | -5.698 | 20.442 | -16.197 | 1.00 | 0.00 | A |
| ATOM | 362 | C | ARG | 246 | -12.345 | 17.582 | -15.651 | 1.00 | 0.00 | A |
| ATOM | 363 | O | ARG | 246 | -12.963 | 18.455 | -15.072 | 1.00 | 0.00 | A |
| ATOM | 364 | N | THR | 247 | -12.270 | 17.569 | -16.942 | 1.00 | 0.00 | A |
| ATOM | 365 | HN | THR | 247 | -11.786 | 16.863 | -17.410 | 1.00 | 0.00 | A |
| ATOM | 366 | CA | THR | 247 | -12.958 | 18.629 | -17.684 | 1.00 | 0.00 | A |
| ATOM | 367 | HA | THR | 247 | -13.029 | 19.495 | -17.059 | 1.00 | 0.00 | A |
| ATOM | 368 | CB | THR | 247 | -12.090 | 18.966 | -18.869 | 1.00 | 0.00 | A |
| ATOM | 369 | HB | THR | 247 | -12.531 | 19.769 | -19.397 | 1.00 | 0.00 | A |
| ATOM | 370 | OG1 | THR | 247 | -11.989 | 17.868 | -19.707 | 1.00 | 0.00 | A |
| ATOM | 371 | HG1 | THR | 247 | -12.415 | 18.090 | -20.538 | 1.00 | 0.00 | A |
| ATOM | 372 | CG2 | THR | 247 | -10.700 | 19.383 | -18.390 | 1.00 | 0.00 | A |
| ATOM | 373 | HG21 | THR | 247 | -10.637 | 19.262 | -17.319 | 1.00 | 0.00 | A |
| ATOM | 374 | HG22 | THR | 247 | -10.527 | 20.418 | -18.646 | 1.00 | 0.00 | A |
| ATOM | 375 | HG23 | THR | 247 | -9.954 | 18.765 | -18.867 | 1.00 | 0.00 | A |
| ATOM | 376 | C | THR | 247 | -14.406 | 18.197 | -18.146 | 1.00 | 0.00 | A |
| ATOM | 377 | O | THR | 247 | -15.032 | 18.942 | -18.874 | 1.00 | 0.00 | A |
| ATOM | 378 | N | PRO | 248 | -14.922 | 17.000 | -17.718 | 1.00 | 0.00 | A |
| ATOM | 379 | CA | PRO | 248 | -16.261 | 16.610 | -18.148 | 1.00 | 0.00 | A |
| ATOM | 380 | HA | PRO | 248 | -16.348 | 16.708 | -19.206 | 1.00 | 0.00 | A |
| ATOM | 381 | CB | PRO | 248 | -16.394 | 15.154 | -17.736 | 1.00 | 0.00 | A |
| ATOM | 382 | HB1 | PRO | 248 | -16.106 | 14.506 | -18.547 | 1.00 | 0.00 | A |
| ATOM | 383 | HB2 | PRO | 248 | -17.408 | 14.943 | -17.422 | 1.00 | 0.00 | A |
| ATOM | 384 | CG | PRO | 248 | -15.456 | 14.999 | -16.605 | 1.00 | 0.00 | A |
| ATOM | 385 | HG1 | PRO | 248 | -15.034 | 14.016 | -16.600 | 1.00 | 0.00 | A |
| ATOM | 386 | HG2 | PRO | 248 | -15.978 | 15.180 | -15.672 | 1.00 | 0.00 | A |
| ATOM | 387 | CD | PRO | 248 | -14.368 | 16.026 | -16.792 | 1.00 | 0.00 | A |
| ATOM | 388 | HD1 | PRO | 248 | -13.474 | 15.582 | -17.209 | 1.00 | 0.00 | A |
| ATOM | 389 | HD2 | PRO | 248 | -14.166 | 16.486 | -15.858 | 1.00 | 0.00 | A |
| ATOM | 390 | C | PRO | 248 | -17.270 | 17.494 | -17.371 | 1.00 | 0.00 | A |
| ATOM | 391 | O | PRO | 248 | -18.483 | 17.497 | -17.611 | 1.00 | 0.00 | A |
| ATOM | 392 | N | LEU | 249 | -16.751 | 18.235 | -16.400 | 1.00 | 0.00 | A |
| ATOM | 393 | HN | LEU | 249 | -15.803 | 18.184 | -16.206 | 1.00 | 0.00 | A |
| ATOM | 394 | CA | LEU | 249 | -17.590 | 19.117 | -15.589 | 1.00 | 0.00 | A |
| ATOM | 395 | HA | LEU | 249 | -18.359 | 18.548 | -15.065 | 1.00 | 0.00 | A |
| ATOM | 396 | CB | LEU | 249 | -16.612 | 19.740 | -14.565 | 1.00 | 0.00 | A |
| ATOM | 397 | HB1 | LEU | 249 | -15.857 | 18.989 | -14.296 | 1.00 | 0.00 | A |
| ATOM | 398 | HB2 | LEU | 249 | -17.148 | 20.026 | -13.682 | 1.00 | 0.00 | A |
| ATOM | 399 | CG | LEU | 249 | -15.900 | 20.960 | -15.167 | 1.00 | 0.00 | A |
| ATOM | 400 | HG | LEU | 249 | -16.634 | 21.654 | -15.550 | 1.00 | 0.00 | A |
| ATOM | 401 | CD1 | LEU | 249 | -15.055 | 21.643 | -14.097 | 1.00 | 0.00 | A |
| ATOM | 402 | HD11 | LEU | 249 | -14.018 | 21.374 | -14.233 | 1.00 | 0.00 | A |

Figure 8-8

| | | | | | | | | | |
|---|---|---|---|---|---|---|---|---|---|
| ATOM | 403 | HD12 | LEU | 249 | -15.386 | 21.323 | -13.121 | 1.00 | 0.00 | A |
| ATOM | 404 | HD13 | LEU | 249 | -15.163 | 22.715 | -14.182 | 1.00 | 0.00 | A |
| ATOM | 405 | CD2 | LEU | 249 | -14.994 | 20.505 | -16.289 | 1.00 | 0.00 | A |
| ATOM | 406 | HD21 | LEU | 249 | -14.557 | 19.559 | -16.023 | 1.00 | 0.00 | A |
| ATOM | 407 | HD22 | LEU | 249 | -14.211 | 21.234 | -16.439 | 1.00 | 0.00 | A |
| ATOM | 408 | HD23 | LEU | 249 | -15.563 | 20.397 | -17.196 | 1.00 | 0.00 | A |
| ATOM | 409 | C | LEU | 249 | -18.244 | 20.168 | -16.514 | 1.00 | 0.00 | A |
| ATOM | 410 | O | LEU | 249 | -19.057 | 20.934 | -16.086 | 1.00 | 0.00 | A |
| ATOM | 411 | N | THR | 250 | -17.807 | 20.257 | -17.774 | 1.00 | 0.00 | A |
| ATOM | 412 | HN | THR | 250 | -17.085 | 19.710 | -18.074 | 1.00 | 0.00 | A |
| ATOM | 413 | CA | THR | 250 | -18.410 | 21.239 | -18.705 | 1.00 | 0.00 | A |
| ATOM | 414 | HA | THR | 250 | -18.484 | 22.204 | -18.257 | 1.00 | 0.00 | A |
| ATOM | 415 | CB | THR | 250 | -17.505 | 21.277 | -19.940 | 1.00 | 0.00 | A |
| ATOM | 416 | HB | THR | 250 | -16.481 | 21.425 | -19.639 | 1.00 | 0.00 | A |
| ATOM | 417 | OG1 | THR | 250 | -17.917 | 22.340 | -20.790 | 1.00 | 0.00 | A |
| ATOM | 418 | HG1 | THR | 250 | -17.370 | 22.320 | -21.576 | 1.00 | 0.00 | A |
| ATOM | 419 | CG2 | THR | 250 | -17.626 | 19.961 | -20.694 | 1.00 | 0.00 | A |
| ATOM | 420 | HG21 | THR | 250 | -18.648 | 19.844 | -21.043 | 1.00 | 0.00 | A |
| ATOM | 421 | HG22 | THR | 250 | -17.380 | 19.146 | -20.031 | 1.00 | 0.00 | A |
| ATOM | 422 | HG23 | THR | 250 | -16.960 | 19.964 | -21.531 | 1.00 | 0.00 | A |
| ATOM | 423 | C | THR | 250 | -19.778 | 20.672 | -19.055 | 1.00 | 0.00 | A |
| ATOM | 424 | O | THR | 250 | -20.750 | 21.359 | -19.209 | 1.00 | 0.00 | A |
| ATOM | 425 | N | ARG | 251 | -19.831 | 19.371 | -19.207 | 1.00 | 0.00 | A |
| ATOM | 426 | HN | ARG | 251 | -19.026 | 18.845 | -19.107 | 1.00 | 0.00 | A |
| ATOM | 427 | CA | ARG | 251 | -21.108 | 18.712 | -19.538 | 1.00 | 0.00 | A |
| ATOM | 428 | HA | ARG | 251 | -21.457 | 19.009 | -20.514 | 1.00 | 0.00 | A |
| ATOM | 429 | CB | ARG | 251 | -20.796 | 17.211 | -19.495 | 1.00 | 0.00 | A |
| ATOM | 430 | HB1 | ARG | 251 | -21.694 | 16.647 | -19.664 | 1.00 | 0.00 | A |
| ATOM | 431 | HB2 | ARG | 251 | -20.382 | 16.957 | -18.527 | 1.00 | 0.00 | A |
| ATOM | 432 | CG | ARG | 251 | -19.772 | 16.879 | -20.583 | 1.00 | 0.00 | A |
| ATOM | 433 | HG1 | ARG | 251 | -18.859 | 17.421 | -20.395 | 1.00 | 0.00 | A |
| ATOM | 434 | HG2 | ARG | 251 | -20.169 | 17.163 | -21.548 | 1.00 | 0.00 | A |
| ATOM | 435 | CD | ARG | 251 | -19.480 | 15.375 | -20.573 | 1.00 | 0.00 | A |
| ATOM | 436 | HD1 | ARG | 251 | -20.381 | 14.816 | -20.762 | 1.00 | 0.00 | A |
| ATOM | 437 | HD2 | ARG | 251 | -19.045 | 15.084 | -19.625 | 1.00 | 0.00 | A |
| ATOM | 438 | NE | ARG | 251 | -18.505 | 15.165 | -21.680 | 1.00 | 0.00 | A |
| ATOM | 439 | HE | ARG | 251 | -18.062 | 15.934 | -22.094 | 1.00 | 0.00 | A |
| ATOM | 440 | CZ | ARG | 251 | -18.242 | 13.958 | -22.098 | 1.00 | 0.00 | A |
| ATOM | 441 | NH1 | ARG | 251 | -19.072 | 13.352 | -22.903 | 1.00 | 0.00 | A |
| ATOM | 442 | HH11 | ARG | 251 | -19.909 | 13.814 | -23.199 | 1.00 | 0.00 | A |
| ATOM | 443 | HH12 | ARG | 251 | -18.871 | 12.426 | -23.225 | 1.00 | 0.00 | A |
| ATOM | 444 | NH2 | ARG | 251 | -17.151 | 13.356 | -21.712 | 1.00 | 0.00 | A |
| ATOM | 445 | HH21 | ARG | 251 | -16.516 | 13.821 | -21.095 | 1.00 | 0.00 | A |
| ATOM | 446 | HH22 | ARG | 251 | -16.950 | 12.431 | -22.033 | 1.00 | 0.00 | A |
| ATOM | 447 | C | ARG | 251 | -22.078 | 19.130 | -18.454 | 1.00 | 0.00 | A |
| ATOM | 448 | O | ARG | 251 | -23.175 | 19.581 | -18.715 | 1.00 | 0.00 | A |
| ATOM | 449 | N | ILE | 252 | -21.671 | 18.974 | -17.221 | 1.00 | 0.00 | A |
| ATOM | 450 | HN | ILE | 252 | -20.786 | 18.577 | -17.044 | 1.00 | 0.00 | A |
| ATOM | 451 | CA | ILE | 252 | -22.568 | 19.377 | -16.091 | 1.00 | 0.00 | A |
| ATOM | 452 | HA | ILE | 252 | -23.571 | 19.017 | -16.247 | 1.00 | 0.00 | A |
| ATOM | 453 | CB | ILE | 252 | -21.987 | 18.805 | -14.841 | 1.00 | 0.00 | A |
| ATOM | 454 | HB | ILE | 252 | -22.540 | 19.150 | -13.975 | 1.00 | 0.00 | A |
| ATOM | 455 | CG1 | ILE | 252 | -20.567 | 19.249 | -14.708 | 1.00 | 0.00 | A |
| ATOM | 456 | HG11 | ILE | 252 | -20.521 | 20.323 | -14.709 | 1.00 | 0.00 | A |
| ATOM | 457 | HG12 | ILE | 252 | -19.991 | 18.861 | -15.528 | 1.00 | 0.00 | A |
| ATOM | 458 | CG2 | ILE | 252 | -22.058 | 17.331 | -14.915 | 1.00 | 0.00 | A |
| ATOM | 459 | HG21 | ILE | 252 | -22.981 | 17.050 | -15.397 | 1.00 | 0.00 | A |
| ATOM | 460 | HG22 | ILE | 252 | -22.028 | 16.929 | -13.920 | 1.00 | 0.00 | A |

Figure 8-9

| ATOM | 461 | HG23 | ILE | 252 | -21.228 | 16.969 | -15.487 | 1.00 | 0.00 | A |
| --- | --- | --- | --- | --- | --- | --- | --- | --- | --- | --- |
| ATOM | 462 | CD1 | ILE | 252 | -20.031 | 18.722 | -13.404 | 1.00 | 0.00 | A |
| ATOM | 463 | HD11 | ILE | 252 | -20.684 | 19.031 | -12.602 | 1.00 | 0.00 | A |
| ATOM | 464 | HD12 | ILE | 252 | -19.043 | 19.109 | -13.240 | 1.00 | 0.00 | A |
| ATOM | 465 | HD13 | ILE | 252 | -19.999 | 17.643 | -13.444 | 1.00 | 0.00 | A |
| ATOM | 466 | C | ILE | 252 | -22.543 | 20.864 | -16.001 | 1.00 | 0.00 | A |
| ATOM | 467 | O | ILE | 252 | -23.405 | 21.468 | -15.470 | 1.00 | 0.00 | A |
| ATOM | 468 | N | ARG | 253 | -21.517 | 21.478 | -16.498 | 1.00 | 0.00 | A |
| ATOM | 469 | HN | ARG | 253 | -20.831 | 20.986 | -16.946 | 1.00 | 0.00 | A |
| ATOM | 470 | CA | ARG | 253 | -21.469 | 22.952 | -16.427 | 1.00 | 0.00 | A |
| ATOM | 471 | HA | ARG | 253 | -21.372 | 23.289 | -15.405 | 1.00 | 0.00 | A |
| ATOM | 472 | CB | ARG | 253 | -20.274 | 23.370 | -17.257 | 1.00 | 0.00 | A |
| ATOM | 473 | HB1 | ARG | 253 | -20.418 | 23.074 | -18.268 | 1.00 | 0.00 | A |
| ATOM | 474 | HB2 | ARG | 253 | -19.393 | 22.900 | -16.863 | 1.00 | 0.00 | A |
| ATOM | 475 | CG | ARG | 253 | -20.097 | 24.864 | -17.204 | 1.00 | 0.00 | A |
| ATOM | 476 | HG1 | ARG | 253 | -21.026 | 25.339 | -17.459 | 1.00 | 0.00 | A |
| ATOM | 477 | HG2 | ARG | 253 | -19.333 | 25.155 | -17.908 | 1.00 | 0.00 | A |
| ATOM | 478 | CD | ARG | 253 | -19.682 | 25.274 | -15.797 | 1.00 | 0.00 | A |
| ATOM | 479 | HD1 | ARG | 253 | -18.744 | 24.809 | -15.534 | 1.00 | 0.00 | A |
| ATOM | 480 | HD2 | ARG | 253 | -20.452 | 25.001 | -15.087 | 1.00 | 0.00 | A |
| ATOM | 481 | NE | ARG | 253 | -19.521 | 26.756 | -15.858 | 1.00 | 0.00 | A |
| ATOM | 482 | HE | ARG | 253 | -20.080 | 27.332 | -15.295 | 1.00 | 0.00 | A |
| ATOM | 483 | CZ | ARG | 253 | -18.636 | 27.288 | -16.663 | 1.00 | 0.00 | A |
| ATOM | 484 | NH1 | ARG | 253 | -19.004 | 28.191 | -17.532 | 1.00 | 0.00 | A |
| ATOM | 485 | HH11 | ARG | 253 | -19.961 | 28.476 | -17.583 | 1.00 | 0.00 | A |
| ATOM | 486 | HH12 | ARG | 253 | -18.327 | 28.597 | -18.148 | 1.00 | 0.00 | A |
| ATOM | 487 | NH2 | ARG | 253 | -17.386 | 26.919 | -16.596 | 1.00 | 0.00 | A |
| ATOM | 488 | HH21 | ARG | 253 | -17.102 | 26.230 | -15.928 | 1.00 | 0.00 | A |
| ATOM | 489 | HH22 | ARG | 253 | -16.710 | 27.327 | -17.212 | 1.00 | 0.00 | A |
| ATOM | 490 | C | ARG | 253 | -22.764 | 23.421 | -17.037 | 1.00 | 0.00 | A |
| ATOM | 491 | O | ARG | 253 | -23.306 | 24.419 | -16.673 | 1.00 | 0.00 | A |
| ATOM | 492 | N | LEU | 254 | -23.270 | 22.620 | -17.971 | 1.00 | 0.00 | A |
| ATOM | 493 | HN | LEU | 254 | -22.790 | 21.807 | -18.223 | 1.00 | 0.00 | A |
| ATOM | 494 | CA | LEU | 254 | -24.521 | 22.935 | -18.645 | 1.00 | 0.00 | A |
| ATOM | 495 | HA | LEU | 254 | -24.651 | 23.984 | -18.704 | 1.00 | 0.00 | A |
| ATOM | 496 | CB | LEU | 254 | -24.391 | 22.325 | -20.048 | 1.00 | 0.00 | A |
| ATOM | 497 | HB1 | LEU | 254 | -25.251 | 22.598 | -20.639 | 1.00 | 0.00 | A |
| ATOM | 498 | HB2 | LEU | 254 | -24.340 | 21.249 | -19.964 | 1.00 | 0.00 | A |
| ATOM | 499 | CG | LEU | 254 | -23.112 | 22.849 | -20.735 | 1.00 | 0.00 | A |
| ATOM | 500 | HG | LEU | 254 | -22.233 | 22.429 | -20.244 | 1.00 | 0.00 | A |
| ATOM | 501 | CD1 | LEU | 254 | -23.111 | 22.414 | -22.199 | 1.00 | 0.00 | A |
| ATOM | 502 | HD11 | LEU | 254 | -22.358 | 22.970 | -22.738 | 1.00 | 0.00 | A |
| ATOM | 503 | HD12 | LEU | 254 | -24.081 | 22.607 | -22.632 | 1.00 | 0.00 | A |
| ATOM | 504 | HD13 | LEU | 254 | -22.891 | 21.358 | -22.260 | 1.00 | 0.00 | A |
| ATOM | 505 | CD2 | LEU | 254 | -23.067 | 24.382 | -20.653 | 1.00 | 0.00 | A |
| ATOM | 506 | HD21 | LEU | 254 | -22.350 | 24.760 | -21.369 | 1.00 | 0.00 | A |
| ATOM | 507 | HD22 | LEU | 254 | -22.772 | 24.681 | -19.657 | 1.00 | 0.00 | A |
| ATOM | 508 | HD23 | LEU | 254 | -24.043 | 24.786 | -20.875 | 1.00 | 0.00 | A |
| ATOM | 509 | C | LEU | 254 | -25.673 | 22.286 | -17.845 | 1.00 | 0.00 | A |
| ATOM | 510 | O | LEU | 254 | -26.726 | 22.866 | -17.674 | 1.00 | 0.00 | A |
| ATOM | 511 | N | ALA | 255 | -25.470 | 21.065 | -17.349 | 1.00 | 0.00 | A |
| ATOM | 512 | HN | ALA | 255 | -24.594 | 20.619 | -17.471 | 1.00 | 0.00 | A |
| ATOM | 513 | CA | ALA | 255 | -26.555 | 20.382 | -16.553 | 1.00 | 0.00 | A |
| ATOM | 514 | HA | ALA | 255 | -27.464 | 20.275 | -17.107 | 1.00 | 0.00 | A |
| ATOM | 515 | CB | ALA | 255 | -25.980 | 19.008 | -16.184 | 1.00 | 0.00 | A |
| ATOM | 516 | HB1 | ALA | 255 | -25.322 | 18.670 | -16.971 | 1.00 | 0.00 | A |
| ATOM | 517 | HB2 | ALA | 255 | -26.788 | 18.301 | -16.060 | 1.00 | 0.00 | A |
| ATOM | 518 | HB3 | ALA | 255 | -25.425 | 19.086 | -15.261 | 1.00 | 0.00 | A |

Figure 8-10

| ATOM | 519 | C | ALA | 255 | -26.768 | 21.217 | -15.326 | 1.00 | 0.00 | A |
| ATOM | 520 | O | ALA | 255 | -27.836 | 21.693 | -15.044 | 1.00 | 0.00 | A |
| ATOM | 521 | N | THR | 256 | -25.732 | 21.387 | -14.609 | 1.00 | 0.00 | A |
| ATOM | 522 | HN | THR | 256 | -24.944 | 20.963 | -14.864 | 1.00 | 0.00 | A |
| ATOM | 523 | CA | THR | 256 | -25.766 | 22.183 | -13.379 | 1.00 | 0.00 | A |
| ATOM | 524 | HA | THR | 256 | -26.521 | 21.830 | -12.706 | 1.00 | 0.00 | A |
| ATOM | 525 | CB | THR | 256 | -24.393 | 22.054 | -12.745 | 1.00 | 0.00 | A |
| ATOM | 526 | HB | THR | 256 | -24.440 | 22.464 | -11.777 | 1.00 | 0.00 | A |
| ATOM | 527 | OG1 | THR | 256 | -23.451 | 22.778 | -13.515 | 1.00 | 0.00 | A |
| ATOM | 528 | HG1 | THR | 256 | -23.332 | 23.638 | -13.105 | 1.00 | 0.00 | A |
| ATOM | 529 | CG2 | THR | 256 | -23.944 | 20.588 | -12.652 | 1.00 | 0.00 | A |
| ATOM | 530 | HG21 | THR | 256 | -24.402 | 20.011 | -13.430 | 1.00 | 0.00 | A |
| ATOM | 531 | HG22 | THR | 256 | -24.227 | 20.187 | -11.699 | 1.00 | 0.00 | A |
| ATOM | 532 | HG23 | THR | 256 | -22.869 | 20.541 | -12.753 | 1.00 | 0.00 | A |
| ATOM | 533 | C | THR | 256 | -25.996 | 23.641 | -13.732 | 1.00 | 0.00 | A |
| ATOM | 534 | O | THR | 256 | -26.331 | 24.428 | -12.890 | 1.00 | 0.00 | A |
| ATOM | 535 | N | GLU | 257 | -25.752 | 24.034 | -14.965 | 1.00 | 0.00 | A |
| ATOM | 536 | HN | GLU | 257 | -25.408 | 23.372 | -15.664 | 1.00 | 0.00 | A |
| ATOM | 537 | CA | GLU | 257 | -25.985 | 25.490 | -15.318 | 1.00 | 0.00 | A |
| ATOM | 538 | HA | GLU | 257 | -25.395 | 26.141 | -14.700 | 1.00 | 0.00 | A |
| ATOM | 539 | CB | GLU | 257 | -25.606 | 25.625 | -16.772 | 1.00 | 0.00 | A |
| ATOM | 540 | HB1 | GLU | 257 | -26.481 | 25.888 | -17.342 | 1.00 | 0.00 | A |
| ATOM | 541 | HB2 | GLU | 257 | -25.231 | 24.691 | -17.122 | 1.00 | 0.00 | A |
| ATOM | 542 | CG | GLU | 257 | -24.550 | 26.726 | -16.931 | 1.00 | 0.00 | A |
| ATOM | 543 | HG1 | GLU | 257 | -23.684 | 26.486 | -16.336 | 1.00 | 0.00 | A |
| ATOM | 544 | HG2 | GLU | 257 | -24.963 | 27.667 | -16.598 | 1.00 | 0.00 | A |
| ATOM | 545 | CD | GLU | 257 | -24.143 | 26.842 | -18.401 | 1.00 | 0.00 | A |
| ATOM | 546 | OE1 | GLU | 257 | -23.307 | 27.678 | -18.700 | 1.00 | 0.00 | A |
| ATOM | 547 | OE2 | GLU | 257 | -24.674 | 26.093 | -19.203 | 1.00 | 0.00 | A |
| ATOM | 548 | C | GLU | 257 | -27.450 | 25.776 | -15.180 | 1.00 | 0.00 | A |
| ATOM | 549 | O | GLU | 257 | -27.892 | 26.576 | -14.388 | 1.00 | 0.00 | A |
| ATOM | 550 | N | MET | 258 | -28.183 | 25.136 | -15.995 | 1.00 | 0.00 | A |
| ATOM | 551 | HN | MET | 258 | -27.755 | 24.523 | -16.633 | 1.00 | 0.00 | A |
| ATOM | 552 | CA | MET | 258 | -29.643 | 25.281 | -16.009 | 1.00 | 0.00 | A |
| ATOM | 553 | HA | MET | 258 | -29.943 | 26.306 | -16.177 | 1.00 | 0.00 | A |
| ATOM | 554 | CB | MET | 258 | -30.024 | 24.390 | -17.196 | 1.00 | 0.00 | A |
| ATOM | 555 | HB1 | MET | 258 | -29.321 | 23.564 | -17.253 | 1.00 | 0.00 | A |
| ATOM | 556 | HB2 | MET | 258 | -29.961 | 24.966 | -18.104 | 1.00 | 0.00 | A |
| ATOM | 557 | CG | MET | 258 | -31.424 | 23.839 | -17.042 | 1.00 | 0.00 | A |
| ATOM | 558 | HG1 | MET | 258 | -31.481 | 23.295 | -16.107 | 1.00 | 0.00 | A |
| ATOM | 559 | HG2 | MET | 258 | -31.628 | 23.169 | -17.859 | 1.00 | 0.00 | A |
| ATOM | 560 | SD | MET | 258 | -32.626 | 25.194 | -17.036 | 1.00 | 0.00 | A |
| ATOM | 561 | CE | MET | 258 | -33.589 | 24.650 | -18.467 | 1.00 | 0.00 | A |
| ATOM | 562 | HE1 | MET | 258 | -33.112 | 24.998 | -19.374 | 1.00 | 0.00 | A |
| ATOM | 563 | HE2 | MET | 258 | -34.584 | 25.057 | -18.409 | 1.00 | 0.00 | A |
| ATOM | 564 | HE3 | MET | 258 | -33.643 | 23.569 | -18.474 | 1.00 | 0.00 | A |
| ATOM | 565 | C | MET | 258 | -30.203 | 24.758 | -14.699 | 1.00 | 0.00 | A |
| ATOM | 566 | O | MET | 258 | -31.234 | 25.192 | -14.224 | 1.00 | 0.00 | A |
| ATOM | 567 | N | MET | 259 | -29.528 | 23.837 | -14.121 | 1.00 | 0.00 | A |
| ATOM | 568 | HN | MET | 259 | -28.701 | 23.545 | -14.497 | 1.00 | 0.00 | A |
| ATOM | 569 | CA | MET | 259 | -29.989 | 23.277 | -12.862 | 1.00 | 0.00 | A |
| ATOM | 570 | HA | MET | 259 | -31.027 | 23.270 | -12.839 | 1.00 | 0.00 | A |
| ATOM | 571 | CB | MET | 259 | -29.457 | 21.854 | -12.827 | 1.00 | 0.00 | A |
| ATOM | 572 | HB1 | MET | 259 | -29.690 | 21.404 | -11.875 | 1.00 | 0.00 | A |
| ATOM | 573 | HB2 | MET | 259 | -28.391 | 21.865 | -12.970 | 1.00 | 0.00 | A |
| ATOM | 574 | CG | MET | 259 | -30.122 | 21.047 | -13.946 | 1.00 | 0.00 | A |
| ATOM | 575 | HG1 | MET | 259 | -29.967 | 21.544 | -14.891 | 1.00 | 0.00 | A |
| ATOM | 576 | HG2 | MET | 259 | -31.181 | 20.970 | -13.752 | 1.00 | 0.00 | A |

Figure 8-11

```
ATOM   577  SD   MET  259     -29.406  19.388 -14.011  1.00  0.00      A
ATOM   578  CE   MET  259     -29.573  19.146 -15.794  1.00  0.00      A
ATOM   579  HE1  MET  259     -29.769  20.100 -16.264  1.00  0.00      A
ATOM   580  HE2  MET  259     -30.389  18.473 -15.993  1.00  0.00      A
ATOM   581  HE3  MET  259     -28.657  18.726 -16.188  1.00  0.00      A
ATOM   582  C    MET  259     -29.469  24.098 -11.730  1.00  0.00      A
ATOM   583  O    MET  259     -29.908  23.968 -10.639  1.00  0.00      A
ATOM   584  N    SER  260     -28.553  24.989 -11.995  1.00  0.00      A
ATOM   585  HN   SER  260     -28.269  25.122 -12.902  1.00  0.00      A
ATOM   586  CA   SER  260     -28.002  25.839 -10.892  1.00  0.00      A
ATOM   587  HA   SER  260     -27.409  25.257 -10.209  1.00  0.00      A
ATOM   588  CB   SER  260     -27.162  26.920 -11.566  1.00  0.00      A
ATOM   589  HB1  SER  260     -26.420  26.457 -12.203  1.00  0.00      A
ATOM   590  HB2  SER  260     -26.668  27.511 -10.817  1.00  0.00      A
ATOM   591  OG   SER  260     -28.012  27.759 -12.339  1.00  0.00      A
ATOM   592  HG   SER  260     -28.322  28.470 -11.772  1.00  0.00      A
ATOM   593  C    SER  260     -29.183  26.456 -10.210  1.00  0.00      A
ATOM   594  O    SER  260     -29.233  26.626  -9.008  1.00  0.00      A
ATOM   595  N    GLU  261     -30.147  26.793 -11.005  1.00  0.00      A
ATOM   596  HN   GLU  261     -30.056  26.641 -11.969  1.00  0.00      A
ATOM   597  CA   GLU  261     -31.360  27.396 -10.491  1.00  0.00      A
ATOM   598  HA   GLU  261     -31.180  27.836  -9.528  1.00  0.00      A
ATOM   599  CB   GLU  261     -31.753  28.438 -11.557  1.00  0.00      A
ATOM   600  HB1  GLU  261     -32.056  27.919 -12.464  1.00  0.00      A
ATOM   601  HB2  GLU  261     -30.896  29.061 -11.780  1.00  0.00      A
ATOM   602  CG   GLU  261     -32.915  29.316 -11.062  1.00  0.00      A
ATOM   603  HG1  GLU  261     -33.138  30.068 -11.806  1.00  0.00      A
ATOM   604  HG2  GLU  261     -32.631  29.800 -10.139  1.00  0.00      A
ATOM   605  CD   GLU  261     -34.159  28.459 -10.826  1.00  0.00      A
ATOM   606  OE1  GLU  261     -34.448  28.176  -9.676  1.00  0.00      A
ATOM   607  OE2  GLU  261     -34.800  28.097 -11.799  1.00  0.00      A
ATOM   608  C    GLU  261     -32.362  26.286 -10.381  1.00  0.00      A
ATOM   609  O    GLU  261     -33.107  26.206  -9.430  1.00  0.00      A
ATOM   610  N    GLN  262     -32.418  25.437 -11.376  1.00  0.00      A
ATOM   611  HN   GLN  262     -31.832  25.548 -12.154  1.00  0.00      A
ATOM   612  CA   GLN  262     -33.369  24.324 -11.318  1.00  0.00      A
ATOM   613  HA   GLN  262     -34.253  24.630 -10.864  1.00  0.00      A
ATOM   614  CB   GLN  262     -33.627  23.884 -12.768  1.00  0.00      A
ATOM   615  HB1  GLN  262     -32.717  23.564 -13.220  1.00  0.00      A
ATOM   616  HB2  GLN  262     -34.032  24.714 -13.327  1.00  0.00      A
ATOM   617  CG   GLN  262     -34.632  22.729 -12.776  1.00  0.00      A
ATOM   618  HG1  GLN  262     -35.550  23.047 -12.305  1.00  0.00      A
ATOM   619  HG2  GLN  262     -34.220  21.888 -12.236  1.00  0.00      A
ATOM   620  CD   GLN  262     -34.920  22.316 -14.219  1.00  0.00      A
ATOM   621  OE1  GLN  262     -34.048  21.825 -14.908  1.00  0.00      A
ATOM   622  NE2  GLN  262     -36.116  22.497 -14.709  1.00  0.00      A
ATOM   623  HE21 GLN  262     -36.818  22.894 -14.152  1.00  0.00      A
ATOM   624  HE22 GLN  262     -36.311  22.236 -15.633  1.00  0.00      A
ATOM   625  C    GLN  262     -32.683  23.249 -10.493  1.00  0.00      A
ATOM   626  O    GLN  262     -32.178  22.276 -11.010  1.00  0.00      A
ATOM   627  N    ASP  263     -32.648  23.453  -9.185  1.00  0.00      A
ATOM   628  HN   ASP  263     -33.069  24.244  -8.815  1.00  0.00      A
ATOM   629  CA   ASP  263     -31.999  22.486  -8.267  1.00  0.00      A
ATOM   630  HA   ASP  263     -32.186  22.758  -7.243  1.00  0.00      A
ATOM   631  CB   ASP  263     -32.608  21.107  -8.573  1.00  0.00      A
ATOM   632  HB1  ASP  263     -32.326  20.795  -9.561  1.00  0.00      A
ATOM   633  HB2  ASP  263     -33.684  21.165  -8.505  1.00  0.00      A
ATOM   634  CG   ASP  263     -32.087  20.090  -7.558  1.00  0.00      A
```

Figure 8-12

| | | | | | | | | | |
|---|---|---|---|---|---|---|---|---|---|
| ATOM | 635 | OD1 | ASP | 263 | -31.513 | 20.511 | -6.578 | 1.00 | 0.00 | A |
| ATOM | 636 | OD2 | ASP | 263 | -32.280 | 18.909 | -7.777 | 1.00 | 0.00 | A |
| ATOM | 637 | C | ASP | 263 | -30.499 | 22.517 | -8.550 | 1.00 | 0.00 | A |
| ATOM | 638 | O | ASP | 263 | -29.942 | 21.568 | -9.063 | 1.00 | 0.00 | A |
| ATOM | 639 | N | GLY | 264 | -29.845 | 23.666 | -8.288 | 1.00 | 0.00 | A |
| ATOM | 640 | HN | GLY | 264 | -30.361 | 24.493 | -8.011 | 1.00 | 0.00 | A |
| ATOM | 641 | CA | GLY | 264 | -28.361 | 23.775 | -8.542 | 1.00 | 0.00 | A |
| ATOM | 642 | HA1 | GLY | 264 | -28.080 | 24.818 | -8.493 | 1.00 | 0.00 | A |
| ATOM | 643 | HA2 | GLY | 264 | -28.148 | 23.402 | -9.533 | 1.00 | 0.00 | A |
| ATOM | 644 | C | GLY | 264 | -27.507 | 22.982 | -7.517 | 1.00 | 0.00 | A |
| ATOM | 645 | O | GLY | 264 | -26.522 | 23.489 | -7.013 | 1.00 | 0.00 | A |
| ATOM | 646 | N | TYR | 265 | -27.861 | 21.764 | -7.200 | 1.00 | 0.00 | A |
| ATOM | 647 | HN | TYR | 265 | -28.643 | 21.369 | -7.584 | 1.00 | 0.00 | A |
| ATOM | 648 | CA | TYR | 265 | -27.053 | 20.992 | -6.227 | 1.00 | 0.00 | A |
| ATOM | 649 | HA | TYR | 265 | -26.591 | 21.661 | -5.518 | 1.00 | 0.00 | A |
| ATOM | 650 | CB | TYR | 265 | -28.034 | 20.071 | -5.502 | 1.00 | 0.00 | A |
| ATOM | 651 | HB1 | TYR | 265 | -27.486 | 19.374 | -4.885 | 1.00 | 0.00 | A |
| ATOM | 652 | HB2 | TYR | 265 | -28.620 | 19.524 | -6.230 | 1.00 | 0.00 | A |
| ATOM | 653 | CG | TYR | 265 | -28.953 | 20.902 | -4.628 | 1.00 | 0.00 | A |
| ATOM | 654 | CD1 | TYR | 265 | -29.792 | 21.896 | -5.200 | 1.00 | 0.00 | A |
| ATOM | 655 | HD1 | TYR | 265 | -29.804 | 22.050 | -6.260 | 1.00 | 0.00 | A |
| ATOM | 656 | CD2 | TYR | 265 | -28.953 | 20.703 | -3.230 | 1.00 | 0.00 | A |
| ATOM | 657 | HD2 | TYR | 265 | -28.315 | 19.948 | -2.793 | 1.00 | 0.00 | A |
| ATOM | 658 | CE1 | TYR | 265 | -30.623 | 22.678 | -4.374 | 1.00 | 0.00 | A |
| ATOM | 659 | HE1 | TYR | 265 | -31.260 | 23.433 | -4.813 | 1.00 | 0.00 | A |
| ATOM | 660 | CE2 | TYR | 265 | -29.790 | 21.485 | -2.404 | 1.00 | 0.00 | A |
| ATOM | 661 | HE2 | TYR | 265 | -29.789 | 21.331 | -1.340 | 1.00 | 0.00 | A |
| ATOM | 662 | CZ | TYR | 265 | -30.625 | 22.472 | -2.973 | 1.00 | 0.00 | A |
| ATOM | 663 | OH | TYR | 265 | -31.438 | 23.237 | -2.164 | 1.00 | 0.00 | A |
| ATOM | 664 | HH | TYR | 265 | -30.995 | 23.348 | -1.318 | 1.00 | 0.00 | A |
| ATOM | 665 | C | TYR | 265 | -25.977 | 20.185 | -6.966 | 1.00 | 0.00 | A |
| ATOM | 666 | O | TYR | 265 | -25.113 | 19.585 | -6.358 | 1.00 | 0.00 | A |
| ATOM | 667 | N | LEU | 266 | -26.019 | 20.166 | -8.284 | 1.00 | 0.00 | A |
| ATOM | 668 | HN | LEU | 266 | -26.623 | 20.725 | -8.757 | 1.00 | 0.00 | A |
| ATOM | 669 | CA | LEU | 266 | -25.015 | 19.413 | -9.028 | 1.00 | 0.00 | A |
| ATOM | 670 | HA | LEU | 266 | -24.627 | 18.616 | -8.408 | 1.00 | 0.00 | A |
| ATOM | 671 | CB | LEU | 266 | -25.701 | 18.805 | -10.297 | 1.00 | 0.00 | A |
| ATOM | 672 | HB1 | LEU | 266 | -26.366 | 18.010 | -9.987 | 1.00 | 0.00 | A |
| ATOM | 673 | HB2 | LEU | 266 | -24.946 | 18.394 | -10.935 | 1.00 | 0.00 | A |
| ATOM | 674 | CG | LEU | 266 | -26.507 | 19.841 | -11.107 | 1.00 | 0.00 | A |
| ATOM | 675 | HG | LEU | 266 | -25.989 | 20.790 | -11.124 | 1.00 | 0.00 | A |
| ATOM | 676 | CD1 | LEU | 266 | -26.679 | 19.302 | -12.528 | 1.00 | 0.00 | A |
| ATOM | 677 | HD11 | LEU | 266 | -26.920 | 20.102 | -13.198 | 1.00 | 0.00 | A |
| ATOM | 678 | HD12 | LEU | 266 | -27.472 | 18.589 | -12.536 | 1.00 | 0.00 | A |
| ATOM | 679 | HD13 | LEU | 266 | -25.766 | 18.824 | -12.848 | 1.00 | 0.00 | A |
| ATOM | 680 | CD2 | LEU | 266 | -27.910 | 20.007 | -10.503 | 1.00 | 0.00 | A |
| ATOM | 681 | HD21 | LEU | 266 | -28.652 | 19.896 | -11.283 | 1.00 | 0.00 | A |
| ATOM | 682 | HD22 | LEU | 266 | -28.000 | 20.987 | -10.061 | 1.00 | 0.00 | A |
| ATOM | 683 | HD23 | LEU | 266 | -28.069 | 19.253 | -9.746 | 1.00 | 0.00 | A |
| ATOM | 684 | C | LEU | 266 | -23.907 | 20.377 | -9.361 | 1.00 | 0.00 | A |
| ATOM | 685 | O | LEU | 266 | -22.770 | 20.015 | -9.498 | 1.00 | 0.00 | A |
| ATOM | 686 | N | ALA | 267 | -24.241 | 21.627 | -9.499 | 1.00 | 0.00 | A |
| ATOM | 687 | HN | ALA | 267 | -25.173 | 21.904 | -9.394 | 1.00 | 0.00 | A |
| ATOM | 688 | CA | ALA | 267 | -23.209 | 22.621 | -9.817 | 1.00 | 0.00 | A |
| ATOM | 689 | HA | ALA | 267 | -22.663 | 22.339 | -10.703 | 1.00 | 0.00 | A |
| ATOM | 690 | CB | ALA | 267 | -23.961 | 23.942 | -10.039 | 1.00 | 0.00 | A |
| ATOM | 691 | HB1 | ALA | 267 | -23.577 | 24.432 | -10.923 | 1.00 | 0.00 | A |
| ATOM | 692 | HB2 | ALA | 267 | -23.822 | 24.585 | -9.183 | 1.00 | 0.00 | A |

Figure 8-13

| | | | | | | | | | | |
|---|---|---|---|---|---|---|---|---|---|---|
| ATOM | 693 | HB3 | ALA | 267 | -25.014 | 23.740 | -10.170 | 1.00 | 0.00 | A |
| ATOM | 694 | C | ALA | 267 | -22.291 | 22.735 | -8.633 | 1.00 | 0.00 | A |
| ATOM | 695 | O | ALA | 267 | -21.140 | 23.058 | -8.758 | 1.00 | 0.00 | A |
| ATOM | 696 | N | GLU | 268 | -22.788 | 22.455 | -7.465 | 1.00 | 0.00 | A |
| ATOM | 697 | HN | GLU | 268 | -23.725 | 22.182 | -7.374 | 1.00 | 0.00 | A |
| ATOM | 698 | CA | GLU | 268 | -21.924 | 22.557 | -6.286 | 1.00 | 0.00 | A |
| ATOM | 699 | HA | GLU | 268 | -21.129 | 23.183 | -6.512 | 1.00 | 0.00 | A |
| ATOM | 700 | CB | GLU | 268 | -22.794 | 23.174 | -5.189 | 1.00 | 0.00 | A |
| ATOM | 701 | HB1 | GLU | 268 | -22.212 | 23.278 | -4.285 | 1.00 | 0.00 | A |
| ATOM | 702 | HB2 | GLU | 268 | -23.642 | 22.531 | -4.998 | 1.00 | 0.00 | A |
| ATOM | 703 | CG | GLU | 268 | -23.289 | 24.554 | -5.635 | 1.00 | 0.00 | A |
| ATOM | 704 | HG1 | GLU | 268 | -23.949 | 24.960 | -4.883 | 1.00 | 0.00 | A |
| ATOM | 705 | HG2 | GLU | 268 | -23.825 | 24.458 | -6.569 | 1.00 | 0.00 | A |
| ATOM | 706 | CD | GLU | 268 | -22.097 | 25.495 | -5.827 | 1.00 | 0.00 | A |
| ATOM | 707 | OE1 | GLU | 268 | -22.315 | 26.610 | -6.270 | 1.00 | 0.00 | A |
| ATOM | 708 | OE2 | GLU | 268 | -20.988 | 25.087 | -5.522 | 1.00 | 0.00 | A |
| ATOM | 709 | C | GLU | 268 | -21.388 | 21.206 | -5.868 | 1.00 | 0.00 | A |
| ATOM | 710 | O | GLU | 268 | -20.204 | 21.035 | -5.697 | 1.00 | 0.00 | A |
| ATOM | 711 | N | SER | 269 | -22.223 | 20.252 | -5.681 | 1.00 | 0.00 | A |
| ATOM | 712 | HN | SER | 269 | -23.184 | 20.398 | -5.805 | 1.00 | 0.00 | A |
| ATOM | 713 | CA | SER | 269 | -21.711 | 18.931 | -5.275 | 1.00 | 0.00 | A |
| ATOM | 714 | HA | SER | 269 | -21.224 | 18.990 | -4.315 | 1.00 | 0.00 | A |
| ATOM | 715 | CB | SER | 269 | -22.945 | 18.036 | -5.187 | 1.00 | 0.00 | A |
| ATOM | 716 | HB1 | SER | 269 | -22.641 | 17.030 | -4.921 | 1.00 | 0.00 | A |
| ATOM | 717 | HB2 | SER | 269 | -23.445 | 18.017 | -6.138 | 1.00 | 0.00 | A |
| ATOM | 718 | OG | SER | 269 | -23.833 | 18.554 | -4.203 | 1.00 | 0.00 | A |
| ATOM | 719 | HG | SER | 269 | -23.310 | 18.828 | -3.447 | 1.00 | 0.00 | A |
| ATOM | 720 | C | SER | 269 | -20.742 | 18.414 | -6.344 | 1.00 | 0.00 | A |
| ATOM | 721 | O | SER | 269 | -19.795 | 17.702 | -6.056 | 1.00 | 0.00 | A |
| ATOM | 722 | N | ILE | 270 | -20.940 | 18.805 | -7.576 | 1.00 | 0.00 | A |
| ATOM | 723 | HN | ILE | 270 | -21.646 | 19.469 | -7.779 | 1.00 | 0.00 | A |
| ATOM | 724 | CA | ILE | 270 | -20.017 | 18.316 | -8.650 | 1.00 | 0.00 | A |
| ATOM | 725 | HA | ILE | 270 | -19.617 | 17.357 | -8.363 | 1.00 | 0.00 | A |
| ATOM | 726 | CB | ILE | 270 | -20.868 | 18.143 | -9.911 | 1.00 | 0.00 | A |
| ATOM | 727 | HB | ILE | 270 | -21.103 | 19.109 | -10.338 | 1.00 | 0.00 | A |
| ATOM | 728 | CG1 | ILE | 270 | -22.152 | 17.388 | -9.558 | 1.00 | 0.00 | A |
| ATOM | 729 | HG11 | ILE | 270 | -22.740 | 17.974 | -8.870 | 1.00 | 0.00 | A |
| ATOM | 730 | HG12 | ILE | 270 | -21.896 | 16.444 | -9.097 | 1.00 | 0.00 | A |
| ATOM | 731 | CG2 | ILE | 270 | -20.086 | 17.302 | -10.925 | 1.00 | 0.00 | A |
| ATOM | 732 | HG21 | ILE | 270 | -20.728 | 17.055 | -11.759 | 1.00 | 0.00 | A |
| ATOM | 733 | HG22 | ILE | 270 | -19.749 | 16.389 | -10.451 | 1.00 | 0.00 | A |
| ATOM | 734 | HG23 | ILE | 270 | -19.235 | 17.859 | -11.279 | 1.00 | 0.00 | A |
| ATOM | 735 | CD1 | ILE | 270 | -22.959 | 17.134 | -10.827 | 1.00 | 0.00 | A |
| ATOM | 736 | HD11 | ILE | 270 | -22.475 | 16.369 | -11.415 | 1.00 | 0.00 | A |
| ATOM | 737 | HD12 | ILE | 270 | -23.023 | 18.046 | -11.403 | 1.00 | 0.00 | A |
| ATOM | 738 | HD13 | ILE | 270 | -23.953 | 16.806 | -10.561 | 1.00 | 0.00 | A |
| ATOM | 739 | C | ILE | 270 | -18.861 | 19.296 | -8.874 | 1.00 | 0.00 | A |
| ATOM | 740 | O | ILE | 270 | -17.723 | 18.906 | -8.848 | 1.00 | 0.00 | A |
| ATOM | 741 | N | ASN | 271 | -19.130 | 20.571 | -9.110 | 1.00 | 0.00 | A |
| ATOM | 742 | HN | ASN | 271 | -20.053 | 20.889 | -9.145 | 1.00 | 0.00 | A |
| ATOM | 743 | CA | ASN | 271 | -17.994 | 21.523 | -9.326 | 1.00 | 0.00 | A |
| ATOM | 744 | HA | ASN | 271 | -17.508 | 21.322 | -10.269 | 1.00 | 0.00 | A |
| ATOM | 745 | CB | ASN | 271 | -18.618 | 22.912 | -9.338 | 1.00 | 0.00 | A |
| ATOM | 746 | HB1 | ASN | 271 | -18.966 | 23.159 | -8.349 | 1.00 | 0.00 | A |
| ATOM | 747 | HB2 | ASN | 271 | -19.450 | 22.920 | -10.028 | 1.00 | 0.00 | A |
| ATOM | 748 | CG | ASN | 271 | -17.585 | 23.939 | -9.787 | 1.00 | 0.00 | A |
| ATOM | 749 | OD1 | ASN | 271 | -16.665 | 24.256 | -9.060 | 1.00 | 0.00 | A |
| ATOM | 750 | ND2 | ASN | 271 | -17.701 | 24.475 | -10.974 | 1.00 | 0.00 | A |

Figure 8-14

| | | | | | | | | | |
|---|---|---|---|---|---|---|---|---|---|
| ATOM | 751 | HD21 | ASN | 271 | -18.446 | 24.213 | -11.560 | 1.00 | 0.00 | A |
| ATOM | 752 | HD22 | ASN | 271 | -17.049 | 25.137 | -11.278 | 1.00 | 0.00 | A |
| ATOM | 753 | C | ASN | 271 | -17.008 | 21.348 | -8.171 | 1.00 | 0.00 | A |
| ATOM | 754 | O | ASN | 271 | -15.811 | 21.482 | -8.324 | 1.00 | 0.00 | A |
| ATOM | 755 | N | LYS | 272 | -17.509 | 21.066 | -7.000 | 1.00 | 0.00 | A |
| ATOM | 756 | HN | LYS | 272 | -18.472 | 20.979 | -6.887 | 1.00 | 0.00 | A |
| ATOM | 757 | CA | LYS | 272 | -16.598 | 20.876 | -5.852 | 1.00 | 0.00 | A |
| ATOM | 758 | HA | LYS | 272 | -15.874 | 21.672 | -5.807 | 1.00 | 0.00 | A |
| ATOM | 759 | CB | LYS | 272 | -17.474 | 20.867 | -4.599 | 1.00 | 0.00 | A |
| ATOM | 760 | HB1 | LYS | 272 | -16.868 | 20.624 | -3.739 | 1.00 | 0.00 | A |
| ATOM | 761 | HB2 | LYS | 272 | -18.258 | 20.130 | -4.708 | 1.00 | 0.00 | A |
| ATOM | 762 | CG | LYS | 272 | -18.093 | 22.253 | -4.407 | 1.00 | 0.00 | A |
| ATOM | 763 | HG1 | LYS | 272 | -18.708 | 22.496 | -5.258 | 1.00 | 0.00 | A |
| ATOM | 764 | HG2 | LYS | 272 | -17.306 | 22.987 | -4.312 | 1.00 | 0.00 | A |
| ATOM | 765 | CD | LYS | 272 | -18.950 | 22.262 | -3.143 | 1.00 | 0.00 | A |
| ATOM | 766 | HD1 | LYS | 272 | -19.723 | 21.515 | -3.229 | 1.00 | 0.00 | A |
| ATOM | 767 | HD2 | LYS | 272 | -19.400 | 23.235 | -3.022 | 1.00 | 0.00 | A |
| ATOM | 768 | CE | LYS | 272 | -18.074 | 21.947 | -1.928 | 1.00 | 0.00 | A |
| ATOM | 769 | HE1 | LYS | 272 | -17.284 | 22.675 | -1.834 | 1.00 | 0.00 | A |
| ATOM | 770 | HE2 | LYS | 272 | -17.661 | 20.949 | -2.012 | 1.00 | 0.00 | A |
| ATOM | 771 | NZ | LYS | 272 | -18.992 | 22.034 | -0.759 | 1.00 | 0.00 | A |
| ATOM | 772 | HZ1 | LYS | 272 | -18.560 | 21.559 | 0.058 | 1.00 | 0.00 | A |
| ATOM | 773 | HZ2 | LYS | 272 | -19.895 | 21.572 | -0.993 | 1.00 | 0.00 | A |
| ATOM | 774 | HZ3 | LYS | 272 | -19.162 | 23.032 | -0.525 | 1.00 | 0.00 | A |
| ATOM | 775 | C | LYS | 272 | -15.913 | 19.542 | -6.075 | 1.00 | 0.00 | A |
| ATOM | 776 | O | LYS | 272 | -14.750 | 19.367 | -5.784 | 1.00 | 0.00 | A |
| ATOM | 777 | N | ASP | 273 | -16.654 | 18.581 | -6.591 | 1.00 | 0.00 | A |
| ATOM | 778 | HN | ASP | 273 | -17.600 | 18.745 | -6.786 | 1.00 | 0.00 | A |
| ATOM | 779 | CA | ASP | 273 | -16.066 | 17.243 | -6.855 | 1.00 | 0.00 | A |
| ATOM | 780 | HA | ASP | 273 | -15.648 | 16.824 | -5.954 | 1.00 | 0.00 | A |
| ATOM | 781 | CB | ASP | 273 | -17.228 | 16.387 | -7.362 | 1.00 | 0.00 | A |
| ATOM | 782 | HB1 | ASP | 273 | -17.643 | 16.833 | -8.252 | 1.00 | 0.00 | A |
| ATOM | 783 | HB2 | ASP | 273 | -17.990 | 16.329 | -6.599 | 1.00 | 0.00 | A |
| ATOM | 784 | CG | ASP | 273 | -16.726 | 14.979 | -7.688 | 1.00 | 0.00 | A |
| ATOM | 785 | OD1 | ASP | 273 | -16.247 | 14.317 | -6.781 | 1.00 | 0.00 | A |
| ATOM | 786 | OD2 | ASP | 273 | -16.832 | 14.585 | -8.837 | 1.00 | 0.00 | A |
| ATOM | 787 | C | ASP | 273 | -14.984 | 17.408 | -7.938 | 1.00 | 0.00 | A |
| ATOM | 788 | O | ASP | 273 | -14.189 | 16.535 | -8.170 | 1.00 | 0.00 | A |
| ATOM | 789 | N | ILE | 274 | -15.002 | 18.541 | -8.622 | 1.00 | 0.00 | A |
| ATOM | 790 | HN | ILE | 274 | -15.651 | 19.191 | -8.421 | 1.00 | 0.00 | A |
| ATOM | 791 | CA | ILE | 274 | -14.016 | 18.834 | -9.687 | 1.00 | 0.00 | A |
| ATOM | 792 | HA | ILE | 274 | -13.738 | 17.939 | -10.203 | 1.00 | 0.00 | A |
| ATOM | 793 | CB | ILE | 274 | -14.728 | 19.797 | -10.633 | 1.00 | 0.00 | A |
| ATOM | 794 | HB | ILE | 274 | -15.102 | 20.632 | -10.074 | 1.00 | 0.00 | A |
| ATOM | 795 | CG1 | ILE | 274 | -15.896 | 19.077 | -11.314 | 1.00 | 0.00 | A |
| ATOM | 796 | HG11 | ILE | 274 | -16.402 | 19.758 | -11.972 | 1.00 | 0.00 | A |
| ATOM | 797 | HG12 | ILE | 274 | -16.581 | 18.725 | -10.570 | 1.00 | 0.00 | A |
| ATOM | 798 | CG2 | ILE | 274 | -13.753 | 20.299 | -11.681 | 1.00 | 0.00 | A |
| ATOM | 799 | HG21 | ILE | 274 | -14.080 | 19.984 | -12.660 | 1.00 | 0.00 | A |
| ATOM | 800 | HG22 | ILE | 274 | -12.773 | 19.895 | -11.479 | 1.00 | 0.00 | A |
| ATOM | 801 | HG23 | ILE | 274 | -13.713 | 21.378 | -11.644 | 1.00 | 0.00 | A |
| ATOM | 802 | CD1 | ILE | 274 | -15.379 | 17.891 | -12.117 | 1.00 | 0.00 | A |
| ATOM | 803 | HD11 | ILE | 274 | -14.405 | 18.120 | -12.514 | 1.00 | 0.00 | A |
| ATOM | 804 | HD12 | ILE | 274 | -16.060 | 17.685 | -12.929 | 1.00 | 0.00 | A |
| ATOM | 805 | HD13 | ILE | 274 | -15.313 | 17.025 | -11.475 | 1.00 | 0.00 | A |
| ATOM | 806 | C | ILE | 274 | -12.810 | 19.505 | -9.012 | 1.00 | 0.00 | A |
| ATOM | 807 | O | ILE | 274 | -11.711 | 19.491 | -9.508 | 1.00 | 0.00 | A |
| ATOM | 808 | N | GLU | 275 | -13.077 | 20.148 | -7.887 | 1.00 | 0.00 | A |

Figure 8-15

| | | | | | | | | | | |
|---|---|---|---|---|---|---|---|---|---|---|
| ATOM | 809 | HN | GLU | 275 | -13.944 | 20.174 | -7.595 | 1.00 | 0.00 | A |
| ATOM | 810 | CA | GLU | 275 | -12.038 | 20.847 | -7.092 | 1.00 | 0.00 | A |
| ATOM | 811 | HA | GLU | 275 | -11.413 | 21.463 | -7.720 | 1.00 | 0.00 | A |
| ATOM | 812 | CB | GLU | 275 | -12.804 | 21.697 | -6.074 | 1.00 | 0.00 | A |
| ATOM | 813 | HB1 | GLU | 275 | -13.400 | 21.055 | -5.443 | 1.00 | 0.00 | A |
| ATOM | 814 | HB2 | GLU | 275 | -13.451 | 22.390 | -6.598 | 1.00 | 0.00 | A |
| ATOM | 815 | CG | GLU | 275 | -11.812 | 22.477 | -5.211 | 1.00 | 0.00 | A |
| ATOM | 816 | HG1 | GLU | 275 | -11.152 | 21.787 | -4.708 | 1.00 | 0.00 | A |
| ATOM | 817 | HG2 | GLU | 275 | -12.351 | 23.059 | -4.479 | 1.00 | 0.00 | A |
| ATOM | 818 | CD | GLU | 275 | -10.988 | 23.407 | -6.098 | 1.00 | 0.00 | A |
| ATOM | 819 | OE1 | GLU | 275 | -11.578 | 24.275 | -6.720 | 1.00 | 0.00 | A |
| ATOM | 820 | OE2 | GLU | 275 | -9.782 | 23.237 | -6.142 | 1.00 | 0.00 | A |
| ATOM | 821 | C | GLU | 275 | -11.239 | 19.767 | -6.408 | 1.00 | 0.00 | A |
| ATOM | 822 | O | GLU | 275 | -10.072 | 19.911 | -6.134 | 1.00 | 0.00 | A |
| ATOM | 823 | N | GLU | 276 | -11.893 | 18.675 | -6.067 | 1.00 | 0.00 | A |
| ATOM | 824 | HN | GLU | 276 | -12.825 | 18.569 | -6.288 | 1.00 | 0.00 | A |
| ATOM | 825 | CA | GLU | 276 | -11.179 | 17.588 | -5.421 | 1.00 | 0.00 | A |
| ATOM | 826 | HA | GLU | 276 | -10.499 | 17.940 | -4.658 | 1.00 | 0.00 | A |
| ATOM | 827 | CB | GLU | 276 | -12.234 | 16.634 | -4.876 | 1.00 | 0.00 | A |
| ATOM | 828 | HB1 | GLU | 276 | -11.752 | 15.812 | -4.370 | 1.00 | 0.00 | A |
| ATOM | 829 | HB2 | GLU | 276 | -12.836 | 16.255 | -5.691 | 1.00 | 0.00 | A |
| ATOM | 830 | CG | GLU | 276 | -13.111 | 17.384 | -3.899 | 1.00 | 0.00 | A |
| ATOM | 831 | HG1 | GLU | 276 | -13.553 | 18.229 | -4.400 | 1.00 | 0.00 | A |
| ATOM | 832 | HG2 | GLU | 276 | -12.508 | 17.726 | -3.075 | 1.00 | 0.00 | A |
| ATOM | 833 | CD | GLU | 276 | -14.215 | 16.462 | -3.379 | 1.00 | 0.00 | A |
| ATOM | 834 | OE1 | GLU | 276 | -14.945 | 16.882 | -2.495 | 1.00 | 0.00 | A |
| ATOM | 835 | OE2 | GLU | 276 | -14.317 | 15.353 | -3.877 | 1.00 | 0.00 | A |
| ATOM | 836 | C | GLU | 276 | -10.482 | 17.020 | -6.578 | 1.00 | 0.00 | A |
| ATOM | 837 | O | GLU | 276 | -9.292 | 16.957 | -6.635 | 1.00 | 0.00 | A |
| ATOM | 838 | N | CYS | 277 | -11.283 | 16.730 | -7.600 | 1.00 | 0.00 | A |
| ATOM | 839 | HN | CYS | 277 | -12.235 | 16.903 | -7.514 | 1.00 | 0.00 | A |
| ATOM | 840 | CA | CYS | 277 | -10.765 | 16.166 | -8.850 | 1.00 | 0.00 | A |
| ATOM | 841 | HA | CYS | 277 | -10.496 | 15.162 | -8.748 | 1.00 | 0.00 | A |
| ATOM | 842 | CB | CYS | 277 | -11.901 | 16.306 | -9.840 | 1.00 | 0.00 | A |
| ATOM | 843 | HB1 | CYS | 277 | -12.152 | 17.340 | -9.930 | 1.00 | 0.00 | A |
| ATOM | 844 | HB2 | CYS | 277 | -12.754 | 15.753 | -9.491 | 1.00 | 0.00 | A |
| ATOM | 845 | SG | CYS | 277 | -11.395 | 15.671 | -11.453 | 1.00 | 0.00 | A |
| ATOM | 846 | HG1 | CYS | 277 | -10.731 | 16.264 | -11.810 | 1.00 | 0.00 | A |
| ATOM | 847 | C | CYS | 277 | -9.611 | 17.040 | -9.286 | 1.00 | 0.00 | A |
| ATOM | 848 | O | CYS | 277 | -8.688 | 16.608 | -9.960 | 1.00 | 0.00 | A |
| ATOM | 849 | N | ASN | 278 | -9.641 | 18.286 | -8.855 | 1.00 | 0.00 | A |
| ATOM | 850 | HN | ASN | 278 | -10.346 | 18.587 | -8.275 | 1.00 | 0.00 | A |
| ATOM | 851 | CA | ASN | 278 | -8.596 | 19.189 | -9.217 | 1.00 | 0.00 | A |
| ATOM | 852 | HA | ASN | 278 | -8.434 | 19.118 | -10.237 | 1.00 | 0.00 | A |
| ATOM | 853 | CB | ASN | 278 | -9.101 | 20.597 | -8.888 | 1.00 | 0.00 | A |
| ATOM | 854 | HB1 | ASN | 278 | -9.272 | 20.685 | -7.840 | 1.00 | 0.00 | A |
| ATOM | 855 | HB2 | ASN | 278 | -10.018 | 20.787 | -9.422 | 1.00 | 0.00 | A |
| ATOM | 856 | CG | ASN | 278 | -8.044 | 21.620 | -9.313 | 1.00 | 0.00 | A |
| ATOM | 857 | OD1 | ASN | 278 | -7.668 | 21.678 | -10.467 | 1.00 | 0.00 | A |
| ATOM | 858 | ND2 | ASN | 278 | -7.544 | 22.434 | -8.423 | 1.00 | 0.00 | A |
| ATOM | 859 | HD21 | ASN | 278 | -7.846 | 22.388 | -7.491 | 1.00 | 0.00 | A |
| ATOM | 860 | HD22 | ASN | 278 | -6.867 | 23.092 | -8.687 | 1.00 | 0.00 | A |
| ATOM | 861 | C | ASN | 278 | -7.337 | 18.878 | -8.406 | 1.00 | 0.00 | A |
| ATOM | 862 | O | ASN | 278 | -6.270 | 18.794 | -8.927 | 1.00 | 0.00 | A |
| ATOM | 863 | N | ALA | 279 | -7.491 | 18.681 | -7.117 | 1.00 | 0.00 | A |
| ATOM | 864 | HN | ALA | 279 | -8.373 | 18.765 | -6.724 | 1.00 | 0.00 | A |
| ATOM | 865 | CA | ALA | 279 | -6.314 | 18.375 | -6.230 | 1.00 | 0.00 | A |
| ATOM | 866 | HA | ALA | 279 | -5.519 | 19.048 | -6.465 | 1.00 | 0.00 | A |

Figure 8-16

```
ATOM    867  CB   ALA   279      -6.814  18.683  -4.824  1.00  0.00           A
ATOM    868  HB1  ALA   279      -7.620  18.009  -4.574  1.00  0.00           A
ATOM    869  HB2  ALA   279      -7.171  19.702  -4.784  1.00  0.00           A
ATOM    870  HB3  ALA   279      -6.006  18.556  -4.119  1.00  0.00           A
ATOM    871  C    ALA   279      -5.786  16.902  -6.288  1.00  0.00           A
ATOM    872  O    ALA   279      -4.765  16.630  -5.745  1.00  0.00           A
ATOM    873  N    ILE   280      -6.430  15.972  -6.941  1.00  0.00           A
ATOM    874  HN   ILE   280      -7.150  16.204  -7.498  1.00  0.00           A
ATOM    875  CA   ILE   280      -5.846  14.551  -6.949  1.00  0.00           A
ATOM    876  HA   ILE   280      -5.049  14.511  -6.309  1.00  0.00           A
ATOM    877  CB   ILE   280      -6.876  13.457  -6.556  1.00  0.00           A
ATOM    878  HB   ILE   280      -6.383  12.533  -6.607  1.00  0.00           A
ATOM    879  CG1  ILE   280      -8.044  13.408  -7.504  1.00  0.00           A
ATOM    880  HG11 ILE   280      -8.702  12.601  -7.227  1.00  0.00           A
ATOM    881  HG12 ILE   280      -7.693  13.262  -8.497  1.00  0.00           A
ATOM    882  CG2  ILE   280      -7.369  13.647  -5.147  1.00  0.00           A
ATOM    883  HG21 ILE   280      -8.443  13.752  -5.158  1.00  0.00           A
ATOM    884  HG22 ILE   280      -6.919  14.528  -4.729  1.00  0.00           A
ATOM    885  HG23 ILE   280      -7.097  12.783  -4.558  1.00  0.00           A
ATOM    886  CD1  ILE   280      -8.767  14.657  -7.424  1.00  0.00           A
ATOM    887  HD11 ILE   280      -9.802  14.458  -7.345  1.00  0.00           A
ATOM    888  HD12 ILE   280      -8.571  15.234  -8.303  1.00  0.00           A
ATOM    889  HD13 ILE   280      -8.441  15.195  -6.566  1.00  0.00           A
ATOM    890  C    ILE   280      -5.374  14.280  -8.260  1.00  0.00           A
ATOM    891  O    ILE   280      -4.382  13.661  -8.446  1.00  0.00           A
ATOM    892  N    ILE   281      -6.079  14.700  -9.190  1.00  0.00           A
ATOM    893  HN   ILE   281      -6.902  15.184  -9.008  1.00  0.00           A
ATOM    894  CA   ILE   281      -5.666  14.469 -10.525  1.00  0.00           A
ATOM    895  HA   ILE   281      -5.359  13.476 -10.650  1.00  0.00           A
ATOM    896  CB   ILE   281      -6.868  14.741 -11.345  1.00  0.00           A
ATOM    897  HB   ILE   281      -7.146  15.782 -11.238  1.00  0.00           A
ATOM    898  CG1  ILE   281      -7.972  13.848 -10.784  1.00  0.00           A
ATOM    899  HG11 ILE   281      -8.351  14.301  -9.873  1.00  0.00           A
ATOM    900  HG12 ILE   281      -7.550  12.877 -10.538  1.00  0.00           A
ATOM    901  CG2  ILE   281      -6.574  14.413 -12.819  1.00  0.00           A
ATOM    902  HG21 ILE   281      -5.551  14.674 -13.047  1.00  0.00           A
ATOM    903  HG22 ILE   281      -7.241  14.978 -13.454  1.00  0.00           A
ATOM    904  HG23 ILE   281      -6.724  13.358 -12.988  1.00  0.00           A
ATOM    905  CD1  ILE   281      -9.100  13.698 -11.783  1.00  0.00           A
ATOM    906  HD11 ILE   281      -8.864  12.897 -12.467  1.00  0.00           A
ATOM    907  HD12 ILE   281      -9.217  14.622 -12.331  1.00  0.00           A
ATOM    908  HD13 ILE   281     -10.010  13.470 -11.260  1.00  0.00           A
ATOM    909  C    ILE   281      -4.567  15.399 -10.793  1.00  0.00           A
ATOM    910  O    ILE   281      -3.644  15.104 -11.523  1.00  0.00           A
ATOM    911  N    GLU   282      -4.591  16.536 -10.171  1.00  0.00           A
ATOM    912  HN   GLU   282      -5.315  16.769  -9.550  1.00  0.00           A
ATOM    913  CA   GLU   282      -3.529  17.429 -10.433  1.00  0.00           A
ATOM    914  HA   GLU   282      -3.220  17.233 -11.383  1.00  0.00           A
ATOM    915  CB   GLU   282      -4.080  18.841 -10.342  1.00  0.00           A
ATOM    916  HB1  GLU   282      -4.289  19.075  -9.314  1.00  0.00           A
ATOM    917  HB2  GLU   282      -4.984  18.921 -10.928  1.00  0.00           A
ATOM    918  CG   GLU   282      -3.032  19.824 -10.867  1.00  0.00           A
ATOM    919  HG1  GLU   282      -2.798  19.587 -11.894  1.00  0.00           A
ATOM    920  HG2  GLU   282      -2.137  19.750 -10.267  1.00  0.00           A
ATOM    921  CD   GLU   282      -3.582  21.247 -10.787  1.00  0.00           A
ATOM    922  OE1  GLU   282      -4.652  21.479 -11.325  1.00  0.00           A
ATOM    923  OE2  GLU   282      -2.924  22.082 -10.191  1.00  0.00           A
ATOM    924  C    GLU   282      -2.378  17.238  -9.453  1.00  0.00           A
```

Figure 8-17

| | | | | | | | | | | |
|---|---|---|---|---|---|---|---|---|---|---|
| ATOM | 925 | O    | GLU | 282 | -1.267 | 16.917 | -9.845  | 1.00 | 0.00 | A |
| ATOM | 926 | N    | GLN | 283 | -2.629 | 17.375 | -8.178  | 1.00 | 0.00 | A |
| ATOM | 927 | HN   | GLN | 283 | -3.546 | 17.552 | -7.857  | 1.00 | 0.00 | A |
| ATOM | 928 | CA   | GLN | 283 | -1.541 | 17.207 | -7.207  | 1.00 | 0.00 | A |
| ATOM | 929 | HA   | GLN | 283 | -0.650 | 17.683 | -7.577  | 1.00 | 0.00 | A |
| ATOM | 930 | CB   | GLN | 283 | -2.025 | 17.947 | -5.971  | 1.00 | 0.00 | A |
| ATOM | 931 | HB1  | GLN | 283 | -2.958 | 17.548 | -5.656  | 1.00 | 0.00 | A |
| ATOM | 932 | HB2  | GLN | 283 | -2.139 | 18.996 | -6.198  | 1.00 | 0.00 | A |
| ATOM | 933 | CG   | GLN | 283 | -1.016 | 17.777 | -4.878  | 1.00 | 0.00 | A |
| ATOM | 934 | HG1  | GLN | 283 | -0.062 | 18.111 | -5.229  | 1.00 | 0.00 | A |
| ATOM | 935 | HG2  | GLN | 283 | -0.965 | 16.732 | -4.613  | 1.00 | 0.00 | A |
| ATOM | 936 | CD   | GLN | 283 | -1.433 | 18.598 | -3.659  | 1.00 | 0.00 | A |
| ATOM | 937 | OE1  | GLN | 283 | -1.660 | 19.788 | -3.761  | 1.00 | 0.00 | A |
| ATOM | 938 | NE2  | GLN | 283 | -1.542 | 18.011 | -2.503  | 1.00 | 0.00 | A |
| ATOM | 939 | HE21 | GLN | 283 | -1.357 | 17.053 | -2.422  | 1.00 | 0.00 | A |
| ATOM | 940 | HE22 | GLN | 283 | -1.812 | 18.526 | -1.717  | 1.00 | 0.00 | A |
| ATOM | 941 | C    | GLN | 283 | -1.248 | 15.738 | -6.903  | 1.00 | 0.00 | A |
| ATOM | 942 | O    | GLN | 283 | -0.229 | 15.428 | -6.315  | 1.00 | 0.00 | A |
| ATOM | 943 | N    | PHE | 284 | -2.099 | 14.818 | -7.277  | 1.00 | 0.00 | A |
| ATOM | 944 | HN   | PHE | 284 | -2.934 | 15.056 | -7.764  | 1.00 | 0.00 | A |
| ATOM | 945 | CA   | PHE | 284 | -1.774 | 13.400 | -6.962  | 1.00 | 0.00 | A |
| ATOM | 946 | HA   | PHE | 284 | -0.860 | 13.365 | -6.395  | 1.00 | 0.00 | A |
| ATOM | 947 | CB   | PHE | 284 | -2.922 | 12.845 | -6.094  | 1.00 | 0.00 | A |
| ATOM | 948 | HB1  | PHE | 284 | -2.814 | 11.774 | -6.005  | 1.00 | 0.00 | A |
| ATOM | 949 | HB2  | PHE | 284 | -3.859 | 13.066 | -6.551  | 1.00 | 0.00 | A |
| ATOM | 950 | CG   | PHE | 284 | -2.879 | 13.465 | -4.717  | 1.00 | 0.00 | A |
| ATOM | 951 | CD1  | PHE | 284 | -2.999 | 14.859 | -4.561  | 1.00 | 0.00 | A |
| ATOM | 952 | HD1  | PHE | 284 | -3.110 | 15.483 | -5.419  | 1.00 | 0.00 | A |
| ATOM | 953 | CD2  | PHE | 284 | -2.725 | 12.638 | -3.579  | 1.00 | 0.00 | A |
| ATOM | 954 | HD2  | PHE | 284 | -2.633 | 11.569 | -3.698  | 1.00 | 0.00 | A |
| ATOM | 955 | CE1  | PHE | 284 | -2.964 | 15.436 | -3.271  | 1.00 | 0.00 | A |
| ATOM | 956 | HE1  | PHE | 284 | -3.059 | 16.503 | -3.156  | 1.00 | 0.00 | A |
| ATOM | 957 | CE2  | PHE | 284 | -2.690 | 13.216 | -2.284  | 1.00 | 0.00 | A |
| ATOM | 958 | HE2  | PHE | 284 | -2.569 | 12.591 | -1.413  | 1.00 | 0.00 | A |
| ATOM | 959 | CZ   | PHE | 284 | -2.810 | 14.614 | -2.133  | 1.00 | 0.00 | A |
| ATOM | 960 | HZ   | PHE | 284 | -2.784 | 15.055 | -1.148  | 1.00 | 0.00 | A |
| ATOM | 961 | C    | PHE | 284 | -1.607 | 12.574 | -8.228  | 1.00 | 0.00 | A |
| ATOM | 962 | O    | PHE | 284 | -0.976 | 11.570 | -8.199  | 1.00 | 0.00 | A |
| ATOM | 963 | N    | ILE | 285 | -2.183 | 12.965 | -9.337  | 1.00 | 0.00 | A |
| ATOM | 964 | HN   | ILE | 285 | -2.664 | 13.824 | -9.387  | 1.00 | 0.00 | A |
| ATOM | 965 | CA   | ILE | 285 | -2.010 | 12.149 | -10.558 | 1.00 | 0.00 | A |
| ATOM | 966 | HA   | ILE | 285 | -1.779 | 11.137 | -10.284 | 1.00 | 0.00 | A |
| ATOM | 967 | CB   | ILE | 285 | -3.366 | 12.195 | -11.255 | 1.00 | 0.00 | A |
| ATOM | 968 | HB   | ILE | 285 | -3.665 | 13.221 | -11.376 | 1.00 | 0.00 | A |
| ATOM | 969 | CG1  | ILE | 285 | -4.425 | 11.436 | -10.389 | 1.00 | 0.00 | A |
| ATOM | 970 | HG11 | ILE | 285 | -5.418 | 11.597 | -10.800 | 1.00 | 0.00 | A |
| ATOM | 971 | HG12 | ILE | 285 | -4.403 | 11.812 | -9.373  | 1.00 | 0.00 | A |
| ATOM | 972 | CG2  | ILE | 285 | -3.254 | 11.533 | -12.630 | 1.00 | 0.00 | A |
| ATOM | 973 | HG21 | ILE | 285 | -2.354 | 10.937 | -12.670 | 1.00 | 0.00 | A |
| ATOM | 974 | HG22 | ILE | 285 | -3.214 | 12.296 | -13.394 | 1.00 | 0.00 | A |
| ATOM | 975 | HG23 | ILE | 285 | -4.113 | 10.900 | -12.797 | 1.00 | 0.00 | A |
| ATOM | 976 | CD1  | ILE | 285 | -4.117 |  9.935 | -10.377 | 1.00 | 0.00 | A |
| ATOM | 977 | HD11 | ILE | 285 | -3.052 |  9.782 | -10.437 | 1.00 | 0.00 | A |
| ATOM | 978 | HD12 | ILE | 285 | -4.595 |  9.464 | -11.221 | 1.00 | 0.00 | A |
| ATOM | 979 | HD13 | ILE | 285 | -4.491 |  9.499 | -9.463  | 1.00 | 0.00 | A |
| ATOM | 980 | C    | ILE | 285 | -0.877 | 12.719 | -11.430 | 1.00 | 0.00 | A |
| ATOM | 981 | O    | ILE | 285 | -0.363 | 12.051 | -12.305 | 1.00 | 0.00 | A |
| ATOM | 982 | N    | ASP | 286 | -0.482 | 13.954 | -11.197 | 1.00 | 0.00 | A |

Figure 8-18

| | | | | | | | | | |
|---|---|---|---|---|---|---|---|---|---|
| ATOM | 983 | HN | ASP | 286 | -0.916 | 14.490 | -10.486 | 1.00 | 0.00 | A |
| ATOM | 984 | CA | ASP | 286 | 0.616 | 14.558 | -12.019 | 1.00 | 0.00 | A |
| ATOM | 985 | HA | ASP | 286 | 0.304 | 14.640 | -13.045 | 1.00 | 0.00 | A |
| ATOM | 986 | CB | ASP | 286 | 0.823 | 15.955 | -11.440 | 1.00 | 0.00 | A |
| ATOM | 987 | HB1 | ASP | 286 | 1.050 | 15.881 | -10.388 | 1.00 | 0.00 | A |
| ATOM | 988 | HB2 | ASP | 286 | -0.077 | 16.537 | -11.578 | 1.00 | 0.00 | A |
| ATOM | 989 | CG | ASP | 286 | 1.985 | 16.636 | -12.165 | 1.00 | 0.00 | A |
| ATOM | 990 | OD1 | ASP | 286 | 3.115 | 16.251 | -11.918 | 1.00 | 0.00 | A |
| ATOM | 991 | OD2 | ASP | 286 | 1.725 | 17.525 | -12.959 | 1.00 | 0.00 | A |
| ATOM | 992 | C | ASP | 286 | 1.927 | 13.748 | -11.932 | 1.00 | 0.00 | A |
| ATOM | 993 | O | ASP | 286 | 2.838 | 13.974 | -12.700 | 1.00 | 0.00 | A |
| ATOM | 994 | N | TYR | 287 | 2.050 | 12.821 | -11.015 | 1.00 | 0.00 | A |
| ATOM | 995 | HN | TYR | 287 | 1.321 | 12.647 | -10.380 | 1.00 | 0.00 | A |
| ATOM | 996 | CA | TYR | 287 | 3.337 | 12.040 | -10.945 | 1.00 | 0.00 | A |
| ATOM | 997 | HA | TYR | 287 | 4.159 | 12.723 | -10.794 | 1.00 | 0.00 | A |
| ATOM | 998 | CB | TYR | 287 | 3.225 | 11.098 | -9.722 | 1.00 | 0.00 | A |
| ATOM | 999 | HB1 | TYR | 287 | 3.097 | 11.697 | -8.831 | 1.00 | 0.00 | A |
| ATOM | 1000 | HB2 | TYR | 287 | 4.138 | 10.530 | -9.632 | 1.00 | 0.00 | A |
| ATOM | 1001 | CG | TYR | 287 | 2.051 | 10.130 | -9.842 | 1.00 | 0.00 | A |
| ATOM | 1002 | CD1 | TYR | 287 | 1.957 | 9.200 | -10.916 | 1.00 | 0.00 | A |
| ATOM | 1003 | HD1 | TYR | 287 | 2.719 | 9.163 | -11.674 | 1.00 | 0.00 | A |
| ATOM | 1004 | CD2 | TYR | 287 | 1.049 | 10.155 | -8.856 | 1.00 | 0.00 | A |
| ATOM | 1005 | HD2 | TYR | 287 | 1.116 | 10.860 | -8.043 | 1.00 | 0.00 | A |
| ATOM | 1006 | CE1 | TYR | 287 | 0.850 | 8.306 | -10.980 | 1.00 | 0.00 | A |
| ATOM | 1007 | HE1 | TYR | 287 | 0.771 | 7.598 | -11.789 | 1.00 | 0.00 | A |
| ATOM | 1008 | CE2 | TYR | 287 | -0.051 | 9.267 | -8.927 | 1.00 | 0.00 | A |
| ATOM | 1009 | HE2 | TYR | 287 | -0.820 | 9.298 | -8.165 | 1.00 | 0.00 | A |
| ATOM | 1010 | CZ | TYR | 287 | -0.150 | 8.347 | -9.982 | 1.00 | 0.00 | A |
| ATOM | 1011 | OH | TYR | 287 | -1.226 | 7.483 | -10.040 | 1.00 | 0.00 | A |
| ATOM | 1012 | HH | TYR | 287 | -2.031 | 8.008 | -10.045 | 1.00 | 0.00 | A |
| ATOM | 1013 | C | TYR | 287 | 3.560 | 11.262 | -12.240 | 1.00 | 0.00 | A |
| ATOM | 1014 | O | TYR | 287 | 4.666 | 10.868 | -12.555 | 1.00 | 0.00 | A |
| ATOM | 1015 | N | LEU | 288 | 2.525 | 11.039 | -12.994 | 1.00 | 0.00 | A |
| ATOM | 1016 | HN | LEU | 288 | 1.643 | 11.365 | -12.723 | 1.00 | 0.00 | A |
| ATOM | 1017 | CA | LEU | 288 | 2.680 | 10.284 | -14.273 | 1.00 | 0.00 | A |
| ATOM | 1018 | HA | LEU | 288 | 2.933 | 9.284 | -14.072 | 1.00 | 0.00 | A |
| ATOM | 1019 | CB | LEU | 288 | 1.306 | 10.359 | -14.940 | 1.00 | 0.00 | A |
| ATOM | 1020 | HB1 | LEU | 288 | 1.358 | 9.918 | -15.923 | 1.00 | 0.00 | A |
| ATOM | 1021 | HB2 | LEU | 288 | 1.002 | 11.394 | -15.023 | 1.00 | 0.00 | A |
| ATOM | 1022 | CG | LEU | 288 | 0.292 | 9.593 | -14.093 | 1.00 | 0.00 | A |
| ATOM | 1023 | HG | LEU | 288 | 0.321 | 9.956 | -13.077 | 1.00 | 0.00 | A |
| ATOM | 1024 | CD1 | LEU | 288 | -1.112 | 9.784 | -14.666 | 1.00 | 0.00 | A |
| ATOM | 1025 | HD11 | LEU | 288 | -1.208 | 9.216 | -15.577 | 1.00 | 0.00 | A |
| ATOM | 1026 | HD12 | LEU | 288 | -1.278 | 10.830 | -14.873 | 1.00 | 0.00 | A |
| ATOM | 1027 | HD13 | LEU | 288 | -1.841 | 9.439 | -13.948 | 1.00 | 0.00 | A |
| ATOM | 1028 | CD2 | LEU | 288 | 0.645 | 8.107 | -14.119 | 1.00 | 0.00 | A |
| ATOM | 1029 | HD21 | LEU | 288 | -0.126 | 7.548 | -13.616 | 1.00 | 0.00 | A |
| ATOM | 1030 | HD22 | LEU | 288 | 1.588 | 7.953 | -13.617 | 1.00 | 0.00 | A |
| ATOM | 1031 | HD23 | LEU | 288 | 0.723 | 7.772 | -15.143 | 1.00 | 0.00 | A |
| ATOM | 1032 | C | LEU | 288 | 3.744 | 10.925 | -15.152 | 1.00 | 0.00 | A |
| ATOM | 1033 | O | LEU | 288 | 4.327 | 10.293 | -16.010 | 1.00 | 0.00 | A |
| ATOM | 1034 | N | ARG | 289 | 4.006 | 12.158 | -14.932 | 1.00 | 0.00 | A |
| ATOM | 1035 | HN | ARG | 289 | 3.538 | 12.620 | -14.222 | 1.00 | 0.00 | A |
| ATOM | 1036 | CA | ARG | 289 | 5.037 | 12.868 | -15.749 | 1.00 | 0.00 | A |
| ATOM | 1037 | HA | ARG | 289 | 4.731 | 12.912 | -16.780 | 1.00 | 0.00 | A |
| ATOM | 1038 | CB | ARG | 289 | 5.105 | 14.278 | -15.174 | 1.00 | 0.00 | A |
| ATOM | 1039 | HB1 | ARG | 289 | 5.860 | 14.845 | -15.697 | 1.00 | 0.00 | A |
| ATOM | 1040 | HB2 | ARG | 289 | 5.352 | 14.228 | -14.123 | 1.00 | 0.00 | A |

Figure 8-19

| ATOM | 1041 | CG   | ARG | 289 | 3.750  | 14.960 | -15.349 | 1.00 | 0.00 | A |
|------|------|------|-----|-----|--------|--------|---------|------|------|---|
| ATOM | 1042 | HG1  | ARG | 289 | 3.000  | 14.419 | -14.793 | 1.00 | 0.00 | A |
| ATOM | 1043 | HG2  | ARG | 289 | 3.485  | 14.971 | -16.397 | 1.00 | 0.00 | A |
| ATOM | 1044 | CD   | ARG | 289 | 3.832  | 16.392 | -14.829 | 1.00 | 0.00 | A |
| ATOM | 1045 | HD1  | ARG | 289 | 4.148  | 16.399 | -13.800 | 1.00 | 0.00 | A |
| ATOM | 1046 | HD2  | ARG | 289 | 2.876  | 16.885 | -14.936 | 1.00 | 0.00 | A |
| ATOM | 1047 | NE   | ARG | 289 | 4.859  | 17.051 | -15.681 | 1.00 | 0.00 | A |
| ATOM | 1048 | HE   | ARG | 289 | 5.221  | 16.583 | -16.462 | 1.00 | 0.00 | A |
| ATOM | 1049 | CZ   | ARG | 289 | 5.274  | 18.252 | -15.388 | 1.00 | 0.00 | A |
| ATOM | 1050 | NH1  | ARG | 289 | 4.726  | 19.289 | -15.958 | 1.00 | 0.00 | A |
| ATOM | 1051 | HH11 | ARG | 289 | 3.986  | 19.164 | -16.619 | 1.00 | 0.00 | A |
| ATOM | 1052 | HH12 | ARG | 289 | 5.045  | 20.210 | -15.732 | 1.00 | 0.00 | A |
| ATOM | 1053 | NH2  | ARG | 289 | 6.240  | 18.414 | -14.525 | 1.00 | 0.00 | A |
| ATOM | 1054 | HH21 | ARG | 289 | 6.660  | 17.619 | -14.088 | 1.00 | 0.00 | A |
| ATOM | 1055 | HH22 | ARG | 289 | 6.559  | 19.335 | -14.299 | 1.00 | 0.00 | A |
| ATOM | 1056 | C    | ARG | 289 | 6.395  | 12.169 | -15.623 | 1.00 | 0.00 | A |
| ATOM | 1057 | OT1  | ARG | 289 | 6.732  | 11.410 | -16.516 | 1.00 | 0.00 | A |
| ATOM | 1058 | OT2  | ARG | 289 | 7.073  | 12.407 | -14.636 | 1.00 | 0.00 | A |
| ATOM | 1059 | CA   | MET | 223 | 20.757 | 7.576  | -2.089  | 1.00 | 0.00 | B |
| ATOM | 1060 | HA   | MET | 223 | 20.343 | 8.263  | -1.370  | 1.00 | 0.00 | B |
| ATOM | 1061 | CB   | MET | 223 | 20.920 | 8.270  | -3.443  | 1.00 | 0.00 | B |
| ATOM | 1062 | HB1  | MET | 223 | 19.956 | 8.600  | -3.798  | 1.00 | 0.00 | B |
| ATOM | 1063 | HB2  | MET | 223 | 21.349 | 7.578  | -4.154  | 1.00 | 0.00 | B |
| ATOM | 1064 | CG   | MET | 223 | 21.843 | 9.478  | -3.285  | 1.00 | 0.00 | B |
| ATOM | 1065 | HG1  | MET | 223 | 22.807 | 9.149  | -2.927  | 1.00 | 0.00 | B |
| ATOM | 1066 | HG2  | MET | 223 | 21.414 | 10.169 | -2.577  | 1.00 | 0.00 | B |
| ATOM | 1067 | SD   | MET | 223 | 22.045 | 10.302 | -4.885  | 1.00 | 0.00 | B |
| ATOM | 1068 | CE   | MET | 223 | 23.085 | 9.041  | -5.660  | 1.00 | 0.00 | B |
| ATOM | 1069 | HE1  | MET | 223 | 22.652 | 8.064  | -5.490  | 1.00 | 0.00 | B |
| ATOM | 1070 | HE2  | MET | 223 | 24.072 | 9.074  | -5.230  | 1.00 | 0.00 | B |
| ATOM | 1071 | HE3  | MET | 223 | 23.150 | 9.233  | -6.723  | 1.00 | 0.00 | B |
| ATOM | 1072 | C    | MET | 223 | 19.863 | 6.340  | -2.224  | 1.00 | 0.00 | B |
| ATOM | 1073 | O    | MET | 223 | 20.328 | 5.218  | -2.171  | 1.00 | 0.00 | B |
| ATOM | 1074 | N    | MET | 223 | 22.142 | 7.172  | -1.689  | 1.00 | 0.00 | B |
| ATOM | 1075 | HT1  | MET | 223 | 22.577 | 7.934  | -1.131  | 1.00 | 0.00 | B |
| ATOM | 1076 | HT2  | MET | 223 | 22.714 | 6.994  | -2.540  | 1.00 | 0.00 | B |
| ATOM | 1077 | HT3  | MET | 223 | 22.097 | 6.306  | -1.115  | 1.00 | 0.00 | B |
| ATOM | 1078 | N    | ALA | 224 | 18.583 | 6.535  | -2.394  | 1.00 | 0.00 | B |
| ATOM | 1079 | HN   | ALA | 224 | 18.226 | 7.447  | -2.432  | 1.00 | 0.00 | B |
| ATOM | 1080 | CA   | ALA | 224 | 17.663 | 5.369  | -2.532  | 1.00 | 0.00 | B |
| ATOM | 1081 | HA   | ALA | 224 | 17.972 | 4.740  | -3.348  | 1.00 | 0.00 | B |
| ATOM | 1082 | CB   | ALA | 224 | 17.789 | 4.610  | -1.210  | 1.00 | 0.00 | B |
| ATOM | 1083 | HB1  | ALA | 224 | 17.936 | 3.560  | -1.412  | 1.00 | 0.00 | B |
| ATOM | 1084 | HB2  | ALA | 224 | 16.888 | 4.743  | -0.629  | 1.00 | 0.00 | B |
| ATOM | 1085 | HB3  | ALA | 224 | 18.635 | 4.991  | -0.657  | 1.00 | 0.00 | B |
| ATOM | 1086 | C    | ALA | 224 | 16.223 | 5.849  | -2.742  | 1.00 | 0.00 | B |
| ATOM | 1087 | O    | ALA | 224 | 15.878 | 6.973  | -2.432  | 1.00 | 0.00 | B |
| ATOM | 1088 | N    | ALA | 225 | 15.382 | 5.002  | -3.265  | 1.00 | 0.00 | B |
| ATOM | 1089 | HN   | ALA | 225 | 15.684 | 4.102  | -3.509  | 1.00 | 0.00 | B |
| ATOM | 1090 | CA   | ALA | 225 | 13.964 | 5.398  | -3.500  | 1.00 | 0.00 | B |
| ATOM | 1091 | HA   | ALA | 225 | 13.510 | 5.737  | -2.584  | 1.00 | 0.00 | B |
| ATOM | 1092 | CB   | ALA | 225 | 14.032 | 6.542  | -4.508  | 1.00 | 0.00 | B |
| ATOM | 1093 | HB1  | ALA | 225 | 13.294 | 7.289  | -4.256  | 1.00 | 0.00 | B |
| ATOM | 1094 | HB2  | ALA | 225 | 13.835 | 6.160  | -5.499  | 1.00 | 0.00 | B |
| ATOM | 1095 | HB3  | ALA | 225 | 15.016 | 6.986  | -4.482  | 1.00 | 0.00 | B |
| ATOM | 1096 | C    | ALA | 225 | 13.190 | 4.217  | -4.080  | 1.00 | 0.00 | B |
| ATOM | 1097 | O    | ALA | 225 | 12.640 | 4.290  | -5.160  | 1.00 | 0.00 | B |
| ATOM | 1098 | N    | GLY | 226 | 13.145 | 3.126  | -3.368  | 1.00 | 0.00 | B |

Figure 8-20

| | | | | | | | | | |
|---|---|---|---|---|---|---|---|---|---|
| ATOM | 1099 | HN | GLY | 226 | 13.593 | 3.092 | -2.497 | 1.00 | 0.00 | B |
| ATOM | 1100 | CA | GLY | 226 | 12.409 | 1.933 | -3.871 | 1.00 | 0.00 | B |
| ATOM | 1101 | HA1 | GLY | 226 | 12.646 | 1.081 | -3.254 | 1.00 | 0.00 | B |
| ATOM | 1102 | HA2 | GLY | 226 | 12.707 | 1.732 | -4.891 | 1.00 | 0.00 | B |
| ATOM | 1103 | C | GLY | 226 | 10.902 | 2.188 | -3.822 | 1.00 | 0.00 | B |
| ATOM | 1104 | O | GLY | 226 | 10.182 | 1.850 | -4.736 | 1.00 | 0.00 | B |
| ATOM | 1105 | N | VAL | 227 | 10.419 | 2.773 | -2.758 | 1.00 | 0.00 | B |
| ATOM | 1106 | HN | VAL | 227 | 11.018 | 3.034 | -2.029 | 1.00 | 0.00 | B |
| ATOM | 1107 | CA | VAL | 227 | 8.951 | 3.048 | -2.653 | 1.00 | 0.00 | B |
| ATOM | 1108 | HA | VAL | 227 | 8.385 | 2.167 | -2.904 | 1.00 | 0.00 | B |
| ATOM | 1109 | CB | VAL | 227 | 8.721 | 3.414 | -1.189 | 1.00 | 0.00 | B |
| ATOM | 1110 | HB | VAL | 227 | 9.323 | 4.275 | -0.935 | 1.00 | 0.00 | B |
| ATOM | 1111 | CG1 | VAL | 227 | 7.243 | 3.742 | -0.971 | 1.00 | 0.00 | B |
| ATOM | 1112 | HG11 | VAL | 227 | 7.155 | 4.542 | -0.251 | 1.00 | 0.00 | B |
| ATOM | 1113 | HG12 | VAL | 227 | 6.730 | 2.867 | -0.601 | 1.00 | 0.00 | B |
| ATOM | 1114 | HG13 | VAL | 227 | 6.801 | 4.051 | -1.907 | 1.00 | 0.00 | B |
| ATOM | 1115 | CG2 | VAL | 227 | 9.117 | 2.232 | -0.301 | 1.00 | 0.00 | B |
| ATOM | 1116 | HG21 | VAL | 227 | 8.360 | 1.465 | -0.363 | 1.00 | 0.00 | B |
| ATOM | 1117 | HG22 | VAL | 227 | 9.207 | 2.566 | 0.722 | 1.00 | 0.00 | B |
| ATOM | 1118 | HG23 | VAL | 227 | 10.064 | 1.832 | -0.634 | 1.00 | 0.00 | B |
| ATOM | 1119 | C | VAL | 227 | 8.558 | 4.213 | -3.566 | 1.00 | 0.00 | B |
| ATOM | 1120 | O | VAL | 227 | 8.404 | 5.335 | -3.125 | 1.00 | 0.00 | B |
| ATOM | 1121 | N | LYS | 228 | 8.390 | 3.955 | -4.833 | 1.00 | 0.00 | B |
| ATOM | 1122 | HN | LYS | 228 | 8.499 | 3.044 | -5.165 | 1.00 | 0.00 | B |
| ATOM | 1123 | CA | LYS | 228 | 8.008 | 5.047 | -5.769 | 1.00 | 0.00 | B |
| ATOM | 1124 | HA | LYS | 228 | 8.603 | 5.923 | -5.590 | 1.00 | 0.00 | B |
| ATOM | 1125 | CB | LYS | 228 | 8.301 | 4.485 | -7.161 | 1.00 | 0.00 | B |
| ATOM | 1126 | HB1 | LYS | 228 | 8.162 | 5.259 | -7.897 | 1.00 | 0.00 | B |
| ATOM | 1127 | HB2 | LYS | 228 | 7.632 | 3.662 | -7.369 | 1.00 | 0.00 | B |
| ATOM | 1128 | CG | LYS | 228 | 9.753 | 3.997 | -7.218 | 1.00 | 0.00 | B |
| ATOM | 1129 | HG1 | LYS | 228 | 9.908 | 3.239 | -6.466 | 1.00 | 0.00 | B |
| ATOM | 1130 | HG2 | LYS | 228 | 10.419 | 4.829 | -7.035 | 1.00 | 0.00 | B |
| ATOM | 1131 | CD | LYS | 228 | 10.043 | 3.406 | -8.601 | 1.00 | 0.00 | B |
| ATOM | 1132 | HD1 | LYS | 228 | 9.900 | 4.165 | -9.356 | 1.00 | 0.00 | B |
| ATOM | 1133 | HD2 | LYS | 228 | 9.370 | 2.580 | -8.787 | 1.00 | 0.00 | B |
| ATOM | 1134 | CE | LYS | 228 | 11.491 | 2.907 | -8.651 | 1.00 | 0.00 | B |
| ATOM | 1135 | HE1 | LYS | 228 | 12.174 | 3.714 | -8.446 | 1.00 | 0.00 | B |
| ATOM | 1136 | HE2 | LYS | 228 | 11.703 | 2.466 | -9.618 | 1.00 | 0.00 | B |
| ATOM | 1137 | NZ | LYS | 228 | 11.580 | 1.878 | -7.578 | 1.00 | 0.00 | B |
| ATOM | 1138 | HZ1 | LYS | 228 | 11.724 | 2.344 | -6.661 | 1.00 | 0.00 | B |
| ATOM | 1139 | HZ2 | LYS | 228 | 12.380 | 1.241 | -7.774 | 1.00 | 0.00 | B |
| ATOM | 1140 | HZ3 | LYS | 228 | 10.698 | 1.329 | -7.550 | 1.00 | 0.00 | B |
| ATOM | 1141 | C | LYS | 228 | 6.514 | 5.366 | -5.595 | 1.00 | 0.00 | B |
| ATOM | 1142 | O | LYS | 228 | 6.135 | 6.487 | -5.323 | 1.00 | 0.00 | B |
| ATOM | 1143 | N | GLN | 229 | 5.672 | 4.384 | -5.750 | 1.00 | 0.00 | B |
| ATOM | 1144 | HN | GLN | 229 | 6.003 | 3.499 | -5.970 | 1.00 | 0.00 | B |
| ATOM | 1145 | CA | GLN | 229 | 4.199 | 4.618 | -5.591 | 1.00 | 0.00 | B |
| ATOM | 1146 | HA | GLN | 229 | 4.017 | 5.216 | -4.712 | 1.00 | 0.00 | B |
| ATOM | 1147 | CB | GLN | 229 | 3.736 | 5.393 | -6.846 | 1.00 | 0.00 | B |
| ATOM | 1148 | HB1 | GLN | 229 | 4.329 | 6.291 | -6.945 | 1.00 | 0.00 | B |
| ATOM | 1149 | HB2 | GLN | 229 | 2.697 | 5.666 | -6.731 | 1.00 | 0.00 | B |
| ATOM | 1150 | CG | GLN | 229 | 3.898 | 4.539 | -8.120 | 1.00 | 0.00 | B |
| ATOM | 1151 | HG1 | GLN | 229 | 3.390 | 5.024 | -8.946 | 1.00 | 0.00 | B |
| ATOM | 1152 | HG2 | GLN | 229 | 3.464 | 3.564 | -7.957 | 1.00 | 0.00 | B |
| ATOM | 1153 | CD | GLN | 229 | 5.373 | 4.385 | -8.462 | 1.00 | 0.00 | B |
| ATOM | 1154 | OE1 | GLN | 229 | 6.120 | 5.333 | -8.383 | 1.00 | 0.00 | B |
| ATOM | 1155 | NE2 | GLN | 229 | 5.825 | 3.226 | -8.864 | 1.00 | 0.00 | B |
| ATOM | 1156 | HE21 | GLN | 229 | 5.215 | 2.466 | -8.947 | 1.00 | 0.00 | B |

Figure 8-21

| ATOM | 1157 | HE22 | GLN | 229 | 6.773 | 3.120 | -9.085 | 1.00 | 0.00 | B |
|---|---|---|---|---|---|---|---|---|---|---|
| ATOM | 1158 | C | GLN | 229 | 3.445 | 3.277 | -5.476 | 1.00 | 0.00 | B |
| ATOM | 1159 | O | GLN | 229 | 2.433 | 3.070 | -6.118 | 1.00 | 0.00 | B |
| ATOM | 1160 | N | LEU | 230 | 3.931 | 2.359 | -4.659 | 1.00 | 0.00 | B |
| ATOM | 1161 | HN | LEU | 230 | 4.743 | 2.537 | -4.151 | 1.00 | 0.00 | B |
| ATOM | 1162 | CA | LEU | 230 | 3.229 | 1.040 | -4.515 | 1.00 | 0.00 | B |
| ATOM | 1163 | HA | LEU | 230 | 2.324 | 1.044 | -5.086 | 1.00 | 0.00 | B |
| ATOM | 1164 | CB | LEU | 230 | 4.189 | -0.034 | -5.064 | 1.00 | 0.00 | B |
| ATOM | 1165 | HB1 | LEU | 230 | 3.760 | -1.012 | -4.899 | 1.00 | 0.00 | B |
| ATOM | 1166 | HB2 | LEU | 230 | 5.133 | 0.032 | -4.541 | 1.00 | 0.00 | B |
| ATOM | 1167 | CG | LEU | 230 | 4.430 | 0.165 | -6.565 | 1.00 | 0.00 | B |
| ATOM | 1168 | HG | LEU | 230 | 3.484 | 0.327 | -7.062 | 1.00 | 0.00 | B |
| ATOM | 1169 | CD1 | LEU | 230 | 5.330 | 1.370 | -6.785 | 1.00 | 0.00 | B |
| ATOM | 1170 | HD11 | LEU | 230 | 6.081 | 1.128 | -7.523 | 1.00 | 0.00 | B |
| ATOM | 1171 | HD12 | LEU | 230 | 5.812 | 1.629 | -5.855 | 1.00 | 0.00 | B |
| ATOM | 1172 | HD13 | LEU | 230 | 4.742 | 2.201 | -7.132 | 1.00 | 0.00 | B |
| ATOM | 1173 | CD2 | LEU | 230 | 5.102 | -1.082 | -7.142 | 1.00 | 0.00 | B |
| ATOM | 1174 | HD21 | LEU | 230 | 6.147 | -1.085 | -6.872 | 1.00 | 0.00 | B |
| ATOM | 1175 | HD22 | LEU | 230 | 5.009 | -1.076 | -8.218 | 1.00 | 0.00 | B |
| ATOM | 1176 | HD23 | LEU | 230 | 4.624 | -1.965 | -6.744 | 1.00 | 0.00 | B |
| ATOM | 1177 | C | LEU | 230 | 2.922 | 0.739 | -3.038 | 1.00 | 0.00 | B |
| ATOM | 1178 | O | LEU | 230 | 2.986 | -0.396 | -2.608 | 1.00 | 0.00 | B |
| ATOM | 1179 | N | ALA | 231 | 2.586 | 1.731 | -2.257 | 1.00 | 0.00 | B |
| ATOM | 1180 | HN | ALA | 231 | 2.546 | 2.639 | -2.607 | 1.00 | 0.00 | B |
| ATOM | 1181 | CA | ALA | 231 | 2.281 | 1.450 | -0.810 | 1.00 | 0.00 | B |
| ATOM | 1182 | HA | ALA | 231 | 1.694 | 0.565 | -0.729 | 1.00 | 0.00 | B |
| ATOM | 1183 | CB | ALA | 231 | 3.645 | 1.231 | -0.157 | 1.00 | 0.00 | B |
| ATOM | 1184 | HB1 | ALA | 231 | 3.656 | 0.274 | 0.342 | 1.00 | 0.00 | B |
| ATOM | 1185 | HB2 | ALA | 231 | 3.829 | 2.016 | 0.562 | 1.00 | 0.00 | B |
| ATOM | 1186 | HB3 | ALA | 231 | 4.415 | 1.251 | -0.915 | 1.00 | 0.00 | B |
| ATOM | 1187 | C | ALA | 231 | 1.551 | 2.622 | -0.138 | 1.00 | 0.00 | B |
| ATOM | 1188 | O | ALA | 231 | 1.458 | 2.685 | 1.071 | 1.00 | 0.00 | B |
| ATOM | 1189 | N | ASP | 232 | 1.006 | 3.515 | -0.909 | 1.00 | 0.00 | B |
| ATOM | 1190 | HN | ASP | 232 | 1.052 | 3.405 | -1.871 | 1.00 | 0.00 | B |
| ATOM | 1191 | CA | ASP | 232 | 0.273 | 4.694 | -0.322 | 1.00 | 0.00 | B |
| ATOM | 1192 | HA | ASP | 232 | -0.296 | 4.395 | 0.511 | 1.00 | 0.00 | B |
| ATOM | 1193 | CB | ASP | 232 | 1.350 | 5.714 | 0.095 | 1.00 | 0.00 | B |
| ATOM | 1194 | HB1 | ASP | 232 | 0.870 | 6.610 | 0.460 | 1.00 | 0.00 | B |
| ATOM | 1195 | HB2 | ASP | 232 | 1.958 | 5.960 | -0.763 | 1.00 | 0.00 | B |
| ATOM | 1196 | CG | ASP | 232 | 2.241 | 5.137 | 1.194 | 1.00 | 0.00 | B |
| ATOM | 1197 | OD1 | ASP | 232 | 3.182 | 4.435 | 0.859 | 1.00 | 0.00 | B |
| ATOM | 1198 | OD2 | ASP | 232 | 1.967 | 5.403 | 2.353 | 1.00 | 0.00 | B |
| ATOM | 1199 | C | ASP | 232 | -0.628 | 5.309 | -1.365 | 1.00 | 0.00 | B |
| ATOM | 1200 | O | ASP | 232 | -1.743 | 5.700 | -1.098 | 1.00 | 0.00 | B |
| ATOM | 1201 | N | ASP | 233 | -0.144 | 5.405 | -2.539 | 1.00 | 0.00 | B |
| ATOM | 1202 | HN | ASP | 233 | 0.753 | 5.084 | -2.701 | 1.00 | 0.00 | B |
| ATOM | 1203 | CA | ASP | 233 | -0.948 | 5.997 | -3.645 | 1.00 | 0.00 | B |
| ATOM | 1204 | HA | ASP | 233 | -1.341 | 6.956 | -3.353 | 1.00 | 0.00 | B |
| ATOM | 1205 | CB | ASP | 233 | 0.036 | 6.166 | -4.806 | 1.00 | 0.00 | B |
| ATOM | 1206 | HB1 | ASP | 233 | -0.479 | 6.588 | -5.655 | 1.00 | 0.00 | B |
| ATOM | 1207 | HB2 | ASP | 233 | 0.445 | 5.202 | -5.075 | 1.00 | 0.00 | B |
| ATOM | 1208 | CG | ASP | 233 | 1.170 | 7.103 | -4.383 | 1.00 | 0.00 | B |
| ATOM | 1209 | OD1 | ASP | 233 | 1.885 | 6.756 | -3.457 | 1.00 | 0.00 | B |
| ATOM | 1210 | OD2 | ASP | 233 | 1.304 | 8.152 | -4.993 | 1.00 | 0.00 | B |
| ATOM | 1211 | C | ASP | 233 | -2.084 | 5.050 | -4.032 | 1.00 | 0.00 | B |
| ATOM | 1212 | O | ASP | 233 | -3.074 | 5.453 | -4.601 | 1.00 | 0.00 | B |
| ATOM | 1213 | N | ARG | 234 | -1.952 | 3.793 | -3.724 | 1.00 | 0.00 | B |
| ATOM | 1214 | HN | ARG | 234 | -1.151 | 3.486 | -3.260 | 1.00 | 0.00 | B |

Figure 8-22

| ATOM | 1215 | CA | ARG | 234 | -3.035 | 2.829 | -4.083 | 1.00 | 0.00 | B |
|---|---|---|---|---|---|---|---|---|---|---|
| ATOM | 1216 | HA | ARG | 234 | -3.332 | 2.984 | -5.108 | 1.00 | 0.00 | B |
| ATOM | 1217 | CB | ARG | 234 | -2.419 | 1.430 | -3.936 | 1.00 | 0.00 | B |
| ATOM | 1218 | HB1 | ARG | 234 | -1.562 | 1.352 | -4.582 | 1.00 | 0.00 | B |
| ATOM | 1219 | HB2 | ARG | 234 | -3.150 | 0.690 | -4.224 | 1.00 | 0.00 | B |
| ATOM | 1220 | CG | ARG | 234 | -1.986 | 1.173 | -2.491 | 1.00 | 0.00 | B |
| ATOM | 1221 | HG1 | ARG | 234 | -2.855 | 1.163 | -1.851 | 1.00 | 0.00 | B |
| ATOM | 1222 | HG2 | ARG | 234 | -1.308 | 1.951 | -2.168 | 1.00 | 0.00 | B |
| ATOM | 1223 | CD | ARG | 234 | -1.289 | -0.189 | -2.414 | 1.00 | 0.00 | B |
| ATOM | 1224 | HD1 | ARG | 234 | -0.420 | -0.201 | -3.051 | 1.00 | 0.00 | B |
| ATOM | 1225 | HD2 | ARG | 234 | -1.976 | -0.976 | -2.697 | 1.00 | 0.00 | B |
| ATOM | 1226 | NE | ARG | 234 | -0.883 | -0.342 | -0.992 | 1.00 | 0.00 | B |
| ATOM | 1227 | HE | ARG | 234 | -1.061 | 0.376 | -0.352 | 1.00 | 0.00 | B |
| ATOM | 1228 | CZ | ARG | 234 | -0.285 | -1.437 | -0.599 | 1.00 | 0.00 | B |
| ATOM | 1229 | NH1 | ARG | 234 | 0.483 | -1.419 | 0.456 | 1.00 | 0.00 | B |
| ATOM | 1230 | HH11 | ARG | 234 | 0.615 | -0.567 | 0.963 | 1.00 | 0.00 | B |
| ATOM | 1231 | HH12 | ARG | 234 | 0.939 | -2.257 | 0.757 | 1.00 | 0.00 | B |
| ATOM | 1232 | NH2 | ARG | 234 | -0.456 | -2.550 | -1.262 | 1.00 | 0.00 | B |
| ATOM | 1233 | HH21 | ARG | 234 | -1.044 | -2.565 | -2.071 | 1.00 | 0.00 | B |
| ATOM | 1234 | HH22 | ARG | 234 | 0.001 | -3.388 | -0.961 | 1.00 | 0.00 | B |
| ATOM | 1235 | C | ARG | 234 | -4.247 | 3.013 | -3.161 | 1.00 | 0.00 | B |
| ATOM | 1236 | O | ARG | 234 | -5.352 | 3.130 | -3.616 | 1.00 | 0.00 | B |
| ATOM | 1237 | N | THR | 235 | -4.048 | 3.053 | -1.875 | 1.00 | 0.00 | B |
| ATOM | 1238 | HN | THR | 235 | -3.142 | 2.991 | -1.516 | 1.00 | 0.00 | B |
| ATOM | 1239 | CA | THR | 235 | -5.206 | 3.231 | -0.944 | 1.00 | 0.00 | B |
| ATOM | 1240 | HA | THR | 235 | -6.047 | 2.644 | -1.263 | 1.00 | 0.00 | B |
| ATOM | 1241 | CB | THR | 235 | -4.688 | 2.747 | 0.414 | 1.00 | 0.00 | B |
| ATOM | 1242 | HB | THR | 235 | -3.795 | 3.306 | 0.680 | 1.00 | 0.00 | B |
| ATOM | 1243 | OG1 | THR | 235 | -4.370 | 1.365 | 0.331 | 1.00 | 0.00 | B |
| ATOM | 1244 | HG1 | THR | 235 | -3.445 | 1.289 | 0.091 | 1.00 | 0.00 | B |
| ATOM | 1245 | CG2 | THR | 235 | -5.756 | 2.967 | 1.488 | 1.00 | 0.00 | B |
| ATOM | 1246 | HG21 | THR | 235 | -5.805 | 2.098 | 2.129 | 1.00 | 0.00 | B |
| ATOM | 1247 | HG22 | THR | 235 | -6.715 | 3.121 | 1.017 | 1.00 | 0.00 | B |
| ATOM | 1248 | HG23 | THR | 235 | -5.500 | 3.835 | 2.077 | 1.00 | 0.00 | B |
| ATOM | 1249 | C | THR | 235 | -5.587 | 4.693 | -0.888 | 1.00 | 0.00 | B |
| ATOM | 1250 | O | THR | 235 | -6.702 | 5.052 | -0.561 | 1.00 | 0.00 | B |
| ATOM | 1251 | N | LEU | 236 | -4.673 | 5.534 | -1.203 | 1.00 | 0.00 | B |
| ATOM | 1252 | HN | LEU | 236 | -3.783 | 5.210 | -1.463 | 1.00 | 0.00 | B |
| ATOM | 1253 | CA | LEU | 236 | -4.950 | 6.979 | -1.179 | 1.00 | 0.00 | B |
| ATOM | 1254 | HA | LEU | 236 | -5.337 | 7.279 | -0.254 | 1.00 | 0.00 | B |
| ATOM | 1255 | CB | LEU | 236 | -3.612 | 7.626 | -1.406 | 1.00 | 0.00 | B |
| ATOM | 1256 | HB1 | LEU | 236 | -3.173 | 7.249 | -2.317 | 1.00 | 0.00 | B |
| ATOM | 1257 | HB2 | LEU | 236 | -2.958 | 7.416 | -0.570 | 1.00 | 0.00 | B |
| ATOM | 1258 | CG | LEU | 236 | -3.823 | 9.108 | -1.526 | 1.00 | 0.00 | B |
| ATOM | 1259 | HG | LEU | 236 | -4.620 | 9.278 | -2.251 | 1.00 | 0.00 | B |
| ATOM | 1260 | CD1 | LEU | 236 | -4.242 | 9.683 | -0.168 | 1.00 | 0.00 | B |
| ATOM | 1261 | HD11 | LEU | 236 | -4.496 | 10.727 | -0.282 | 1.00 | 0.00 | B |
| ATOM | 1262 | HD12 | LEU | 236 | -3.427 | 9.585 | 0.532 | 1.00 | 0.00 | B |
| ATOM | 1263 | HD13 | LEU | 236 | -5.101 | 9.142 | 0.202 | 1.00 | 0.00 | B |
| ATOM | 1264 | CD2 | LEU | 236 | -2.533 | 9.759 | -1.999 | 1.00 | 0.00 | B |
| ATOM | 1265 | HD21 | LEU | 236 | -1.723 | 9.464 | -1.349 | 1.00 | 0.00 | B |
| ATOM | 1266 | HD22 | LEU | 236 | -2.644 | 10.823 | -1.973 | 1.00 | 0.00 | B |
| ATOM | 1267 | HD23 | LEU | 236 | -2.318 | 9.442 | -3.009 | 1.00 | 0.00 | B |
| ATOM | 1268 | C | LEU | 236 | -5.906 | 7.372 | -2.277 | 1.00 | 0.00 | B |
| ATOM | 1269 | O | LEU | 236 | -6.867 | 8.081 | -2.050 | 1.00 | 0.00 | B |
| ATOM | 1270 | N | LEU | 237 | -5.669 | 6.932 | -3.458 | 1.00 | 0.00 | B |
| ATOM | 1271 | HN | LEU | 237 | -4.892 | 6.359 | -3.629 | 1.00 | 0.00 | B |
| ATOM | 1272 | CA | LEU | 237 | -6.582 | 7.302 | -4.559 | 1.00 | 0.00 | B |

Figure 8-23

| | | | | | | | | | |
|---|---|---|---|---|---|---|---|---|---|
| ATOM | 1273 | HA | LEU | 237 | -6.919 | 8.303 | -4.411 | 1.00 | 0.00 | B |
| ATOM | 1274 | CB | LEU | 237 | -5.715 | 7.241 | -5.797 | 1.00 | 0.00 | B |
| ATOM | 1275 | HB1 | LEU | 237 | -6.231 | 7.681 | -6.628 | 1.00 | 0.00 | B |
| ATOM | 1276 | HB2 | LEU | 237 | -5.476 | 6.211 | -6.022 | 1.00 | 0.00 | B |
| ATOM | 1277 | CG | LEU | 237 | -4.409 | 8.036 | -5.520 | 1.00 | 0.00 | B |
| ATOM | 1278 | HG | LEU | 237 | -3.768 | 7.440 | -4.889 | 1.00 | 0.00 | B |
| ATOM | 1279 | CD1 | LEU | 237 | -3.699 | 8.292 | -6.816 | 1.00 | 0.00 | B |
| ATOM | 1280 | HD11 | LEU | 237 | -4.343 | 8.859 | -7.466 | 1.00 | 0.00 | B |
| ATOM | 1281 | HD12 | LEU | 237 | -3.455 | 7.352 | -7.275 | 1.00 | 0.00 | B |
| ATOM | 1282 | HD13 | LEU | 237 | -2.798 | 8.848 | -6.623 | 1.00 | 0.00 | B |
| ATOM | 1283 | CD2 | LEU | 237 | -4.712 | 9.385 | -4.802 | 1.00 | 0.00 | B |
| ATOM | 1284 | HD21 | LEU | 237 | -3.790 | 9.823 | -4.454 | 1.00 | 0.00 | B |
| ATOM | 1285 | HD22 | LEU | 237 | -5.357 | 9.212 | -3.954 | 1.00 | 0.00 | B |
| ATOM | 1286 | HD23 | LEU | 237 | -5.195 | 10.059 | -5.483 | 1.00 | 0.00 | B |
| ATOM | 1287 | C | LEU | 237 | -7.784 | 6.383 | -4.595 | 1.00 | 0.00 | B |
| ATOM | 1288 | O | LEU | 237 | -8.482 | 6.261 | -5.573 | 1.00 | 0.00 | B |
| ATOM | 1289 | N | MET | 238 | -7.984 | 5.708 | -3.547 | 1.00 | 0.00 | B |
| ATOM | 1290 | HN | MET | 238 | -7.460 | 5.892 | -2.781 | 1.00 | 0.00 | B |
| ATOM | 1291 | CA | MET | 238 | -9.116 | 4.793 | -3.447 | 1.00 | 0.00 | B |
| ATOM | 1292 | HA | MET | 238 | -9.492 | 4.580 | -4.427 | 1.00 | 0.00 | B |
| ATOM | 1293 | CB | MET | 238 | -8.625 | 3.526 | -2.756 | 1.00 | 0.00 | B |
| ATOM | 1294 | HB1 | MET | 238 | -9.455 | 3.030 | -2.277 | 1.00 | 0.00 | B |
| ATOM | 1295 | HB2 | MET | 238 | -7.879 | 3.783 | -2.016 | 1.00 | 0.00 | B |
| ATOM | 1296 | CG | MET | 238 | -8.013 | 2.595 | -3.802 | 1.00 | 0.00 | B |
| ATOM | 1297 | HG1 | MET | 238 | -7.270 | 3.126 | -4.366 | 1.00 | 0.00 | B |
| ATOM | 1298 | HG2 | MET | 238 | -8.789 | 2.254 | -4.472 | 1.00 | 0.00 | B |
| ATOM | 1299 | SD | MET | 238 | -7.262 | 1.166 | -2.982 | 1.00 | 0.00 | B |
| ATOM | 1300 | CE | MET | 238 | -6.963 | 0.181 | -4.471 | 1.00 | 0.00 | B |
| ATOM | 1301 | HE1 | MET | 238 | -6.403 | 0.770 | -5.185 | 1.00 | 0.00 | B |
| ATOM | 1302 | HE2 | MET | 238 | -7.904 | -0.108 | -4.907 | 1.00 | 0.00 | B |
| ATOM | 1303 | HE3 | MET | 238 | -6.402 | -0.706 | -4.208 | 1.00 | 0.00 | B |
| ATOM | 1304 | C | MET | 238 | -10.129 | 5.534 | -2.645 | 1.00 | 0.00 | B |
| ATOM | 1305 | O | MET | 238 | -11.297 | 5.521 | -2.905 | 1.00 | 0.00 | B |
| ATOM | 1306 | N | ALA | 239 | -9.647 | 6.106 | -1.574 | 1.00 | 0.00 | B |
| ATOM | 1307 | HN | ALA | 239 | -8.699 | 6.003 | -1.367 | 1.00 | 0.00 | B |
| ATOM | 1308 | CA | ALA | 239 | -10.488 | 6.888 | -0.667 | 1.00 | 0.00 | B |
| ATOM | 1309 | HA | ALA | 239 | -11.509 | 6.557 | -0.698 | 1.00 | 0.00 | B |
| ATOM | 1310 | CB | ALA | 239 | -9.880 | 6.660 | 0.718 | 1.00 | 0.00 | B |
| ATOM | 1311 | HB1 | ALA | 239 | -9.179 | 7.456 | 0.938 | 1.00 | 0.00 | B |
| ATOM | 1312 | HB2 | ALA | 239 | -9.359 | 5.712 | 0.731 | 1.00 | 0.00 | B |
| ATOM | 1313 | HB3 | ALA | 239 | -10.661 | 6.652 | 1.459 | 1.00 | 0.00 | B |
| ATOM | 1314 | C | ALA | 239 | -10.360 | 8.361 | -1.074 | 1.00 | 0.00 | B |
| ATOM | 1315 | O | ALA | 239 | -10.608 | 9.256 | -0.291 | 1.00 | 0.00 | B |
| ATOM | 1316 | N | GLY | 240 | -9.967 | 8.620 | -2.311 | 1.00 | 0.00 | B |
| ATOM | 1317 | HN | GLY | 240 | -9.811 | 7.890 | -2.956 | 1.00 | 0.00 | B |
| ATOM | 1318 | CA | GLY | 240 | -9.817 | 10.000 | -2.767 | 1.00 | 0.00 | B |
| ATOM | 1319 | HA1 | GLY | 240 | -8.801 | 10.334 | -2.586 | 1.00 | 0.00 | B |
| ATOM | 1320 | HA2 | GLY | 240 | -10.510 | 10.638 | -2.254 | 1.00 | 0.00 | B |
| ATOM | 1321 | C | GLY | 240 | -10.080 | 10.026 | -4.239 | 1.00 | 0.00 | B |
| ATOM | 1322 | O | GLY | 240 | -10.754 | 10.893 | -4.748 | 1.00 | 0.00 | B |
| ATOM | 1323 | N | VAL | 241 | -9.510 | 9.116 | -4.960 | 1.00 | 0.00 | B |
| ATOM | 1324 | HN | VAL | 241 | -8.957 | 8.417 | -4.550 | 1.00 | 0.00 | B |
| ATOM | 1325 | CA | VAL | 241 | -9.755 | 9.124 | -6.383 | 1.00 | 0.00 | B |
| ATOM | 1326 | HA | VAL | 241 | -10.058 | 10.087 | -6.638 | 1.00 | 0.00 | B |
| ATOM | 1327 | CB | VAL | 241 | -8.397 | 8.827 | -7.042 | 1.00 | 0.00 | B |
| ATOM | 1328 | HB | VAL | 241 | -8.097 | 7.829 | -6.827 | 1.00 | 0.00 | B |
| ATOM | 1329 | CG1 | VAL | 241 | -8.491 | 9.018 | -8.545 | 1.00 | 0.00 | B |
| ATOM | 1330 | HG11 | VAL | 241 | -7.493 | 9.117 | -8.953 | 1.00 | 0.00 | B |

Figure 8-24

| | | | | | | | | | |
|---|---|---|---|---|---|---|---|---|---|
| ATOM | 1331 | HG12 | VAL | 241 | -9.056 | 9.915 | -8.756 | 1.00 | 0.00 | B |
| ATOM | 1332 | HG13 | VAL | 241 | -8.980 | 8.171 | -8.985 | 1.00 | 0.00 | B |
| ATOM | 1333 | CG2 | VAL | 241 | -7.355 | 9.813 | -6.500 | 1.00 | 0.00 | B |
| ATOM | 1334 | HG21 | VAL | 241 | -6.380 | 9.551 | -6.876 | 1.00 | 0.00 | B |
| ATOM | 1335 | HG22 | VAL | 241 | -7.350 | 9.781 | -5.424 | 1.00 | 0.00 | B |
| ATOM | 1336 | HG23 | VAL | 241 | -7.606 | 10.813 | -6.824 | 1.00 | 0.00 | B |
| ATOM | 1337 | C | VAL | 241 | -10.891 | 8.110 | -6.742 | 1.00 | 0.00 | B |
| ATOM | 1338 | O | VAL | 241 | -11.599 | 8.269 | -7.718 | 1.00 | 0.00 | B |
| ATOM | 1339 | N | SER | 242 | -11.031 | 7.046 | -5.978 | 1.00 | 0.00 | B |
| ATOM | 1340 | HN | SER | 242 | -10.447 | 6.922 | -5.205 | 1.00 | 0.00 | B |
| ATOM | 1341 | CA | SER | 242 | -12.111 | 6.033 | -6.272 | 1.00 | 0.00 | B |
| ATOM | 1342 | HA | SER | 242 | -12.368 | 6.062 | -7.319 | 1.00 | 0.00 | B |
| ATOM | 1343 | CB | SER | 242 | -11.493 | 4.683 | -5.936 | 1.00 | 0.00 | B |
| ATOM | 1344 | HB1 | SER | 242 | -11.269 | 4.649 | -4.881 | 1.00 | 0.00 | B |
| ATOM | 1345 | HB2 | SER | 242 | -10.589 | 4.545 | -6.498 | 1.00 | 0.00 | B |
| ATOM | 1346 | OG | SER | 242 | -12.415 | 3.650 | -6.265 | 1.00 | 0.00 | B |
| ATOM | 1347 | HG | SER | 242 | -12.800 | 3.325 | -5.448 | 1.00 | 0.00 | B |
| ATOM | 1348 | C | SER | 242 | -13.388 | 6.260 | -5.403 | 1.00 | 0.00 | B |
| ATOM | 1349 | O | SER | 242 | -14.493 | 6.058 | -5.843 | 1.00 | 0.00 | B |
| ATOM | 1350 | N | HIS | 243 | -13.224 | 6.651 | -4.166 | 1.00 | 0.00 | B |
| ATOM | 1351 | HN | HIS | 243 | -12.339 | 6.853 | -3.843 | 1.00 | 0.00 | B |
| ATOM | 1352 | CA | HIS | 243 | -14.416 | 6.880 | -3.270 | 1.00 | 0.00 | B |
| ATOM | 1353 | HA | HIS | 243 | -15.219 | 6.234 | -3.560 | 1.00 | 0.00 | B |
| ATOM | 1354 | CB | HIS | 243 | -13.926 | 6.492 | -1.869 | 1.00 | 0.00 | B |
| ATOM | 1355 | HB1 | HIS | 243 | -13.113 | 7.143 | -1.582 | 1.00 | 0.00 | B |
| ATOM | 1356 | HB2 | HIS | 243 | -13.579 | 5.469 | -1.882 | 1.00 | 0.00 | B |
| ATOM | 1357 | CG | HIS | 243 | -15.051 | 6.625 | -0.872 | 1.00 | 0.00 | B |
| ATOM | 1358 | ND1 | HIS | 243 | -15.698 | 7.831 | -0.629 | 1.00 | 0.00 | B |
| ATOM | 1359 | HD1 | HIS | 243 | -15.489 | 8.694 | -1.036 | 1.00 | 0.00 | B |
| ATOM | 1360 | CD2 | HIS | 243 | -15.665 | 5.704 | -0.061 | 1.00 | 0.00 | B |
| ATOM | 1361 | HD2 | HIS | 243 | -15.408 | 4.656 | -0.007 | 1.00 | 0.00 | B |
| ATOM | 1362 | CE1 | HIS | 243 | -16.653 | 7.599 | 0.293 | 1.00 | 0.00 | B |
| ATOM | 1363 | HE1 | HIS | 243 | -17.317 | 8.357 | 0.682 | 1.00 | 0.00 | B |
| ATOM | 1364 | NE2 | HIS | 243 | -16.675 | 6.318 | 0.671 | 1.00 | 0.00 | B |
| ATOM | 1365 | C | HIS | 243 | -14.861 | 8.342 | -3.313 | 1.00 | 0.00 | B |
| ATOM | 1366 | O | HIS | 243 | -16.004 | 8.680 | -3.103 | 1.00 | 0.00 | B |
| ATOM | 1367 | N | ASP | 244 | -13.962 | 9.201 | -3.527 | 1.00 | 0.00 | B |
| ATOM | 1368 | HN | ASP | 244 | -13.094 | 8.919 | -3.755 | 1.00 | 0.00 | B |
| ATOM | 1369 | CA | ASP | 244 | -14.303 | 10.612 | -3.582 | 1.00 | 0.00 | B |
| ATOM | 1370 | HA | ASP | 244 | -15.215 | 10.795 | -3.037 | 1.00 | 0.00 | B |
| ATOM | 1371 | CB | ASP | 244 | -13.142 | 11.356 | -2.925 | 1.00 | 0.00 | B |
| ATOM | 1372 | HB1 | ASP | 244 | -12.245 | 11.146 | -3.446 | 1.00 | 0.00 | B |
| ATOM | 1373 | HB2 | ASP | 244 | -13.044 | 11.032 | -1.900 | 1.00 | 0.00 | B |
| ATOM | 1374 | CG | ASP | 244 | -13.411 | 12.861 | -2.959 | 1.00 | 0.00 | B |
| ATOM | 1375 | OD1 | ASP | 244 | -14.468 | 13.265 | -2.505 | 1.00 | 0.00 | B |
| ATOM | 1376 | OD2 | ASP | 244 | -12.551 | 13.584 | -3.434 | 1.00 | 0.00 | B |
| ATOM | 1377 | C | ASP | 244 | -14.475 | 10.976 | -5.026 | 1.00 | 0.00 | B |
| ATOM | 1378 | O | ASP | 244 | -15.340 | 11.741 | -5.375 | 1.00 | 0.00 | B |
| ATOM | 1379 | N | LEU | 245 | -13.623 | 10.440 | -5.894 | 1.00 | 0.00 | B |
| ATOM | 1380 | HN | LEU | 245 | -12.856 | 9.801 | -5.564 | 1.00 | 0.00 | B |
| ATOM | 1381 | CA | LEU | 245 | -13.766 | 10.783 | -7.362 | 1.00 | 0.00 | B |
| ATOM | 1382 | HA | LEU | 245 | -14.200 | 11.768 | -7.451 | 1.00 | 0.00 | B |
| ATOM | 1383 | CB | LEU | 245 | -12.348 | 10.826 | -7.902 | 1.00 | 0.00 | B |
| ATOM | 1384 | HB1 | LEU | 245 | -12.320 | 10.409 | -8.895 | 1.00 | 0.00 | B |
| ATOM | 1385 | HB2 | LEU | 245 | -11.723 | 10.264 | -7.259 | 1.00 | 0.00 | B |
| ATOM | 1386 | CG | LEU | 245 | -11.849 | 12.273 | -7.940 | 1.00 | 0.00 | B |
| ATOM | 1387 | HG | LEU | 245 | -10.835 | 12.292 | -8.315 | 1.00 | 0.00 | B |
| ATOM | 1388 | CD1 | LEU | 245 | -12.749 | 13.092 | -8.867 | 1.00 | 0.00 | B |

Figure 8-25

```
ATOM   1389 HD11 LEU   245     -13.238  13.870  -8.301  1.00  0.00      B
ATOM   1390 HD12 LEU   245     -13.493  12.446  -9.310  1.00  0.00      B
ATOM   1391 HD13 LEU   245     -12.150  13.538  -9.649  1.00  0.00      B
ATOM   1392  CD2 LEU   245     -11.886  12.875  -6.531  1.00  0.00      B
ATOM   1393 HD21 LEU   245     -12.150  12.112  -5.820  1.00  0.00      B
ATOM   1394 HD22 LEU   245     -12.619  13.666  -6.496  1.00  0.00      B
ATOM   1395 HD23 LEU   245     -10.913  13.275  -6.286  1.00  0.00      B
ATOM   1396    C  LEU   245     -14.650   9.770  -8.160  1.00  0.00      B
ATOM   1397    O  LEU   245     -15.378  10.164  -9.050  1.00  0.00      B
ATOM   1398    N  ARG   246     -14.603   8.483  -7.866  1.00  0.00      B
ATOM   1399   HN  ARG   246     -14.067   8.168  -7.118  1.00  0.00      B
ATOM   1400   CA  ARG   246     -15.470   7.510  -8.661  1.00  0.00      B
ATOM   1401   HA  ARG   246     -15.683   7.934  -9.618  1.00  0.00      B
ATOM   1402   CB  ARG   246     -14.653   6.221  -8.831  1.00  0.00      B
ATOM   1403  HB1  ARG   246     -14.397   5.826  -7.875  1.00  0.00      B
ATOM   1404  HB2  ARG   246     -13.751   6.439  -9.383  1.00  0.00      B
ATOM   1405   CG  ARG   246     -15.485   5.192  -9.603  1.00  0.00      B
ATOM   1406  HG1  ARG   246     -15.723   5.583 -10.579  1.00  0.00      B
ATOM   1407  HG2  ARG   246     -16.400   4.994  -9.062  1.00  0.00      B
ATOM   1408   CD  ARG   246     -14.692   3.888  -9.758  1.00  0.00      B
ATOM   1409  HD1  ARG   246     -13.735   4.083 -10.213  1.00  0.00      B
ATOM   1410  HD2  ARG   246     -15.254   3.175 -10.349  1.00  0.00      B
ATOM   1411   NE  ARG   246     -14.501   3.375  -8.370  1.00  0.00      B
ATOM   1412   HE  ARG   246     -14.655   3.965  -7.604  1.00  0.00      B
ATOM   1413   CZ  ARG   246     -14.132   2.135  -8.177  1.00  0.00      B
ATOM   1414  NH1  ARG   246     -13.514   1.480  -9.124  1.00  0.00      B
ATOM   1415 HH11 ARG   246     -13.322   1.926  -9.998  1.00  0.00      B
ATOM   1416 HH12 ARG   246     -13.236   0.530  -8.977  1.00  0.00      B
ATOM   1417  NH2  ARG   246     -14.375   1.553  -7.034  1.00  0.00      B
ATOM   1418 HH21 ARG   246     -14.841   2.053  -6.307  1.00  0.00      B
ATOM   1419 HH22 ARG   246     -14.093   0.604  -6.887  1.00  0.00      B
ATOM   1420    C  ARG   246     -16.790   7.249  -7.987  1.00  0.00      B
ATOM   1421    O  ARG   246     -17.786   7.024  -8.648  1.00  0.00      B
ATOM   1422    N  THR   247     -16.844   7.267  -6.695  1.00  0.00      B
ATOM   1423   HN  THR   247     -16.049   7.459  -6.162  1.00  0.00      B
ATOM   1424   CA  THR   247     -18.138   7.018  -6.054  1.00  0.00      B
ATOM   1425   HA  THR   247     -18.735   6.417  -6.708  1.00  0.00      B
ATOM   1426   CB  THR   247     -17.859   6.228  -4.802  1.00  0.00      B
ATOM   1427   HB  THR   247     -18.781   5.983  -4.342  1.00  0.00      B
ATOM   1428  OG1  THR   247     -17.098   6.984  -3.926  1.00  0.00      B
ATOM   1429  HG1  THR   247     -17.631   7.159  -3.146  1.00  0.00      B
ATOM   1430  CG2  THR   247     -17.116   4.940  -5.157  1.00  0.00      B
ATOM   1431 HG21 THR   247     -16.891   4.934  -6.213  1.00  0.00      B
ATOM   1432 HG22 THR   247     -17.737   4.089  -4.916  1.00  0.00      B
ATOM   1433 HG23 THR   247     -16.198   4.888  -4.592  1.00  0.00      B
ATOM   1434    C  THR   247     -18.910   8.356  -5.721  1.00  0.00      B
ATOM   1435    O  THR   247     -19.939   8.291  -5.080  1.00  0.00      B
ATOM   1436    N  PRO   248     -18.406   9.554  -6.162  1.00  0.00      B
ATOM   1437   CA  PRO   248     -19.127  10.784  -5.853  1.00  0.00      B
ATOM   1438   HA  PRO   248     -19.351  10.823  -4.812  1.00  0.00      B
ATOM   1439   CB  PRO   248     -18.172  11.901  -6.233  1.00  0.00      B
ATOM   1440  HB1  PRO   248     -17.589  12.205  -5.379  1.00  0.00      B
ATOM   1441  HB2  PRO   248     -18.720  12.743  -6.637  1.00  0.00      B
ATOM   1442   CG  PRO   248     -17.295  11.309  -7.263  1.00  0.00      B
ATOM   1443  HG1  PRO   248     -16.310  11.721  -7.199  1.00  0.00      B
ATOM   1444  HG2  PRO   248     -17.710  11.498  -8.246  1.00  0.00      B
ATOM   1445   CD  PRO   248     -17.251   9.825  -7.002  1.00  0.00      B
ATOM   1446  HD1  PRO   248     -16.343   9.541  -6.488  1.00  0.00      B
```

Figure 8-26

```
ATOM   1447  HD2  PRO  248   -17.344   9.311   -7.926  1.00  0.00      B
ATOM   1448  C    PRO  248   -20.392  10.815   -6.749  1.00  0.00      B
ATOM   1449  O    PRO  248   -21.280  11.667   -6.627  1.00  0.00      B
ATOM   1450  N    LEU  249   -20.451   9.878   -7.686  1.00  0.00      B
ATOM   1451  HN   LEU  249   -19.723   9.247   -7.786  1.00  0.00      B
ATOM   1452  CA   LEU  249   -21.590   9.790   -8.599  1.00  0.00      B
ATOM   1453  HA   LEU  249   -21.696  10.708   -9.178  1.00  0.00      B
ATOM   1454  CB   LEU  249   -21.236   8.616   -9.543  1.00  0.00      B
ATOM   1455  HB1  LEU  249   -20.151   8.618   -9.715  1.00  0.00      B
ATOM   1456  HB2  LEU  249   -21.738   8.742  -10.480  1.00  0.00      B
ATOM   1457  CG   LEU  249   -21.631   7.273   -8.910  1.00  0.00      B
ATOM   1458  HG   LEU  249   -22.671   7.303   -8.620  1.00  0.00      B
ATOM   1459  CD1  LEU  249   -21.409   6.147   -9.913  1.00  0.00      B
ATOM   1460  HD11 LEU  249   -20.495   5.625   -9.671  1.00  0.00      B
ATOM   1461  HD12 LEU  249   -21.335   6.560  -10.907  1.00  0.00      B
ATOM   1462  HD13 LEU  249   -22.239   5.457   -9.870  1.00  0.00      B
ATOM   1463  CD2  LEU  249   -20.769   7.022   -7.693  1.00  0.00      B
ATOM   1464  HD21 LEU  249   -19.776   7.386   -7.888  1.00  0.00      B
ATOM   1465  HD22 LEU  249   -20.732   5.962   -7.490  1.00  0.00      B
ATOM   1466  HD23 LEU  249   -21.181   7.537   -6.842  1.00  0.00      B
ATOM   1467  C    LEU  249   -22.870   9.533   -7.773  1.00  0.00      B
ATOM   1468  O    LEU  249   -23.945   9.529   -8.299  1.00  0.00      B
ATOM   1469  N    THR  250   -22.734   9.225   -6.480  1.00  0.00      B
ATOM   1470  HN   THR  250   -21.865   9.129   -6.095  1.00  0.00      B
ATOM   1471  CA   THR  250   -23.930   8.982   -5.640  1.00  0.00      B
ATOM   1472  HA   THR  250   -24.614   8.320   -6.121  1.00  0.00      B
ATOM   1473  CB   THR  250   -23.421   8.383   -4.325  1.00  0.00      B
ATOM   1474  HB   THR  250   -22.769   7.551   -4.530  1.00  0.00      B
ATOM   1475  OG1  THR  250   -24.531   7.947   -3.550  1.00  0.00      B
ATOM   1476  HG1  THR  250   -24.198   7.616   -2.715  1.00  0.00      B
ATOM   1477  CG2  THR  250   -22.660   9.447   -3.548  1.00  0.00      B
ATOM   1478  HG21 THR  250   -23.338  10.257   -3.296  1.00  0.00      B
ATOM   1479  HG22 THR  250   -21.859   9.829   -4.160  1.00  0.00      B
ATOM   1480  HG23 THR  250   -22.262   9.020   -2.652  1.00  0.00      B
ATOM   1481  C    THR  250   -24.542  10.356   -5.408  1.00  0.00      B
ATOM   1482  O    THR  250   -25.726  10.545   -5.367  1.00  0.00      B
ATOM   1483  N    ARG  251   -23.688  11.333   -5.224  1.00  0.00      B
ATOM   1484  HN   ARG  251   -22.739  11.146   -5.230  1.00  0.00      B
ATOM   1485  CA   ARG  251   -24.168  12.708   -4.998  1.00  0.00      B
ATOM   1486  HA   ARG  251   -24.711  12.783   -4.069  1.00  0.00      B
ATOM   1487  CB   ARG  251   -22.898  13.566   -4.967  1.00  0.00      B
ATOM   1488  HB1  ARG  251   -23.160  14.603   -4.868  1.00  0.00      B
ATOM   1489  HB2  ARG  251   -22.340  13.415   -5.883  1.00  0.00      B
ATOM   1490  CG   ARG  251   -22.034  13.144   -3.776  1.00  0.00      B
ATOM   1491  HG1  ARG  251   -21.745  12.111   -3.890  1.00  0.00      B
ATOM   1492  HG2  ARG  251   -22.601  13.260   -2.863  1.00  0.00      B
ATOM   1493  CD   ARG  251   -20.779  14.020   -3.714  1.00  0.00      B
ATOM   1494  HD1  ARG  251   -21.048  15.056   -3.596  1.00  0.00      B
ATOM   1495  HD2  ARG  251   -20.182  13.882   -4.607  1.00  0.00      B
ATOM   1496  NE   ARG  251   -20.037  13.544   -2.513  1.00  0.00      B
ATOM   1497  HE   ARG  251   -20.294  12.704   -2.080  1.00  0.00      B
ATOM   1498  CZ   ARG  251   -19.047  14.247   -2.036  1.00  0.00      B
ATOM   1499  NH1  ARG  251   -19.288  15.295   -1.298  1.00  0.00      B
ATOM   1500  HH11 ARG  251   -20.232  15.559   -1.097  1.00  0.00      B
ATOM   1501  HH12 ARG  251   -18.530  15.835   -0.931  1.00  0.00      B
ATOM   1502  NH2  ARG  251   -17.816  13.902   -2.298  1.00  0.00      B
ATOM   1503  HH21 ARG  251   -17.631  13.098   -2.864  1.00  0.00      B
ATOM   1504  HH22 ARG  251   -17.057  14.442   -1.932  1.00  0.00      B
```

Figure 8-27

| | | | | | | | | | |
|---|---|---|---|---|---|---|---|---|---|
| ATOM | 1505 | C | ARG | 251 | -25.054 | 13.033 | -6.182 | 1.00 | 0.00 | B |
| ATOM | 1506 | O | ARG | 251 | -26.172 | 13.483 | -6.041 | 1.00 | 0.00 | B |
| ATOM | 1507 | N | ILE | 252 | -24.545 | 12.804 | -7.365 | 1.00 | 0.00 | B |
| ATOM | 1508 | HN | ILE | 252 | -23.622 | 12.466 | -7.445 | 1.00 | 0.00 | B |
| ATOM | 1509 | CA | ILE | 252 | -25.364 | 13.086 | -8.587 | 1.00 | 0.00 | B |
| ATOM | 1510 | HA | ILE | 252 | -25.841 | 14.050 | -8.518 | 1.00 | 0.00 | B |
| ATOM | 1511 | CB | ILE | 252 | -24.440 | 13.034 | -9.759 | 1.00 | 0.00 | B |
| ATOM | 1512 | HB | ILE | 252 | -24.996 | 13.131 | -10.683 | 1.00 | 0.00 | B |
| ATOM | 1513 | CG1 | ILE | 252 | -23.725 | 11.723 | -9.767 | 1.00 | 0.00 | B |
| ATOM | 1514 | HG11 | ILE | 252 | -24.440 | 10.920 | -9.793 | 1.00 | 0.00 | B |
| ATOM | 1515 | HG12 | ILE | 252 | -23.118 | 11.639 | -8.884 | 1.00 | 0.00 | B |
| ATOM | 1516 | CG2 | ILE | 252 | -23.471 | 14.146 | -9.649 | 1.00 | 0.00 | B |
| ATOM | 1517 | HG21 | ILE | 252 | -23.977 | 15.011 | -9.251 | 1.00 | 0.00 | B |
| ATOM | 1518 | HG22 | ILE | 252 | -23.081 | 14.366 | -10.623 | 1.00 | 0.00 | B |
| ATOM | 1519 | HG23 | ILE | 252 | -22.678 | 13.855 | -8.989 | 1.00 | 0.00 | B |
| ATOM | 1520 | CD1 | ILE | 252 | -22.860 | 11.668 | -10.997 | 1.00 | 0.00 | B |
| ATOM | 1521 | HD11 | ILE | 252 | -23.469 | 11.863 | -11.867 | 1.00 | 0.00 | B |
| ATOM | 1522 | HD12 | ILE | 252 | -22.412 | 10.696 | -11.076 | 1.00 | 0.00 | B |
| ATOM | 1523 | HD13 | ILE | 252 | -22.091 | 12.422 | -10.923 | 1.00 | 0.00 | B |
| ATOM | 1524 | C | ILE | 252 | -26.372 | 11.998 | -8.718 | 1.00 | 0.00 | B |
| ATOM | 1525 | O | ILE | 252 | -27.360 | 12.139 | -9.346 | 1.00 | 0.00 | B |
| ATOM | 1526 | N | ARG | 253 | -26.113 | 10.867 | -8.142 | 1.00 | 0.00 | B |
| ATOM | 1527 | HN | ARG | 253 | -25.322 | 10.765 | -7.616 | 1.00 | 0.00 | B |
| ATOM | 1528 | CA | ARG | 253 | -27.098 | 9.772 | -8.251 | 1.00 | 0.00 | B |
| ATOM | 1529 | HA | ARG | 253 | -27.172 | 9.416 | -9.269 | 1.00 | 0.00 | B |
| ATOM | 1530 | CB | ARG | 253 | -26.611 | 8.681 | -7.322 | 1.00 | 0.00 | B |
| ATOM | 1531 | HB1 | ARG | 253 | -26.599 | 9.040 | -6.322 | 1.00 | 0.00 | B |
| ATOM | 1532 | HB2 | ARG | 253 | -25.621 | 8.388 | -7.616 | 1.00 | 0.00 | B |
| ATOM | 1533 | CG | ARG | 253 | -27.521 | 7.483 | -7.402 | 1.00 | 0.00 | B |
| ATOM | 1534 | HG1 | ARG | 253 | -28.537 | 7.799 | -7.251 | 1.00 | 0.00 | B |
| ATOM | 1535 | HG2 | ARG | 253 | -27.242 | 6.777 | -6.636 | 1.00 | 0.00 | B |
| ATOM | 1536 | CD | ARG | 253 | -27.384 | 6.836 | -8.773 | 1.00 | 0.00 | B |
| ATOM | 1537 | HD1 | ARG | 253 | -26.369 | 6.505 | -8.931 | 1.00 | 0.00 | B |
| ATOM | 1538 | HD2 | ARG | 253 | -27.679 | 7.535 | -9.546 | 1.00 | 0.00 | B |
| ATOM | 1539 | NE | ARG | 253 | -28.306 | 5.664 | -8.741 | 1.00 | 0.00 | B |
| ATOM | 1540 | HE | ARG | 253 | -29.055 | 5.612 | -9.371 | 1.00 | 0.00 | B |
| ATOM | 1541 | CZ | ARG | 253 | -28.118 | 4.704 | -7.870 | 1.00 | 0.00 | B |
| ATOM | 1542 | NH1 | ARG | 253 | -29.086 | 4.352 | -7.066 | 1.00 | 0.00 | B |
| ATOM | 1543 | HH11 | ARG | 253 | -29.971 | 4.815 | -7.116 | 1.00 | 0.00 | B |
| ATOM | 1544 | HH12 | ARG | 253 | -28.942 | 3.619 | -6.401 | 1.00 | 0.00 | B |
| ATOM | 1545 | NH2 | ARG | 253 | -26.964 | 4.096 | -7.805 | 1.00 | 0.00 | B |
| ATOM | 1546 | HH21 | ARG | 253 | -26.224 | 4.363 | -8.421 | 1.00 | 0.00 | B |
| ATOM | 1547 | HH22 | ARG | 253 | -26.821 | 3.363 | -7.139 | 1.00 | 0.00 | B |
| ATOM | 1548 | C | ARG | 253 | -28.401 | 10.365 | -7.782 | 1.00 | 0.00 | B |
| ATOM | 1549 | O | ARG | 253 | -29.450 | 10.008 | -8.226 | 1.00 | 0.00 | B |
| ATOM | 1550 | N | LEU | 254 | -28.288 | 11.333 | -6.878 | 1.00 | 0.00 | B |
| ATOM | 1551 | HN | LEU | 254 | -27.403 | 11.596 | -6.559 | 1.00 | 0.00 | B |
| ATOM | 1552 | CA | LEU | 254 | -29.459 | 12.009 | -6.338 | 1.00 | 0.00 | B |
| ATOM | 1553 | HA | LEU | 254 | -30.287 | 11.349 | -6.323 | 1.00 | 0.00 | B |
| ATOM | 1554 | CB | LEU | 254 | -29.068 | 12.421 | -4.913 | 1.00 | 0.00 | B |
| ATOM | 1555 | HB1 | LEU | 254 | -29.924 | 12.850 | -4.415 | 1.00 | 0.00 | B |
| ATOM | 1556 | HB2 | LEU | 254 | -28.275 | 13.154 | -4.959 | 1.00 | 0.00 | B |
| ATOM | 1557 | CG | LEU | 254 | -28.582 | 11.188 | -4.120 | 1.00 | 0.00 | B |
| ATOM | 1558 | HG | LEU | 254 | -27.620 | 10.856 | -4.512 | 1.00 | 0.00 | B |
| ATOM | 1559 | CD1 | LEU | 254 | -28.409 | 11.567 | -2.651 | 1.00 | 0.00 | B |
| ATOM | 1560 | HD11 | LEU | 254 | -28.308 | 10.671 | -2.058 | 1.00 | 0.00 | B |
| ATOM | 1561 | HD12 | LEU | 254 | -29.273 | 12.123 | -2.319 | 1.00 | 0.00 | B |
| ATOM | 1562 | HD13 | LEU | 254 | -27.524 | 12.175 | -2.539 | 1.00 | 0.00 | B |

Figure 8-28

| | | | | | | | | | |
|---|---|---|---|---|---|---|---|---|---|
| ATOM | 1563 | CD2 | LEU | 254 | -29.610 | 10.052 | -4.242 | 1.00 | 0.00 | B |
| ATOM | 1564 | HD21 | LEU | 254 | -29.427 | 9.316 | -3.472 | 1.00 | 0.00 | B |
| ATOM | 1565 | HD22 | LEU | 254 | -29.519 | 9.588 | -5.213 | 1.00 | 0.00 | B |
| ATOM | 1566 | HD23 | LEU | 254 | -30.606 | 10.452 | -4.127 | 1.00 | 0.00 | B |
| ATOM | 1567 | C | LEU | 254 | -29.756 | 13.238 | -7.226 | 1.00 | 0.00 | B |
| ATOM | 1568 | O | LEU | 254 | -30.895 | 13.546 | -7.515 | 1.00 | 0.00 | B |
| ATOM | 1569 | N | ALA | 255 | -28.718 | 13.949 | -7.665 | 1.00 | 0.00 | B |
| ATOM | 1570 | HN | ALA | 255 | -27.795 | 13.666 | -7.446 | 1.00 | 0.00 | B |
| ATOM | 1571 | CA | ALA | 255 | -28.946 | 15.156 | -8.541 | 1.00 | 0.00 | B |
| ATOM | 1572 | HA | ALA | 255 | -29.570 | 15.890 | -8.072 | 1.00 | 0.00 | B |
| ATOM | 1573 | CB | ALA | 255 | -27.547 | 15.726 | -8.813 | 1.00 | 0.00 | B |
| ATOM | 1574 | HB1 | ALA | 255 | -26.913 | 15.548 | -7.957 | 1.00 | 0.00 | B |
| ATOM | 1575 | HB2 | ALA | 255 | -27.619 | 16.789 | -8.993 | 1.00 | 0.00 | B |
| ATOM | 1576 | HB3 | ALA | 255 | -27.123 | 15.243 | -9.681 | 1.00 | 0.00 | B |
| ATOM | 1577 | C | ALA | 255 | -29.569 | 14.648 | -9.807 | 1.00 | 0.00 | B |
| ATOM | 1578 | O | ALA | 255 | -30.635 | 15.037 | -10.204 | 1.00 | 0.00 | B |
| ATOM | 1579 | N | THR | 256 | -28.884 | 13.774 | -10.425 | 1.00 | 0.00 | B |
| ATOM | 1580 | HN | THR | 256 | -28.050 | 13.543 | -10.084 | 1.00 | 0.00 | B |
| ATOM | 1581 | CA | THR | 256 | -29.353 | 13.170 | -11.675 | 1.00 | 0.00 | B |
| ATOM | 1582 | HA | THR | 256 | -29.584 | 13.917 | -12.407 | 1.00 | 0.00 | B |
| ATOM | 1583 | CB | THR | 256 | -28.228 | 12.279 | -12.170 | 1.00 | 0.00 | B |
| ATOM | 1584 | HB | THR | 256 | -28.460 | 11.973 | -13.150 | 1.00 | 0.00 | B |
| ATOM | 1585 | OG1 | THR | 256 | -28.129 | 11.140 | -11.334 | 1.00 | 0.00 | B |
| ATOM | 1586 | HG1 | THR | 256 | -28.606 | 10.421 | -11.756 | 1.00 | 0.00 | B |
| ATOM | 1587 | CG2 | THR | 256 | -26.880 | 13.014 | -12.177 | 1.00 | 0.00 | B |
| ATOM | 1588 | HG21 | THR | 256 | -26.874 | 13.782 | -11.429 | 1.00 | 0.00 | B |
| ATOM | 1589 | HG22 | THR | 256 | -26.717 | 13.454 | -13.141 | 1.00 | 0.00 | B |
| ATOM | 1590 | HG23 | THR | 256 | -26.090 | 12.305 | -11.972 | 1.00 | 0.00 | B |
| ATOM | 1591 | C | THR | 256 | -30.562 | 12.300 | -11.389 | 1.00 | 0.00 | B |
| ATOM | 1592 | O | THR | 256 | -31.274 | 11.929 | -12.282 | 1.00 | 0.00 | B |
| ATOM | 1593 | N | GLU | 257 | -30.772 | 11.905 | -10.149 | 1.00 | 0.00 | B |
| ATOM | 1594 | HN | GLU | 257 | -30.129 | 12.174 | -9.402 | 1.00 | 0.00 | B |
| ATOM | 1595 | CA | GLU | 257 | -31.983 | 11.039 | -9.864 | 1.00 | 0.00 | B |
| ATOM | 1596 | HA | GLU | 257 | -31.961 | 10.133 | -10.441 | 1.00 | 0.00 | B |
| ATOM | 1597 | CB | GLU | 257 | -31.937 | 10.746 | -8.384 | 1.00 | 0.00 | B |
| ATOM | 1598 | HB1 | GLU | 257 | -32.794 | 11.191 | -7.909 | 1.00 | 0.00 | B |
| ATOM | 1599 | HB2 | GLU | 257 | -31.051 | 11.171 | -7.973 | 1.00 | 0.00 | B |
| ATOM | 1600 | CG | GLU | 257 | -31.965 | 9.229 | -8.157 | 1.00 | 0.00 | B |
| ATOM | 1601 | HG1 | GLU | 257 | -31.128 | 8.771 | -8.658 | 1.00 | 0.00 | B |
| ATOM | 1602 | HG2 | GLU | 257 | -32.884 | 8.825 | -8.555 | 1.00 | 0.00 | B |
| ATOM | 1603 | CD | GLU | 257 | -31.887 | 8.931 | -6.658 | 1.00 | 0.00 | B |
| ATOM | 1604 | OE1 | GLU | 257 | -31.900 | 7.764 | -6.304 | 1.00 | 0.00 | B |
| ATOM | 1605 | OE2 | GLU | 257 | -31.816 | 9.875 | -5.890 | 1.00 | 0.00 | B |
| ATOM | 1606 | C | GLU | 257 | -33.214 | 11.845 | -10.150 | 1.00 | 0.00 | B |
| ATOM | 1607 | O | GLU | 257 | -34.015 | 11.542 | -11.004 | 1.00 | 0.00 | B |
| ATOM | 1608 | N | MET | 258 | -33.364 | 12.852 | -9.392 | 1.00 | 0.00 | B |
| ATOM | 1609 | HN | MET | 258 | -32.690 | 13.023 | -8.697 | 1.00 | 0.00 | B |
| ATOM | 1610 | CA | MET | 258 | -34.506 | 13.763 | -9.522 | 1.00 | 0.00 | B |
| ATOM | 1611 | HA | MET | 258 | -35.448 | 13.244 | -9.414 | 1.00 | 0.00 | B |
| ATOM | 1612 | CB | MET | 258 | -34.263 | 14.721 | -8.352 | 1.00 | 0.00 | B |
| ATOM | 1613 | HB1 | MET | 258 | -33.192 | 14.828 | -8.204 | 1.00 | 0.00 | B |
| ATOM | 1614 | HB2 | MET | 258 | -34.701 | 14.308 | -7.460 | 1.00 | 0.00 | B |
| ATOM | 1615 | CG | MET | 258 | -34.864 | 16.083 | -8.625 | 1.00 | 0.00 | B |
| ATOM | 1616 | HG1 | MET | 258 | -34.442 | 16.470 | -9.545 | 1.00 | 0.00 | B |
| ATOM | 1617 | HG2 | MET | 258 | -34.616 | 16.743 | -7.812 | 1.00 | 0.00 | B |
| ATOM | 1618 | SD | MET | 258 | -36.662 | 15.945 | -8.786 | 1.00 | 0.00 | B |
| ATOM | 1619 | CE | MET | 258 | -37.098 | 17.072 | -7.439 | 1.00 | 0.00 | B |
| ATOM | 1620 | HE1 | MET | 258 | -37.082 | 16.533 | -6.501 | 1.00 | 0.00 | B |

Figure 8-29

```
ATOM   1621  HE2  MET  258   -38.085   17.469   -7.605  1.00  0.00           B
ATOM   1622  HE3  MET  258   -36.386   17.886   -7.405  1.00  0.00           B
ATOM   1623  C    MET  258   -34.424   14.466  -10.864  1.00  0.00           B
ATOM   1624  O    MET  258   -35.418   14.849  -11.449  1.00  0.00           B
ATOM   1625  N    MET  259   -33.250   14.632  -11.349  1.00  0.00           B
ATOM   1626  HN   MET  259   -32.492   14.283  -10.886  1.00  0.00           B
ATOM   1627  CA   MET  259   -33.076   15.295  -12.629  1.00  0.00           B
ATOM   1628  HA   MET  259   -33.810   16.021  -12.751  1.00  0.00           B
ATOM   1629  CB   MET  259   -31.704   15.945  -12.571  1.00  0.00           B
ATOM   1630  HB1  MET  259   -31.472   16.386  -13.527  1.00  0.00           B
ATOM   1631  HB2  MET  259   -30.965   15.203  -12.326  1.00  0.00           B
ATOM   1632  CG   MET  259   -31.717   17.038  -11.498  1.00  0.00           B
ATOM   1633  HG1  MET  259   -32.037   16.617  -10.558  1.00  0.00           B
ATOM   1634  HG2  MET  259   -32.400   17.820  -11.790  1.00  0.00           B
ATOM   1635  SD   MET  259   -30.059   17.732  -11.316  1.00  0.00           B
ATOM   1636  CE   MET  259   -30.168   18.107   -9.551  1.00  0.00           B
ATOM   1637  HE1  MET  259   -31.016   17.585   -9.127  1.00  0.00           B
ATOM   1638  HE2  MET  259   -30.297   19.167   -9.414  1.00  0.00           B
ATOM   1639  HE3  MET  259   -29.259   17.788   -9.058  1.00  0.00           B
ATOM   1640  C    MET  259   -33.176   14.293  -13.729  1.00  0.00           B
ATOM   1641  O    MET  259   -33.302   14.640  -14.853  1.00  0.00           B
ATOM   1642  N    SER  260   -33.167   13.029  -13.403  1.00  0.00           B
ATOM   1643  HN   SER  260   -33.139   12.778  -12.477  1.00  0.00           B
ATOM   1644  CA   SER  260   -33.268   11.985  -14.472  1.00  0.00           B
ATOM   1645  HA   SER  260   -32.379   11.959  -15.077  1.00  0.00           B
ATOM   1646  CB   SER  260   -33.482   10.657  -13.752  1.00  0.00           B
ATOM   1647  HB1  SER  260   -32.688   10.503  -13.033  1.00  0.00           B
ATOM   1648  HB2  SER  260   -33.474    9.855  -14.466  1.00  0.00           B
ATOM   1649  OG   SER  260   -34.741   10.682  -13.089  1.00  0.00           B
ATOM   1650  HG   SER  260   -35.405   10.360  -13.703  1.00  0.00           B
ATOM   1651  C    SER  260   -34.477   12.332  -15.282  1.00  0.00           B
ATOM   1652  O    SER  260   -34.523   12.189  -16.488  1.00  0.00           B
ATOM   1653  N    GLU  261   -35.470   12.796  -14.593  1.00  0.00           B
ATOM   1654  HN   GLU  261   -35.385   12.887  -13.622  1.00  0.00           B
ATOM   1655  CA   GLU  261   -36.708   13.183  -15.239  1.00  0.00           B
ATOM   1656  HA   GLU  261   -36.800   12.698  -16.193  1.00  0.00           B
ATOM   1657  CB   GLU  261   -37.808   12.757  -14.247  1.00  0.00           B
ATOM   1658  HB1  GLU  261   -37.745   13.383  -13.359  1.00  0.00           B
ATOM   1659  HB2  GLU  261   -37.651   11.725  -13.960  1.00  0.00           B
ATOM   1660  CG   GLU  261   -39.203   12.913  -14.878  1.00  0.00           B
ATOM   1661  HG1  GLU  261   -39.952   12.562  -14.180  1.00  0.00           B
ATOM   1662  HG2  GLU  261   -39.255   12.325  -15.783  1.00  0.00           B
ATOM   1663  CD   GLU  261   -39.472   14.381  -15.208  1.00  0.00           B
ATOM   1664  OE1  GLU  261   -39.377   14.732  -16.371  1.00  0.00           B
ATOM   1665  OE2  GLU  261   -39.764   15.131  -14.290  1.00  0.00           B
ATOM   1666  C    GLU  261   -36.640   14.671  -15.414  1.00  0.00           B
ATOM   1667  O    GLU  261   -37.030   15.202  -16.429  1.00  0.00           B
ATOM   1668  N    GLN  262   -36.178   15.365  -14.403  1.00  0.00           B
ATOM   1669  HN   GLN  262   -35.907   14.914  -13.577  1.00  0.00           B
ATOM   1670  CA   GLN  262   -36.076   16.822  -14.521  1.00  0.00           B
ATOM   1671  HA   GLN  262   -36.878   17.195  -15.067  1.00  0.00           B
ATOM   1672  CB   GLN  262   -36.083   17.384  -13.090  1.00  0.00           B
ATOM   1673  HB1  GLN  262   -35.252   17.002  -12.544  1.00  0.00           B
ATOM   1674  HB2  GLN  262   -36.999   17.096  -12.597  1.00  0.00           B
ATOM   1675  CG   GLN  262   -35.996   18.911  -13.145  1.00  0.00           B
ATOM   1676  HG1  GLN  262   -36.829   19.299  -13.712  1.00  0.00           B
ATOM   1677  HG2  GLN  262   -35.070   19.203  -13.620  1.00  0.00           B
ATOM   1678  CD   GLN  262   -36.043   19.474  -11.726  1.00  0.00           B
```

Figure 8-30

| | | | | | | | | | |
|---|---|---|---|---|---|---|---|---|---|
| ATOM | 1679 | OE1 | GLN | 262 | -35.142 | 19.253 | -10.942 | 1.00 | 0.00 | B |
| ATOM | 1680 | NE2 | GLN | 262 | -37.064 | 20.198 | -11.360 | 1.00 | 0.00 | B |
| ATOM | 1681 | HE21 | GLN | 262 | -37.791 | 20.375 | -11.992 | 1.00 | 0.00 | B |
| ATOM | 1682 | HE22 | GLN | 262 | -37.104 | 20.564 | -10.451 | 1.00 | 0.00 | B |
| ATOM | 1683 | C | GLN | 262 | -34.765 | 17.078 | -15.245 | 1.00 | 0.00 | B |
| ATOM | 1684 | O | GLN | 262 | -33.775 | 17.450 | -14.653 | 1.00 | 0.00 | B |
| ATOM | 1685 | N | ASP | 263 | -34.766 | 16.846 | -16.548 | 1.00 | 0.00 | B |
| ATOM | 1686 | HN | ASP | 263 | -35.582 | 16.554 | -16.980 | 1.00 | 0.00 | B |
| ATOM | 1687 | CA | ASP | 263 | -33.548 | 17.047 | -17.371 | 1.00 | 0.00 | B |
| ATOM | 1688 | HA | ASP | 263 | -33.779 | 16.934 | -18.417 | 1.00 | 0.00 | B |
| ATOM | 1689 | CB | ASP | 263 | -33.050 | 18.473 | -17.086 | 1.00 | 0.00 | B |
| ATOM | 1690 | HB1 | ASP | 263 | -32.718 | 18.547 | -16.066 | 1.00 | 0.00 | B |
| ATOM | 1691 | HB2 | ASP | 263 | -33.851 | 19.177 | -17.258 | 1.00 | 0.00 | B |
| ATOM | 1692 | CG | ASP | 263 | -31.881 | 18.794 | -18.017 | 1.00 | 0.00 | B |
| ATOM | 1693 | OD1 | ASP | 263 | -31.676 | 18.046 | -18.947 | 1.00 | 0.00 | B |
| ATOM | 1694 | OD2 | ASP | 263 | -31.220 | 19.788 | -17.786 | 1.00 | 0.00 | B |
| ATOM | 1695 | C | ASP | 263 | -32.526 | 15.995 | -16.946 | 1.00 | 0.00 | B |
| ATOM | 1696 | O | ASP | 263 | -31.514 | 16.313 | -16.354 | 1.00 | 0.00 | B |
| ATOM | 1697 | N | GLY | 264 | -32.836 | 14.705 | -17.176 | 1.00 | 0.00 | B |
| ATOM | 1698 | HN | GLY | 264 | -33.755 | 14.456 | -17.527 | 1.00 | 0.00 | B |
| ATOM | 1699 | CA | GLY | 264 | -31.877 | 13.606 | -16.784 | 1.00 | 0.00 | B |
| ATOM | 1700 | HA1 | GLY | 264 | -32.399 | 12.661 | -16.836 | 1.00 | 0.00 | B |
| ATOM | 1701 | HA2 | GLY | 264 | -31.555 | 13.772 | -15.767 | 1.00 | 0.00 | B |
| ATOM | 1702 | C | GLY | 264 | -30.625 | 13.534 | -17.699 | 1.00 | 0.00 | B |
| ATOM | 1703 | O | GLY | 264 | -30.231 | 12.463 | -18.120 | 1.00 | 0.00 | B |
| ATOM | 1704 | N | TYR | 265 | -30.001 | 14.640 | -18.012 | 1.00 | 0.00 | B |
| ATOM | 1705 | HN | TYR | 265 | -30.318 | 15.485 | -17.694 | 1.00 | 0.00 | B |
| ATOM | 1706 | CA | TYR | 265 | -28.801 | 14.587 | -18.881 | 1.00 | 0.00 | B |
| ATOM | 1707 | HA | TYR | 265 | -28.874 | 13.753 | -19.561 | 1.00 | 0.00 | B |
| ATOM | 1708 | CB | TYR | 265 | -28.794 | 15.896 | -19.670 | 1.00 | 0.00 | B |
| ATOM | 1709 | HB1 | TYR | 265 | -27.863 | 15.987 | -20.210 | 1.00 | 0.00 | B |
| ATOM | 1710 | HB2 | TYR | 265 | -28.898 | 16.729 | -18.986 | 1.00 | 0.00 | B |
| ATOM | 1711 | CG | TYR | 265 | -29.950 | 15.898 | -20.652 | 1.00 | 0.00 | B |
| ATOM | 1712 | CD1 | TYR | 265 | -31.290 | 15.793 | -20.194 | 1.00 | 0.00 | B |
| ATOM | 1713 | HD1 | TYR | 265 | -31.501 | 15.740 | -19.144 | 1.00 | 0.00 | B |
| ATOM | 1714 | CD2 | TYR | 265 | -29.686 | 15.977 | -22.036 | 1.00 | 0.00 | B |
| ATOM | 1715 | HD2 | TYR | 265 | -28.667 | 16.054 | -22.388 | 1.00 | 0.00 | B |
| ATOM | 1716 | CE1 | TYR | 265 | -32.353 | 15.773 | -21.118 | 1.00 | 0.00 | B |
| ATOM | 1717 | HE1 | TYR | 265 | -33.372 | 15.694 | -20.763 | 1.00 | 0.00 | B |
| ATOM | 1718 | CE2 | TYR | 265 | -30.753 | 15.958 | -22.962 | 1.00 | 0.00 | B |
| ATOM | 1719 | HE2 | TYR | 265 | -30.550 | 16.020 | -24.017 | 1.00 | 0.00 | B |
| ATOM | 1720 | CZ | TYR | 265 | -32.086 | 15.856 | -22.505 | 1.00 | 0.00 | B |
| ATOM | 1721 | OH | TYR | 265 | -33.126 | 15.835 | -23.411 | 1.00 | 0.00 | B |
| ATOM | 1722 | HH | TYR | 265 | -32.812 | 15.409 | -24.213 | 1.00 | 0.00 | B |
| ATOM | 1723 | C | TYR | 265 | -27.539 | 14.453 | -18.018 | 1.00 | 0.00 | B |
| ATOM | 1724 | O | TYR | 265 | -26.451 | 14.255 | -18.523 | 1.00 | 0.00 | B |
| ATOM | 1725 | N | LEU | 266 | -27.673 | 14.557 | -16.710 | 1.00 | 0.00 | B |
| ATOM | 1726 | HN | LEU | 266 | -28.536 | 14.597 | -16.314 | 1.00 | 0.00 | B |
| ATOM | 1727 | CA | LEU | 266 | -26.500 | 14.434 | -15.852 | 1.00 | 0.00 | B |
| ATOM | 1728 | HA | LEU | 266 | -25.615 | 14.707 | -16.408 | 1.00 | 0.00 | B |
| ATOM | 1729 | CB | LEU | 266 | -26.680 | 15.406 | -14.637 | 1.00 | 0.00 | B |
| ATOM | 1730 | HB1 | LEU | 266 | -26.573 | 16.424 | -14.987 | 1.00 | 0.00 | B |
| ATOM | 1731 | HB2 | LEU | 266 | -25.913 | 15.206 | -13.919 | 1.00 | 0.00 | B |
| ATOM | 1732 | CG | LEU | 266 | -28.047 | 15.260 | -13.940 | 1.00 | 0.00 | B |
| ATOM | 1733 | HG | LEU | 266 | -28.340 | 14.220 | -13.900 | 1.00 | 0.00 | B |
| ATOM | 1734 | CD1 | LEU | 266 | -27.921 | 15.832 | -12.526 | 1.00 | 0.00 | B |
| ATOM | 1735 | HD11 | LEU | 266 | -28.710 | 15.458 | -11.907 | 1.00 | 0.00 | B |
| ATOM | 1736 | HD12 | LEU | 266 | -27.989 | 16.895 | -12.574 | 1.00 | 0.00 | B |

Figure 8-31

```
ATOM   1737 HD13 LEU  266    -26.967  15.553 -12.106  1.00  0.00      B
ATOM   1738  CD2 LEU  266    -29.109  16.089 -14.680  1.00  0.00      B
ATOM   1739 HD21 LEU  266    -29.629  16.721 -13.973  1.00  0.00      B
ATOM   1740 HD22 LEU  266    -29.815  15.428 -15.156  1.00  0.00      B
ATOM   1741 HD23 LEU  266    -28.630  16.705 -15.427  1.00  0.00      B
ATOM   1742    C LEU  266    -26.412  12.987 -15.441  1.00  0.00      B
ATOM   1743    O LEU  266    -25.362  12.463 -15.185  1.00  0.00      B
ATOM   1744    N ALA  267    -27.532  12.329 -15.373  1.00  0.00      B
ATOM   1745   HN ALA  267    -28.380  12.773 -15.575  1.00  0.00      B
ATOM   1746   CA ALA  267    -27.517  10.913 -14.985  1.00  0.00      B
ATOM   1747   HA ALA  267    -27.011  10.777 -14.043  1.00  0.00      B
ATOM   1748   CB ALA  267    -28.992  10.498 -14.875  1.00  0.00      B
ATOM   1749  HB1 ALA  267    -29.138   9.920 -13.974  1.00  0.00      B
ATOM   1750  HB2 ALA  267    -29.264   9.900 -15.733  1.00  0.00      B
ATOM   1751  HB3 ALA  267    -29.614  11.381 -14.841  1.00  0.00      B
ATOM   1752    C ALA  267    -26.836  10.139 -16.079  1.00  0.00      B
ATOM   1753    O ALA  267    -26.251   9.113 -15.853  1.00  0.00      B
ATOM   1754    N GLU  268    -26.892  10.631 -17.281  1.00  0.00      B
ATOM   1755   HN GLU  268    -27.360  11.474 -17.453  1.00  0.00      B
ATOM   1756   CA GLU  268    -26.241   9.903 -18.373  1.00  0.00      B
ATOM   1757   HA GLU  268    -26.131   8.912 -18.090  1.00  0.00      B
ATOM   1758   CB GLU  268    -27.192  10.013 -19.567  1.00  0.00      B
ATOM   1759  HB1 GLU  268    -26.769   9.492 -20.413  1.00  0.00      B
ATOM   1760  HB2 GLU  268    -27.332  11.055 -19.819  1.00  0.00      B
ATOM   1761   CG GLU  268    -28.545   9.388 -19.210  1.00  0.00      B
ATOM   1762  HG1 GLU  268    -29.230   9.520 -20.034  1.00  0.00      B
ATOM   1763  HG2 GLU  268    -28.944   9.873 -18.330  1.00  0.00      B
ATOM   1764   CD GLU  268    -28.368   7.894 -18.932  1.00  0.00      B
ATOM   1765  OE1 GLU  268    -29.340   7.265 -18.544  1.00  0.00      B
ATOM   1766  OE2 GLU  268    -27.267   7.401 -19.117  1.00  0.00      B
ATOM   1767    C GLU  268    -24.882  10.481 -18.698  1.00  0.00      B
ATOM   1768    O GLU  268    -23.903   9.772 -18.749  1.00  0.00      B
ATOM   1769    N SER  269    -24.796  11.736 -18.937  1.00  0.00      B
ATOM   1770   HN SER  269    -25.594  12.305 -18.910  1.00  0.00      B
ATOM   1771   CA SER  269    -23.476  12.309 -19.253  1.00  0.00      B
ATOM   1772   HA SER  269    -23.084  11.884 -20.162  1.00  0.00      B
ATOM   1773   CB SER  269    -23.724  13.805 -19.433  1.00  0.00      B
ATOM   1774  HB1 SER  269    -22.784  14.303 -19.639  1.00  0.00      B
ATOM   1775  HB2 SER  269    -24.152  14.211 -18.534  1.00  0.00      B
ATOM   1776   OG SER  269    -24.629  14.005 -20.513  1.00  0.00      B
ATOM   1777   HG SER  269    -24.380  13.410 -21.223  1.00  0.00      B
ATOM   1778    C SER  269    -22.521  12.056 -18.081  1.00  0.00      B
ATOM   1779    O SER  269    -21.325  11.896 -18.256  1.00  0.00      B
ATOM   1780    N ILE  270    -23.045  11.970 -16.886  1.00  0.00      B
ATOM   1781   HN ILE  270    -24.027  11.994 -16.771  1.00  0.00      B
ATOM   1782   CA ILE  270    -22.143  11.730 -15.714  1.00  0.00      B
ATOM   1783   HA ILE  270    -21.164  12.127 -15.933  1.00  0.00      B
ATOM   1784   CB ILE  270    -22.741  12.504 -14.536  1.00  0.00      B
ATOM   1785   HB ILE  270    -23.618  11.994 -14.162  1.00  0.00      B
ATOM   1786  CG1 ILE  270    -23.099  13.922 -14.990  1.00  0.00      B
ATOM   1787 HG11 ILE  270    -23.865  13.877 -15.747  1.00  0.00      B
ATOM   1788 HG12 ILE  270    -22.219  14.400 -15.396  1.00  0.00      B
ATOM   1789  CG2 ILE  270    -21.689  12.612 -13.427  1.00  0.00      B
ATOM   1790 HG21 ILE  270    -22.050  13.275 -12.653  1.00  0.00      B
ATOM   1791 HG22 ILE  270    -20.771  13.011 -13.840  1.00  0.00      B
ATOM   1792 HG23 ILE  270    -21.502  11.638 -13.009  1.00  0.00      B
ATOM   1793  CD1 ILE  270    -23.611  14.724 -13.797  1.00  0.00      B
ATOM   1794 HD11 ILE  270    -22.786  14.963 -13.143  1.00  0.00      B
```

Figure 8-32

| | | | | | | | | | |
|---|---|---|---|---|---|---|---|---|---|
| ATOM | 1795 | HD12 | ILE | 270 | -24.343 | 14.140 | -13.257 | 1.00 | 0.00 | B |
| ATOM | 1796 | HD13 | ILE | 270 | -24.067 | 15.637 | -14.148 | 1.00 | 0.00 | B |
| ATOM | 1797 | C | ILE | 270 | -22.021 | 10.234 | -15.408 | 1.00 | 0.00 | B |
| ATOM | 1798 | O | ILE | 270 | -20.936 | 9.721 | -15.312 | 1.00 | 0.00 | B |
| ATOM | 1799 | N | ASN | 271 | -23.120 | 9.517 | -15.236 | 1.00 | 0.00 | B |
| ATOM | 1800 | HN | ASN | 271 | -24.003 | 9.932 | -15.300 | 1.00 | 0.00 | B |
| ATOM | 1801 | CA | ASN | 271 | -22.993 | 8.054 | -14.939 | 1.00 | 0.00 | B |
| ATOM | 1802 | HA | ASN | 271 | -22.590 | 7.904 | -13.948 | 1.00 | 0.00 | B |
| ATOM | 1803 | CB | ASN | 271 | -24.405 | 7.492 | -15.028 | 1.00 | 0.00 | B |
| ATOM | 1804 | HB1 | ASN | 271 | -24.737 | 7.512 | -16.053 | 1.00 | 0.00 | B |
| ATOM | 1805 | HB2 | ASN | 271 | -25.066 | 8.095 | -14.422 | 1.00 | 0.00 | B |
| ATOM | 1806 | CG | ASN | 271 | -24.424 | 6.058 | -14.513 | 1.00 | 0.00 | B |
| ATOM | 1807 | OD1 | ASN | 271 | -23.924 | 5.157 | -15.155 | 1.00 | 0.00 | B |
| ATOM | 1808 | ND2 | ASN | 271 | -24.986 | 5.809 | -13.358 | 1.00 | 0.00 | B |
| ATOM | 1809 | HD21 | ASN | 271 | -25.387 | 6.542 | -12.838 | 1.00 | 0.00 | B |
| ATOM | 1810 | HD22 | ASN | 271 | -25.009 | 4.895 | -13.012 | 1.00 | 0.00 | B |
| ATOM | 1811 | C | ASN | 271 | -22.066 | 7.441 | -15.989 | 1.00 | 0.00 | B |
| ATOM | 1812 | O | ASN | 271 | -21.320 | 6.520 | -15.725 | 1.00 | 0.00 | B |
| ATOM | 1813 | N | LYS | 272 | -22.122 | 7.937 | -17.194 | 1.00 | 0.00 | B |
| ATOM | 1814 | HN | LYS | 272 | -22.737 | 8.664 | -17.397 | 1.00 | 0.00 | B |
| ATOM | 1815 | CA | LYS | 272 | -21.237 | 7.387 | -18.243 | 1.00 | 0.00 | B |
| ATOM | 1816 | HA | LYS | 272 | -21.271 | 6.311 | -18.241 | 1.00 | 0.00 | B |
| ATOM | 1817 | CB | LYS | 272 | -21.743 | 7.944 | -19.574 | 1.00 | 0.00 | B |
| ATOM | 1818 | HB1 | LYS | 272 | -21.066 | 7.657 | -20.364 | 1.00 | 0.00 | B |
| ATOM | 1819 | HB2 | LYS | 272 | -21.799 | 9.023 | -19.519 | 1.00 | 0.00 | B |
| ATOM | 1820 | CG | LYS | 272 | -23.133 | 7.371 | -19.864 | 1.00 | 0.00 | B |
| ATOM | 1821 | HG1 | LYS | 272 | -23.815 | 7.663 | -19.083 | 1.00 | 0.00 | B |
| ATOM | 1822 | HG2 | LYS | 272 | -23.074 | 6.293 | -19.905 | 1.00 | 0.00 | B |
| ATOM | 1823 | CD | LYS | 272 | -23.636 | 7.902 | -21.205 | 1.00 | 0.00 | B |
| ATOM | 1824 | HD1 | LYS | 272 | -23.674 | 8.979 | -21.171 | 1.00 | 0.00 | B |
| ATOM | 1825 | HD2 | LYS | 272 | -24.623 | 7.511 | -21.397 | 1.00 | 0.00 | B |
| ATOM | 1826 | CE | LYS | 272 | -22.683 | 7.463 | -22.320 | 1.00 | 0.00 | B |
| ATOM | 1827 | HE1 | LYS | 272 | -22.620 | 6.387 | -22.358 | 1.00 | 0.00 | B |
| ATOM | 1828 | HE2 | LYS | 272 | -21.702 | 7.896 | -22.167 | 1.00 | 0.00 | B |
| ATOM | 1829 | NZ | LYS | 272 | -23.293 | 7.984 | -23.574 | 1.00 | 0.00 | B |
| ATOM | 1830 | HZ1 | LYS | 272 | -22.582 | 7.987 | -24.332 | 1.00 | 0.00 | B |
| ATOM | 1831 | HZ2 | LYS | 272 | -23.637 | 8.954 | -23.415 | 1.00 | 0.00 | B |
| ATOM | 1832 | HZ3 | LYS | 272 | -24.088 | 7.375 | -23.852 | 1.00 | 0.00 | B |
| ATOM | 1833 | C | LYS | 272 | -19.841 | 7.878 | -17.915 | 1.00 | 0.00 | B |
| ATOM | 1834 | O | LYS | 272 | -18.864 | 7.183 | -18.089 | 1.00 | 0.00 | B |
| ATOM | 1835 | N | ASP | 273 | -19.745 | 9.107 | -17.445 | 1.00 | 0.00 | B |
| ATOM | 1836 | HN | ASP | 273 | -20.552 | 9.657 | -17.348 | 1.00 | 0.00 | B |
| ATOM | 1837 | CA | ASP | 273 | -18.420 | 9.671 | -17.087 | 1.00 | 0.00 | B |
| ATOM | 1838 | HA | ASP | 273 | -17.750 | 9.640 | -17.931 | 1.00 | 0.00 | B |
| ATOM | 1839 | CB | ASP | 273 | -18.697 | 11.116 | -16.670 | 1.00 | 0.00 | B |
| ATOM | 1840 | HB1 | ASP | 273 | -19.383 | 11.126 | -15.838 | 1.00 | 0.00 | B |
| ATOM | 1841 | HB2 | ASP | 273 | -19.132 | 11.651 | -17.501 | 1.00 | 0.00 | B |
| ATOM | 1842 | CG | ASP | 273 | -17.389 | 11.793 | -16.257 | 1.00 | 0.00 | B |
| ATOM | 1843 | OD1 | ASP | 273 | -16.505 | 11.893 | -17.093 | 1.00 | 0.00 | B |
| ATOM | 1844 | OD2 | ASP | 273 | -17.294 | 12.203 | -15.112 | 1.00 | 0.00 | B |
| ATOM | 1845 | C | ASP | 273 | -17.861 | 8.851 | -15.910 | 1.00 | 0.00 | B |
| ATOM | 1846 | O | ASP | 273 | -16.708 | 8.936 | -15.577 | 1.00 | 0.00 | B |
| ATOM | 1847 | N | ILE | 274 | -18.723 | 8.082 | -15.265 | 1.00 | 0.00 | B |
| ATOM | 1848 | HN | ILE | 274 | -19.620 | 8.058 | -15.546 | 1.00 | 0.00 | B |
| ATOM | 1849 | CA | ILE | 274 | -18.320 | 7.236 | -14.119 | 1.00 | 0.00 | B |
| ATOM | 1850 | HA | ILE | 274 | -17.544 | 7.708 | -13.553 | 1.00 | 0.00 | B |
| ATOM | 1851 | CB | ILE | 274 | -19.582 | 7.083 | -13.274 | 1.00 | 0.00 | B |
| ATOM | 1852 | HB | ILE | 274 | -20.380 | 6.718 | -13.890 | 1.00 | 0.00 | B |

Figure 8-33

| | | | | | | | | | |
|---|---|---|---|---|---|---|---|---|---|
| ATOM | 1853 | CG1 | ILE | 274 | -19.974 | 8.443 | -12.688 | 1.00 | 0.00 | B |
| ATOM | 1854 | HG11 | ILE | 274 | -20.867 | 8.336 | -12.102 | 1.00 | 0.00 | B |
| ATOM | 1855 | HG12 | ILE | 274 | -20.150 | 9.137 | -13.484 | 1.00 | 0.00 | B |
| ATOM | 1856 | CG2 | ILE | 274 | -19.330 | 6.094 | -12.152 | 1.00 | 0.00 | B |
| ATOM | 1857 | HG21 | ILE | 274 | -19.432 | 6.593 | -11.200 | 1.00 | 0.00 | B |
| ATOM | 1858 | HG22 | ILE | 274 | -18.333 | 5.693 | -12.247 | 1.00 | 0.00 | B |
| ATOM | 1859 | HG23 | ILE | 274 | -20.049 | 5.291 | -12.216 | 1.00 | 0.00 | B |
| ATOM | 1860 | CD1 | ILE | 274 | -18.851 | 8.973 | -11.805 | 1.00 | 0.00 | B |
| ATOM | 1861 | HD11 | ILE | 274 | -18.353 | 8.150 | -11.323 | 1.00 | 0.00 | B |
| ATOM | 1862 | HD12 | ILE | 274 | -19.266 | 9.631 | -11.057 | 1.00 | 0.00 | B |
| ATOM | 1863 | HD13 | ILE | 274 | -18.144 | 9.518 | -12.412 | 1.00 | 0.00 | B |
| ATOM | 1864 | C | ILE | 274 | -17.867 | 5.885 | -14.693 | 1.00 | 0.00 | B |
| ATOM | 1865 | O | ILE | 274 | -17.118 | 5.155 | -14.093 | 1.00 | 0.00 | B |
| ATOM | 1866 | N | GLU | 275 | -18.404 | 5.557 | -15.857 | 1.00 | 0.00 | B |
| ATOM | 1867 | HN | GLU | 275 | -19.013 | 6.127 | -16.232 | 1.00 | 0.00 | B |
| ATOM | 1868 | CA | GLU | 275 | -18.080 | 4.297 | -16.569 | 1.00 | 0.00 | B |
| ATOM | 1869 | HA | GLU | 275 | -18.118 | 3.449 | -15.902 | 1.00 | 0.00 | B |
| ATOM | 1870 | CB | GLU | 275 | -19.126 | 4.172 | -17.680 | 1.00 | 0.00 | B |
| ATOM | 1871 | HB1 | GLU | 275 | -19.046 | 5.017 | -18.347 | 1.00 | 0.00 | B |
| ATOM | 1872 | HB2 | GLU | 275 | -20.115 | 4.148 | -17.242 | 1.00 | 0.00 | B |
| ATOM | 1873 | CG | GLU | 275 | -18.884 | 2.883 | -18.465 | 1.00 | 0.00 | B |
| ATOM | 1874 | HG1 | GLU | 275 | -17.888 | 2.896 | -18.882 | 1.00 | 0.00 | B |
| ATOM | 1875 | HG2 | GLU | 275 | -19.608 | 2.805 | -19.263 | 1.00 | 0.00 | B |
| ATOM | 1876 | CD | GLU | 275 | -19.024 | 1.684 | -17.531 | 1.00 | 0.00 | B |
| ATOM | 1877 | OE1 | GLU | 275 | -20.103 | 1.500 | -16.994 | 1.00 | 0.00 | B |
| ATOM | 1878 | OE2 | GLU | 275 | -18.049 | 0.969 | -17.366 | 1.00 | 0.00 | B |
| ATOM | 1879 | C | GLU | 275 | -16.697 | 4.485 | -17.140 | 1.00 | 0.00 | B |
| ATOM | 1880 | O | GLU | 275 | -15.942 | 3.558 | -17.305 | 1.00 | 0.00 | B |
| ATOM | 1881 | N | GLU | 276 | -16.372 | 5.707 | -17.511 | 1.00 | 0.00 | B |
| ATOM | 1882 | HN | GLU | 276 | -16.983 | 6.440 | -17.379 | 1.00 | 0.00 | B |
| ATOM | 1883 | CA | GLU | 276 | -15.049 | 5.960 | -18.053 | 1.00 | 0.00 | B |
| ATOM | 1884 | HA | GLU | 276 | -14.741 | 5.200 | -18.757 | 1.00 | 0.00 | B |
| ATOM | 1885 | CB | GLU | 276 | -15.088 | 7.353 | -18.670 | 1.00 | 0.00 | B |
| ATOM | 1886 | HB1 | GLU | 276 | -14.128 | 7.584 | -19.104 | 1.00 | 0.00 | B |
| ATOM | 1887 | HB2 | GLU | 276 | -15.326 | 8.081 | -17.906 | 1.00 | 0.00 | B |
| ATOM | 1888 | CG | GLU | 276 | -16.149 | 7.379 | -19.749 | 1.00 | 0.00 | B |
| ATOM | 1889 | HG1 | GLU | 276 | -17.096 | 7.102 | -19.316 | 1.00 | 0.00 | B |
| ATOM | 1890 | HG2 | GLU | 276 | -15.882 | 6.677 | -20.520 | 1.00 | 0.00 | B |
| ATOM | 1891 | CD | GLU | 276 | -16.251 | 8.784 | -20.345 | 1.00 | 0.00 | B |
| ATOM | 1892 | OE1 | GLU | 276 | -16.979 | 8.946 | -21.309 | 1.00 | 0.00 | B |
| ATOM | 1893 | OE2 | GLU | 276 | -15.606 | 9.675 | -19.823 | 1.00 | 0.00 | B |
| ATOM | 1894 | C | GLU | 276 | -14.261 | 5.938 | -16.819 | 1.00 | 0.00 | B |
| ATOM | 1895 | O | GLU | 276 | -13.373 | 5.160 | -16.646 | 1.00 | 0.00 | B |
| ATOM | 1896 | N | CYS | 277 | -14.721 | 6.750 | -15.870 | 1.00 | 0.00 | B |
| ATOM | 1897 | HN | CYS | 277 | -15.512 | 7.283 | -16.053 | 1.00 | 0.00 | B |
| ATOM | 1898 | CA | CYS | 277 | -14.071 | 6.852 | -14.560 | 1.00 | 0.00 | B |
| ATOM | 1899 | HA | CYS | 277 | -13.172 | 7.381 | -14.606 | 1.00 | 0.00 | B |
| ATOM | 1900 | CB | CYS | 277 | -15.067 | 7.587 | -13.689 | 1.00 | 0.00 | B |
| ATOM | 1901 | HB1 | CYS | 277 | -15.973 | 7.023 | -13.654 | 1.00 | 0.00 | B |
| ATOM | 1902 | HB2 | CYS | 277 | -15.258 | 8.560 | -14.102 | 1.00 | 0.00 | B |
| ATOM | 1903 | SG | CYS | 277 | -14.409 | 7.766 | -12.017 | 1.00 | 0.00 | B |
| ATOM | 1904 | HG1 | CYS | 277 | -14.380 | 6.895 | -11.615 | 1.00 | 0.00 | B |
| ATOM | 1905 | C | CYS | 277 | -13.896 | 5.444 | -14.041 | 1.00 | 0.00 | B |
| ATOM | 1906 | O | CYS | 277 | -12.998 | 5.143 | -13.268 | 1.00 | 0.00 | B |
| ATOM | 1907 | N | ASN | 278 | -14.746 | 4.550 | -14.509 | 1.00 | 0.00 | B |
| ATOM | 1908 | HN | ASN | 278 | -15.406 | 4.797 | -15.162 | 1.00 | 0.00 | B |
| ATOM | 1909 | CA | ASN | 278 | -14.662 | 3.192 | -14.075 | 1.00 | 0.00 | B |
| ATOM | 1910 | HA | ASN | 278 | -14.588 | 3.179 | -13.042 | 1.00 | 0.00 | B |

Figure 8-34

| | | | | | | | | | | |
|---|---|---|---|---|---|---|---|---|---|---|
| ATOM | 1911 | CB | ASN | 278 | -15.973 | 2.518 | -14.491 | 1.00 | 0.00 | B |
| ATOM | 1912 | HB1 | ASN | 278 | -16.061 | 2.524 | -15.553 | 1.00 | 0.00 | B |
| ATOM | 1913 | HB2 | ASN | 278 | -16.806 | 3.045 | -14.054 | 1.00 | 0.00 | B |
| ATOM | 1914 | CG | ASN | 278 | -15.969 | 1.069 | -13.996 | 1.00 | 0.00 | B |
| ATOM | 1915 | OD1 | ASN | 278 | -15.844 | 0.820 | -12.814 | 1.00 | 0.00 | B |
| ATOM | 1916 | ND2 | ASN | 278 | -16.100 | 0.096 | -14.857 | 1.00 | 0.00 | B |
| ATOM | 1917 | HD21 | ASN | 278 | -16.200 | 0.296 | -15.812 | 1.00 | 0.00 | B |
| ATOM | 1918 | HD22 | ASN | 278 | -16.099 | -0.834 | -14.549 | 1.00 | 0.00 | B |
| ATOM | 1919 | C | ASN | 278 | -13.476 | 2.503 | -14.751 | 1.00 | 0.00 | B |
| ATOM | 1920 | O | ASN | 278 | -12.704 | 1.845 | -14.127 | 1.00 | 0.00 | B |
| ATOM | 1921 | N | ALA | 279 | -13.333 | 2.692 | -16.043 | 1.00 | 0.00 | B |
| ATOM | 1922 | HN | ALA | 279 | -13.985 | 3.226 | -16.521 | 1.00 | 0.00 | B |
| ATOM | 1923 | CA | ALA | 279 | -12.203 | 2.053 | -16.802 | 1.00 | 0.00 | B |
| ATOM | 1924 | HA | ALA | 279 | -12.126 | 1.028 | -16.511 | 1.00 | 0.00 | B |
| ATOM | 1925 | CB | ALA | 279 | -12.648 | 2.114 | -18.258 | 1.00 | 0.00 | B |
| ATOM | 1926 | HB1 | ALA | 279 | -12.730 | 3.145 | -18.566 | 1.00 | 0.00 | B |
| ATOM | 1927 | HB2 | ALA | 279 | -13.608 | 1.628 | -18.362 | 1.00 | 0.00 | B |
| ATOM | 1928 | HB3 | ALA | 279 | -11.921 | 1.611 | -18.878 | 1.00 | 0.00 | B |
| ATOM | 1929 | C | ALA | 279 | -10.807 | 2.745 | -16.651 | 1.00 | 0.00 | B |
| ATOM | 1930 | O | ALA | 279 | -9.841 | 2.204 | -17.085 | 1.00 | 0.00 | B |
| ATOM | 1931 | N | ILE | 280 | -10.677 | 3.890 | -16.036 | 1.00 | 0.00 | B |
| ATOM | 1932 | HN | ILE | 280 | -11.402 | 4.251 | -15.558 | 1.00 | 0.00 | B |
| ATOM | 1933 | CA | ILE | 280 | -9.273 | 4.504 | -15.931 | 1.00 | 0.00 | B |
| ATOM | 1934 | HA | ILE | 280 | -8.620 | 3.950 | -16.490 | 1.00 | 0.00 | B |
| ATOM | 1935 | CB | ILE | 280 | -9.210 | 5.987 | -16.390 | 1.00 | 0.00 | B |
| ATOM | 1936 | HB | ILE | 280 | -8.220 | 6.309 | -16.264 | 1.00 | 0.00 | B |
| ATOM | 1937 | CG1 | ILE | 280 | -10.092 | 6.877 | -15.557 | 1.00 | 0.00 | B |
| ATOM | 1938 | HG11 | ILE | 280 | -9.976 | 7.902 | -15.872 | 1.00 | 0.00 | B |
| ATOM | 1939 | HG12 | ILE | 280 | -9.830 | 6.785 | -14.531 | 1.00 | 0.00 | B |
| ATOM | 1940 | CG2 | ILE | 280 | -9.568 | 6.128 | -17.844 | 1.00 | 0.00 | B |
| ATOM | 1941 | HG21 | ILE | 280 | -10.408 | 6.801 | -17.939 | 1.00 | 0.00 | B |
| ATOM | 1942 | HG22 | ILE | 280 | -9.823 | 5.165 | -18.242 | 1.00 | 0.00 | B |
| ATOM | 1943 | HG23 | ILE | 280 | -8.720 | 6.533 | -18.378 | 1.00 | 0.00 | B |
| ATOM | 1944 | CD1 | ILE | 280 | -11.470 | 6.481 | -15.742 | 1.00 | 0.00 | B |
| ATOM | 1945 | HD11 | ILE | 280 | -12.061 | 7.339 | -15.915 | 1.00 | 0.00 | B |
| ATOM | 1946 | HD12 | ILE | 280 | -11.810 | 5.971 | -14.866 | 1.00 | 0.00 | B |
| ATOM | 1947 | HD13 | ILE | 280 | -11.535 | 5.828 | -16.581 | 1.00 | 0.00 | B |
| ATOM | 1948 | C | ILE | 280 | -8.865 | 4.432 | -14.573 | 1.00 | 0.00 | B |
| ATOM | 1949 | O | ILE | 280 | -7.743 | 4.195 | -14.274 | 1.00 | 0.00 | B |
| ATOM | 1950 | N | ILE | 281 | -9.743 | 4.663 | -13.728 | 1.00 | 0.00 | B |
| ATOM | 1951 | HN | ILE | 281 | -10.650 | 4.879 | -14.002 | 1.00 | 0.00 | B |
| ATOM | 1952 | CA | ILE | 281 | -9.407 | 4.604 | -12.353 | 1.00 | 0.00 | B |
| ATOM | 1953 | HA | ILE | 281 | -8.507 | 5.109 | -12.170 | 1.00 | 0.00 | B |
| ATOM | 1954 | CB | ILE | 281 | -10.526 | 5.282 | -11.662 | 1.00 | 0.00 | B |
| ATOM | 1955 | HB | ILE | 281 | -11.439 | 4.723 | -11.825 | 1.00 | 0.00 | B |
| ATOM | 1956 | CG1 | ILE | 281 | -10.641 | 6.664 | -12.300 | 1.00 | 0.00 | B |
| ATOM | 1957 | HG11 | ILE | 281 | -11.146 | 6.560 | -13.256 | 1.00 | 0.00 | B |
| ATOM | 1958 | HG12 | ILE | 281 | -9.643 | 7.055 | -12.476 | 1.00 | 0.00 | B |
| ATOM | 1959 | CG2 | ILE | 281 | -10.221 | 5.381 | -10.157 | 1.00 | 0.00 | B |
| ATOM | 1960 | HG21 | ILE | 281 | -9.693 | 4.494 | -9.838 | 1.00 | 0.00 | B |
| ATOM | 1961 | HG22 | ILE | 281 | -11.145 | 5.468 | -9.606 | 1.00 | 0.00 | B |
| ATOM | 1962 | HG23 | ILE | 281 | -9.608 | 6.251 | -9.972 | 1.00 | 0.00 | B |
| ATOM | 1963 | CD1 | ILE | 281 | -11.430 | 7.602 | -11.410 | 1.00 | 0.00 | B |
| ATOM | 1964 | HD11 | ILE | 281 | -10.765 | 8.044 | -10.683 | 1.00 | 0.00 | B |
| ATOM | 1965 | HD12 | ILE | 281 | -12.205 | 7.045 | -10.903 | 1.00 | 0.00 | B |
| ATOM | 1966 | HD13 | ILE | 281 | -11.873 | 8.374 | -12.012 | 1.00 | 0.00 | B |
| ATOM | 1967 | C | ILE | 281 | -9.295 | 3.185 | -12.008 | 1.00 | 0.00 | B |
| ATOM | 1968 | O | ILE | 281 | -8.497 | 2.789 | -11.184 | 1.00 | 0.00 | B |

Figure 8-35

| ATOM | 1969 | N | GLU | 282 | -10.047 | 2.357 | -12.662 | 1.00 | 0.00 | B |
|---|---|---|---|---|---|---|---|---|---|---|
| ATOM | 1970 | HN | GLU | 282 | -10.670 | 2.664 | -13.357 | 1.00 | 0.00 | B |
| ATOM | 1971 | CA | GLU | 282 | -9.935 | 0.990 | -12.325 | 1.00 | 0.00 | B |
| ATOM | 1972 | HA | GLU | 282 | -9.663 | 0.960 | -11.344 | 1.00 | 0.00 | B |
| ATOM | 1973 | CB | GLU | 282 | -11.302 | 0.356 | -12.510 | 1.00 | 0.00 | B |
| ATOM | 1974 | HB1 | GLU | 282 | -11.522 | 0.286 | -13.559 | 1.00 | 0.00 | B |
| ATOM | 1975 | HB2 | GLU | 282 | -12.055 | 0.954 | -12.017 | 1.00 | 0.00 | B |
| ATOM | 1976 | CG | GLU | 282 | -11.287 | -1.053 | -11.915 | 1.00 | 0.00 | B |
| ATOM | 1977 | HG1 | GLU | 282 | -11.047 | -0.998 | -10.864 | 1.00 | 0.00 | B |
| ATOM | 1978 | HG2 | GLU | 282 | -10.544 | -1.650 | -12.423 | 1.00 | 0.00 | B |
| ATOM | 1979 | CD | GLU | 282 | -12.662 | -1.695 | -12.089 | 1.00 | 0.00 | B |
| ATOM | 1980 | OE1 | GLU | 282 | -13.634 | -1.094 | -11.663 | 1.00 | 0.00 | B |
| ATOM | 1981 | OE2 | GLU | 282 | -12.721 | -2.780 | -12.643 | 1.00 | 0.00 | B |
| ATOM | 1982 | C | GLU | 282 | -8.894 | 0.282 | -13.183 | 1.00 | 0.00 | B |
| ATOM | 1983 | O | GLU | 282 | -7.915 | -0.240 | -12.677 | 1.00 | 0.00 | B |
| ATOM | 1984 | N | GLN | 283 | -9.055 | 0.299 | -14.480 | 1.00 | 0.00 | B |
| ATOM | 1985 | HN | GLN | 283 | -9.803 | 0.795 | -14.892 | 1.00 | 0.00 | B |
| ATOM | 1986 | CA | GLN | 283 | -8.077 | -0.381 | -15.337 | 1.00 | 0.00 | B |
| ATOM | 1987 | HA | GLN | 283 | -7.805 | -1.325 | -14.897 | 1.00 | 0.00 | B |
| ATOM | 1988 | CB | GLN | 283 | -8.826 | -0.634 | -16.634 | 1.00 | 0.00 | B |
| ATOM | 1989 | HB1 | GLN | 283 | -9.184 | 0.287 | -17.026 | 1.00 | 0.00 | B |
| ATOM | 1990 | HB2 | GLN | 283 | -9.657 | -1.297 | -16.450 | 1.00 | 0.00 | B |
| ATOM | 1991 | CG | GLN | 283 | -7.891 | -1.263 | -17.620 | 1.00 | 0.00 | B |
| ATOM | 1992 | HG1 | GLN | 283 | -7.474 | -2.150 | -17.188 | 1.00 | 0.00 | B |
| ATOM | 1993 | HG2 | GLN | 283 | -7.103 | -0.561 | -17.848 | 1.00 | 0.00 | B |
| ATOM | 1994 | CD | GLN | 283 | -8.650 | -1.619 | -18.896 | 1.00 | 0.00 | B |
| ATOM | 1995 | OE1 | GLN | 283 | -9.648 | -2.310 | -18.851 | 1.00 | 0.00 | B |
| ATOM | 1996 | NE2 | GLN | 283 | -8.216 | -1.175 | -20.039 | 1.00 | 0.00 | B |
| ATOM | 1997 | HE21 | GLN | 283 | -7.410 | -0.620 | -20.074 | 1.00 | 0.00 | B |
| ATOM | 1998 | HE22 | GLN | 283 | -8.697 | -1.393 | -20.863 | 1.00 | 0.00 | B |
| ATOM | 1999 | C | GLN | 283 | -6.818 | 0.455 | -15.568 | 1.00 | 0.00 | B |
| ATOM | 2000 | O | GLN | 283 | -5.824 | -0.058 | -16.046 | 1.00 | 0.00 | B |
| ATOM | 2001 | N | PHE | 284 | -6.819 | 1.724 | -15.251 | 1.00 | 0.00 | B |
| ATOM | 2002 | HN | PHE | 284 | -7.622 | 2.156 | -14.853 | 1.00 | 0.00 | B |
| ATOM | 2003 | CA | PHE | 284 | -5.571 | 2.501 | -15.492 | 1.00 | 0.00 | B |
| ATOM | 2004 | HA | PHE | 284 | -4.844 | 1.865 | -15.968 | 1.00 | 0.00 | B |
| ATOM | 2005 | CB | PHE | 284 | -5.925 | 3.657 | -16.450 | 1.00 | 0.00 | B |
| ATOM | 2006 | HB1 | PHE | 284 | -5.095 | 4.346 | -16.497 | 1.00 | 0.00 | B |
| ATOM | 2007 | HB2 | PHE | 284 | -6.788 | 4.172 | -16.093 | 1.00 | 0.00 | B |
| ATOM | 2008 | CG | PHE | 284 | -6.202 | 3.120 | -17.835 | 1.00 | 0.00 | B |
| ATOM | 2009 | CD1 | PHE | 284 | -7.244 | 2.194 | -18.042 | 1.00 | 0.00 | B |
| ATOM | 2010 | HD1 | PHE | 284 | -7.834 | 1.864 | -17.217 | 1.00 | 0.00 | B |
| ATOM | 2011 | CD2 | PHE | 284 | -5.415 | 3.552 | -18.929 | 1.00 | 0.00 | B |
| ATOM | 2012 | HD2 | PHE | 284 | -4.615 | 4.261 | -18.773 | 1.00 | 0.00 | B |
| ATOM | 2013 | CE1 | PHE | 284 | -7.506 | 1.697 | -19.339 | 1.00 | 0.00 | B |
| ATOM | 2014 | HE1 | PHE | 284 | -8.306 | 0.990 | -19.493 | 1.00 | 0.00 | B |
| ATOM | 2015 | CE2 | PHE | 284 | -5.675 | 3.054 | -20.229 | 1.00 | 0.00 | B |
| ATOM | 2016 | HE2 | PHE | 284 | -5.075 | 3.381 | -21.064 | 1.00 | 0.00 | B |
| ATOM | 2017 | CZ | PHE | 284 | -6.721 | 2.126 | -20.432 | 1.00 | 0.00 | B |
| ATOM | 2018 | HZ | PHE | 284 | -6.922 | 1.746 | -21.422 | 1.00 | 0.00 | B |
| ATOM | 2019 | C | PHE | 284 | -4.991 | 3.036 | -14.192 | 1.00 | 0.00 | B |
| ATOM | 2020 | O | PHE | 284 | -3.840 | 3.317 | -14.131 | 1.00 | 0.00 | B |
| ATOM | 2021 | N | ILE | 285 | -5.772 | 3.207 | -13.156 | 1.00 | 0.00 | B |
| ATOM | 2022 | HN | ILE | 285 | -6.717 | 2.928 | -13.178 | 1.00 | 0.00 | B |
| ATOM | 2023 | CA | ILE | 285 | -5.190 | 3.729 | -11.901 | 1.00 | 0.00 | B |
| ATOM | 2024 | HA | ILE | 285 | -4.297 | 4.282 | -12.122 | 1.00 | 0.00 | B |
| ATOM | 2025 | CB | ILE | 285 | -6.251 | 4.671 | -11.339 | 1.00 | 0.00 | B |
| ATOM | 2026 | HB | ILE | 285 | -7.189 | 4.148 | -11.278 | 1.00 | 0.00 | B |

Figure 8-36

```
ATOM   2027  CG1  ILE  285   -6.400   5.912 -12.280  1.00  0.00      B
ATOM   2028  HG11 ILE  285   -7.256   6.505 -11.972  1.00  0.00      B
ATOM   2029  HG12 ILE  285   -6.554   5.579 -13.300  1.00  0.00      B
ATOM   2030  CG2  ILE  285   -5.833   5.131  -9.941  1.00  0.00      B
ATOM   2031  HG21 ILE  285   -4.780   4.936  -9.798  1.00  0.00      B
ATOM   2032  HG22 ILE  285   -6.404   4.592  -9.199  1.00  0.00      B
ATOM   2033  HG23 ILE  285   -6.019   6.191  -9.839  1.00  0.00      B
ATOM   2034  CD1  ILE  285   -5.134   6.773 -12.219  1.00  0.00      B
ATOM   2035  HD11 ILE  285   -4.275   6.146 -12.052  1.00  0.00      B
ATOM   2036  HD12 ILE  285   -5.222   7.483 -11.411  1.00  0.00      B
ATOM   2037  HD13 ILE  285   -5.016   7.304 -13.152  1.00  0.00      B
ATOM   2038  C    ILE  285   -4.858   2.574 -10.940  1.00  0.00      B
ATOM   2039  O    ILE  285   -4.106   2.735 -10.001  1.00  0.00      B
ATOM   2040  N    ASP  286   -5.415   1.402 -11.171  1.00  0.00      B
ATOM   2041  HN   ASP  286   -6.033   1.286 -11.936  1.00  0.00      B
ATOM   2042  CA   ASP  286   -5.126   0.244 -10.264  1.00  0.00      B
ATOM   2043  HA   ASP  286   -5.497   0.450  -9.275  1.00  0.00      B
ATOM   2044  CB   ASP  286   -5.899  -0.930 -10.860  1.00  0.00      B
ATOM   2045  HB1  ASP  286   -5.593  -1.083 -11.883  1.00  0.00      B
ATOM   2046  HB2  ASP  286   -6.957  -0.715 -10.827  1.00  0.00      B
ATOM   2047  CG   ASP  286   -5.609  -2.192 -10.048  1.00  0.00      B
ATOM   2048  OD1  ASP  286   -4.514  -2.713 -10.172  1.00  0.00      B
ATOM   2049  OD2  ASP  286   -6.485  -2.613  -9.308  1.00  0.00      B
ATOM   2050  C    ASP  286   -3.620  -0.090 -10.200  1.00  0.00      B
ATOM   2051  O    ASP  286   -3.197  -0.850  -9.355  1.00  0.00      B
ATOM   2052  N    TYR  287   -2.806   0.447 -11.074  1.00  0.00      B
ATOM   2053  HN   TYR  287   -3.147   1.048 -11.772  1.00  0.00      B
ATOM   2054  CA   TYR  287   -1.339   0.109 -10.997  1.00  0.00      B
ATOM   2055  HA   TYR  287   -1.215  -0.958 -11.088  1.00  0.00      B
ATOM   2056  CB   TYR  287   -0.652   0.807 -12.197  1.00  0.00      B
ATOM   2057  HB1  TYR  287   -1.082   0.425 -13.114  1.00  0.00      B
ATOM   2058  HB2  TYR  287    0.401   0.576 -12.182  1.00  0.00      B
ATOM   2059  CG   TYR  287   -0.828   2.323 -12.163  1.00  0.00      B
ATOM   2060  CD1  TYR  287   -0.344   3.107 -11.076  1.00  0.00      B
ATOM   2061  HD1  TYR  287    0.158   2.639 -10.247  1.00  0.00      B
ATOM   2062  CD2  TYR  287   -1.472   2.956 -13.241  1.00  0.00      B
ATOM   2063  HD2  TYR  287   -1.842   2.365 -14.064  1.00  0.00      B
ATOM   2064  CE1  TYR  287   -0.520   4.521 -11.094  1.00  0.00      B
ATOM   2065  HE1  TYR  287   -0.159   5.123 -10.277  1.00  0.00      B
ATOM   2066  CE2  TYR  287   -1.646   4.362 -13.250  1.00  0.00      B
ATOM   2067  HE2  TYR  287   -2.151   4.842 -14.084  1.00  0.00      B
ATOM   2068  CZ   TYR  287   -1.171   5.139 -12.182  1.00  0.00      B
ATOM   2069  OH   TYR  287   -1.342   6.508 -12.201  1.00  0.00      B
ATOM   2070  HH   TYR  287   -2.280   6.691 -12.293  1.00  0.00      B
ATOM   2071  C    TYR  287   -0.753   0.573  -9.665  1.00  0.00      B
ATOM   2072  O    TYR  287    0.280   0.102  -9.233  1.00  0.00      B
ATOM   2073  N    LEU  288   -1.404   1.488  -9.008  1.00  0.00      B
ATOM   2074  HN   LEU  288   -2.235   1.854  -9.372  1.00  0.00      B
ATOM   2075  CA   LEU  288   -0.882   1.981  -7.698  1.00  0.00      B
ATOM   2076  HA   LEU  288    0.012   2.513  -7.844  1.00  0.00      B
ATOM   2077  CB   LEU  288   -1.973   2.912  -7.169  1.00  0.00      B
ATOM   2078  HB1  LEU  288   -1.717   3.239  -6.173  1.00  0.00      B
ATOM   2079  HB2  LEU  288   -2.918   2.384  -7.146  1.00  0.00      B
ATOM   2080  CG   LEU  288   -2.088   4.128  -8.088  1.00  0.00      B
ATOM   2081  HG   LEU  288   -2.229   3.800  -9.106  1.00  0.00      B
ATOM   2082  CD1  LEU  288   -3.271   4.993  -7.659  1.00  0.00      B
ATOM   2083  HD11 LEU  288   -3.026   5.509  -6.745  1.00  0.00      B
ATOM   2084  HD12 LEU  288   -4.137   4.368  -7.498  1.00  0.00      B
```

Figure 8-37

| | | | | | | | | | |
|---|---|---|---|---|---|---|---|---|---|
| ATOM | 2085 | HD13 | LEU | 288 | -3.487 | 5.715 | -8.432 | 1.00 | 0.00 | B |
| ATOM | 2086 | CD2 | LEU | 288 | -0.804 | 4.951 | -7.986 | 1.00 | 0.00 | B |
| ATOM | 2087 | HD21 | LEU | 288 | -0.920 | 5.867 | -8.547 | 1.00 | 0.00 | B |
| ATOM | 2088 | HD22 | LEU | 288 | 0.020 | 4.382 | -8.390 | 1.00 | 0.00 | B |
| ATOM | 2089 | HD23 | LEU | 288 | -0.607 | 5.185 | -6.949 | 1.00 | 0.00 | B |
| ATOM | 2090 | C | LEU | 288 | -0.648 | 0.822 | -6.740 | 1.00 | 0.00 | B |
| ATOM | 2091 | O | LEU | 288 | 0.130 | 0.910 | -5.812 | 1.00 | 0.00 | B |
| ATOM | 2092 | N | ARG | 289 | -1.300 | -0.256 | -6.969 | 1.00 | 0.00 | B |
| ATOM | 2093 | HN | ARG | 289 | -1.893 | -0.295 | -7.734 | 1.00 | 0.00 | B |
| ATOM | 2094 | CA | ARG | 289 | -1.133 | -1.444 | -6.078 | 1.00 | 0.00 | B |
| ATOM | 2095 | HA | ARG | 289 | -1.473 | -1.214 | -5.084 | 1.00 | 0.00 | B |
| ATOM | 2096 | CB | ARG | 289 | -2.015 | -2.529 | -6.684 | 1.00 | 0.00 | B |
| ATOM | 2097 | HB1 | ARG | 289 | -1.918 | -3.436 | -6.107 | 1.00 | 0.00 | B |
| ATOM | 2098 | HB2 | ARG | 289 | -1.710 | -2.714 | -7.705 | 1.00 | 0.00 | B |
| ATOM | 2099 | CG | ARG | 289 | -3.470 | -2.068 | -6.661 | 1.00 | 0.00 | B |
| ATOM | 2100 | HG1 | ARG | 289 | -3.578 | -1.185 | -7.270 | 1.00 | 0.00 | B |
| ATOM | 2101 | HG2 | ARG | 289 | -3.761 | -1.843 | -5.644 | 1.00 | 0.00 | B |
| ATOM | 2102 | CD | ARG | 289 | -4.361 | -3.177 | -7.212 | 1.00 | 0.00 | B |
| ATOM | 2103 | HD1 | ARG | 289 | -4.050 | -3.449 | -8.205 | 1.00 | 0.00 | B |
| ATOM | 2104 | HD2 | ARG | 289 | -5.396 | -2.861 | -7.211 | 1.00 | 0.00 | B |
| ATOM | 2105 | NE | ARG | 289 | -4.165 | -4.324 | -6.284 | 1.00 | 0.00 | B |
| ATOM | 2106 | HE | ARG | 289 | -3.651 | -4.205 | -5.459 | 1.00 | 0.00 | B |
| ATOM | 2107 | CZ | ARG | 289 | -4.678 | -5.488 | -6.570 | 1.00 | 0.00 | B |
| ATOM | 2108 | NH1 | ARG | 289 | -5.842 | -5.825 | -6.087 | 1.00 | 0.00 | B |
| ATOM | 2109 | HH11 | ARG | 289 | -6.341 | -5.191 | -5.497 | 1.00 | 0.00 | B |
| ATOM | 2110 | HH12 | ARG | 289 | -6.236 | -6.718 | -6.308 | 1.00 | 0.00 | B |
| ATOM | 2111 | NH2 | ARG | 289 | -4.026 | -6.316 | -7.341 | 1.00 | 0.00 | B |
| ATOM | 2112 | HH21 | ARG | 289 | -3.134 | -6.057 | -7.712 | 1.00 | 0.00 | B |
| ATOM | 2113 | HH22 | ARG | 289 | -4.420 | -7.209 | -7.562 | 1.00 | 0.00 | B |
| ATOM | 2114 | C | ARG | 289 | 0.332 | -1.892 | -6.052 | 1.00 | 0.00 | B |
| ATOM | 2115 | OT1 | ARG | 289 | 1.021 | -1.540 | -5.109 | 1.00 | 0.00 | B |
| ATOM | 2116 | OT2 | ARG | 289 | 0.738 | -2.579 | -6.975 | 1.00 | 0.00 | B |

Figure 9-1

Coordinates determined by NMR for sub-domain A [EnvZ(C)(290-450), SEQ ID NO:14]

```
REMARK final envZ structures
REMARK DATE:18-Feb-98   13:12:56      created by user:
ATOM     1  CA   THR   290    13.696 -20.007  11.535  1.00  0.00
ATOM     2  HA   THR   290    12.665 -19.951  11.842  1.00  0.00
ATOM     3  CB   THR   290    14.180 -18.628  11.081  1.00  0.00
ATOM     4  HB   THR   290    13.750 -18.395  10.121  1.00  0.00
ATOM     5  OG1  THR   290    15.598 -18.633  10.977  1.00  0.00
ATOM     6  HG1  THR   290    15.839 -19.184  10.228  1.00  0.00
ATOM     7  CG2  THR   290    13.744 -17.573  12.098  1.00  0.00
ATOM     8  HG21 THR   290    14.505 -16.810  12.173  1.00  0.00
ATOM     9  HG22 THR   290    13.604 -18.038  13.062  1.00  0.00
ATOM    10  HG23 THR   290    12.815 -17.124  11.776  1.00  0.00
ATOM    11  C    THR   290    13.862 -21.033  10.411  1.00  0.00
ATOM    12  O    THR   290    14.757 -21.855  10.433  1.00  0.00
ATOM    13  N    THR   290    14.564 -20.365  12.694  1.00  0.00
ATOM    14  HT1  THR   290    14.206 -19.898  13.552  1.00  0.00
ATOM    15  HT2  THR   290    15.537 -20.052  12.510  1.00  0.00
ATOM    16  HT3  THR   290    14.551 -21.396  12.830  1.00  0.00
ATOM    17  N    GLY   291    13.008 -20.989   9.430  1.00  0.00
ATOM    18  HN   GLY   291    12.295 -20.317   9.433  1.00  0.00
ATOM    19  CA   GLY   291    13.111 -21.958   8.304  1.00  0.00
ATOM    20  HA1  GLY   291    13.566 -22.871   8.654  1.00  0.00
ATOM    21  HA2  GLY   291    13.716 -21.530   7.515  1.00  0.00
ATOM    22  C    GLY   291    11.711 -22.262   7.771  1.00  0.00
ATOM    23  O    GLY   291    11.539 -22.650   6.633  1.00  0.00
ATOM    24  N    GLN   292    10.710 -22.087   8.588  1.00  0.00
ATOM    25  HN   GLN   292    10.872 -21.774   9.502  1.00  0.00
ATOM    26  CA   GLN   292     9.318 -22.364   8.134  1.00  0.00
ATOM    27  HA   GLN   292     9.322 -23.028   7.287  1.00  0.00
ATOM    28  CB   GLN   292     8.645 -23.042   9.327  1.00  0.00
ATOM    29  HB1  GLN   292     7.595 -23.175   9.121  1.00  0.00
ATOM    30  HB2  GLN   292     8.767 -22.426  10.207  1.00  0.00
ATOM    31  CG   GLN   292     9.293 -24.407   9.565  1.00  0.00
ATOM    32  HG1  GLN   292    10.356 -24.335   9.391  1.00  0.00
ATOM    33  HG2  GLN   292     8.864 -25.131   8.887  1.00  0.00
ATOM    34  CD   GLN   292     9.044 -24.848  11.008  1.00  0.00
ATOM    35  OE1  GLN   292     8.609 -25.957  11.249  1.00  0.00
ATOM    36  NE2  GLN   292     9.304 -24.022  11.985  1.00  0.00
ATOM    37  HE21 GLN   292     9.654 -23.127  11.791  1.00  0.00
ATOM    38  HE22 GLN   292     9.151 -24.297  12.913  1.00  0.00
ATOM    39  C    GLN   292     8.610 -21.052   7.786  1.00  0.00
ATOM    40  O    GLN   292     8.870 -20.021   8.374  1.00  0.00
ATOM    41  N    GLU   293     7.718 -21.081   6.835  1.00  0.00
ATOM    42  HN   GLU   293     7.521 -21.921   6.371  1.00  0.00
ATOM    43  CA   GLU   293     6.998 -19.831   6.455  1.00  0.00
ATOM    44  HA   GLU   293     7.223 -19.041   7.152  1.00  0.00
ATOM    45  CB   GLU   293     7.536 -19.473   5.070  1.00  0.00
ATOM    46  HB1  GLU   293     7.471 -20.335   4.425  1.00  0.00
ATOM    47  HB2  GLU   293     8.569 -19.164   5.155  1.00  0.00
ATOM    48  CG   GLU   293     6.708 -18.331   4.479  1.00  0.00
ATOM    49  HG1  GLU   293     7.357 -17.502   4.241  1.00  0.00
ATOM    50  HG2  GLU   293     5.968 -18.013   5.199  1.00  0.00
ATOM    51  CD   GLU   293     6.011 -18.811   3.205  1.00  0.00
ATOM    52  OE1  GLU   293     4.793 -18.881   3.211  1.00  0.00
ATOM    53  OE2  GLU   293     6.706 -19.101   2.245  1.00  0.00
ATOM    54  C    GLU   293     5.486 -20.081   6.399  1.00  0.00
```

Figure 9-2

```
ATOM     55   O    GLU   293      4.864  -19.946   5.364  1.00  0.00
ATOM     56   N    MET   294      4.892  -20.445   7.505  1.00  0.00
ATOM     57   HN   MET   294      5.413  -20.550   8.328  1.00  0.00
ATOM     58   CA   MET   294      3.419  -20.703   7.514  1.00  0.00
ATOM     59   HA   MET   294      2.989  -20.471   6.549  1.00  0.00
ATOM     60   CB   MET   294      3.278  -22.197   7.812  1.00  0.00
ATOM     61   HB1  MET   294      2.239  -22.481   7.749  1.00  0.00
ATOM     62   HB2  MET   294      3.649  -22.401   8.807  1.00  0.00
ATOM     63   CG   MET   294      4.088  -23.002   6.790  1.00  0.00
ATOM     64   HG1  MET   294      4.730  -23.699   7.309  1.00  0.00
ATOM     65   HG2  MET   294      4.690  -22.329   6.198  1.00  0.00
ATOM     66   SD   MET   294      2.958  -23.913   5.706  1.00  0.00
ATOM     67   CE   MET   294      3.153  -25.536   6.482  1.00  0.00
ATOM     68   HE1  MET   294      2.837  -26.306   5.790  1.00  0.00
ATOM     69   HE2  MET   294      2.549  -25.585   7.372  1.00  0.00
ATOM     70   HE3  MET   294      4.192  -25.685   6.746  1.00  0.00
ATOM     71   C    MET   294      2.748  -19.863   8.603  1.00  0.00
ATOM     72   O    MET   294      2.768  -20.210   9.768  1.00  0.00
ATOM     73   N    PRO   295      2.171  -18.784   8.169  1.00  0.00
ATOM     74   CA   PRO   295      1.477  -17.860   9.086  1.00  0.00
ATOM     75   HA   PRO   295      2.049  -17.707   9.983  1.00  0.00
ATOM     76   CB   PRO   295      1.399  -16.571   8.290  1.00  0.00
ATOM     77   HB1  PRO   295      2.242  -15.939   8.515  1.00  0.00
ATOM     78   HB2  PRO   295      0.472  -16.055   8.502  1.00  0.00
ATOM     79   CG   PRO   295      1.447  -16.994   6.846  1.00  0.00
ATOM     80   HG1  PRO   295      2.007  -16.280   6.271  1.00  0.00
ATOM     81   HG2  PRO   295      0.444  -17.080   6.456  1.00  0.00
ATOM     82   CD   PRO   295      2.128  -18.331   6.784  1.00  0.00
ATOM     83   HD1  PRO   295      3.127  -18.228   6.395  1.00  0.00
ATOM     84   HD2  PRO   295      1.551  -19.018   6.176  1.00  0.00
ATOM     85   C    PRO   295      0.071  -18.369   9.419  1.00  0.00
ATOM     86   O    PRO   295     -0.900  -17.964   8.817  1.00  0.00
ATOM     87   N    MET   296     -0.044  -19.239  10.379  1.00  0.00
ATOM     88   HN   MET   296      0.742  -19.531  10.866  1.00  0.00
ATOM     89   CA   MET   296     -1.375  -19.771  10.752  1.00  0.00
ATOM     90   HA   MET   296     -2.155  -19.128  10.370  1.00  0.00
ATOM     91   CB   MET   296     -1.464  -21.126  10.102  1.00  0.00
ATOM     92   HB1  MET   296     -2.402  -21.589  10.355  1.00  0.00
ATOM     93   HB2  MET   296     -0.645  -21.745  10.441  1.00  0.00
ATOM     94   CG   MET   296     -1.380  -20.931   8.601  1.00  0.00
ATOM     95   HG1  MET   296     -0.395  -21.194   8.263  1.00  0.00
ATOM     96   HG2  MET   296     -1.574  -19.892   8.372  1.00  0.00
ATOM     97   SD   MET   296     -2.607  -21.962   7.768  1.00  0.00
ATOM     98   CE   MET   296     -3.050  -20.768   6.480  1.00  0.00
ATOM     99   HE1  MET   296     -3.390  -19.851   6.943  1.00  0.00
ATOM    100   HE2  MET   296     -3.837  -21.171   5.868  1.00  0.00
ATOM    101   HE3  MET   296     -2.183  -20.566   5.865  1.00  0.00
ATOM    102   C    MET   296     -1.462  -19.864  12.261  1.00  0.00
ATOM    103   O    MET   296     -0.980  -20.788  12.884  1.00  0.00
ATOM    104   N    GLU   297     -2.074  -18.904  12.827  1.00  0.00
ATOM    105   HN   GLU   297     -2.452  -18.215  12.269  1.00  0.00
ATOM    106   CA   GLU   297     -2.240  -18.849  14.315  1.00  0.00
ATOM    107   HA   GLU   297     -1.652  -19.615  14.791  1.00  0.00
ATOM    108   CB   GLU   297     -1.725  -17.467  14.725  1.00  0.00
ATOM    109   HB1  GLU   297     -0.677  -17.387  14.480  1.00  0.00
ATOM    110   HB2  GLU   297     -1.856  -17.336  15.790  1.00  0.00
ATOM    111   CG   GLU   297     -2.505  -16.383  13.977  1.00  0.00
ATOM    112   HG1  GLU   297     -3.560  -16.495  14.178  1.00  0.00
```

Figure 9-3

```
ATOM    113  HG2  GLU  297    -2.328  -16.478  12.916  1.00  0.00
ATOM    114  CD   GLU  297    -2.043  -15.005  14.449  1.00  0.00
ATOM    115  OE1  GLU  297    -1.414  -14.938  15.493  1.00  0.00
ATOM    116  OE2  GLU  297    -2.323  -14.039  13.759  1.00  0.00
ATOM    117  C    GLU  297    -3.708  -19.004  14.688  1.00  0.00
ATOM    118  O    GLU  297    -4.556  -19.130  13.839  1.00  0.00
ATOM    119  N    MET  298    -4.017  -18.944  15.951  1.00  0.00
ATOM    120  HN   MET  298    -3.316  -18.811  16.619  1.00  0.00
ATOM    121  CA   MET  298    -5.440  -19.093  16.376  1.00  0.00
ATOM    122  HA   MET  298    -5.940  -19.823  15.766  1.00  0.00
ATOM    123  CB   MET  298    -5.367  -19.587  17.824  1.00  0.00
ATOM    124  HB1  MET  298    -6.351  -19.883  18.154  1.00  0.00
ATOM    125  HB2  MET  298    -4.999  -18.792  18.457  1.00  0.00
ATOM    126  CG   MET  298    -4.420  -20.787  17.910  1.00  0.00
ATOM    127  HG1  MET  298    -3.647  -20.585  18.636  1.00  0.00
ATOM    128  HG2  MET  298    -3.971  -20.961  16.944  1.00  0.00
ATOM    129  SD   MET  298    -5.353  -22.252  18.414  1.00  0.00
ATOM    130  CE   MET  298    -6.752  -22.016  17.294  1.00  0.00
ATOM    131  HE1  MET  298    -7.472  -21.350  17.753  1.00  0.00
ATOM    132  HE2  MET  298    -7.220  -22.964  17.095  1.00  0.00
ATOM    133  HE3  MET  298    -6.399  -21.587  16.364  1.00  0.00
ATOM    134  C    MET  298    -6.170  -17.749  16.310  1.00  0.00
ATOM    135  O    MET  298    -6.057  -16.915  17.187  1.00  0.00
ATOM    136  N    ALA  299    -6.922  -17.546  15.260  1.00  0.00
ATOM    137  HN   ALA  299    -6.980  -18.231  14.572  1.00  0.00
ATOM    138  CA   ALA  299    -7.675  -16.277  15.096  1.00  0.00
ATOM    139  HA   ALA  299    -7.429  -15.585  15.877  1.00  0.00
ATOM    140  CB   ALA  299    -7.220  -15.731  13.745  1.00  0.00
ATOM    141  HB1  ALA  299    -7.621  -14.740  13.604  1.00  0.00
ATOM    142  HB2  ALA  299    -7.580  -16.380  12.956  1.00  0.00
ATOM    143  HB3  ALA  299    -6.143  -15.694  13.716  1.00  0.00
ATOM    144  C    ALA  299    -9.181  -16.554  15.065  1.00  0.00
ATOM    145  O    ALA  299    -9.614  -17.644  14.745  1.00  0.00
ATOM    146  N    ASP  300    -9.981  -15.579  15.393  1.00  0.00
ATOM    147  HN   ASP  300    -9.613  -14.710  15.650  1.00  0.00
ATOM    148  CA   ASP  300   -11.456  -15.788  15.380  1.00  0.00
ATOM    149  HA   ASP  300   -11.708  -16.745  15.793  1.00  0.00
ATOM    150  CB   ASP  300   -12.024  -14.672  16.255  1.00  0.00
ATOM    151  HB1  ASP  300   -13.081  -14.567  16.064  1.00  0.00
ATOM    152  HB2  ASP  300   -11.522  -13.743  16.026  1.00  0.00
ATOM    153  CG   ASP  300   -11.808  -15.022  17.727  1.00  0.00
ATOM    154  OD1  ASP  300   -12.102  -14.184  18.564  1.00  0.00
ATOM    155  OD2  ASP  300   -11.352  -16.121  17.992  1.00  0.00
ATOM    156  C    ASP  300   -11.977  -15.669  13.951  1.00  0.00
ATOM    157  O    ASP  300   -11.860  -14.634  13.326  1.00  0.00
ATOM    158  N    LEU  301   -12.542  -16.717  13.419  1.00  0.00
ATOM    159  HN   LEU  301   -12.622  -17.549  13.931  1.00  0.00
ATOM    160  CA   LEU  301   -13.061  -16.637  12.029  1.00  0.00
ATOM    161  HA   LEU  301   -12.266  -16.388  11.354  1.00  0.00
ATOM    162  CB   LEU  301   -13.613  -18.033  11.711  1.00  0.00
ATOM    163  HB1  LEU  301   -14.514  -17.939  11.123  1.00  0.00
ATOM    164  HB2  LEU  301   -13.839  -18.549  12.634  1.00  0.00
ATOM    165  CG   LEU  301   -12.571  -18.839  10.917  1.00  0.00
ATOM    166  HG   LEU  301   -11.759  -19.120  11.573  1.00  0.00
ATOM    167  CD1  LEU  301   -13.223  -20.099  10.348  1.00  0.00
ATOM    168  HD11 LEU  301   -12.476  -20.870  10.236  1.00  0.00
ATOM    169  HD12 LEU  301   -13.657  -19.875   9.384  1.00  0.00
ATOM    170  HD13 LEU  301   -13.995  -20.440  11.020  1.00  0.00
```

Figure 9-4

| | | | | | | | | |
|---|---|---|---|---|---|---|---|---|
| ATOM | 171 | CD2 | LEU | 301 | -12.030 | -17.994 | 9.762 | 1.00 | 0.00 |
| ATOM | 172 | HD21 | LEU | 301 | -12.795 | -17.310 | 9.428 | 1.00 | 0.00 |
| ATOM | 173 | HD22 | LEU | 301 | -11.743 | -18.640 | 8.947 | 1.00 | 0.00 |
| ATOM | 174 | HD23 | LEU | 301 | -11.169 | -17.434 | 10.099 | 1.00 | 0.00 |
| ATOM | 175 | C | LEU | 301 | -14.163 | -15.583 | 11.952 | 1.00 | 0.00 |
| ATOM | 176 | O | LEU | 301 | -14.428 | -15.025 | 10.909 | 1.00 | 0.00 |
| ATOM | 177 | N | ASN | 302 | -14.806 | -15.300 | 13.048 | 1.00 | 0.00 |
| ATOM | 178 | HN | ASN | 302 | -14.574 | -15.755 | 13.888 | 1.00 | 0.00 |
| ATOM | 179 | CA | ASN | 302 | -15.887 | -14.278 | 13.021 | 1.00 | 0.00 |
| ATOM | 180 | HA | ASN | 302 | -16.465 | -14.369 | 12.118 | 1.00 | 0.00 |
| ATOM | 181 | CB | ASN | 302 | -16.757 | -14.577 | 14.240 | 1.00 | 0.00 |
| ATOM | 182 | HB1 | ASN | 302 | -16.267 | -14.215 | 15.131 | 1.00 | 0.00 |
| ATOM | 183 | HB2 | ASN | 302 | -16.912 | -15.644 | 14.321 | 1.00 | 0.00 |
| ATOM | 184 | CG | ASN | 302 | -18.103 | -13.876 | 14.083 | 1.00 | 0.00 |
| ATOM | 185 | OD1 | ASN | 302 | -18.248 | -12.995 | 13.259 | 1.00 | 0.00 |
| ATOM | 186 | ND2 | ASN | 302 | -19.105 | -14.233 | 14.838 | 1.00 | 0.00 |
| ATOM | 187 | HD21 | ASN | 302 | -18.990 | -14.946 | 15.501 | 1.00 | 0.00 |
| ATOM | 188 | HD22 | ASN | 302 | -19.975 | -13.792 | 14.739 | 1.00 | 0.00 |
| ATOM | 189 | C | ASN | 302 | -15.271 | -12.886 | 13.123 | 1.00 | 0.00 |
| ATOM | 190 | O | ASN | 302 | -15.877 | -11.892 | 12.769 | 1.00 | 0.00 |
| ATOM | 191 | N | ALA | 303 | -14.064 | -12.813 | 13.602 | 1.00 | 0.00 |
| ATOM | 192 | HN | ALA | 303 | -13.599 | -13.627 | 13.866 | 1.00 | 0.00 |
| ATOM | 193 | CA | ALA | 303 | -13.387 | -11.497 | 13.735 | 1.00 | 0.00 |
| ATOM | 194 | HA | ALA | 303 | -14.077 | -10.749 | 14.078 | 1.00 | 0.00 |
| ATOM | 195 | CB | ALA | 303 | -12.287 | -11.719 | 14.774 | 1.00 | 0.00 |
| ATOM | 196 | HB1 | ALA | 303 | -11.901 | -10.765 | 15.099 | 1.00 | 0.00 |
| ATOM | 197 | HB2 | ALA | 303 | -11.489 | -12.300 | 14.335 | 1.00 | 0.00 |
| ATOM | 198 | HB3 | ALA | 303 | -12.695 | -12.250 | 15.622 | 1.00 | 0.00 |
| ATOM | 199 | C | ALA | 303 | -12.788 | -11.102 | 12.390 | 1.00 | 0.00 |
| ATOM | 200 | O | ALA | 303 | -12.851 | -9.961 | 11.978 | 1.00 | 0.00 |
| ATOM | 201 | N | VAL | 304 | -12.206 | -12.044 | 11.701 | 1.00 | 0.00 |
| ATOM | 202 | HN | VAL | 304 | -12.167 | -12.956 | 12.057 | 1.00 | 0.00 |
| ATOM | 203 | CA | VAL | 304 | -11.602 | -11.735 | 10.377 | 1.00 | 0.00 |
| ATOM | 204 | HA | VAL | 304 | -10.924 | -10.900 | 10.456 | 1.00 | 0.00 |
| ATOM | 205 | CB | VAL | 304 | -10.838 | -12.998 | 9.979 | 1.00 | 0.00 |
| ATOM | 206 | HB | VAL | 304 | -11.529 | -13.828 | 9.903 | 1.00 | 0.00 |
| ATOM | 207 | CG1 | VAL | 304 | -10.155 | -12.779 | 8.630 | 1.00 | 0.00 |
| ATOM | 208 | HG11 | VAL | 304 | -9.337 | -12.085 | 8.751 | 1.00 | 0.00 |
| ATOM | 209 | HG12 | VAL | 304 | -10.868 | -12.376 | 7.927 | 1.00 | 0.00 |
| ATOM | 210 | HG13 | VAL | 304 | -9.776 | -13.721 | 8.261 | 1.00 | 0.00 |
| ATOM | 211 | CG2 | VAL | 304 | -9.778 | -13.309 | 11.039 | 1.00 | 0.00 |
| ATOM | 212 | HG21 | VAL | 304 | -9.387 | -14.303 | 10.877 | 1.00 | 0.00 |
| ATOM | 213 | HG22 | VAL | 304 | -10.222 | -13.252 | 12.021 | 1.00 | 0.00 |
| ATOM | 214 | HG23 | VAL | 304 | -8.975 | -12.590 | 10.965 | 1.00 | 0.00 |
| ATOM | 215 | C | VAL | 304 | -12.712 | -11.434 | 9.370 | 1.00 | 0.00 |
| ATOM | 216 | O | VAL | 304 | -12.606 | -10.528 | 8.561 | 1.00 | 0.00 |
| ATOM | 217 | N | LEU | 305 | -13.783 | -12.186 | 9.410 | 1.00 | 0.00 |
| ATOM | 218 | HN | LEU | 305 | -13.858 | -12.912 | 10.074 | 1.00 | 0.00 |
| ATOM | 219 | CA | LEU | 305 | -14.891 | -11.935 | 8.454 | 1.00 | 0.00 |
| ATOM | 220 | HA | LEU | 305 | -14.514 | -11.880 | 7.446 | 1.00 | 0.00 |
| ATOM | 221 | CB | LEU | 305 | -15.821 | -13.133 | 8.601 | 1.00 | 0.00 |
| ATOM | 222 | HB1 | LEU | 305 | -16.681 | -13.004 | 7.961 | 1.00 | 0.00 |
| ATOM | 223 | HB2 | LEU | 305 | -16.143 | -13.219 | 9.630 | 1.00 | 0.00 |
| ATOM | 224 | CG | LEU | 305 | -15.068 | -14.397 | 8.190 | 1.00 | 0.00 |
| ATOM | 225 | HG | LEU | 305 | -14.273 | -14.586 | 8.897 | 1.00 | 0.00 |
| ATOM | 226 | CD1 | LEU | 305 | -16.029 | -15.588 | 8.169 | 1.00 | 0.00 |
| ATOM | 227 | HD11 | LEU | 305 | -15.747 | -16.263 | 7.373 | 1.00 | 0.00 |
| ATOM | 228 | HD12 | LEU | 305 | -17.036 | -15.235 | 8.003 | 1.00 | 0.00 |

Figure 9-5

| | | | | | | | | | |
|---|---|---|---|---|---|---|---|---|---|
| ATOM | 229 | HD13 | LEU | 305 | -15.981 | -16.107 | 9.114 | 1.00 | 0.00 |
| ATOM | 230 | CD2 | LEU | 305 | -14.470 | -14.196 | 6.798 | 1.00 | 0.00 |
| ATOM | 231 | HD21 | LEU | 305 | -14.146 | -15.147 | 6.404 | 1.00 | 0.00 |
| ATOM | 232 | HD22 | LEU | 305 | -13.624 | -13.526 | 6.864 | 1.00 | 0.00 |
| ATOM | 233 | HD23 | LEU | 305 | -15.215 | -13.770 | 6.145 | 1.00 | 0.00 |
| ATOM | 234 | C | LEU | 305 | -15.596 | -10.637 | 8.834 | 1.00 | 0.00 |
| ATOM | 235 | O | LEU | 305 | -16.113 | -9.929 | 7.993 | 1.00 | 0.00 |
| ATOM | 236 | N | GLY | 306 | -15.622 | -10.318 | 10.100 | 1.00 | 0.00 |
| ATOM | 237 | HN | GLY | 306 | -15.204 | -10.907 | 10.764 | 1.00 | 0.00 |
| ATOM | 238 | CA | GLY | 306 | -16.290 | -9.066 | 10.533 | 1.00 | 0.00 |
| ATOM | 239 | HA1 | GLY | 306 | -16.286 | -9.004 | 11.609 | 1.00 | 0.00 |
| ATOM | 240 | HA2 | GLY | 306 | -17.308 | -9.051 | 10.168 | 1.00 | 0.00 |
| ATOM | 241 | C | GLY | 306 | -15.517 | -7.884 | 9.955 | 1.00 | 0.00 |
| ATOM | 242 | O | GLY | 306 | -16.029 | -6.788 | 9.834 | 1.00 | 0.00 |
| ATOM | 243 | N | GLU | 307 | -14.280 | -8.106 | 9.589 | 1.00 | 0.00 |
| ATOM | 244 | HN | GLU | 307 | -13.896 | -9.001 | 9.681 | 1.00 | 0.00 |
| ATOM | 245 | CA | GLU | 307 | -13.462 | -7.007 | 9.017 | 1.00 | 0.00 |
| ATOM | 246 | HA | GLU | 307 | -13.719 | -6.071 | 9.473 | 1.00 | 0.00 |
| ATOM | 247 | CB | GLU | 307 | -12.012 | -7.373 | 9.342 | 1.00 | 0.00 |
| ATOM | 248 | HB1 | GLU | 307 | -11.350 | -6.856 | 8.665 | 1.00 | 0.00 |
| ATOM | 249 | HB2 | GLU | 307 | -11.878 | -8.439 | 9.233 | 1.00 | 0.00 |
| ATOM | 250 | CG | GLU | 307 | -11.689 | -6.961 | 10.781 | 1.00 | 0.00 |
| ATOM | 251 | HG1 | GLU | 307 | -11.788 | -7.816 | 11.432 | 1.00 | 0.00 |
| ATOM | 252 | HG2 | GLU | 307 | -12.375 | -6.186 | 11.097 | 1.00 | 0.00 |
| ATOM | 253 | CD | GLU | 307 | -10.254 | -6.433 | 10.852 | 1.00 | 0.00 |
| ATOM | 254 | OE1 | GLU | 307 | -9.392 | -7.032 | 10.231 | 1.00 | 0.00 |
| ATOM | 255 | OE2 | GLU | 307 | -10.043 | -5.439 | 11.527 | 1.00 | 0.00 |
| ATOM | 256 | C | GLU | 307 | -13.682 | -6.947 | 7.509 | 1.00 | 0.00 |
| ATOM | 257 | O | GLU | 307 | -13.649 | -5.895 | 6.905 | 1.00 | 0.00 |
| ATOM | 258 | N | VAL | 308 | -13.905 | -8.077 | 6.896 | 1.00 | 0.00 |
| ATOM | 259 | HN | VAL | 308 | -13.928 | -8.916 | 7.405 | 1.00 | 0.00 |
| ATOM | 260 | CA | VAL | 308 | -14.131 | -8.095 | 5.424 | 1.00 | 0.00 |
| ATOM | 261 | HA | VAL | 308 | -13.418 | -7.464 | 4.923 | 1.00 | 0.00 |
| ATOM | 262 | CB | VAL | 308 | -13.934 | -9.549 | 5.014 | 1.00 | 0.00 |
| ATOM | 263 | HB | VAL | 308 | -14.685 | -10.163 | 5.490 | 1.00 | 0.00 |
| ATOM | 264 | CG1 | VAL | 308 | -14.058 | -9.674 | 3.498 | 1.00 | 0.00 |
| ATOM | 265 | HG11 | VAL | 308 | -13.923 | -8.704 | 3.046 | 1.00 | 0.00 |
| ATOM | 266 | HG12 | VAL | 308 | -15.036 | -10.056 | 3.248 | 1.00 | 0.00 |
| ATOM | 267 | HG13 | VAL | 308 | -13.302 | -10.351 | 3.131 | 1.00 | 0.00 |
| ATOM | 268 | CG2 | VAL | 308 | -12.547 | -10.009 | 5.449 | 1.00 | 0.00 |
| ATOM | 269 | HG21 | VAL | 308 | -12.398 | -11.034 | 5.150 | 1.00 | 0.00 |
| ATOM | 270 | HG22 | VAL | 308 | -12.464 | -9.930 | 6.523 | 1.00 | 0.00 |
| ATOM | 271 | HG23 | VAL | 308 | -11.800 | -9.384 | 4.983 | 1.00 | 0.00 |
| ATOM | 272 | C | VAL | 308 | -15.556 | -7.640 | 5.138 | 1.00 | 0.00 |
| ATOM | 273 | O | VAL | 308 | -15.882 | -7.200 | 4.053 | 1.00 | 0.00 |
| ATOM | 274 | N | ILE | 309 | -16.402 | -7.743 | 6.120 | 1.00 | 0.00 |
| ATOM | 275 | HN | ILE | 309 | -16.102 | -8.088 | 6.983 | 1.00 | 0.00 |
| ATOM | 276 | CA | ILE | 309 | -17.813 | -7.329 | 5.955 | 1.00 | 0.00 |
| ATOM | 277 | HA | ILE | 309 | -18.192 | -7.619 | 4.991 | 1.00 | 0.00 |
| ATOM | 278 | CB | ILE | 309 | -18.547 | -8.090 | 7.072 | 1.00 | 0.00 |
| ATOM | 279 | HB | ILE | 309 | -17.838 | -8.359 | 7.842 | 1.00 | 0.00 |
| ATOM | 280 | CG1 | ILE | 309 | -19.157 | -9.361 | 6.481 | 1.00 | 0.00 |
| ATOM | 281 | HG11 | ILE | 309 | -18.716 | -9.554 | 5.515 | 1.00 | 0.00 |
| ATOM | 282 | HG12 | ILE | 309 | -20.219 | -9.232 | 6.368 | 1.00 | 0.00 |
| ATOM | 283 | CG2 | ILE | 309 | -19.655 | -7.216 | 7.690 | 1.00 | 0.00 |
| ATOM | 284 | HG21 | ILE | 309 | -19.241 | -6.258 | 7.975 | 1.00 | 0.00 |
| ATOM | 285 | HG22 | ILE | 309 | -20.051 | -7.703 | 8.563 | 1.00 | 0.00 |
| ATOM | 286 | HG23 | ILE | 309 | -20.442 | -7.068 | 6.968 | 1.00 | 0.00 |

Figure 9-6

```
ATOM    287  CD1  ILE   309     -18.874  -10.546   7.409  1.00  0.00
ATOM    288  HD11 ILE   309     -18.248  -10.222   8.227  1.00  0.00
ATOM    289  HD12 ILE   309     -18.369  -11.322   6.855  1.00  0.00
ATOM    290  HD13 ILE   309     -19.805  -10.930   7.799  1.00  0.00
ATOM    291  C    ILE   309     -17.900   -5.821   6.157  1.00  0.00
ATOM    292  O    ILE   309     -18.489   -5.099   5.376  1.00  0.00
ATOM    293  N    ALA   310     -17.317   -5.358   7.216  1.00  0.00
ATOM    294  HN   ALA   310     -16.848   -5.974   7.820  1.00  0.00
ATOM    295  CA   ALA   310     -17.337   -3.908   7.514  1.00  0.00
ATOM    296  HA   ALA   310     -18.307   -3.498   7.312  1.00  0.00
ATOM    297  CB   ALA   310     -17.014   -3.801   9.004  1.00  0.00
ATOM    298  HB1  ALA   310     -16.284   -4.552   9.269  1.00  0.00
ATOM    299  HB2  ALA   310     -17.915   -3.955   9.580  1.00  0.00
ATOM    300  HB3  ALA   310     -16.615   -2.821   9.217  1.00  0.00
ATOM    301  C    ALA   310     -16.272   -3.212   6.677  1.00  0.00
ATOM    302  O    ALA   310     -16.282   -2.008   6.509  1.00  0.00
ATOM    303  N    ALA   311     -15.349   -3.974   6.152  1.00  0.00
ATOM    304  HN   ALA   311     -15.405   -4.934   6.262  1.00  0.00
ATOM    305  CA   ALA   311     -14.264   -3.386   5.318  1.00  0.00
ATOM    306  HA   ALA   311     -13.491   -2.959   5.931  1.00  0.00
ATOM    307  CB   ALA   311     -13.719   -4.555   4.501  1.00  0.00
ATOM    308  HB1  ALA   311     -14.520   -5.252   4.294  1.00  0.00
ATOM    309  HB2  ALA   311     -12.943   -5.054   5.058  1.00  0.00
ATOM    310  HB3  ALA   311     -13.315   -4.187   3.568  1.00  0.00
ATOM    311  C    ALA   311     -14.866   -2.356   4.407  1.00  0.00
ATOM    312  O    ALA   311     -14.524   -1.191   4.433  1.00  0.00
ATOM    313  N    GLU   312     -15.763   -2.785   3.602  1.00  0.00
ATOM    314  HN   GLU   312     -16.008   -3.735   3.611  1.00  0.00
ATOM    315  CA   GLU   312     -16.422   -1.869   2.670  1.00  0.00
ATOM    316  HA   GLU   312     -16.567   -0.921   3.133  1.00  0.00
ATOM    317  CB   GLU   312     -15.475   -1.747   1.476  1.00  0.00
ATOM    318  HB1  GLU   312     -15.583   -2.612   0.840  1.00  0.00
ATOM    319  HB2  GLU   312     -14.454   -1.685   1.831  1.00  0.00
ATOM    320  CG   GLU   312     -15.817   -0.486   0.680  1.00  0.00
ATOM    321  HG1  GLU   312     -16.183    0.276   1.352  1.00  0.00
ATOM    322  HG2  GLU   312     -16.579   -0.718  -0.051  1.00  0.00
ATOM    323  CD   GLU   312     -14.564    0.027  -0.033  1.00  0.00
ATOM    324  OE1  GLU   312     -14.599    0.133  -1.248  1.00  0.00
ATOM    325  OE2  GLU   312     -13.591    0.306   0.649  1.00  0.00
ATOM    326  C    GLU   312     -17.750   -2.471   2.258  1.00  0.00
ATOM    327  O    GLU   312     -18.292   -2.166   1.213  1.00  0.00
ATOM    328  N    SER   313     -18.282   -3.328   3.085  1.00  0.00
ATOM    329  HN   SER   313     -17.817   -3.548   3.927  1.00  0.00
ATOM    330  CA   SER   313     -19.584   -3.970   2.764  1.00  0.00
ATOM    331  HA   SER   313     -19.741   -4.835   3.385  1.00  0.00
ATOM    332  CB   SER   313     -20.635   -2.905   3.071  1.00  0.00
ATOM    333  HB1  SER   313     -20.233   -2.200   3.792  1.00  0.00
ATOM    334  HB2  SER   313     -21.511   -3.372   3.483  1.00  0.00
ATOM    335  OG   SER   313     -20.985   -2.227   1.871  1.00  0.00
ATOM    336  HG   SER   313     -21.176   -1.312   2.091  1.00  0.00
ATOM    337  C    SER   313     -19.617   -4.359   1.285  1.00  0.00
ATOM    338  O    SER   313     -20.608   -4.181   0.606  1.00  0.00
ATOM    339  N    GLY   314     -18.534   -4.891   0.780  1.00  0.00
ATOM    340  HN   GLY   314     -17.742   -5.029   1.348  1.00  0.00
ATOM    341  CA   GLY   314     -18.500   -5.292  -0.653  1.00  0.00
ATOM    342  HA1  GLY   314     -19.258   -6.036  -0.838  1.00  0.00
ATOM    343  HA2  GLY   314     -17.526   -5.700  -0.891  1.00  0.00
ATOM    344  C    GLY   314     -18.769   -4.068  -1.527  1.00  0.00
```

Figure 9-7

| | | | | | | | | | |
|---|---|---|---|---|---|---|---|---|---|
| ATOM | 345 | O | GLY | 314 | -18.348 | -2.970 | -1.222 | 1.00 | 0.00 |
| ATOM | 346 | N | TYR | 315 | -19.469 | -4.245 | -2.608 | 1.00 | 0.00 |
| ATOM | 347 | HN | TYR | 315 | -19.802 | -5.138 | -2.835 | 1.00 | 0.00 |
| ATOM | 348 | CA | TYR | 315 | -19.764 | -3.090 | -3.501 | 1.00 | 0.00 |
| ATOM | 349 | HA | TYR | 315 | -19.094 | -2.272 | -3.297 | 1.00 | 0.00 |
| ATOM | 350 | CB | TYR | 315 | -19.532 | -3.618 | -4.912 | 1.00 | 0.00 |
| ATOM | 351 | HB1 | TYR | 315 | -19.966 | -2.935 | -5.626 | 1.00 | 0.00 |
| ATOM | 352 | HB2 | TYR | 315 | -20.001 | -4.588 | -5.013 | 1.00 | 0.00 |
| ATOM | 353 | CG | TYR | 315 | -18.049 | -3.744 | -5.173 | 1.00 | 0.00 |
| ATOM | 354 | CD1 | TYR | 315 | -17.433 | -5.002 | -5.126 | 1.00 | 0.00 |
| ATOM | 355 | HD1 | TYR | 315 | -18.018 | -5.881 | -4.901 | 1.00 | 0.00 |
| ATOM | 356 | CD2 | TYR | 315 | -17.290 | -2.605 | -5.466 | 1.00 | 0.00 |
| ATOM | 357 | HD2 | TYR | 315 | -17.763 | -1.635 | -5.503 | 1.00 | 0.00 |
| ATOM | 358 | CE1 | TYR | 315 | -16.059 | -5.120 | -5.371 | 1.00 | 0.00 |
| ATOM | 359 | HE1 | TYR | 315 | -15.584 | -6.090 | -5.335 | 1.00 | 0.00 |
| ATOM | 360 | CE2 | TYR | 315 | -15.916 | -2.723 | -5.709 | 1.00 | 0.00 |
| ATOM | 361 | HE2 | TYR | 315 | -15.330 | -1.843 | -5.934 | 1.00 | 0.00 |
| ATOM | 362 | CZ | TYR | 315 | -15.300 | -3.979 | -5.662 | 1.00 | 0.00 |
| ATOM | 363 | OH | TYR | 315 | -13.947 | -4.094 | -5.906 | 1.00 | 0.00 |
| ATOM | 364 | HH | TYR | 315 | -13.565 | -3.214 | -5.882 | 1.00 | 0.00 |
| ATOM | 365 | C | TYR | 315 | -21.218 | -2.652 | -3.331 | 1.00 | 0.00 |
| ATOM | 366 | O | TYR | 315 | -22.048 | -2.899 | -4.181 | 1.00 | 0.00 |
| ATOM | 367 | N | GLU | 316 | -21.537 | -1.998 | -2.250 | 1.00 | 0.00 |
| ATOM | 368 | HN | GLU | 316 | -20.858 | -1.794 | -1.578 | 1.00 | 0.00 |
| ATOM | 369 | CA | GLU | 316 | -22.941 | -1.557 | -2.049 | 1.00 | 0.00 |
| ATOM | 370 | HA | GLU | 316 | -23.061 | -1.093 | -1.087 | 1.00 | 0.00 |
| ATOM | 371 | CB | GLU | 316 | -23.191 | -0.551 | -3.155 | 1.00 | 0.00 |
| ATOM | 372 | HB1 | GLU | 316 | -24.248 | -0.375 | -3.244 | 1.00 | 0.00 |
| ATOM | 373 | HB2 | GLU | 316 | -22.809 | -0.946 | -4.086 | 1.00 | 0.00 |
| ATOM | 374 | CG | GLU | 316 | -22.478 | 0.764 | -2.828 | 1.00 | 0.00 |
| ATOM | 375 | HG1 | GLU | 316 | -21.531 | 0.553 | -2.356 | 1.00 | 0.00 |
| ATOM | 376 | HG2 | GLU | 316 | -23.093 | 1.351 | -2.159 | 1.00 | 0.00 |
| ATOM | 377 | CD | GLU | 316 | -22.237 | 1.546 | -4.120 | 1.00 | 0.00 |
| ATOM | 378 | OE1 | GLU | 316 | -21.112 | 1.964 | -4.334 | 1.00 | 0.00 |
| ATOM | 379 | OE2 | GLU | 316 | -23.182 | 1.713 | -4.874 | 1.00 | 0.00 |
| ATOM | 380 | C | GLU | 316 | -23.875 | -2.752 | -2.194 | 1.00 | 0.00 |
| ATOM | 381 | O | GLU | 316 | -25.000 | -2.634 | -2.638 | 1.00 | 0.00 |
| ATOM | 382 | N | ARG | 317 | -23.405 | -3.901 | -1.829 | 1.00 | 0.00 |
| ATOM | 383 | HN | ARG | 317 | -22.535 | -3.972 | -1.515 | 1.00 | 0.00 |
| ATOM | 384 | CA | ARG | 317 | -24.190 | -5.091 | -1.920 | 1.00 | 0.00 |
| ATOM | 385 | HA | ARG | 317 | -24.829 | -5.046 | -2.762 | 1.00 | 0.00 |
| ATOM | 386 | CB | ARG | 317 | -23.170 | -6.210 | -2.098 | 1.00 | 0.00 |
| ATOM | 387 | HB1 | ARG | 317 | -23.435 | -7.045 | -1.469 | 1.00 | 0.00 |
| ATOM | 388 | HB2 | ARG | 317 | -22.186 | -5.848 | -1.822 | 1.00 | 0.00 |
| ATOM | 389 | CG | ARG | 317 | -23.159 | -6.656 | -3.555 | 1.00 | 0.00 |
| ATOM | 390 | HG1 | ARG | 317 | -24.112 | -7.096 | -3.802 | 1.00 | 0.00 |
| ATOM | 391 | HG2 | ARG | 317 | -22.376 | -7.384 | -3.700 | 1.00 | 0.00 |
| ATOM | 392 | CD | ARG | 317 | -22.910 | -5.449 | -4.459 | 1.00 | 0.00 |
| ATOM | 393 | HD1 | ARG | 317 | -21.857 | -5.337 | -4.655 | 1.00 | 0.00 |
| ATOM | 394 | HD2 | ARG | 317 | -23.310 | -4.552 | -4.005 | 1.00 | 0.00 |
| ATOM | 395 | NE | ARG | 317 | -23.634 | -5.757 | -5.720 | 1.00 | 0.00 |
| ATOM | 396 | HE | ARG | 317 | -23.686 | -6.681 | -6.043 | 1.00 | 0.00 |
| ATOM | 397 | CZ | ARG | 317 | -24.200 | -4.797 | -6.396 | 1.00 | 0.00 |
| ATOM | 398 | NH1 | ARG | 317 | -25.486 | -4.822 | -6.613 | 1.00 | 0.00 |
| ATOM | 399 | HH11 | ARG | 317 | -26.037 | -5.578 | -6.261 | 1.00 | 0.00 |
| ATOM | 400 | HH12 | ARG | 317 | -25.921 | -4.085 | -7.131 | 1.00 | 0.00 |
| ATOM | 401 | NH2 | ARG | 317 | -23.479 | -3.810 | -6.854 | 1.00 | 0.00 |
| ATOM | 402 | HH21 | ARG | 317 | -22.493 | -3.792 | -6.687 | 1.00 | 0.00 |

Figure 9-8

```
ATOM    403  HH22 ARG    317     -23.912   -3.071   -7.371  1.00  0.00
ATOM    404  C    ARG    317     -24.978   -5.293   -0.649  1.00  0.00
ATOM    405  O    ARG    317     -24.961   -4.490    0.262  1.00  0.00
ATOM    406  N    GLU    318     -25.659   -6.351   -0.603  1.00  0.00
ATOM    407  HN   GLU    318     -25.604   -6.955   -1.337  1.00  0.00
ATOM    408  CA   GLU    318     -26.484   -6.684    0.581  1.00  0.00
ATOM    409  HA   GLU    318     -26.415   -5.903    1.320  1.00  0.00
ATOM    410  CB   GLU    318     -27.909   -6.783    0.057  1.00  0.00
ATOM    411  HB1  GLU    318     -28.437   -7.563    0.585  1.00  0.00
ATOM    412  HB2  GLU    318     -27.892   -7.007   -1.000  1.00  0.00
ATOM    413  CG   GLU    318     -28.610   -5.452    0.288  1.00  0.00
ATOM    414  HG1  GLU    318     -27.921   -4.647    0.083  1.00  0.00
ATOM    415  HG2  GLU    318     -28.935   -5.394    1.316  1.00  0.00
ATOM    416  CD   GLU    318     -29.818   -5.338   -0.642  1.00  0.00
ATOM    417  OE1  GLU    318     -29.661   -5.613   -1.819  1.00  0.00
ATOM    418  OE2  GLU    318     -30.879   -4.975   -0.160  1.00  0.00
ATOM    419  C    GLU    318     -26.021   -8.012    1.164  1.00  0.00
ATOM    420  O    GLU    318     -26.537   -9.068    0.843  1.00  0.00
ATOM    421  N    ILE    319     -25.040   -7.962    2.004  1.00  0.00
ATOM    422  HN   ILE    319     -24.636   -7.098    2.219  1.00  0.00
ATOM    423  CA   ILE    319     -24.515   -9.211    2.627  1.00  0.00
ATOM    424  HA   ILE    319     -24.630  -10.046    1.960  1.00  0.00
ATOM    425  CB   ILE    319     -23.036   -8.937    2.864  1.00  0.00
ATOM    426  HB   ILE    319     -22.940   -8.157    3.594  1.00  0.00
ATOM    427  CG1  ILE    319     -22.377   -8.502    1.558  1.00  0.00
ATOM    428  HG11 ILE    319     -22.924   -8.912    0.723  1.00  0.00
ATOM    429  HG12 ILE    319     -21.357   -8.860    1.533  1.00  0.00
ATOM    430  CG2  ILE    319     -22.350  -10.198    3.392  1.00  0.00
ATOM    431  HG21 ILE    319     -22.771  -10.460    4.352  1.00  0.00
ATOM    432  HG22 ILE    319     -21.290  -10.011    3.504  1.00  0.00
ATOM    433  HG23 ILE    319     -22.501  -11.009    2.698  1.00  0.00
ATOM    434  CD1  ILE    319     -22.385   -6.976    1.470  1.00  0.00
ATOM    435  HD11 ILE    319     -21.464   -6.635    1.021  1.00  0.00
ATOM    436  HD12 ILE    319     -22.478   -6.559    2.462  1.00  0.00
ATOM    437  HD13 ILE    319     -23.221   -6.655    0.866  1.00  0.00
ATOM    438  C    ILE    319     -25.191   -9.491    3.966  1.00  0.00
ATOM    439  O    ILE    319     -25.707   -8.608    4.621  1.00  0.00
ATOM    440  N    GLU    320     -25.183  -10.721    4.366  1.00  0.00
ATOM    441  HN   GLU    320     -24.760  -11.400    3.809  1.00  0.00
ATOM    442  CA   GLU    320     -25.811  -11.106    5.661  1.00  0.00
ATOM    443  HA   GLU    320     -26.273  -10.254    6.123  1.00  0.00
ATOM    444  CB   GLU    320     -26.858  -12.159    5.311  1.00  0.00
ATOM    445  HB1  GLU    320     -26.536  -13.122    5.673  1.00  0.00
ATOM    446  HB2  GLU    320     -26.985  -12.199    4.238  1.00  0.00
ATOM    447  CG   GLU    320     -28.186  -11.787    5.971  1.00  0.00
ATOM    448  HG1  GLU    320     -28.250  -10.714    6.070  1.00  0.00
ATOM    449  HG2  GLU    320     -28.241  -12.243    6.949  1.00  0.00
ATOM    450  CD   GLU    320     -29.344  -12.286    5.108  1.00  0.00
ATOM    451  OE1  GLU    320     -30.474  -11.938    5.410  1.00  0.00
ATOM    452  OE2  GLU    320     -29.082  -13.007    4.160  1.00  0.00
ATOM    453  C    GLU    320     -24.727  -11.694    6.565  1.00  0.00
ATOM    454  O    GLU    320     -24.205  -12.757    6.305  1.00  0.00
ATOM    455  N    THR    321     -24.386  -11.022    7.626  1.00  0.00
ATOM    456  HN   THR    321     -24.811  -10.168    7.826  1.00  0.00
ATOM    457  CA   THR    321     -23.330  -11.563    8.524  1.00  0.00
ATOM    458  HA   THR    321     -22.627  -12.135    7.949  1.00  0.00
ATOM    459  CB   THR    321     -22.631  -10.345    9.084  1.00  0.00
ATOM    460  HB   THR    321     -21.993  -10.644    9.897  1.00  0.00
```

Figure 9-9

```
ATOM    461  OG1  THR  321  -23.597   -9.411   9.550  1.00  0.00
ATOM    462  HG1  THR  321  -23.470   -9.298  10.495  1.00  0.00
ATOM    463  CG2  THR  321  -21.787   -9.713   7.993  1.00  0.00
ATOM    464 HG21  THR  321  -21.535  -10.461   7.255  1.00  0.00
ATOM    465 HG22  THR  321  -20.883   -9.319   8.425  1.00  0.00
ATOM    466 HG23  THR  321  -22.341   -8.916   7.522  1.00  0.00
ATOM    467  C    THR  321  -23.882  -12.419   9.663  1.00  0.00
ATOM    468  O    THR  321  -24.658  -11.979  10.486  1.00  0.00
ATOM    469  N    ALA  322  -23.467  -13.646   9.691  1.00  0.00
ATOM    470  HN   ALA  322  -22.845  -13.953   9.002  1.00  0.00
ATOM    471  CA   ALA  322  -23.910  -14.600  10.742  1.00  0.00
ATOM    472  HA   ALA  322  -24.128  -14.086  11.664  1.00  0.00
ATOM    473  CB   ALA  322  -25.162  -15.271  10.179  1.00  0.00
ATOM    474  HB1  ALA  322  -25.346  -14.908   9.179  1.00  0.00
ATOM    475  HB2  ALA  322  -26.009  -15.040  10.808  1.00  0.00
ATOM    476  HB3  ALA  322  -25.014  -16.340  10.153  1.00  0.00
ATOM    477  C    ALA  322  -22.781  -15.611  10.924  1.00  0.00
ATOM    478  O    ALA  322  -22.859  -16.725  10.462  1.00  0.00
ATOM    479  N    LEU  323  -21.739  -15.230  11.617  1.00  0.00
ATOM    480  HN   LEU  323  -21.710  -14.327  11.999  1.00  0.00
ATOM    481  CA   LEU  323  -20.589  -16.163  11.831  1.00  0.00
ATOM    482  HA   LEU  323  -20.530  -16.872  11.032  1.00  0.00
ATOM    483  CB   LEU  323  -19.365  -15.253  11.796  1.00  0.00
ATOM    484  HB1  LEU  323  -18.522  -15.774  12.224  1.00  0.00
ATOM    485  HB2  LEU  323  -19.571  -14.370  12.377  1.00  0.00
ATOM    486  CG   LEU  323  -19.021  -14.834  10.344  1.00  0.00
ATOM    487  HG   LEU  323  -18.297  -15.522   9.933  1.00  0.00
ATOM    488  CD1  LEU  323  -20.274  -14.821   9.458  1.00  0.00
ATOM    489 HD11  LEU  323  -20.797  -15.759   9.555  1.00  0.00
ATOM    490 HD12  LEU  323  -19.983  -14.676   8.429  1.00  0.00
ATOM    491 HD13  LEU  323  -20.922  -14.013   9.765  1.00  0.00
ATOM    492  CD2  LEU  323  -18.429  -13.431  10.369  1.00  0.00
ATOM    493 HD21  LEU  323  -17.518  -13.435  10.941  1.00  0.00
ATOM    494 HD22  LEU  323  -19.137  -12.754  10.825  1.00  0.00
ATOM    495 HD23  LEU  323  -18.222  -13.111   9.361  1.00  0.00
ATOM    496  C    LEU  323  -20.672  -16.882  13.170  1.00  0.00
ATOM    497  O    LEU  323  -19.937  -16.584  14.087  1.00  0.00
ATOM    498  N    TYR  324  -21.538  -17.843  13.279  1.00  0.00
ATOM    499  HN   TYR  324  -22.098  -18.082  12.514  1.00  0.00
ATOM    500  CA   TYR  324  -21.668  -18.589  14.563  1.00  0.00
ATOM    501  HA   TYR  324  -22.432  -19.343  14.485  1.00  0.00
ATOM    502  CB   TYR  324  -20.304  -19.250  14.762  1.00  0.00
ATOM    503  HB1  TYR  324  -19.688  -18.621  15.388  1.00  0.00
ATOM    504  HB2  TYR  324  -19.826  -19.382  13.803  1.00  0.00
ATOM    505  CG   TYR  324  -20.482  -20.592  15.423  1.00  0.00
ATOM    506  CD1  TYR  324  -19.891  -20.838  16.666  1.00  0.00
ATOM    507  HD1  TYR  324  -19.310  -20.068  17.148  1.00  0.00
ATOM    508  CD2  TYR  324  -21.235  -21.591  14.794  1.00  0.00
ATOM    509  HD2  TYR  324  -21.690  -21.402  13.833  1.00  0.00
ATOM    510  CE1  TYR  324  -20.051  -22.082  17.284  1.00  0.00
ATOM    511  HE1  TYR  324  -19.594  -22.270  18.244  1.00  0.00
ATOM    512  CE2  TYR  324  -21.396  -22.838  15.413  1.00  0.00
ATOM    513  HE2  TYR  324  -21.977  -23.609  14.930  1.00  0.00
ATOM    514  CZ   TYR  324  -20.803  -23.083  16.659  1.00  0.00
ATOM    515  OH   TYR  324  -20.959  -24.310  17.271  1.00  0.00
ATOM    516  HH   TYR  324  -21.779  -24.696  16.957  1.00  0.00
ATOM    517  C    TYR  324  -21.969  -17.630  15.724  1.00  0.00
ATOM    518  O    TYR  324  -21.264  -16.665  15.935  1.00  0.00
```

Figure 9-10

| | | | | | | | | |
|---|---|---|---|---|---|---|---|---|
| ATOM | 519 | N | PRO | 325 | -23.008 | -17.930 | 16.447 | 1.00 0.00 |
| ATOM | 520 | CA | PRO | 325 | -23.394 | -17.083 | 17.589 | 1.00 0.00 |
| ATOM | 521 | HA | PRO | 325 | -23.257 | -16.053 | 17.360 | 1.00 0.00 |
| ATOM | 522 | CB | PRO | 325 | -24.858 | -17.402 | 17.793 | 1.00 0.00 |
| ATOM | 523 | HB1 | PRO | 325 | -25.475 | -16.708 | 17.246 | 1.00 0.00 |
| ATOM | 524 | HB2 | PRO | 325 | -25.104 | -17.378 | 18.850 | 1.00 0.00 |
| ATOM | 525 | CG | PRO | 325 | -25.035 | -18.791 | 17.242 | 1.00 0.00 |
| ATOM | 526 | HG1 | PRO | 325 | -25.983 | -18.870 | 16.749 | 1.00 0.00 |
| ATOM | 527 | HG2 | PRO | 325 | -24.973 | -19.510 | 18.046 | 1.00 0.00 |
| ATOM | 528 | CD | PRO | 325 | -23.923 | -19.043 | 16.248 | 1.00 0.00 |
| ATOM | 529 | HD1 | PRO | 325 | -24.306 | -19.035 | 15.240 | 1.00 0.00 |
| ATOM | 530 | HD2 | PRO | 325 | -23.432 | -19.984 | 16.462 | 1.00 0.00 |
| ATOM | 531 | C | PRO | 325 | -22.594 | -17.469 | 18.827 | 1.00 0.00 |
| ATOM | 532 | O | PRO | 325 | -23.107 | -17.506 | 19.927 | 1.00 0.00 |
| ATOM | 533 | N | GLY | 326 | -21.351 | -17.754 | 18.654 | 1.00 0.00 |
| ATOM | 534 | HN | GLY | 326 | -20.978 | -17.720 | 17.765 | 1.00 0.00 |
| ATOM | 535 | CA | GLY | 326 | -20.506 | -18.142 | 19.826 | 1.00 0.00 |
| ATOM | 536 | HA1 | GLY | 326 | -20.558 | -19.212 | 19.960 | 1.00 0.00 |
| ATOM | 537 | HA2 | GLY | 326 | -20.889 | -17.656 | 20.712 | 1.00 0.00 |
| ATOM | 538 | C | GLY | 326 | -19.030 | -17.730 | 19.620 | 1.00 0.00 |
| ATOM | 539 | O | GLY | 326 | -18.201 | -17.950 | 20.481 | 1.00 0.00 |
| ATOM | 540 | N | SER | 327 | -18.688 | -17.141 | 18.494 | 1.00 0.00 |
| ATOM | 541 | HN | SER | 327 | -19.347 | -16.981 | 17.801 | 1.00 0.00 |
| ATOM | 542 | CA | SER | 327 | -17.270 | -16.732 | 18.266 | 1.00 0.00 |
| ATOM | 543 | HA | SER | 327 | -17.201 | -16.077 | 17.413 | 1.00 0.00 |
| ATOM | 544 | CB | SER | 327 | -16.846 | -15.992 | 19.521 | 1.00 0.00 |
| ATOM | 545 | HB1 | SER | 327 | -16.124 | -16.594 | 20.061 | 1.00 0.00 |
| ATOM | 546 | HB2 | SER | 327 | -17.701 | -15.819 | 20.139 | 1.00 0.00 |
| ATOM | 547 | OG | SER | 327 | -16.264 | -14.744 | 19.159 | 1.00 0.00 |
| ATOM | 548 | HG | SER | 327 | -15.342 | -14.757 | 19.428 | 1.00 0.00 |
| ATOM | 549 | C | SER | 327 | -16.399 | -17.957 | 18.064 | 1.00 0.00 |
| ATOM | 550 | O | SER | 327 | -16.243 | -18.781 | 18.944 | 1.00 0.00 |
| ATOM | 551 | N | ILE | 328 | -15.837 | -18.081 | 16.917 | 1.00 0.00 |
| ATOM | 552 | HN | ILE | 328 | -15.993 | -17.406 | 16.234 | 1.00 0.00 |
| ATOM | 553 | CA | ILE | 328 | -14.961 | -19.265 | 16.637 | 1.00 0.00 |
| ATOM | 554 | HA | ILE | 328 | -15.234 | -20.084 | 17.273 | 1.00 0.00 |
| ATOM | 555 | CB | ILE | 328 | -15.187 | -19.665 | 15.175 | 1.00 0.00 |
| ATOM | 556 | HB | ILE | 328 | -14.366 | -19.304 | 14.570 | 1.00 0.00 |
| ATOM | 557 | CG1 | ILE | 328 | -16.511 | -19.086 | 14.654 | 1.00 0.00 |
| ATOM | 558 | HG11 | ILE | 328 | -16.381 | -18.037 | 14.435 | 1.00 0.00 |
| ATOM | 559 | HG12 | ILE | 328 | -17.277 | -19.206 | 15.405 | 1.00 0.00 |
| ATOM | 560 | CG2 | ILE | 328 | -15.231 | -21.190 | 15.094 | 1.00 0.00 |
| ATOM | 561 | HG21 | ILE | 328 | -14.979 | -21.507 | 14.093 | 1.00 0.00 |
| ATOM | 562 | HG22 | ILE | 328 | -16.219 | -21.528 | 15.342 | 1.00 0.00 |
| ATOM | 563 | HG23 | ILE | 328 | -14.522 | -21.608 | 15.794 | 1.00 0.00 |
| ATOM | 564 | CD1 | ILE | 328 | -16.920 | -19.819 | 13.386 | 1.00 0.00 |
| ATOM | 565 | HD11 | ILE | 328 | -16.052 | -19.957 | 12.758 | 1.00 0.00 |
| ATOM | 566 | HD12 | ILE | 328 | -17.660 | -19.241 | 12.861 | 1.00 0.00 |
| ATOM | 567 | HD13 | ILE | 328 | -17.329 | -20.782 | 13.649 | 1.00 0.00 |
| ATOM | 568 | C | ILE | 328 | -13.500 | -18.914 | 16.847 | 1.00 0.00 |
| ATOM | 569 | O | ILE | 328 | -13.159 | -17.829 | 17.275 | 1.00 0.00 |
| ATOM | 570 | N | GLU | 329 | -12.638 | -19.829 | 16.531 | 1.00 0.00 |
| ATOM | 571 | HN | GLU | 329 | -12.946 | -20.670 | 16.185 | 1.00 0.00 |
| ATOM | 572 | CA | GLU | 329 | -11.193 | -19.594 | 16.695 | 1.00 0.00 |
| ATOM | 573 | HA | GLU | 329 | -10.892 | -18.704 | 16.170 | 1.00 0.00 |
| ATOM | 574 | CB | GLU | 329 | -11.014 | -19.406 | 18.176 | 1.00 0.00 |
| ATOM | 575 | HB1 | GLU | 329 | -11.722 | -18.678 | 18.523 | 1.00 0.00 |
| ATOM | 576 | HB2 | GLU | 329 | -10.017 | -19.066 | 18.367 | 1.00 0.00 |

Figure 9-11

| | | | | | | | | |
|---|---|---|---|---|---|---|---|---|
| ATOM | 577 | CG | GLU | 329 | -11.255 | -20.730 | 18.903 | 1.00 0.00 |
| ATOM | 578 | HG1 | GLU | 329 | -10.334 | -21.289 | 18.947 | 1.00 0.00 |
| ATOM | 579 | HG2 | GLU | 329 | -11.999 | -21.303 | 18.367 | 1.00 0.00 |
| ATOM | 580 | CD | GLU | 329 | -11.749 | -20.452 | 20.322 | 1.00 0.00 |
| ATOM | 581 | OE1 | GLU | 329 | -12.304 | -19.387 | 20.537 | 1.00 0.00 |
| ATOM | 582 | OE2 | GLU | 329 | -11.565 | -21.309 | 21.170 | 1.00 0.00 |
| ATOM | 583 | C | GLU | 329 | -10.404 | -20.807 | 16.199 | 1.00 0.00 |
| ATOM | 584 | O | GLU | 329 | -10.414 | -21.864 | 16.798 | 1.00 0.00 |
| ATOM | 585 | N | VAL | 330 | -9.733 | -20.663 | 15.107 | 1.00 0.00 |
| ATOM | 586 | HN | VAL | 330 | -9.760 | -19.822 | 14.636 | 1.00 0.00 |
| ATOM | 587 | CA | VAL | 330 | -8.944 | -21.797 | 14.564 | 1.00 0.00 |
| ATOM | 588 | HA | VAL | 330 | -8.896 | -22.605 | 15.269 | 1.00 0.00 |
| ATOM | 589 | CB | VAL | 330 | -9.710 | -22.226 | 13.334 | 1.00 0.00 |
| ATOM | 590 | HB | VAL | 330 | -9.307 | -23.145 | 12.972 | 1.00 0.00 |
| ATOM | 591 | CG1 | VAL | 330 | -11.170 | -22.423 | 13.691 | 1.00 0.00 |
| ATOM | 592 | HG11 | VAL | 330 | -11.504 | -23.366 | 13.302 | 1.00 0.00 |
| ATOM | 593 | HG12 | VAL | 330 | -11.756 | -21.625 | 13.264 | 1.00 0.00 |
| ATOM | 594 | HG13 | VAL | 330 | -11.281 | -22.418 | 14.763 | 1.00 0.00 |
| ATOM | 595 | CG2 | VAL | 330 | -9.575 | -21.142 | 12.243 | 1.00 0.00 |
| ATOM | 596 | HG21 | VAL | 330 | -9.952 | -20.201 | 12.618 | 1.00 0.00 |
| ATOM | 597 | HG22 | VAL | 330 | -10.137 | -21.434 | 11.369 | 1.00 0.00 |
| ATOM | 598 | HG23 | VAL | 330 | -8.532 | -21.028 | 11.977 | 1.00 0.00 |
| ATOM | 599 | C | VAL | 330 | -7.556 | -21.357 | 14.142 | 1.00 0.00 |
| ATOM | 600 | O | VAL | 330 | -7.260 | -20.190 | 14.057 | 1.00 0.00 |
| ATOM | 601 | N | LYS | 331 | -6.707 | -22.292 | 13.866 | 1.00 0.00 |
| ATOM | 602 | HN | LYS | 331 | -6.974 | -23.229 | 13.938 | 1.00 0.00 |
| ATOM | 603 | CA | LYS | 331 | -5.337 | -21.936 | 13.441 | 1.00 0.00 |
| ATOM | 604 | HA | LYS | 331 | -4.969 | -21.105 | 14.009 | 1.00 0.00 |
| ATOM | 605 | CB | LYS | 331 | -4.491 | -23.173 | 13.695 | 1.00 0.00 |
| ATOM | 606 | HB1 | LYS | 331 | -4.205 | -23.614 | 12.754 | 1.00 0.00 |
| ATOM | 607 | HB2 | LYS | 331 | -5.061 | -23.888 | 14.271 | 1.00 0.00 |
| ATOM | 608 | CG | LYS | 331 | -3.240 | -22.771 | 14.468 | 1.00 0.00 |
| ATOM | 609 | HG1 | LYS | 331 | -3.241 | -21.700 | 14.627 | 1.00 0.00 |
| ATOM | 610 | HG2 | LYS | 331 | -2.361 | -23.050 | 13.903 | 1.00 0.00 |
| ATOM | 611 | CD | LYS | 331 | -3.235 | -23.485 | 15.817 | 1.00 0.00 |
| ATOM | 612 | HD1 | LYS | 331 | -3.104 | -24.544 | 15.662 | 1.00 0.00 |
| ATOM | 613 | HD2 | LYS | 331 | -4.178 | -23.308 | 16.319 | 1.00 0.00 |
| ATOM | 614 | CE | LYS | 331 | -2.089 | -22.950 | 16.677 | 1.00 0.00 |
| ATOM | 615 | HE1 | LYS | 331 | -2.227 | -21.901 | 16.879 | 1.00 0.00 |
| ATOM | 616 | HE2 | LYS | 331 | -1.139 | -23.120 | 16.186 | 1.00 0.00 |
| ATOM | 617 | NZ | LYS | 331 | -2.169 | -23.728 | 17.943 | 1.00 0.00 |
| ATOM | 618 | HZ1 | LYS | 331 | -1.277 | -23.630 | 18.468 | 1.00 0.00 |
| ATOM | 619 | HZ2 | LYS | 331 | -2.334 | -24.733 | 17.722 | 1.00 0.00 |
| ATOM | 620 | HZ3 | LYS | 331 | -2.951 | -23.367 | 18.523 | 1.00 0.00 |
| ATOM | 621 | C | LYS | 331 | -5.383 | -21.609 | 11.958 | 1.00 0.00 |
| ATOM | 622 | O | LYS | 331 | -5.164 | -22.459 | 11.117 | 1.00 0.00 |
| ATOM | 623 | N | MET | 332 | -5.666 | -20.386 | 11.624 | 1.00 0.00 |
| ATOM | 624 | HN | MET | 332 | -5.820 | -19.711 | 12.314 | 1.00 0.00 |
| ATOM | 625 | CA | MET | 332 | -5.731 | -20.013 | 10.194 | 1.00 0.00 |
| ATOM | 626 | HA | MET | 332 | -5.145 | -20.692 | 9.599 | 1.00 0.00 |
| ATOM | 627 | CB | MET | 332 | -7.224 | -20.178 | 9.852 | 1.00 0.00 |
| ATOM | 628 | HB1 | MET | 332 | -7.816 | -19.873 | 10.702 | 1.00 0.00 |
| ATOM | 629 | HB2 | MET | 332 | -7.423 | -21.217 | 9.639 | 1.00 0.00 |
| ATOM | 630 | CG | MET | 332 | -7.620 | -19.332 | 8.635 | 1.00 0.00 |
| ATOM | 631 | HG1 | MET | 332 | -7.688 | -19.966 | 7.765 | 1.00 0.00 |
| ATOM | 632 | HG2 | MET | 332 | -6.889 | -18.567 | 8.462 | 1.00 0.00 |
| ATOM | 633 | SD | MET | 332 | -9.231 | -18.571 | 8.949 | 1.00 0.00 |
| ATOM | 634 | CE | MET | 332 | -8.702 | -17.451 | 10.271 | 1.00 0.00 |

Figure 9-12

| | | | | | | | | |
|---|---|---|---|---|---|---|---|---|
| ATOM | 635 | HE1 | MET | 332 | -8.945 | -17.888 | 11.232 | 1.00 | 0.00 |
| ATOM | 636 | HE2 | MET | 332 | -9.210 | -16.509 | 10.169 | 1.00 | 0.00 |
| ATOM | 637 | HE3 | MET | 332 | -7.635 | -17.291 | 10.202 | 1.00 | 0.00 |
| ATOM | 638 | C | MET | 332 | -5.255 | -18.570 | 9.993 | 1.00 | 0.00 |
| ATOM | 639 | O | MET | 332 | -5.635 | -17.666 | 10.710 | 1.00 | 0.00 |
| ATOM | 640 | N | HIS | 333 | -4.421 | -18.366 | 9.019 | 1.00 | 0.00 |
| ATOM | 641 | HN | HIS | 333 | -4.129 | -19.117 | 8.479 | 1.00 | 0.00 |
| ATOM | 642 | CA | HIS | 333 | -3.893 | -16.998 | 8.731 | 1.00 | 0.00 |
| ATOM | 643 | HA | HIS | 333 | -3.265 | -16.653 | 9.534 | 1.00 | 0.00 |
| ATOM | 644 | CB | HIS | 333 | -3.067 | -17.167 | 7.451 | 1.00 | 0.00 |
| ATOM | 645 | HB1 | HIS | 333 | -3.733 | -17.208 | 6.600 | 1.00 | 0.00 |
| ATOM | 646 | HB2 | HIS | 333 | -2.502 | -18.084 | 7.505 | 1.00 | 0.00 |
| ATOM | 647 | CG | HIS | 333 | -2.127 | -16.003 | 7.292 | 1.00 | 0.00 |
| ATOM | 648 | ND1 | HIS | 333 | -1.579 | -15.656 | 6.065 | 1.00 | 0.00 |
| ATOM | 649 | HD1 | HIS | 333 | -1.729 | -16.114 | 5.213 | 1.00 | 0.00 |
| ATOM | 650 | CD2 | HIS | 333 | -1.634 | -15.095 | 8.190 | 1.00 | 0.00 |
| ATOM | 651 | HD2 | HIS | 333 | -1.858 | -15.081 | 9.242 | 1.00 | 0.00 |
| ATOM | 652 | CE1 | HIS | 333 | -0.796 | -14.578 | 6.262 | 1.00 | 0.00 |
| ATOM | 653 | HE1 | HIS | 333 | -0.241 | -14.081 | 5.481 | 1.00 | 0.00 |
| ATOM | 654 | NE2 | HIS | 333 | -0.795 | -14.196 | 7.541 | 1.00 | 0.00 |
| ATOM | 655 | C | HIS | 333 | -5.046 | -16.022 | 8.482 | 1.00 | 0.00 |
| ATOM | 656 | O | HIS | 333 | -5.742 | -16.133 | 7.497 | 1.00 | 0.00 |
| ATOM | 657 | N | PRO | 334 | -5.202 | -15.086 | 9.378 | 1.00 | 0.00 |
| ATOM | 658 | CA | PRO | 334 | -6.283 | -14.086 | 9.240 | 1.00 | 0.00 |
| ATOM | 659 | HA | PRO | 334 | -7.233 | -14.570 | 9.102 | 1.00 | 0.00 |
| ATOM | 660 | CB | PRO | 334 | -6.258 | -13.340 | 10.570 | 1.00 | 0.00 |
| ATOM | 661 | HB1 | PRO | 334 | -6.964 | -13.775 | 11.259 | 1.00 | 0.00 |
| ATOM | 662 | HB2 | PRO | 334 | -6.475 | -12.289 | 10.416 | 1.00 | 0.00 |
| ATOM | 663 | CG | PRO | 334 | -4.863 | -13.522 | 11.081 | 1.00 | 0.00 |
| ATOM | 664 | HG1 | PRO | 334 | -4.858 | -13.517 | 12.158 | 1.00 | 0.00 |
| ATOM | 665 | HG2 | PRO | 334 | -4.224 | -12.733 | 10.701 | 1.00 | 0.00 |
| ATOM | 666 | CD | PRO | 334 | -4.390 | -14.865 | 10.576 | 1.00 | 0.00 |
| ATOM | 667 | HD1 | PRO | 334 | -4.581 | -15.635 | 11.304 | 1.00 | 0.00 |
| ATOM | 668 | HD2 | PRO | 334 | -3.339 | -14.825 | 10.326 | 1.00 | 0.00 |
| ATOM | 669 | C | PRO | 334 | -5.979 | -13.148 | 8.072 | 1.00 | 0.00 |
| ATOM | 670 | O | PRO | 334 | -6.867 | -12.652 | 7.411 | 1.00 | 0.00 |
| ATOM | 671 | N | LEU | 335 | -4.727 | -12.906 | 7.812 | 1.00 | 0.00 |
| ATOM | 672 | HN | LEU | 335 | -4.026 | -13.319 | 8.355 | 1.00 | 0.00 |
| ATOM | 673 | CA | LEU | 335 | -4.355 | -12.007 | 6.694 | 1.00 | 0.00 |
| ATOM | 674 | HA | LEU | 335 | -4.854 | -11.063 | 6.788 | 1.00 | 0.00 |
| ATOM | 675 | CB | LEU | 335 | -2.834 | -11.823 | 6.852 | 1.00 | 0.00 |
| ATOM | 676 | HB1 | LEU | 335 | -2.418 | -12.695 | 7.333 | 1.00 | 0.00 |
| ATOM | 677 | HB2 | LEU | 335 | -2.642 | -10.954 | 7.463 | 1.00 | 0.00 |
| ATOM | 678 | CG | LEU | 335 | -2.170 | -11.635 | 5.488 | 1.00 | 0.00 |
| ATOM | 679 | HG | LEU | 335 | -2.301 | -12.532 | 4.898 | 1.00 | 0.00 |
| ATOM | 680 | CD1 | LEU | 335 | -2.817 | -10.451 | 4.768 | 1.00 | 0.00 |
| ATOM | 681 | HD11 | LEU | 335 | -3.764 | -10.760 | 4.350 | 1.00 | 0.00 |
| ATOM | 682 | HD12 | LEU | 335 | -2.167 | -10.112 | 3.977 | 1.00 | 0.00 |
| ATOM | 683 | HD13 | LEU | 335 | -2.980 | -9.648 | 5.472 | 1.00 | 0.00 |
| ATOM | 684 | CD2 | LEU | 335 | -0.678 | -11.364 | 5.686 | 1.00 | 0.00 |
| ATOM | 685 | HD21 | LEU | 335 | -0.523 | -10.308 | 5.852 | 1.00 | 0.00 |
| ATOM | 686 | HD22 | LEU | 335 | -0.135 | -11.675 | 4.807 | 1.00 | 0.00 |
| ATOM | 687 | HD23 | LEU | 335 | -0.324 | -11.919 | 6.543 | 1.00 | 0.00 |
| ATOM | 688 | C | LEU | 335 | -4.710 | -12.674 | 5.358 | 1.00 | 0.00 |
| ATOM | 689 | O | LEU | 335 | -5.421 | -12.118 | 4.541 | 1.00 | 0.00 |
| ATOM | 690 | N | SER | 336 | -4.223 | -13.858 | 5.138 | 1.00 | 0.00 |
| ATOM | 691 | HN | SER | 336 | -3.660 | -14.286 | 5.813 | 1.00 | 0.00 |
| ATOM | 692 | CA | SER | 336 | -4.527 | -14.563 | 3.863 | 1.00 | 0.00 |

Figure 9-13

| ATOM | 693 | HA | SER | 336 | -4.172 | -13.990 | 3.022 | 1.00 | 0.00 |
| ATOM | 694 | CB | SER | 336 | -3.769 | -15.883 | 3.951 | 1.00 | 0.00 |
| ATOM | 695 | HB1 | SER | 336 | -4.360 | -16.669 | 3.494 | 1.00 | 0.00 |
| ATOM | 696 | HB2 | SER | 336 | -3.589 | -16.127 | 4.983 | 1.00 | 0.00 |
| ATOM | 697 | OG | SER | 336 | -2.523 | -15.754 | 3.275 | 1.00 | 0.00 |
| ATOM | 698 | HG | SER | 336 | -2.086 | -14.965 | 3.605 | 1.00 | 0.00 |
| ATOM | 699 | C | SER | 336 | -6.031 | -14.811 | 3.744 | 1.00 | 0.00 |
| ATOM | 700 | O | SER | 336 | -6.586 | -14.805 | 2.663 | 1.00 | 0.00 |
| ATOM | 701 | N | ILE | 337 | -6.699 | -15.028 | 4.846 | 1.00 | 0.00 |
| ATOM | 702 | HN | ILE | 337 | -6.236 | -15.026 | 5.714 | 1.00 | 0.00 |
| ATOM | 703 | CA | ILE | 337 | -8.168 | -15.274 | 4.782 | 1.00 | 0.00 |
| ATOM | 704 | HA | ILE | 337 | -8.387 | -16.030 | 4.047 | 1.00 | 0.00 |
| ATOM | 705 | CB | ILE | 337 | -8.543 | -15.777 | 6.172 | 1.00 | 0.00 |
| ATOM | 706 | HB | ILE | 337 | -8.223 | -15.058 | 6.912 | 1.00 | 0.00 |
| ATOM | 707 | CG1 | ILE | 337 | -7.829 | -17.114 | 6.416 | 1.00 | 0.00 |
| ATOM | 708 | HG11 | ILE | 337 | -7.734 | -17.276 | 7.471 | 1.00 | 0.00 |
| ATOM | 709 | HG12 | ILE | 337 | -6.845 | -17.076 | 5.971 | 1.00 | 0.00 |
| ATOM | 710 | CG2 | ILE | 337 | -10.065 | -15.972 | 6.275 | 1.00 | 0.00 |
| ATOM | 711 | HG21 | ILE | 337 | -10.527 | -15.052 | 6.595 | 1.00 | 0.00 |
| ATOM | 712 | HG22 | ILE | 337 | -10.280 | -16.752 | 6.995 | 1.00 | 0.00 |
| ATOM | 713 | HG23 | ILE | 337 | -10.458 | -16.259 | 5.310 | 1.00 | 0.00 |
| ATOM | 714 | CD1 | ILE | 337 | -8.626 | -18.268 | 5.788 | 1.00 | 0.00 |
| ATOM | 715 | HD11 | ILE | 337 | -9.572 | -18.372 | 6.298 | 1.00 | 0.00 |
| ATOM | 716 | HD12 | ILE | 337 | -8.065 | -19.185 | 5.880 | 1.00 | 0.00 |
| ATOM | 717 | HD13 | ILE | 337 | -8.803 | -18.058 | 4.744 | 1.00 | 0.00 |
| ATOM | 718 | C | ILE | 337 | -8.893 | -13.972 | 4.435 | 1.00 | 0.00 |
| ATOM | 719 | O | ILE | 337 | -9.898 | -13.978 | 3.755 | 1.00 | 0.00 |
| ATOM | 720 | N | LYS | 338 | -8.394 | -12.852 | 4.895 | 1.00 | 0.00 |
| ATOM | 721 | HN | LYS | 338 | -7.581 | -12.860 | 5.444 | 1.00 | 0.00 |
| ATOM | 722 | CA | LYS | 338 | -9.069 | -11.561 | 4.574 | 1.00 | 0.00 |
| ATOM | 723 | HA | LYS | 338 | -10.099 | -11.579 | 4.890 | 1.00 | 0.00 |
| ATOM | 724 | CB | LYS | 338 | -8.291 | -10.491 | 5.340 | 1.00 | 0.00 |
| ATOM | 725 | HB1 | LYS | 338 | -8.487 | -9.523 | 4.905 | 1.00 | 0.00 |
| ATOM | 726 | HB2 | LYS | 338 | -7.233 | -10.704 | 5.283 | 1.00 | 0.00 |
| ATOM | 727 | CG | LYS | 338 | -8.732 | -10.487 | 6.800 | 1.00 | 0.00 |
| ATOM | 728 | HG1 | LYS | 338 | -7.929 | -10.854 | 7.416 | 1.00 | 0.00 |
| ATOM | 729 | HG2 | LYS | 338 | -9.596 | -11.126 | 6.914 | 1.00 | 0.00 |
| ATOM | 730 | CD | LYS | 338 | -9.088 | -9.060 | 7.225 | 1.00 | 0.00 |
| ATOM | 731 | HD1 | LYS | 338 | -9.894 | -9.089 | 7.943 | 1.00 | 0.00 |
| ATOM | 732 | HD2 | LYS | 338 | -9.399 | -8.493 | 6.358 | 1.00 | 0.00 |
| ATOM | 733 | CE | LYS | 338 | -7.864 | -8.393 | 7.862 | 1.00 | 0.00 |
| ATOM | 734 | HE1 | LYS | 338 | -6.957 | -8.868 | 7.523 | 1.00 | 0.00 |
| ATOM | 735 | HE2 | LYS | 338 | -7.933 | -8.435 | 8.942 | 1.00 | 0.00 |
| ATOM | 736 | NZ | LYS | 338 | -7.906 | -6.979 | 7.392 | 1.00 | 0.00 |
| ATOM | 737 | HZ1 | LYS | 338 | -6.968 | -6.547 | 7.507 | 1.00 | 0.00 |
| ATOM | 738 | HZ2 | LYS | 338 | -8.604 | -6.448 | 7.954 | 1.00 | 0.00 |
| ATOM | 739 | HZ3 | LYS | 338 | -8.176 | -6.955 | 6.390 | 1.00 | 0.00 |
| ATOM | 740 | C | LYS | 338 | -8.964 | -11.326 | 3.074 | 1.00 | 0.00 |
| ATOM | 741 | O | LYS | 338 | -9.841 | -10.761 | 2.451 | 1.00 | 0.00 |
| ATOM | 742 | N | ARG | 339 | -7.882 | -11.764 | 2.496 | 1.00 | 0.00 |
| ATOM | 743 | HN | ARG | 339 | -7.193 | -12.211 | 3.034 | 1.00 | 0.00 |
| ATOM | 744 | CA | ARG | 339 | -7.681 | -11.588 | 1.033 | 1.00 | 0.00 |
| ATOM | 745 | HA | ARG | 339 | -7.926 | -10.582 | 0.735 | 1.00 | 0.00 |
| ATOM | 746 | CB | ARG | 339 | -6.175 | -11.852 | 0.819 | 1.00 | 0.00 |
| ATOM | 747 | HB1 | ARG | 339 | -5.839 | -12.595 | 1.527 | 1.00 | 0.00 |
| ATOM | 748 | HB2 | ARG | 339 | -5.627 | -10.934 | 0.977 | 1.00 | 0.00 |
| ATOM | 749 | CG | ARG | 339 | -5.912 | -12.357 | -0.607 | 1.00 | 0.00 |
| ATOM | 750 | HG1 | ARG | 339 | -6.585 | -13.167 | -0.835 | 1.00 | 0.00 |

Figure 9-14

| ATOM | 751 | HG2 | ARG | 339 | -4.891 | -12.706 | -0.681 | 1.00 | 0.00 |
| ATOM | 752 | CD | ARG | 339 | -6.132 | -11.218 | -1.599 | 1.00 | 0.00 |
| ATOM | 753 | HD1 | ARG | 339 | -7.049 | -10.700 | -1.378 | 1.00 | 0.00 |
| ATOM | 754 | HD2 | ARG | 339 | -6.147 | -11.602 | -2.611 | 1.00 | 0.00 |
| ATOM | 755 | NE | ARG | 339 | -4.969 | -10.306 | -1.402 | 1.00 | 0.00 |
| ATOM | 756 | HE | ARG | 339 | -4.494 | -10.297 | -0.545 | 1.00 | 0.00 |
| ATOM | 757 | CZ | ARG | 339 | -4.585 | -9.520 | -2.371 | 1.00 | 0.00 |
| ATOM | 758 | NH1 | ARG | 339 | -3.312 | -9.353 | -2.612 | 1.00 | 0.00 |
| ATOM | 759 | HH11 | ARG | 339 | -2.631 | -9.828 | -2.054 | 1.00 | 0.00 |
| ATOM | 760 | HH12 | ARG | 339 | -3.019 | -8.751 | -3.355 | 1.00 | 0.00 |
| ATOM | 761 | NH2 | ARG | 339 | -5.474 | -8.900 | -3.097 | 1.00 | 0.00 |
| ATOM | 762 | HH21 | ARG | 339 | -6.448 | -9.027 | -2.912 | 1.00 | 0.00 |
| ATOM | 763 | HH22 | ARG | 339 | -5.181 | -8.297 | -3.839 | 1.00 | 0.00 |
| ATOM | 764 | C | ARG | 339 | -8.544 | -12.605 | 0.270 | 1.00 | 0.00 |
| ATOM | 765 | O | ARG | 339 | -8.950 | -12.375 | -0.852 | 1.00 | 0.00 |
| ATOM | 766 | N | ALA | 340 | -8.828 | -13.727 | 0.880 | 1.00 | 0.00 |
| ATOM | 767 | HN | ALA | 340 | -8.488 | -13.892 | 1.783 | 1.00 | 0.00 |
| ATOM | 768 | CA | ALA | 340 | -9.663 | -14.762 | 0.201 | 1.00 | 0.00 |
| ATOM | 769 | HA | ALA | 340 | -9.371 | -14.861 | -0.829 | 1.00 | 0.00 |
| ATOM | 770 | CB | ALA | 340 | -9.369 | -16.060 | 0.952 | 1.00 | 0.00 |
| ATOM | 771 | HB1 | ALA | 340 | -8.582 | -16.600 | 0.445 | 1.00 | 0.00 |
| ATOM | 772 | HB2 | ALA | 340 | -10.261 | -16.668 | 0.983 | 1.00 | 0.00 |
| ATOM | 773 | HB3 | ALA | 340 | -9.056 | -15.830 | 1.960 | 1.00 | 0.00 |
| ATOM | 774 | C | ALA | 340 | -11.157 | -14.409 | 0.306 | 1.00 | 0.00 |
| ATOM | 775 | O | ALA | 340 | -11.950 | -14.779 | -0.536 | 1.00 | 0.00 |
| ATOM | 776 | N | VAL | 341 | -11.545 | -13.696 | 1.335 | 1.00 | 0.00 |
| ATOM | 777 | HN | VAL | 341 | -10.894 | -13.405 | 2.004 | 1.00 | 0.00 |
| ATOM | 778 | CA | VAL | 341 | -12.986 | -13.325 | 1.487 | 1.00 | 0.00 |
| ATOM | 779 | HA | VAL | 341 | -13.616 | -14.152 | 1.210 | 1.00 | 0.00 |
| ATOM | 780 | CB | VAL | 341 | -13.164 | -13.009 | 2.977 | 1.00 | 0.00 |
| ATOM | 781 | HB | VAL | 341 | -12.420 | -12.287 | 3.283 | 1.00 | 0.00 |
| ATOM | 782 | CG1 | VAL | 341 | -14.559 | -12.431 | 3.210 | 1.00 | 0.00 |
| ATOM | 783 | HG11 | VAL | 341 | -14.823 | -11.782 | 2.389 | 1.00 | 0.00 |
| ATOM | 784 | HG12 | VAL | 341 | -14.564 | -11.867 | 4.131 | 1.00 | 0.00 |
| ATOM | 785 | HG13 | VAL | 341 | -15.275 | -13.236 | 3.277 | 1.00 | 0.00 |
| ATOM | 786 | CG2 | VAL | 341 | -13.004 | -14.292 | 3.802 | 1.00 | 0.00 |
| ATOM | 787 | HG21 | VAL | 341 | -12.174 | -14.866 | 3.420 | 1.00 | 0.00 |
| ATOM | 788 | HG22 | VAL | 341 | -13.909 | -14.878 | 3.737 | 1.00 | 0.00 |
| ATOM | 789 | HG23 | VAL | 341 | -12.817 | -14.034 | 4.836 | 1.00 | 0.00 |
| ATOM | 790 | C | VAL | 341 | -13.314 | -12.090 | 0.633 | 1.00 | 0.00 |
| ATOM | 791 | O | VAL | 341 | -14.437 | -11.894 | 0.212 | 1.00 | 0.00 |
| ATOM | 792 | N | ALA | 342 | -12.341 | -11.257 | 0.380 | 1.00 | 0.00 |
| ATOM | 793 | HN | ALA | 342 | -11.445 | -11.430 | 0.738 | 1.00 | 0.00 |
| ATOM | 794 | CA | ALA | 342 | -12.592 | -10.033 | -0.445 | 1.00 | 0.00 |
| ATOM | 795 | HA | ALA | 342 | -13.372 | -9.436 | -0.003 | 1.00 | 0.00 |
| ATOM | 796 | CB | ALA | 342 | -11.273 | -9.263 | -0.415 | 1.00 | 0.00 |
| ATOM | 797 | HB1 | ALA | 342 | -10.513 | -9.832 | -0.932 | 1.00 | 0.00 |
| ATOM | 798 | HB2 | ALA | 342 | -10.970 | -9.106 | 0.609 | 1.00 | 0.00 |
| ATOM | 799 | HB3 | ALA | 342 | -11.401 | -8.309 | -0.903 | 1.00 | 0.00 |
| ATOM | 800 | C | ALA | 342 | -12.959 | -10.408 | -1.890 | 1.00 | 0.00 |
| ATOM | 801 | O | ALA | 342 | -13.676 | -9.693 | -2.562 | 1.00 | 0.00 |
| ATOM | 802 | N | ASN | 343 | -12.472 | -11.517 | -2.373 | 1.00 | 0.00 |
| ATOM | 803 | HN | ASN | 343 | -11.892 | -12.080 | -1.819 | 1.00 | 0.00 |
| ATOM | 804 | CA | ASN | 343 | -12.797 | -11.928 | -3.776 | 1.00 | 0.00 |
| ATOM | 805 | HA | ASN | 343 | -12.915 | -11.060 | -4.403 | 1.00 | 0.00 |
| ATOM | 806 | CB | ASN | 343 | -11.588 | -12.743 | -4.238 | 1.00 | 0.00 |
| ATOM | 807 | HB1 | ASN | 343 | -11.894 | -13.759 | -4.436 | 1.00 | 0.00 |
| ATOM | 808 | HB2 | ASN | 343 | -10.833 | -12.738 | -3.465 | 1.00 | 0.00 |

Figure 9-15

```
ATOM    809   CG   ASN   343   -11.016  -12.129   -5.516   1.00   0.00
ATOM    810   OD1  ASN   343   -11.745  -11.842   -6.445   1.00   0.00
ATOM    811   ND2  ASN   343    -9.732  -11.913   -5.603   1.00   0.00
ATOM    812   HD21 ASN   343    -9.144  -12.146   -4.855   1.00   0.00
ATOM    813   HD22 ASN   343    -9.357  -11.516   -6.417   1.00   0.00
ATOM    814   C    ASN   343   -14.068  -12.788   -3.809   1.00   0.00
ATOM    815   O    ASN   343   -14.700  -12.939   -4.835   1.00   0.00
ATOM    816   N    MET   344   -14.443  -13.351   -2.697   1.00   0.00
ATOM    817   HN   MET   344   -13.919  -13.215   -1.880   1.00   0.00
ATOM    818   CA   MET   344   -15.672  -14.205   -2.660   1.00   0.00
ATOM    819   HA   MET   344   -15.547  -15.067   -3.293   1.00   0.00
ATOM    820   CB   MET   344   -15.790  -14.647   -1.206   1.00   0.00
ATOM    821   HB1  MET   344   -16.748  -15.119   -1.050   1.00   0.00
ATOM    822   HB2  MET   344   -15.702  -13.786   -0.559   1.00   0.00
ATOM    823   CG   MET   344   -14.677  -15.642   -0.888   1.00   0.00
ATOM    824   HG1  MET   344   -14.490  -15.644    0.176   1.00   0.00
ATOM    825   HG2  MET   344   -13.777  -15.354   -1.411   1.00   0.00
ATOM    826   SD   MET   344   -15.179  -17.297   -1.417   1.00   0.00
ATOM    827   CE   MET   344   -14.288  -18.220   -0.144   1.00   0.00
ATOM    828   HE1  MET   344   -13.228  -18.025   -0.236   1.00   0.00
ATOM    829   HE2  MET   344   -14.468  -19.274   -0.270   1.00   0.00
ATOM    830   HE3  MET   344   -14.634  -17.909    0.834   1.00   0.00
ATOM    831   C    MET   344   -16.921  -13.412   -3.077   1.00   0.00
ATOM    832   O    MET   344   -17.975  -13.977   -3.292   1.00   0.00
ATOM    833   N    VAL   345   -16.820  -12.116   -3.195   1.00   0.00
ATOM    834   HN   VAL   345   -15.967  -11.669   -3.019   1.00   0.00
ATOM    835   CA   VAL   345   -18.019  -11.318   -3.599   1.00   0.00
ATOM    836   HA   VAL   345   -18.917  -11.898   -3.459   1.00   0.00
ATOM    837   CB   VAL   345   -18.030  -10.114   -2.662   1.00   0.00
ATOM    838   HB   VAL   345   -18.779   -9.408   -2.992   1.00   0.00
ATOM    839   CG1  VAL   345   -18.359  -10.578   -1.241   1.00   0.00
ATOM    840   HG11 VAL   345   -18.281   -9.742   -0.562   1.00   0.00
ATOM    841   HG12 VAL   345   -17.664  -11.350   -0.945   1.00   0.00
ATOM    842   HG13 VAL   345   -19.364  -10.971   -1.215   1.00   0.00
ATOM    843   CG2  VAL   345   -16.653   -9.446   -2.677   1.00   0.00
ATOM    844   HG21 VAL   345   -16.233   -9.507   -3.671   1.00   0.00
ATOM    845   HG22 VAL   345   -16.001   -9.950   -1.979   1.00   0.00
ATOM    846   HG23 VAL   345   -16.753   -8.409   -2.392   1.00   0.00
ATOM    847   C    VAL   345   -17.905  -10.863   -5.058   1.00   0.00
ATOM    848   O    VAL   345   -18.551   -9.919   -5.473   1.00   0.00
ATOM    849   N    VAL   346   -17.094  -11.520   -5.841   1.00   0.00
ATOM    850   HN   VAL   346   -16.581  -12.279   -5.493   1.00   0.00
ATOM    851   CA   VAL   346   -16.952  -11.113   -7.269   1.00   0.00
ATOM    852   HA   VAL   346   -17.181  -10.067   -7.385   1.00   0.00
ATOM    853   CB   VAL   346   -15.489  -11.369   -7.620   1.00   0.00
ATOM    854   HB   VAL   346   -14.855  -10.946   -6.855   1.00   0.00
ATOM    855   CG1  VAL   346   -15.240  -12.874   -7.713   1.00   0.00
ATOM    856   HG11 VAL   346   -15.664  -13.253   -8.632   1.00   0.00
ATOM    857   HG12 VAL   346   -15.704  -13.368   -6.873   1.00   0.00
ATOM    858   HG13 VAL   346   -14.177  -13.065   -7.701   1.00   0.00
ATOM    859   CG2  VAL   346   -15.172  -10.716   -8.968   1.00   0.00
ATOM    860   HG21 VAL   346   -15.009  -11.483   -9.710   1.00   0.00
ATOM    861   HG22 VAL   346   -14.282  -10.111   -8.875   1.00   0.00
ATOM    862   HG23 VAL   346   -16.001  -10.094   -9.271   1.00   0.00
ATOM    863   C    VAL   346   -17.875  -11.961   -8.146   1.00   0.00
ATOM    864   O    VAL   346   -18.300  -11.542   -9.204   1.00   0.00
ATOM    865   N    ASN   347   -18.189  -13.151   -7.712   1.00   0.00
ATOM    866   HN   ASN   347   -17.836  -13.468   -6.855   1.00   0.00
```

Figure 9-16

| ATOM | 867 | CA | ASN | 347 | -19.086 | -14.026 | -8.520 | 1.00 | 0.00 |
| --- | --- | --- | --- | --- | --- | --- | --- | --- | --- |
| ATOM | 868 | HA | ASN | 347 | -19.101 | -13.705 | -9.548 | 1.00 | 0.00 |
| ATOM | 869 | CB | ASN | 347 | -18.480 | -15.426 | -8.417 | 1.00 | 0.00 |
| ATOM | 870 | HB1 | ASN | 347 | -17.417 | -15.371 | -8.597 | 1.00 | 0.00 |
| ATOM | 871 | HB2 | ASN | 347 | -18.938 | -16.070 | -9.154 | 1.00 | 0.00 |
| ATOM | 872 | CG | ASN | 347 | -18.729 | -15.991 | -7.017 | 1.00 | 0.00 |
| ATOM | 873 | OD1 | ASN | 347 | -19.860 | -16.199 | -6.626 | 1.00 | 0.00 |
| ATOM | 874 | ND2 | ASN | 347 | -17.713 | -16.249 | -6.241 | 1.00 | 0.00 |
| ATOM | 875 | HD21 | ASN | 347 | -16.801 | -16.081 | -6.555 | 1.00 | 0.00 |
| ATOM | 876 | HD22 | ASN | 347 | -17.863 | -16.611 | -5.342 | 1.00 | 0.00 |
| ATOM | 877 | C | ASN | 347 | -20.496 | -14.005 | -7.930 | 1.00 | 0.00 |
| ATOM | 878 | O | ASN | 347 | -21.343 | -14.798 | -8.288 | 1.00 | 0.00 |
| ATOM | 879 | N | ALA | 348 | -20.750 | -13.101 | -7.025 | 1.00 | 0.00 |
| ATOM | 880 | HN | ALA | 348 | -20.048 | -12.473 | -6.752 | 1.00 | 0.00 |
| ATOM | 881 | CA | ALA | 348 | -22.104 | -13.018 | -6.403 | 1.00 | 0.00 |
| ATOM | 882 | HA | ALA | 348 | -22.843 | -13.466 | -7.047 | 1.00 | 0.00 |
| ATOM | 883 | CB | ALA | 348 | -21.993 | -13.810 | -5.101 | 1.00 | 0.00 |
| ATOM | 884 | HB1 | ALA | 348 | -22.717 | -13.438 | -4.390 | 1.00 | 0.00 |
| ATOM | 885 | HB2 | ALA | 348 | -20.998 | -13.697 | -4.694 | 1.00 | 0.00 |
| ATOM | 886 | HB3 | ALA | 348 | -22.185 | -14.854 | -5.297 | 1.00 | 0.00 |
| ATOM | 887 | C | ALA | 348 | -22.457 | -11.555 | -6.118 | 1.00 | 0.00 |
| ATOM | 888 | O | ALA | 348 | -23.270 | -11.254 | -5.264 | 1.00 | 0.00 |
| ATOM | 889 | N | ALA | 349 | -21.849 | -10.645 | -6.828 | 1.00 | 0.00 |
| ATOM | 890 | HN | ALA | 349 | -21.202 | -10.912 | -7.509 | 1.00 | 0.00 |
| ATOM | 891 | CA | ALA | 349 | -22.139 | -9.202 | -6.609 | 1.00 | 0.00 |
| ATOM | 892 | HA | ALA | 349 | -23.082 | -9.082 | -6.111 | 1.00 | 0.00 |
| ATOM | 893 | CB | ALA | 349 | -21.004 | -8.698 | -5.717 | 1.00 | 0.00 |
| ATOM | 894 | HB1 | ALA | 349 | -20.146 | -8.459 | -6.328 | 1.00 | 0.00 |
| ATOM | 895 | HB2 | ALA | 349 | -20.737 | -9.466 | -5.006 | 1.00 | 0.00 |
| ATOM | 896 | HB3 | ALA | 349 | -21.327 | -7.814 | -5.189 | 1.00 | 0.00 |
| ATOM | 897 | C | ALA | 349 | -22.138 | -8.462 | -7.949 | 1.00 | 0.00 |
| ATOM | 898 | O | ALA | 349 | -21.948 | -7.264 | -8.009 | 1.00 | 0.00 |
| ATOM | 899 | N | ARG | 350 | -22.347 | -9.171 | -9.024 | 1.00 | 0.00 |
| ATOM | 900 | HN | ARG | 350 | -22.496 | -10.137 | -8.951 | 1.00 | 0.00 |
| ATOM | 901 | CA | ARG | 350 | -22.359 | -8.516 | -10.363 | 1.00 | 0.00 |
| ATOM | 902 | HA | ARG | 350 | -21.357 | -8.269 | -10.669 | 1.00 | 0.00 |
| ATOM | 903 | CB | ARG | 350 | -22.947 | -9.563 | -11.307 | 1.00 | 0.00 |
| ATOM | 904 | HB1 | ARG | 350 | -23.220 | -9.094 | -12.241 | 1.00 | 0.00 |
| ATOM | 905 | HB2 | ARG | 350 | -23.824 | -10.005 | -10.854 | 1.00 | 0.00 |
| ATOM | 906 | CG | ARG | 350 | -21.905 | -10.651 | -11.571 | 1.00 | 0.00 |
| ATOM | 907 | HG1 | ARG | 350 | -22.294 | -11.357 | -12.288 | 1.00 | 0.00 |
| ATOM | 908 | HG2 | ARG | 350 | -21.677 | -11.163 | -10.646 | 1.00 | 0.00 |
| ATOM | 909 | CD | ARG | 350 | -20.631 | -10.011 | -12.127 | 1.00 | 0.00 |
| ATOM | 910 | HD1 | ARG | 350 | -20.082 | -9.520 | -11.339 | 1.00 | 0.00 |
| ATOM | 911 | HD2 | ARG | 350 | -20.877 | -9.308 | -12.914 | 1.00 | 0.00 |
| ATOM | 912 | NE | ARG | 350 | -19.838 | -11.147 | -12.670 | 1.00 | 0.00 |
| ATOM | 913 | HE | ARG | 350 | -19.308 | -11.709 | -12.067 | 1.00 | 0.00 |
| ATOM | 914 | CZ | ARG | 350 | -19.847 | -11.393 | -13.952 | 1.00 | 0.00 |
| ATOM | 915 | NH1 | ARG | 350 | -19.846 | -12.625 | -14.378 | 1.00 | 0.00 |
| ATOM | 916 | HH11 | ARG | 350 | -19.838 | -13.379 | -13.723 | 1.00 | 0.00 |
| ATOM | 917 | HH12 | ARG | 350 | -19.852 | -12.816 | -15.360 | 1.00 | 0.00 |
| ATOM | 918 | NH2 | ARG | 350 | -19.857 | -10.406 | -14.807 | 1.00 | 0.00 |
| ATOM | 919 | HH21 | ARG | 350 | -19.857 | -9.460 | -14.481 | 1.00 | 0.00 |
| ATOM | 920 | HH22 | ARG | 350 | -19.862 | -10.596 | -15.788 | 1.00 | 0.00 |
| ATOM | 921 | C | ARG | 350 | -23.234 | -7.260 | -10.338 | 1.00 | 0.00 |
| ATOM | 922 | O | ARG | 350 | -22.756 | -6.165 | -10.115 | 1.00 | 0.00 |
| ATOM | 923 | N | TYR | 351 | -24.511 | -7.406 | -10.562 | 1.00 | 0.00 |
| ATOM | 924 | HN | TYR | 351 | -24.879 | -8.297 | -10.736 | 1.00 | 0.00 |

Figure 9-17

| | | | | | | | | |
|---|---|---|---|---|---|---|---|---|
| ATOM | 925 | CA | TYR | 351 | -25.409 | -6.212 | -10.550 | 1.00 0.00 |
| ATOM | 926 | HA | TYR | 351 | -25.303 | -5.669 | -9.627 | 1.00 0.00 |
| ATOM | 927 | CB | TYR | 351 | -24.929 | -5.354 | -11.719 | 1.00 0.00 |
| ATOM | 928 | HB1 | TYR | 351 | -25.294 | -5.772 | -12.646 | 1.00 0.00 |
| ATOM | 929 | HB2 | TYR | 351 | -23.849 | -5.337 | -11.733 | 1.00 0.00 |
| ATOM | 930 | CG | TYR | 351 | -25.452 | -3.948 | -11.564 | 1.00 0.00 |
| ATOM | 931 | CD1 | TYR | 351 | -26.403 | -3.453 | -12.465 | 1.00 0.00 |
| ATOM | 932 | HD1 | TYR | 351 | -26.765 | -4.079 | -13.268 | 1.00 0.00 |
| ATOM | 933 | CD2 | TYR | 351 | -24.984 | -3.137 | -10.523 | 1.00 0.00 |
| ATOM | 934 | HD2 | TYR | 351 | -24.251 | -3.519 | -9.828 | 1.00 0.00 |
| ATOM | 935 | CE1 | TYR | 351 | -26.887 | -2.148 | -12.324 | 1.00 0.00 |
| ATOM | 936 | HE1 | TYR | 351 | -27.619 | -1.767 | -13.018 | 1.00 0.00 |
| ATOM | 937 | CE2 | TYR | 351 | -25.469 | -1.831 | -10.382 | 1.00 0.00 |
| ATOM | 938 | HE2 | TYR | 351 | -25.111 | -1.206 | -9.579 | 1.00 0.00 |
| ATOM | 939 | CZ | TYR | 351 | -26.421 | -1.337 | -11.283 | 1.00 0.00 |
| ATOM | 940 | OH | TYR | 351 | -26.899 | -0.051 | -11.144 | 1.00 0.00 |
| ATOM | 941 | HH | TYR | 351 | -26.987 | 0.328 | -12.021 | 1.00 0.00 |
| ATOM | 942 | C | TYR | 351 | -26.867 | -6.637 | -10.761 | 1.00 0.00 |
| ATOM | 943 | O | TYR | 351 | -27.360 | -6.668 | -11.872 | 1.00 0.00 |
| ATOM | 944 | N | GLY | 352 | -27.563 | -6.962 | -9.704 | 1.00 0.00 |
| ATOM | 945 | HN | GLY | 352 | -27.150 | -6.929 | -8.815 | 1.00 0.00 |
| ATOM | 946 | CA | GLY | 352 | -28.985 | -7.383 | -9.850 | 1.00 0.00 |
| ATOM | 947 | HA1 | GLY | 352 | -29.185 | -7.621 | -10.883 | 1.00 0.00 |
| ATOM | 948 | HA2 | GLY | 352 | -29.633 | -6.576 | -9.534 | 1.00 0.00 |
| ATOM | 949 | C | GLY | 352 | -29.248 | -8.619 | -8.987 | 1.00 0.00 |
| ATOM | 950 | O | GLY | 352 | -28.580 | -8.854 | -8.000 | 1.00 0.00 |
| ATOM | 951 | N | ASN | 353 | -30.218 | -9.414 | -9.354 | 1.00 0.00 |
| ATOM | 952 | HN | ASN | 353 | -30.741 | -9.209 | -10.156 | 1.00 0.00 |
| ATOM | 953 | CA | ASN | 353 | -30.526 | -10.637 | -8.554 | 1.00 0.00 |
| ATOM | 954 | HA | ASN | 353 | -31.092 | -10.379 | -7.676 | 1.00 0.00 |
| ATOM | 955 | CB | ASN | 353 | -31.368 | -11.516 | -9.479 | 1.00 0.00 |
| ATOM | 956 | HB1 | ASN | 353 | -30.805 | -11.744 | -10.370 | 1.00 0.00 |
| ATOM | 957 | HB2 | ASN | 353 | -32.274 | -10.991 | -9.748 | 1.00 0.00 |
| ATOM | 958 | CG | ASN | 353 | -31.726 | -12.817 | -8.758 | 1.00 0.00 |
| ATOM | 959 | OD1 | ASN | 353 | -31.375 | -13.005 | -7.610 | 1.00 0.00 |
| ATOM | 960 | ND2 | ASN | 353 | -32.417 | -13.730 | -9.387 | 1.00 0.00 |
| ATOM | 961 | HD21 | ASN | 353 | -32.702 | -13.578 | -10.313 | 1.00 0.00 |
| ATOM | 962 | HD22 | ASN | 353 | -32.648 | -14.569 | -8.934 | 1.00 0.00 |
| ATOM | 963 | C | ASN | 353 | -29.232 | -11.354 | -8.164 | 1.00 0.00 |
| ATOM | 964 | O | ASN | 353 | -28.686 | -12.127 | -8.927 | 1.00 0.00 |
| ATOM | 965 | N | GLY | 354 | -28.736 | -11.107 | -6.982 | 1.00 0.00 |
| ATOM | 966 | HN | GLY | 354 | -29.190 | -10.482 | -6.380 | 1.00 0.00 |
| ATOM | 967 | CA | GLY | 354 | -27.478 | -11.778 | -6.551 | 1.00 0.00 |
| ATOM | 968 | HA1 | GLY | 354 | -26.676 | -11.501 | -7.217 | 1.00 0.00 |
| ATOM | 969 | HA2 | GLY | 354 | -27.617 | -12.847 | -6.581 | 1.00 0.00 |
| ATOM | 970 | C | GLY | 354 | -27.120 | -11.352 | -5.126 | 1.00 0.00 |
| ATOM | 971 | O | GLY | 354 | -26.054 | -10.826 | -4.876 | 1.00 0.00 |
| ATOM | 972 | N | TRP | 355 | -28.001 | -11.573 | -4.188 | 1.00 0.00 |
| ATOM | 973 | HN | TRP | 355 | -28.857 | -11.999 | -4.408 | 1.00 0.00 |
| ATOM | 974 | CA | TRP | 355 | -27.706 | -11.179 | -2.777 | 1.00 0.00 |
| ATOM | 975 | HA | TRP | 355 | -27.415 | -10.142 | -2.734 | 1.00 0.00 |
| ATOM | 976 | CB | TRP | 355 | -29.050 | -11.382 | -2.026 | 1.00 0.00 |
| ATOM | 977 | HB1 | TRP | 355 | -29.725 | -11.946 | -2.654 | 1.00 0.00 |
| ATOM | 978 | HB2 | TRP | 355 | -29.487 | -10.419 | -1.816 | 1.00 0.00 |
| ATOM | 979 | CG | TRP | 355 | -28.842 | -12.119 | -0.734 | 1.00 0.00 |
| ATOM | 980 | CD1 | TRP | 355 | -28.475 | -11.550 | 0.437 | 1.00 0.00 |
| ATOM | 981 | HD1 | TRP | 355 | -28.286 | -10.498 | 0.592 | 1.00 0.00 |
| ATOM | 982 | CD2 | TRP | 355 | -28.983 | -13.543 | -0.471 | 1.00 0.00 |

Figure 9-18

| | | | | | | | | |
|---|---|---|---|---|---|---|---|---|
| ATOM | 983 | NE1 | TRP | 355 | -28.382 | -12.538 | 1.402 | 1.00 | 0.00 |
| ATOM | 984 | HE1 | TRP | 355 | -28.132 | -12.392 | 2.338 | 1.00 | 0.00 |
| ATOM | 985 | CE2 | TRP | 355 | -28.686 | -13.783 | 0.889 | 1.00 | 0.00 |
| ATOM | 986 | CE3 | TRP | 355 | -29.338 | -14.640 | -1.276 | 1.00 | 0.00 |
| ATOM | 987 | HE3 | TRP | 355 | -29.571 | -14.487 | -2.320 | 1.00 | 0.00 |
| ATOM | 988 | CZ2 | TRP | 355 | -28.739 | -15.063 | 1.434 | 1.00 | 0.00 |
| ATOM | 989 | HZ2 | TRP | 355 | -28.507 | -15.219 | 2.476 | 1.00 | 0.00 |
| ATOM | 990 | CZ3 | TRP | 355 | -29.392 | -15.934 | -0.730 | 1.00 | 0.00 |
| ATOM | 991 | HZ3 | TRP | 355 | -29.665 | -16.771 | -1.355 | 1.00 | 0.00 |
| ATOM | 992 | CH2 | TRP | 355 | -29.092 | -16.143 | 0.624 | 1.00 | 0.00 |
| ATOM | 993 | HH2 | TRP | 355 | -29.135 | -17.137 | 1.038 | 1.00 | 0.00 |
| ATOM | 994 | C | TRP | 355 | -26.577 | -12.072 | -2.217 | 1.00 | 0.00 |
| ATOM | 995 | O | TRP | 355 | -26.290 | -13.129 | -2.753 | 1.00 | 0.00 |
| ATOM | 996 | N | ILE | 356 | -25.942 | -11.657 | -1.143 | 1.00 | 0.00 |
| ATOM | 997 | HN | ILE | 356 | -26.184 | -10.807 | -0.724 | 1.00 | 0.00 |
| ATOM | 998 | CA | ILE | 356 | -24.843 | -12.483 | -0.564 | 1.00 | 0.00 |
| ATOM | 999 | HA | ILE | 356 | -24.765 | -13.426 | -1.083 | 1.00 | 0.00 |
| ATOM | 1000 | CB | ILE | 356 | -23.576 | -11.665 | -0.780 | 1.00 | 0.00 |
| ATOM | 1001 | HB | ILE | 356 | -23.513 | -10.901 | -0.023 | 1.00 | 0.00 |
| ATOM | 1002 | CG1 | ILE | 356 | -23.603 | -11.015 | -2.170 | 1.00 | 0.00 |
| ATOM | 1003 | HG11 | ILE | 356 | -24.501 | -10.427 | -2.274 | 1.00 | 0.00 |
| ATOM | 1004 | HG12 | ILE | 356 | -23.587 | -11.786 | -2.927 | 1.00 | 0.00 |
| ATOM | 1005 | CG2 | ILE | 356 | -22.368 | -12.579 | -0.676 | 1.00 | 0.00 |
| ATOM | 1006 | HG21 | ILE | 356 | -21.482 | -12.036 | -0.965 | 1.00 | 0.00 |
| ATOM | 1007 | HG22 | ILE | 356 | -22.504 | -13.425 | -1.332 | 1.00 | 0.00 |
| ATOM | 1008 | HG23 | ILE | 356 | -22.266 | -12.922 | 0.341 | 1.00 | 0.00 |
| ATOM | 1009 | CD1 | ILE | 356 | -22.380 | -10.110 | -2.336 | 1.00 | 0.00 |
| ATOM | 1010 | HD11 | ILE | 356 | -21.878 | -10.005 | -1.386 | 1.00 | 0.00 |
| ATOM | 1011 | HD12 | ILE | 356 | -22.697 | -9.139 | -2.686 | 1.00 | 0.00 |
| ATOM | 1012 | HD13 | ILE | 356 | -21.703 | -10.548 | -3.055 | 1.00 | 0.00 |
| ATOM | 1013 | C | ILE | 356 | -25.070 | -12.721 | 0.931 | 1.00 | 0.00 |
| ATOM | 1014 | O | ILE | 356 | -25.722 | -11.950 | 1.613 | 1.00 | 0.00 |
| ATOM | 1015 | N | LYS | 357 | -24.509 | -13.771 | 1.448 | 1.00 | 0.00 |
| ATOM | 1016 | HN | LYS | 357 | -23.958 | -14.352 | 0.889 | 1.00 | 0.00 |
| ATOM | 1017 | CA | LYS | 357 | -24.680 | -14.076 | 2.891 | 1.00 | 0.00 |
| ATOM | 1018 | HA | LYS | 357 | -25.026 | -13.208 | 3.423 | 1.00 | 0.00 |
| ATOM | 1019 | CB | LYS | 357 | -25.742 | -15.175 | 2.935 | 1.00 | 0.00 |
| ATOM | 1020 | HB1 | LYS | 357 | -25.390 | -16.037 | 2.390 | 1.00 | 0.00 |
| ATOM | 1021 | HB2 | LYS | 357 | -26.657 | -14.812 | 2.485 | 1.00 | 0.00 |
| ATOM | 1022 | CG | LYS | 357 | -26.007 | -15.568 | 4.389 | 1.00 | 0.00 |
| ATOM | 1023 | HG1 | LYS | 357 | -26.593 | -14.800 | 4.866 | 1.00 | 0.00 |
| ATOM | 1024 | HG2 | LYS | 357 | -25.066 | -15.679 | 4.909 | 1.00 | 0.00 |
| ATOM | 1025 | CD | LYS | 357 | -26.774 | -16.892 | 4.431 | 1.00 | 0.00 |
| ATOM | 1026 | HD1 | LYS | 357 | -26.078 | -17.716 | 4.370 | 1.00 | 0.00 |
| ATOM | 1027 | HD2 | LYS | 357 | -27.460 | -16.937 | 3.599 | 1.00 | 0.00 |
| ATOM | 1028 | CE | LYS | 357 | -27.556 | -16.987 | 5.744 | 1.00 | 0.00 |
| ATOM | 1029 | HE1 | LYS | 357 | -27.168 | -16.286 | 6.464 | 1.00 | 0.00 |
| ATOM | 1030 | HE2 | LYS | 357 | -27.514 | -17.995 | 6.134 | 1.00 | 0.00 |
| ATOM | 1031 | NZ | LYS | 357 | -28.955 | -16.627 | 5.385 | 1.00 | 0.00 |
| ATOM | 1032 | HZ1 | LYS | 357 | -29.611 | -17.087 | 6.045 | 1.00 | 0.00 |
| ATOM | 1033 | HZ2 | LYS | 357 | -29.156 | -16.947 | 4.415 | 1.00 | 0.00 |
| ATOM | 1034 | HZ3 | LYS | 357 | -29.074 | -15.597 | 5.441 | 1.00 | 0.00 |
| ATOM | 1035 | C | LYS | 357 | -23.369 | -14.587 | 3.484 | 1.00 | 0.00 |
| ATOM | 1036 | O | LYS | 357 | -22.928 | -15.678 | 3.185 | 1.00 | 0.00 |
| ATOM | 1037 | N | VAL | 358 | -22.738 | -13.814 | 4.318 | 1.00 | 0.00 |
| ATOM | 1038 | HN | VAL | 358 | -23.101 | -12.933 | 4.546 | 1.00 | 0.00 |
| ATOM | 1039 | CA | VAL | 358 | -21.460 | -14.275 | 4.919 | 1.00 | 0.00 |
| ATOM | 1040 | HA | VAL | 358 | -20.923 | -14.895 | 4.228 | 1.00 | 0.00 |

Figure 9-19

| ATOM | 1041 | CB   | VAL | 358 | -20.670 | -13.008 | 5.208  | 1.00 | 0.00 |
|------|------|------|-----|-----|---------|---------|--------|------|------|
| ATOM | 1042 | HB   | VAL | 358 | -21.330 | -12.258 | 5.601  | 1.00 | 0.00 |
| ATOM | 1043 | CG1  | VAL | 358 | -19.566 | -13.307 | 6.232  | 1.00 | 0.00 |
| ATOM | 1044 | HG11 | VAL | 358 | -19.810 | -12.835 | 7.172  | 1.00 | 0.00 |
| ATOM | 1045 | HG12 | VAL | 358 | -18.625 | -12.921 | 5.869  | 1.00 | 0.00 |
| ATOM | 1046 | HG13 | VAL | 358 | -19.486 | -14.375 | 6.375  | 1.00 | 0.00 |
| ATOM | 1047 | CG2  | VAL | 358 | -20.039 | -12.509 | 3.911  | 1.00 | 0.00 |
| ATOM | 1048 | HG21 | VAL | 358 | -20.650 | -12.816 | 3.074  | 1.00 | 0.00 |
| ATOM | 1049 | HG22 | VAL | 358 | -19.050 | -12.931 | 3.808  | 1.00 | 0.00 |
| ATOM | 1050 | HG23 | VAL | 358 | -19.972 | -11.434 | 3.934  | 1.00 | 0.00 |
| ATOM | 1051 | C    | VAL | 358 | -21.760 | -15.035 | 6.198  | 1.00 | 0.00 |
| ATOM | 1052 | O    | VAL | 358 | -21.768 | -14.482 | 7.278  | 1.00 | 0.00 |
| ATOM | 1053 | N    | SER | 359 | -22.010 | -16.303 | 6.084  | 1.00 | 0.00 |
| ATOM | 1054 | HN   | SER | 359 | -21.990 | -16.729 | 5.199  | 1.00 | 0.00 |
| ATOM | 1055 | CA   | SER | 359 | -22.313 | -17.109 | 7.291  | 1.00 | 0.00 |
| ATOM | 1056 | HA   | SER | 359 | -22.543 | -16.467 | 8.123  | 1.00 | 0.00 |
| ATOM | 1057 | CB   | SER | 359 | -23.541 | -17.936 | 6.918  | 1.00 | 0.00 |
| ATOM | 1058 | HB1  | SER | 359 | -23.238 | -18.760 | 6.281  | 1.00 | 0.00 |
| ATOM | 1059 | HB2  | SER | 359 | -24.247 | -17.320 | 6.392  | 1.00 | 0.00 |
| ATOM | 1060 | OG   | SER | 359 | -24.147 | -18.436 | 8.104  | 1.00 | 0.00 |
| ATOM | 1061 | HG   | SER | 359 | -23.690 | -19.244 | 8.352  | 1.00 | 0.00 |
| ATOM | 1062 | C    | SER | 359 | -21.140 | -18.019 | 7.626  | 1.00 | 0.00 |
| ATOM | 1063 | O    | SER | 359 | -20.554 | -18.631 | 6.764  | 1.00 | 0.00 |
| ATOM | 1064 | N    | SER | 360 | -20.793 | -18.102 | 8.871  | 1.00 | 0.00 |
| ATOM | 1065 | HN   | SER | 360 | -21.273 | -17.597 | 9.536  | 1.00 | 0.00 |
| ATOM | 1066 | CA   | SER | 360 | -19.662 | -18.968 | 9.279  | 1.00 | 0.00 |
| ATOM | 1067 | HA   | SER | 360 | -19.308 | -19.539 | 8.441  | 1.00 | 0.00 |
| ATOM | 1068 | CB   | SER | 360 | -18.575 | -18.013 | 9.759  | 1.00 | 0.00 |
| ATOM | 1069 | HB1  | SER | 360 | -18.851 | -17.612 | 10.727 | 1.00 | 0.00 |
| ATOM | 1070 | HB2  | SER | 360 | -18.466 | -17.207 | 9.058  | 1.00 | 0.00 |
| ATOM | 1071 | OG   | SER | 360 | -17.344 | -18.719 | 9.859  | 1.00 | 0.00 |
| ATOM | 1072 | HG   | SER | 360 | -17.296 | -19.108 | 10.737 | 1.00 | 0.00 |
| ATOM | 1073 | C    | SER | 360 | -20.104 | -19.894 | 10.412 | 1.00 | 0.00 |
| ATOM | 1074 | O    | SER | 360 | -21.109 | -19.666 | 11.062 | 1.00 | 0.00 |
| ATOM | 1075 | N    | GLY | 361 | -19.359 | -20.925 | 10.661 | 1.00 | 0.00 |
| ATOM | 1076 | HN   | GLY | 361 | -18.542 | -21.071 | 10.142 | 1.00 | 0.00 |
| ATOM | 1077 | CA   | GLY | 361 | -19.726 | -21.872 | 11.750 | 1.00 | 0.00 |
| ATOM | 1078 | HA1  | GLY | 361 | -20.554 | -22.486 | 11.432 | 1.00 | 0.00 |
| ATOM | 1079 | HA2  | GLY | 361 | -20.005 | -21.315 | 12.635 | 1.00 | 0.00 |
| ATOM | 1080 | C    | GLY | 361 | -18.526 | -22.759 | 12.059 | 1.00 | 0.00 |
| ATOM | 1081 | O    | GLY | 361 | -17.400 | -22.395 | 11.795 | 1.00 | 0.00 |
| ATOM | 1082 | N    | THR | 362 | -18.747 | -23.930 | 12.602 | 1.00 | 0.00 |
| ATOM | 1083 | HN   | THR | 362 | -19.663 | -24.225 | 12.790 | 1.00 | 0.00 |
| ATOM | 1084 | CA   | THR | 362 | -17.593 | -24.817 | 12.916 | 1.00 | 0.00 |
| ATOM | 1085 | HA   | THR | 362 | -17.059 | -25.066 | 12.018 | 1.00 | 0.00 |
| ATOM | 1086 | CB   | THR | 362 | -16.699 | -23.988 | 13.841 | 1.00 | 0.00 |
| ATOM | 1087 | HB   | THR | 362 | -16.202 | -23.220 | 13.276 | 1.00 | 0.00 |
| ATOM | 1088 | OG1  | THR | 362 | -15.729 | -24.833 | 14.443 | 1.00 | 0.00 |
| ATOM | 1089 | HG1  | THR | 362 | -15.573 | -24.518 | 15.337 | 1.00 | 0.00 |
| ATOM | 1090 | CG2  | THR | 362 | -17.557 | -23.342 | 14.927 | 1.00 | 0.00 |
| ATOM | 1091 | HG21 | THR | 362 | -17.825 | -22.340 | 14.626 | 1.00 | 0.00 |
| ATOM | 1092 | HG22 | THR | 362 | -16.998 | -23.303 | 15.851 | 1.00 | 0.00 |
| ATOM | 1093 | HG23 | THR | 362 | -18.453 | -23.926 | 15.074 | 1.00 | 0.00 |
| ATOM | 1094 | C    | THR | 362 | -18.051 | -26.083 | 13.637 | 1.00 | 0.00 |
| ATOM | 1095 | O    | THR | 362 | -19.220 | -26.283 | 13.900 | 1.00 | 0.00 |
| ATOM | 1096 | N    | GLU | 363 | -17.122 | -26.933 | 13.960 | 1.00 | 0.00 |
| ATOM | 1097 | HN   | GLU | 363 | -16.191 | -26.732 | 13.744 | 1.00 | 0.00 |
| ATOM | 1098 | CA   | GLU | 363 | -17.456 | -28.197 | 14.666 | 1.00 | 0.00 |

Figure 9-20

| ATOM | 1099 | HA | GLU | 363 | -18.438 | -28.140 | 15.107 | 1.00 | 0.00 |
| ATOM | 1100 | CB | GLU | 363 | -17.419 | -29.280 | 13.586 | 1.00 | 0.00 |
| ATOM | 1101 | HB1 | GLU | 363 | -16.745 | -30.067 | 13.887 | 1.00 | 0.00 |
| ATOM | 1102 | HB2 | GLU | 363 | -17.078 | -28.849 | 12.655 | 1.00 | 0.00 |
| ATOM | 1103 | CG | GLU | 363 | -18.824 | -29.860 | 13.395 | 1.00 | 0.00 |
| ATOM | 1104 | HG1 | GLU | 363 | -19.380 | -29.237 | 12.711 | 1.00 | 0.00 |
| ATOM | 1105 | HG2 | GLU | 363 | -19.332 | -29.892 | 14.349 | 1.00 | 0.00 |
| ATOM | 1106 | CD | GLU | 363 | -18.719 | -31.275 | 12.822 | 1.00 | 0.00 |
| ATOM | 1107 | OE1 | GLU | 363 | -19.088 | -32.205 | 13.522 | 1.00 | 0.00 |
| ATOM | 1108 | OE2 | GLU | 363 | -18.271 | -31.406 | 11.695 | 1.00 | 0.00 |
| ATOM | 1109 | C | GLU | 363 | -16.394 | -28.452 | 15.738 | 1.00 | 0.00 |
| ATOM | 1110 | O | GLU | 363 | -15.441 | -27.708 | 15.845 | 1.00 | 0.00 |
| ATOM | 1111 | N | PRO | 364 | -16.585 | -29.488 | 16.500 | 1.00 | 0.00 |
| ATOM | 1112 | CA | PRO | 364 | -15.619 | -29.813 | 17.560 | 1.00 | 0.00 |
| ATOM | 1113 | HA | PRO | 364 | -15.275 | -28.923 | 18.011 | 1.00 | 0.00 |
| ATOM | 1114 | CB | PRO | 364 | -16.428 | -30.637 | 18.545 | 1.00 | 0.00 |
| ATOM | 1115 | HB1 | PRO | 364 | -16.828 | -30.007 | 19.322 | 1.00 | 0.00 |
| ATOM | 1116 | HB2 | PRO | 364 | -15.812 | -31.418 | 18.973 | 1.00 | 0.00 |
| ATOM | 1117 | CG | PRO | 364 | -17.556 | -31.237 | 17.736 | 1.00 | 0.00 |
| ATOM | 1118 | HG1 | PRO | 364 | -18.473 | -31.196 | 18.302 | 1.00 | 0.00 |
| ATOM | 1119 | HG2 | PRO | 364 | -17.323 | -32.264 | 17.488 | 1.00 | 0.00 |
| ATOM | 1120 | CD | PRO | 364 | -17.707 | -30.418 | 16.464 | 1.00 | 0.00 |
| ATOM | 1121 | HD1 | PRO | 364 | -18.640 | -29.876 | 16.470 | 1.00 | 0.00 |
| ATOM | 1122 | HD2 | PRO | 364 | -17.644 | -31.057 | 15.593 | 1.00 | 0.00 |
| ATOM | 1123 | C | PRO | 364 | -14.434 | -30.594 | 17.015 | 1.00 | 0.00 |
| ATOM | 1124 | O | PRO | 364 | -13.622 | -31.120 | 17.751 | 1.00 | 0.00 |
| ATOM | 1125 | N | ASN | 365 | -14.331 | -30.662 | 15.751 | 1.00 | 0.00 |
| ATOM | 1126 | HN | ASN | 365 | -15.000 | -30.229 | 15.193 | 1.00 | 0.00 |
| ATOM | 1127 | CA | ASN | 365 | -13.211 | -31.395 | 15.126 | 1.00 | 0.00 |
| ATOM | 1128 | HA | ASN | 365 | -12.328 | -31.318 | 15.729 | 1.00 | 0.00 |
| ATOM | 1129 | CB | ASN | 365 | -13.670 | -32.848 | 15.030 | 1.00 | 0.00 |
| ATOM | 1130 | HB1 | ASN | 365 | -13.145 | -33.339 | 14.226 | 1.00 | 0.00 |
| ATOM | 1131 | HB2 | ASN | 365 | -14.733 | -32.877 | 14.838 | 1.00 | 0.00 |
| ATOM | 1132 | CG | ASN | 365 | -13.368 | -33.566 | 16.348 | 1.00 | 0.00 |
| ATOM | 1133 | OD1 | ASN | 365 | -14.142 | -33.496 | 17.281 | 1.00 | 0.00 |
| ATOM | 1134 | ND2 | ASN | 365 | -12.264 | -34.256 | 16.464 | 1.00 | 0.00 |
| ATOM | 1135 | HD21 | ASN | 365 | -11.637 | -34.308 | 15.713 | 1.00 | 0.00 |
| ATOM | 1136 | HD22 | ASN | 365 | -12.065 | -34.724 | 17.302 | 1.00 | 0.00 |
| ATOM | 1137 | C | ASN | 365 | -12.971 | -30.807 | 13.756 | 1.00 | 0.00 |
| ATOM | 1138 | O | ASN | 365 | -12.397 | -31.429 | 12.885 | 1.00 | 0.00 |
| ATOM | 1139 | N | ARG | 366 | -13.408 | -29.590 | 13.561 | 1.00 | 0.00 |
| ATOM | 1140 | HN | ARG | 366 | -13.853 | -29.099 | 14.310 | 1.00 | 0.00 |
| ATOM | 1141 | CA | ARG | 366 | -13.214 | -28.926 | 12.227 | 1.00 | 0.00 |
| ATOM | 1142 | HA | ARG | 366 | -12.178 | -28.678 | 12.074 | 1.00 | 0.00 |
| ATOM | 1143 | CB | ARG | 366 | -13.663 | -29.962 | 11.190 | 1.00 | 0.00 |
| ATOM | 1144 | HB1 | ARG | 366 | -14.456 | -29.545 | 10.588 | 1.00 | 0.00 |
| ATOM | 1145 | HB2 | ARG | 366 | -14.024 | -30.846 | 11.692 | 1.00 | 0.00 |
| ATOM | 1146 | CG | ARG | 366 | -12.490 | -30.331 | 10.287 | 1.00 | 0.00 |
| ATOM | 1147 | HG1 | ARG | 366 | -11.912 | -31.115 | 10.750 | 1.00 | 0.00 |
| ATOM | 1148 | HG2 | ARG | 366 | -11.865 | -29.462 | 10.135 | 1.00 | 0.00 |
| ATOM | 1149 | CD | ARG | 366 | -13.023 | -30.821 | 8.938 | 1.00 | 0.00 |
| ATOM | 1150 | HD1 | ARG | 366 | -12.379 | -30.498 | 8.137 | 1.00 | 0.00 |
| ATOM | 1151 | HD2 | ARG | 366 | -14.033 | -30.460 | 8.781 | 1.00 | 0.00 |
| ATOM | 1152 | NE | ARG | 366 | -13.010 | -32.306 | 9.037 | 1.00 | 0.00 |
| ATOM | 1153 | HE | ARG | 366 | -12.331 | -32.823 | 8.554 | 1.00 | 0.00 |
| ATOM | 1154 | CZ | ARG | 366 | -13.901 | -32.918 | 9.766 | 1.00 | 0.00 |
| ATOM | 1155 | NH1 | ARG | 366 | -15.172 | -32.755 | 9.518 | 1.00 | 0.00 |
| ATOM | 1156 | HH11 | ARG | 366 | -15.463 | -32.162 | 8.767 | 1.00 | 0.00 |

Figure 9-21

```
ATOM   1157  HH12 ARG   366     -15.856 -33.223  10.079  1.00  0.00
ATOM   1158  NH2  ARG   366     -13.520 -33.696  10.743  1.00  0.00
ATOM   1159  HH21 ARG   366     -12.547 -33.823  10.931  1.00  0.00
ATOM   1160  HH22 ARG   366     -14.203 -34.165  11.303  1.00  0.00
ATOM   1161  C    ARG   366     -14.091 -27.677  12.108  1.00  0.00
ATOM   1162  O    ARG   366     -15.299 -27.751  12.184  1.00  0.00
ATOM   1163  N    ALA   367     -13.495 -26.532  11.908  1.00  0.00
ATOM   1164  HN   ALA   367     -12.508 -26.495  11.825  1.00  0.00
ATOM   1165  CA   ALA   367     -14.316 -25.277  11.782  1.00  0.00
ATOM   1166  HA   ALA   367     -15.270 -25.400  12.262  1.00  0.00
ATOM   1167  CB   ALA   367     -13.507 -24.182  12.477  1.00  0.00
ATOM   1168  HB1  ALA   367     -13.297 -24.478  13.494  1.00  0.00
ATOM   1169  HB2  ALA   367     -14.075 -23.262  12.480  1.00  0.00
ATOM   1170  HB3  ALA   367     -12.579 -24.030  11.946  1.00  0.00
ATOM   1171  C    ALA   367     -14.494 -24.953  10.300  1.00  0.00
ATOM   1172  O    ALA   367     -13.830 -25.516   9.474  1.00  0.00
ATOM   1173  N    TRP   368     -15.391 -24.071   9.939  1.00  0.00
ATOM   1174  HN   TRP   368     -15.952 -23.613  10.609  1.00  0.00
ATOM   1175  CA   TRP   368     -15.548 -23.769   8.482  1.00  0.00
ATOM   1176  HA   TRP   368     -14.585 -23.576   8.040  1.00  0.00
ATOM   1177  CB   TRP   368     -16.146 -25.040   7.871  1.00  0.00
ATOM   1178  HB1  TRP   368     -15.464 -25.865   8.023  1.00  0.00
ATOM   1179  HB2  TRP   368     -16.299 -24.893   6.811  1.00  0.00
ATOM   1180  CG   TRP   368     -17.456 -25.348   8.527  1.00  0.00
ATOM   1181  CD1  TRP   368     -17.663 -26.343   9.421  1.00  0.00
ATOM   1182  HD1  TRP   368     -16.915 -27.039   9.770  1.00  0.00
ATOM   1183  CD2  TRP   368     -18.740 -24.680   8.357  1.00  0.00
ATOM   1184  NE1  TRP   368     -18.989 -26.317   9.819  1.00  0.00
ATOM   1185  HE1  TRP   368     -19.398 -26.927  10.468  1.00  0.00
ATOM   1186  CE2  TRP   368     -19.692 -25.313   9.188  1.00  0.00
ATOM   1187  CE3  TRP   368     -19.166 -23.593   7.571  1.00  0.00
ATOM   1188  HE3  TRP   368     -18.463 -23.088   6.925  1.00  0.00
ATOM   1189  CZ2  TRP   368     -21.015 -24.888   9.241  1.00  0.00
ATOM   1190  HZ2  TRP   368     -21.721 -25.390   9.886  1.00  0.00
ATOM   1191  CZ3  TRP   368     -20.504 -23.161   7.623  1.00  0.00
ATOM   1192  HZ3  TRP   368     -20.823 -22.327   7.017  1.00  0.00
ATOM   1193  CH2  TRP   368     -21.425 -23.810   8.458  1.00  0.00
ATOM   1194  HH2  TRP   368     -22.451 -23.475   8.494  1.00  0.00
ATOM   1195  C    TRP   368     -16.472 -22.575   8.256  1.00  0.00
ATOM   1196  O    TRP   368     -17.414 -22.358   8.984  1.00  0.00
ATOM   1197  N    PHE   369     -16.196 -21.797   7.245  1.00  0.00
ATOM   1198  HN   PHE   369     -15.423 -21.994   6.680  1.00  0.00
ATOM   1199  CA   PHE   369     -17.045 -20.611   6.948  1.00  0.00
ATOM   1200  HA   PHE   369     -17.856 -20.542   7.654  1.00  0.00
ATOM   1201  CB   PHE   369     -16.109 -19.404   7.099  1.00  0.00
ATOM   1202  HB1  PHE   369     -15.506 -19.525   7.987  1.00  0.00
ATOM   1203  HB2  PHE   369     -16.696 -18.501   7.183  1.00  0.00
ATOM   1204  CG   PHE   369     -15.208 -19.303   5.893  1.00  0.00
ATOM   1205  CD1  PHE   369     -15.691 -18.738   4.709  1.00  0.00
ATOM   1206  HD1  PHE   369     -16.708 -18.379   4.658  1.00  0.00
ATOM   1207  CD2  PHE   369     -13.889 -19.768   5.962  1.00  0.00
ATOM   1208  HD2  PHE   369     -13.517 -20.205   6.877  1.00  0.00
ATOM   1209  CE1  PHE   369     -14.857 -18.639   3.590  1.00  0.00
ATOM   1210  HE1  PHE   369     -15.231 -18.202   2.675  1.00  0.00
ATOM   1211  CE2  PHE   369     -13.054 -19.670   4.843  1.00  0.00
ATOM   1212  HE2  PHE   369     -12.038 -20.030   4.894  1.00  0.00
ATOM   1213  CZ   PHE   369     -13.538 -19.105   3.656  1.00  0.00
ATOM   1214  HZ   PHE   369     -12.894 -19.027   2.792  1.00  0.00
```

Figure 9-22

```
ATOM   1215   C    PHE   369    -17.585  -20.720   5.511  1.00  0.00
ATOM   1216   O    PHE   369    -16.863  -21.054   4.591  1.00  0.00
ATOM   1217   N    GLN   370    -18.844  -20.450   5.314  1.00  0.00
ATOM   1218   HN   GLN   370    -19.411  -20.196   6.062  1.00  0.00
ATOM   1219   CA   GLN   370    -19.416  -20.543   3.938  1.00  0.00
ATOM   1220   HA   GLN   370    -18.636  -20.721   3.220  1.00  0.00
ATOM   1221   CB   GLN   370    -20.352  -21.754   3.998  1.00  0.00
ATOM   1222   HB1  GLN   370    -21.030  -21.642   4.831  1.00  0.00
ATOM   1223   HB2  GLN   370    -19.768  -22.653   4.128  1.00  0.00
ATOM   1224   CG   GLN   370    -21.158  -21.854   2.700  1.00  0.00
ATOM   1225   HG1  GLN   370    -20.612  -22.443   1.983  1.00  0.00
ATOM   1226   HG2  GLN   370    -21.326  -20.866   2.300  1.00  0.00
ATOM   1227   CD   GLN   370    -22.505  -22.523   2.986  1.00  0.00
ATOM   1228   OE1  GLN   370    -22.586  -23.432   3.788  1.00  0.00
ATOM   1229   NE2  GLN   370    -23.574  -22.108   2.360  1.00  0.00
ATOM   1230   HE21 GLN   370    -23.510  -21.373   1.714  1.00  0.00
ATOM   1231   HE22 GLN   370    -24.440  -22.533   2.534  1.00  0.00
ATOM   1232   C    GLN   370    -20.203  -19.272   3.574  1.00  0.00
ATOM   1233   O    GLN   370    -20.744  -18.591   4.427  1.00  0.00
ATOM   1234   N    VAL   371    -20.260  -18.950   2.303  1.00  0.00
ATOM   1235   HN   VAL   371    -19.807  -19.514   1.638  1.00  0.00
ATOM   1236   CA   VAL   371    -21.006  -17.731   1.860  1.00  0.00
ATOM   1237   HA   VAL   371    -21.422  -17.215   2.703  1.00  0.00
ATOM   1238   CB   VAL   371    -19.967  -16.856   1.170  1.00  0.00
ATOM   1239   HB   VAL   371    -19.710  -17.291   0.222  1.00  0.00
ATOM   1240   CG1  VAL   371    -20.542  -15.453   0.949  1.00  0.00
ATOM   1241   HG11 VAL   371    -21.232  -15.473   0.118  1.00  0.00
ATOM   1242   HG12 VAL   371    -19.738  -14.765   0.731  1.00  0.00
ATOM   1243   HG13 VAL   371    -21.060  -15.130   1.840  1.00  0.00
ATOM   1244   CG2  VAL   371    -18.719  -16.763   2.049  1.00  0.00
ATOM   1245   HG21 VAL   371    -18.330  -17.755   2.226  1.00  0.00
ATOM   1246   HG22 VAL   371    -18.977  -16.305   2.992  1.00  0.00
ATOM   1247   HG23 VAL   371    -17.970  -16.165   1.550  1.00  0.00
ATOM   1248   C    VAL   371    -22.112  -18.135   0.875  1.00  0.00
ATOM   1249   O    VAL   371    -21.854  -18.744  -0.145  1.00  0.00
ATOM   1250   N    GLU   372    -23.339  -17.796   1.168  1.00  0.00
ATOM   1251   HN   GLU   372    -23.525  -17.289   1.984  1.00  0.00
ATOM   1252   CA   GLU   372    -24.459  -18.164   0.248  1.00  0.00
ATOM   1253   HA   GLU   372    -24.200  -19.034  -0.331  1.00  0.00
ATOM   1254   CB   GLU   372    -25.635  -18.481   1.170  1.00  0.00
ATOM   1255   HB1  GLU   372    -26.497  -17.910   0.864  1.00  0.00
ATOM   1256   HB2  GLU   372    -25.374  -18.223   2.187  1.00  0.00
ATOM   1257   CG   GLU   372    -25.960  -19.972   1.089  1.00  0.00
ATOM   1258   HG1  GLU   372    -25.183  -20.538   1.581  1.00  0.00
ATOM   1259   HG2  GLU   372    -26.023  -20.270   0.052  1.00  0.00
ATOM   1260   CD   GLU   372    -27.297  -20.241   1.780  1.00  0.00
ATOM   1261   OE1  GLU   372    -28.301  -19.747   1.295  1.00  0.00
ATOM   1262   OE2  GLU   372    -27.293  -20.936   2.782  1.00  0.00
ATOM   1263   C    GLU   372    -24.804  -16.994  -0.670  1.00  0.00
ATOM   1264   O    GLU   372    -24.822  -15.855  -0.255  1.00  0.00
ATOM   1265   N    ASP   373    -25.086  -17.264  -1.915  1.00  0.00
ATOM   1266   HN   ASP   373    -25.071  -18.194  -2.234  1.00  0.00
ATOM   1267   CA   ASP   373    -25.430  -16.155  -2.853  1.00  0.00
ATOM   1268   HA   ASP   373    -25.851  -15.322  -2.311  1.00  0.00
ATOM   1269   CB   ASP   373    -24.103  -15.747  -3.489  1.00  0.00
ATOM   1270   HB1  ASP   373    -23.518  -15.189  -2.775  1.00  0.00
ATOM   1271   HB2  ASP   373    -24.295  -15.133  -4.358  1.00  0.00
ATOM   1272   CG   ASP   373    -23.332  -17.000  -3.909  1.00  0.00
```

Figure 9-23

| | | | | | | | | | |
|---|---|---|---|---|---|---|---|---|---|
| ATOM | 1273 | OD1 | ASP | 373 | -22.298 | -17.263 | -3.317 | 1.00 | 0.00 |
| ATOM | 1274 | OD2 | ASP | 373 | -23.789 | -17.678 | -4.816 | 1.00 | 0.00 |
| ATOM | 1275 | C | ASP | 373 | -26.408 | -16.647 | -3.919 | 1.00 | 0.00 |
| ATOM | 1276 | O | ASP | 373 | -26.502 | -17.827 | -4.191 | 1.00 | 0.00 |
| ATOM | 1277 | N | ASP | 374 | -27.139 | -15.754 | -4.525 | 1.00 | 0.00 |
| ATOM | 1278 | HN | ASP | 374 | -27.053 | -14.801 | -4.288 | 1.00 | 0.00 |
| ATOM | 1279 | CA | ASP | 374 | -28.110 | -16.182 | -5.574 | 1.00 | 0.00 |
| ATOM | 1280 | HA | ASP | 374 | -28.334 | -17.230 | -5.471 | 1.00 | 0.00 |
| ATOM | 1281 | CB | ASP | 374 | -29.367 | -15.355 | -5.313 | 1.00 | 0.00 |
| ATOM | 1282 | HB1 | ASP | 374 | -29.793 | -15.041 | -6.253 | 1.00 | 0.00 |
| ATOM | 1283 | HB2 | ASP | 374 | -29.109 | -14.486 | -4.723 | 1.00 | 0.00 |
| ATOM | 1284 | CG | ASP | 374 | -30.385 | -16.207 | -4.551 | 1.00 | 0.00 |
| ATOM | 1285 | OD1 | ASP | 374 | -31.296 | -15.634 | -3.976 | 1.00 | 0.00 |
| ATOM | 1286 | OD2 | ASP | 374 | -30.237 | -17.419 | -4.555 | 1.00 | 0.00 |
| ATOM | 1287 | C | ASP | 374 | -27.552 | -15.892 | -6.973 | 1.00 | 0.00 |
| ATOM | 1288 | O | ASP | 374 | -27.408 | -14.758 | -7.371 | 1.00 | 0.00 |
| ATOM | 1289 | N | GLY | 375 | -27.236 | -16.915 | -7.719 | 1.00 | 0.00 |
| ATOM | 1290 | HN | GLY | 375 | -27.357 | -17.826 | -7.377 | 1.00 | 0.00 |
| ATOM | 1291 | CA | GLY | 375 | -26.687 | -16.699 | -9.092 | 1.00 | 0.00 |
| ATOM | 1292 | HA1 | GLY | 375 | -25.929 | -15.933 | -9.062 | 1.00 | 0.00 |
| ATOM | 1293 | HA2 | GLY | 375 | -27.485 | -16.392 | -9.755 | 1.00 | 0.00 |
| ATOM | 1294 | C | GLY | 375 | -26.069 | -18.002 | -9.603 | 1.00 | 0.00 |
| ATOM | 1295 | O | GLY | 375 | -25.988 | -18.973 | -8.880 | 1.00 | 0.00 |
| ATOM | 1296 | N | PRO | 376 | -25.647 | -17.980 | -10.839 | 1.00 | 0.00 |
| ATOM | 1297 | CA | PRO | 376 | -25.029 | -19.181 | -11.447 | 1.00 | 0.00 |
| ATOM | 1298 | HA | PRO | 376 | -25.671 | -20.038 | -11.336 | 1.00 | 0.00 |
| ATOM | 1299 | CB | PRO | 376 | -24.897 | -18.813 | -12.922 | 1.00 | 0.00 |
| ATOM | 1300 | HB1 | PRO | 376 | -25.750 | -19.169 | -13.476 | 1.00 | 0.00 |
| ATOM | 1301 | HB2 | PRO | 376 | -23.980 | -19.222 | -13.329 | 1.00 | 0.00 |
| ATOM | 1302 | CG | PRO | 376 | -24.861 | -17.316 | -12.942 | 1.00 | 0.00 |
| ATOM | 1303 | HG1 | PRO | 376 | -25.288 | -16.948 | -13.860 | 1.00 | 0.00 |
| ATOM | 1304 | HG2 | PRO | 376 | -23.840 | -16.969 | -12.839 | 1.00 | 0.00 |
| ATOM | 1305 | CD | PRO | 376 | -25.693 | -16.848 | -11.769 | 1.00 | 0.00 |
| ATOM | 1306 | HD1 | PRO | 376 | -26.708 | -16.658 | -12.075 | 1.00 | 0.00 |
| ATOM | 1307 | HD2 | PRO | 376 | -25.255 | -15.964 | -11.322 | 1.00 | 0.00 |
| ATOM | 1308 | C | PRO | 376 | -23.658 | -19.445 | -10.816 | 1.00 | 0.00 |
| ATOM | 1309 | O | PRO | 376 | -22.916 | -18.531 | -10.517 | 1.00 | 0.00 |
| ATOM | 1310 | N | GLY | 377 | -23.316 | -20.689 | -10.612 | 1.00 | 0.00 |
| ATOM | 1311 | HN | GLY | 377 | -23.927 | -21.413 | -10.860 | 1.00 | 0.00 |
| ATOM | 1312 | CA | GLY | 377 | -21.995 | -21.003 | -10.000 | 1.00 | 0.00 |
| ATOM | 1313 | HA1 | GLY | 377 | -22.144 | -21.394 | -9.007 | 1.00 | 0.00 |
| ATOM | 1314 | HA2 | GLY | 377 | -21.402 | -20.100 | -9.946 | 1.00 | 0.00 |
| ATOM | 1315 | C | GLY | 377 | -21.261 | -22.044 | -10.847 | 1.00 | 0.00 |
| ATOM | 1316 | O | GLY | 377 | -20.506 | -21.711 | -11.738 | 1.00 | 0.00 |
| ATOM | 1317 | N | ILE | 378 | -21.476 | -23.304 | -10.577 | 1.00 | 0.00 |
| ATOM | 1318 | HN | ILE | 378 | -22.093 | -23.555 | -9.855 | 1.00 | 0.00 |
| ATOM | 1319 | CA | ILE | 378 | -20.782 | -24.363 | -11.374 | 1.00 | 0.00 |
| ATOM | 1320 | HA | ILE | 378 | -20.247 | -23.921 | -12.198 | 1.00 | 0.00 |
| ATOM | 1321 | CB | ILE | 378 | -19.792 | -25.011 | -10.395 | 1.00 | 0.00 |
| ATOM | 1322 | HB | ILE | 378 | -20.317 | -25.709 | -9.759 | 1.00 | 0.00 |
| ATOM | 1323 | CG1 | ILE | 378 | -19.129 | -23.925 | -9.533 | 1.00 | 0.00 |
| ATOM | 1324 | HG11 | ILE | 378 | -18.990 | -23.033 | -10.125 | 1.00 | 0.00 |
| ATOM | 1325 | HG12 | ILE | 378 | -18.170 | -24.280 | -9.185 | 1.00 | 0.00 |
| ATOM | 1326 | CG2 | ILE | 378 | -18.709 | -25.754 | -11.179 | 1.00 | 0.00 |
| ATOM | 1327 | HG21 | ILE | 378 | -18.381 | -25.143 | -12.007 | 1.00 | 0.00 |
| ATOM | 1328 | HG22 | ILE | 378 | -19.109 | -26.683 | -11.553 | 1.00 | 0.00 |
| ATOM | 1329 | HG23 | ILE | 378 | -17.870 | -25.959 | -10.528 | 1.00 | 0.00 |
| ATOM | 1330 | CD1 | ILE | 378 | -20.022 | -23.604 | -8.332 | 1.00 | 0.00 |

Figure 9-24

| | | | | | | | | |
|---|---|---|---|---|---|---|---|---|
| ATOM | 1331 | HD11 | ILE | 378 | -20.155 | -22.536 | -8.256 | 1.00 | 0.00 |
| ATOM | 1332 | HD12 | ILE | 378 | -19.558 | -23.974 | -7.427 | 1.00 | 0.00 |
| ATOM | 1333 | HD13 | ILE | 378 | -20.984 | -24.078 | -8.461 | 1.00 | 0.00 |
| ATOM | 1334 | C | ILE | 378 | -21.800 | -25.393 | -11.890 | 1.00 | 0.00 |
| ATOM | 1335 | O | ILE | 378 | -22.941 | -25.414 | -11.475 | 1.00 | 0.00 |
| ATOM | 1336 | N | ALA | 379 | -21.391 | -26.247 | -12.792 | 1.00 | 0.00 |
| ATOM | 1337 | HN | ALA | 379 | -20.465 | -26.215 | -13.111 | 1.00 | 0.00 |
| ATOM | 1338 | CA | ALA | 379 | -22.334 | -27.275 | -13.338 | 1.00 | 0.00 |
| ATOM | 1339 | HA | ALA | 379 | -23.297 | -26.836 | -13.532 | 1.00 | 0.00 |
| ATOM | 1340 | CB | ALA | 379 | -21.699 | -27.739 | -14.647 | 1.00 | 0.00 |
| ATOM | 1341 | HB1 | ALA | 379 | -21.420 | -28.779 | -14.562 | 1.00 | 0.00 |
| ATOM | 1342 | HB2 | ALA | 379 | -20.820 | -27.146 | -14.851 | 1.00 | 0.00 |
| ATOM | 1343 | HB3 | ALA | 379 | -22.408 | -27.621 | -15.452 | 1.00 | 0.00 |
| ATOM | 1344 | C | ALA | 379 | -22.468 | -28.452 | -12.369 | 1.00 | 0.00 |
| ATOM | 1345 | O | ALA | 379 | -21.893 | -28.446 | -11.302 | 1.00 | 0.00 |
| ATOM | 1346 | N | PRO | 380 | -23.237 | -29.426 | -12.783 | 1.00 | 0.00 |
| ATOM | 1347 | CA | PRO | 380 | -23.456 | -30.626 | -11.950 | 1.00 | 0.00 |
| ATOM | 1348 | HA | PRO | 380 | -23.639 | -30.351 | -10.926 | 1.00 | 0.00 |
| ATOM | 1349 | CB | PRO | 380 | -24.701 | -31.260 | -12.550 | 1.00 | 0.00 |
| ATOM | 1350 | HB1 | PRO | 380 | -25.582 | -30.927 | -12.026 | 1.00 | 0.00 |
| ATOM | 1351 | HB2 | PRO | 380 | -24.625 | -32.340 | -12.513 | 1.00 | 0.00 |
| ATOM | 1352 | CG | PRO | 380 | -24.742 | -30.787 | -13.977 | 1.00 | 0.00 |
| ATOM | 1353 | HG1 | PRO | 380 | -25.763 | -30.620 | -14.278 | 1.00 | 0.00 |
| ATOM | 1354 | HG2 | PRO | 380 | -24.283 | -31.525 | -14.620 | 1.00 | 0.00 |
| ATOM | 1355 | CD | PRO | 380 | -23.971 | -29.484 | -14.048 | 1.00 | 0.00 |
| ATOM | 1356 | HD1 | PRO | 380 | -24.648 | -28.649 | -14.124 | 1.00 | 0.00 |
| ATOM | 1357 | HD2 | PRO | 380 | -23.287 | -29.499 | -14.887 | 1.00 | 0.00 |
| ATOM | 1358 | C | PRO | 380 | -22.260 | -31.581 | -12.053 | 1.00 | 0.00 |
| ATOM | 1359 | O | PRO | 380 | -21.983 | -32.342 | -11.147 | 1.00 | 0.00 |
| ATOM | 1360 | N | GLU | 381 | -21.551 | -31.549 | -13.149 | 1.00 | 0.00 |
| ATOM | 1361 | HN | GLU | 381 | -21.788 | -30.930 | -13.871 | 1.00 | 0.00 |
| ATOM | 1362 | CA | GLU | 381 | -20.377 | -32.459 | -13.298 | 1.00 | 0.00 |
| ATOM | 1363 | HA | GLU | 381 | -20.554 | -33.380 | -12.778 | 1.00 | 0.00 |
| ATOM | 1364 | CB | GLU | 381 | -20.262 | -32.723 | -14.798 | 1.00 | 0.00 |
| ATOM | 1365 | HB1 | GLU | 381 | -19.221 | -32.721 | -15.085 | 1.00 | 0.00 |
| ATOM | 1366 | HB2 | GLU | 381 | -20.789 | -31.951 | -15.341 | 1.00 | 0.00 |
| ATOM | 1367 | CG | GLU | 381 | -20.874 | -34.088 | -15.121 | 1.00 | 0.00 |
| ATOM | 1368 | HG1 | GLU | 381 | -21.951 | -34.011 | -15.113 | 1.00 | 0.00 |
| ATOM | 1369 | HG2 | GLU | 381 | -20.558 | -34.809 | -14.379 | 1.00 | 0.00 |
| ATOM | 1370 | CD | GLU | 381 | -20.409 | -34.544 | -16.504 | 1.00 | 0.00 |
| ATOM | 1371 | OE1 | GLU | 381 | -19.649 | -35.497 | -16.568 | 1.00 | 0.00 |
| ATOM | 1372 | OE2 | GLU | 381 | -20.820 | -33.933 | -17.476 | 1.00 | 0.00 |
| ATOM | 1373 | C | GLU | 381 | -19.110 | -31.786 | -12.766 | 1.00 | 0.00 |
| ATOM | 1374 | O | GLU | 381 | -18.378 | -32.356 | -11.985 | 1.00 | 0.00 |
| ATOM | 1375 | N | GLN | 382 | -18.846 | -30.581 | -13.183 | 1.00 | 0.00 |
| ATOM | 1376 | HN | GLN | 382 | -19.452 | -30.139 | -13.813 | 1.00 | 0.00 |
| ATOM | 1377 | CA | GLN | 382 | -17.621 | -29.873 | -12.698 | 1.00 | 0.00 |
| ATOM | 1378 | HA | GLN | 382 | -16.734 | -30.404 | -12.997 | 1.00 | 0.00 |
| ATOM | 1379 | CB | GLN | 382 | -17.662 | -28.503 | -13.372 | 1.00 | 0.00 |
| ATOM | 1380 | HB1 | GLN | 382 | -16.982 | -27.833 | -12.869 | 1.00 | 0.00 |
| ATOM | 1381 | HB2 | GLN | 382 | -18.666 | -28.106 | -13.321 | 1.00 | 0.00 |
| ATOM | 1382 | CG | GLN | 382 | -17.242 | -28.646 | -14.836 | 1.00 | 0.00 |
| ATOM | 1383 | HG1 | GLN | 382 | -18.036 | -28.289 | -15.474 | 1.00 | 0.00 |
| ATOM | 1384 | HG2 | GLN | 382 | -17.046 | -29.687 | -15.053 | 1.00 | 0.00 |
| ATOM | 1385 | CD | GLN | 382 | -15.977 | -27.824 | -15.090 | 1.00 | 0.00 |
| ATOM | 1386 | OE1 | GLN | 382 | -15.526 | -27.098 | -14.227 | 1.00 | 0.00 |
| ATOM | 1387 | NE2 | GLN | 382 | -15.382 | -27.909 | -16.248 | 1.00 | 0.00 |
| ATOM | 1388 | HE21 | GLN | 382 | -15.746 | -28.495 | -16.944 | 1.00 | 0.00 |

Figure 9-25

| | | | | | | | | |
|---|---|---|---|---|---|---|---|---|
| ATOM | 1389 | HE22 | GLN | 382 | -14.572 | -27.386 | -16.422 | 1.00 0.00 |
| ATOM | 1390 | C | GLN | 382 | -17.662 | -29.732 | -11.176 | 1.00 0.00 |
| ATOM | 1391 | O | GLN | 382 | -16.642 | -29.740 | -10.516 | 1.00 0.00 |
| ATOM | 1392 | N | ARG | 383 | -18.829 | -29.602 | -10.613 | 1.00 0.00 |
| ATOM | 1393 | HN | ARG | 383 | -19.642 | -29.599 | -11.161 | 1.00 0.00 |
| ATOM | 1394 | CA | ARG | 383 | -18.923 | -29.462 | -9.135 | 1.00 0.00 |
| ATOM | 1395 | HA | ARG | 383 | -18.607 | -28.481 | -8.825 | 1.00 0.00 |
| ATOM | 1396 | CB | ARG | 383 | -20.401 | -29.666 | -8.815 | 1.00 0.00 |
| ATOM | 1397 | HB1 | ARG | 383 | -20.621 | -30.723 | -8.791 | 1.00 0.00 |
| ATOM | 1398 | HB2 | ARG | 383 | -21.002 | -29.191 | -9.573 | 1.00 0.00 |
| ATOM | 1399 | CG | ARG | 383 | -20.718 | -29.053 | -7.455 | 1.00 0.00 |
| ATOM | 1400 | HG1 | ARG | 383 | -21.783 | -28.909 | -7.363 | 1.00 0.00 |
| ATOM | 1401 | HG2 | ARG | 383 | -20.214 | -28.100 | -7.363 | 1.00 0.00 |
| ATOM | 1402 | CD | ARG | 383 | -20.236 | -29.995 | -6.352 | 1.00 0.00 |
| ATOM | 1403 | HD1 | ARG | 383 | -19.579 | -29.476 | -5.673 | 1.00 0.00 |
| ATOM | 1404 | HD2 | ARG | 383 | -19.735 | -30.853 | -6.784 | 1.00 0.00 |
| ATOM | 1405 | NE | ARG | 383 | -21.470 | -30.418 | -5.643 | 1.00 0.00 |
| ATOM | 1406 | HE | ARG | 383 | -22.319 | -30.480 | -6.129 | 1.00 0.00 |
| ATOM | 1407 | CZ | ARG | 383 | -21.421 | -30.707 | -4.374 | 1.00 0.00 |
| ATOM | 1408 | NH1 | ARG | 383 | -20.844 | -29.885 | -3.543 | 1.00 0.00 |
| ATOM | 1409 | HH11 | ARG | 383 | -20.440 | -29.034 | -3.880 | 1.00 0.00 |
| ATOM | 1410 | HH12 | ARG | 383 | -20.805 | -30.104 | -2.569 | 1.00 0.00 |
| ATOM | 1411 | NH2 | ARG | 383 | -21.946 | -31.818 | -3.936 | 1.00 0.00 |
| ATOM | 1412 | HH21 | ARG | 383 | -22.385 | -32.449 | -4.576 | 1.00 0.00 |
| ATOM | 1413 | HH22 | ARG | 383 | -21.907 | -32.040 | -2.962 | 1.00 0.00 |
| ATOM | 1414 | C | ARG | 383 | -18.075 | -30.543 | -8.462 | 1.00 0.00 |
| ATOM | 1415 | O | ARG | 383 | -17.557 | -30.359 | -7.378 | 1.00 0.00 |
| ATOM | 1416 | N | LYS | 384 | -17.933 | -31.671 | -9.102 | 1.00 0.00 |
| ATOM | 1417 | HN | LYS | 384 | -18.362 | -31.795 | -9.973 | 1.00 0.00 |
| ATOM | 1418 | CA | LYS | 384 | -17.121 | -32.771 | -8.512 | 1.00 0.00 |
| ATOM | 1419 | HA | LYS | 384 | -17.191 | -32.753 | -7.437 | 1.00 0.00 |
| ATOM | 1420 | CB | LYS | 384 | -17.745 | -34.057 | -9.052 | 1.00 0.00 |
| ATOM | 1421 | HB1 | LYS | 384 | -16.989 | -34.826 | -9.114 | 1.00 0.00 |
| ATOM | 1422 | HB2 | LYS | 384 | -18.154 | -33.873 | -10.036 | 1.00 0.00 |
| ATOM | 1423 | CG | LYS | 384 | -18.860 | -34.516 | -8.110 | 1.00 0.00 |
| ATOM | 1424 | HG1 | LYS | 384 | -19.808 | -34.460 | -8.621 | 1.00 0.00 |
| ATOM | 1425 | HG2 | LYS | 384 | -18.880 | -33.876 | -7.239 | 1.00 0.00 |
| ATOM | 1426 | CD | LYS | 384 | -18.603 | -35.959 | -7.676 | 1.00 0.00 |
| ATOM | 1427 | HD1 | LYS | 384 | -18.141 | -35.966 | -6.700 | 1.00 0.00 |
| ATOM | 1428 | HD2 | LYS | 384 | -17.947 | -36.439 | -8.389 | 1.00 0.00 |
| ATOM | 1429 | CE | LYS | 384 | -19.932 | -36.714 | -7.613 | 1.00 0.00 |
| ATOM | 1430 | HE1 | LYS | 384 | -20.757 | -36.021 | -7.580 | 1.00 0.00 |
| ATOM | 1431 | HE2 | LYS | 384 | -19.952 | -37.370 | -6.751 | 1.00 0.00 |
| ATOM | 1432 | NZ | LYS | 384 | -19.982 | -37.507 | -8.873 | 1.00 0.00 |
| ATOM | 1433 | HZ1 | LYS | 384 | -19.551 | -36.961 | -9.644 | 1.00 0.00 |
| ATOM | 1434 | HZ2 | LYS | 384 | -20.974 | -37.719 | -9.109 | 1.00 0.00 |
| ATOM | 1435 | HZ3 | LYS | 384 | -19.458 | -38.395 | -8.745 | 1.00 0.00 |
| ATOM | 1436 | C | LYS | 384 | -15.659 | -32.654 | -8.954 | 1.00 0.00 |
| ATOM | 1437 | O | LYS | 384 | -14.751 | -32.914 | -8.190 | 1.00 0.00 |
| ATOM | 1438 | N | HIS | 385 | -15.416 | -32.265 | -10.182 | 1.00 0.00 |
| ATOM | 1439 | HN | HIS | 385 | -16.157 | -32.062 | -10.791 | 1.00 0.00 |
| ATOM | 1440 | CA | HIS | 385 | -14.002 | -32.140 | -10.646 | 1.00 0.00 |
| ATOM | 1441 | HA | HIS | 385 | -13.334 | -32.535 | -9.897 | 1.00 0.00 |
| ATOM | 1442 | CB | HIS | 385 | -13.908 | -33.000 | -11.916 | 1.00 0.00 |
| ATOM | 1443 | HB1 | HIS | 385 | -14.253 | -34.000 | -11.694 | 1.00 0.00 |
| ATOM | 1444 | HB2 | HIS | 385 | -12.881 | -33.042 | -12.240 | 1.00 0.00 |
| ATOM | 1445 | CG | HIS | 385 | -14.750 | -32.418 | -13.021 | 1.00 0.00 |
| ATOM | 1446 | ND1 | HIS | 385 | -14.242 | -31.510 | -13.939 | 1.00 0.00 |

Figure 9-26

```
ATOM   1447  HD1  HIS  385    -13.332 -31.148 -13.953  1.00  0.00
ATOM   1448  CD2  HIS  385    -16.052 -32.639 -13.394  1.00  0.00
ATOM   1449  HD2  HIS  385    -16.739 -33.301 -12.889  1.00  0.00
ATOM   1450  CE1  HIS  385    -15.227 -31.224 -14.812  1.00  0.00
ATOM   1451  HE1  HIS  385    -15.119 -30.545 -15.645  1.00  0.00
ATOM   1452  NE2  HIS  385    -16.351 -31.886 -14.526  1.00  0.00
ATOM   1453  C    HIS  385    -13.642 -30.676 -10.941  1.00  0.00
ATOM   1454  O    HIS  385    -13.240 -30.333 -12.034  1.00  0.00
ATOM   1455  N    LEU  386    -13.782 -29.808  -9.970  1.00  0.00
ATOM   1456  HN   LEU  386    -14.110 -30.098  -9.096  1.00  0.00
ATOM   1457  CA   LEU  386    -13.444 -28.372 -10.199  1.00  0.00
ATOM   1458  HA   LEU  386    -13.464 -28.155 -11.234  1.00  0.00
ATOM   1459  CB   LEU  386    -14.527 -27.582  -9.462  1.00  0.00
ATOM   1460  HB1  LEU  386    -14.236 -27.452  -8.431  1.00  0.00
ATOM   1461  HB2  LEU  386    -15.460 -28.127  -9.506  1.00  0.00
ATOM   1462  CG   LEU  386    -14.709 -26.209 -10.113  1.00  0.00
ATOM   1463  HG   LEU  386    -15.589 -25.736  -9.708  1.00  0.00
ATOM   1464  CD1  LEU  386    -13.488 -25.339  -9.823  1.00  0.00
ATOM   1465  HD11 LEU  386    -12.992 -25.702  -8.935  1.00  0.00
ATOM   1466  HD12 LEU  386    -13.800 -24.317  -9.668  1.00  0.00
ATOM   1467  HD13 LEU  386    -12.805 -25.385 -10.659  1.00  0.00
ATOM   1468  CD2  LEU  386    -14.871 -26.373 -11.626  1.00  0.00
ATOM   1469  HD21 LEU  386    -15.506 -27.224 -11.830  1.00  0.00
ATOM   1470  HD22 LEU  386    -13.902 -26.530 -12.077  1.00  0.00
ATOM   1471  HD23 LEU  386    -15.320 -25.483 -12.039  1.00  0.00
ATOM   1472  C    LEU  386    -12.056 -28.070  -9.626  1.00  0.00
ATOM   1473  O    LEU  386    -11.537 -26.980  -9.745  1.00  0.00
ATOM   1474  N    PHE  387    -11.460 -29.039  -9.025  1.00  0.00
ATOM   1475  HN   PHE  387    -11.896 -29.902  -8.970  1.00  0.00
ATOM   1476  CA   PHE  387    -10.106 -28.854  -8.432  1.00  0.00
ATOM   1477  HA   PHE  387     -9.506 -28.219  -9.054  1.00  0.00
ATOM   1478  CB   PHE  387    -10.341 -28.200  -7.070  1.00  0.00
ATOM   1479  HB1  PHE  387     -9.441 -28.273  -6.476  1.00  0.00
ATOM   1480  HB2  PHE  387    -11.148 -28.708  -6.563  1.00  0.00
ATOM   1481  CG   PHE  387    -10.702 -26.744  -7.255  1.00  0.00
ATOM   1482  CD1  PHE  387     -9.848 -25.890  -7.965  1.00  0.00
ATOM   1483  HD1  PHE  387     -8.927 -26.270  -8.384  1.00  0.00
ATOM   1484  CD2  PHE  387    -11.894 -26.249  -6.713  1.00  0.00
ATOM   1485  HD2  PHE  387    -12.551 -26.907  -6.165  1.00  0.00
ATOM   1486  CE1  PHE  387    -10.189 -24.541  -8.133  1.00  0.00
ATOM   1487  HE1  PHE  387     -9.531 -23.881  -8.678  1.00  0.00
ATOM   1488  CE2  PHE  387    -12.233 -24.902  -6.881  1.00  0.00
ATOM   1489  HE2  PHE  387    -13.154 -24.522  -6.463  1.00  0.00
ATOM   1490  CZ   PHE  387    -11.382 -24.048  -7.590  1.00  0.00
ATOM   1491  HZ   PHE  387    -11.645 -23.007  -7.720  1.00  0.00
ATOM   1492  C    PHE  387     -9.446 -30.215  -8.262  1.00  0.00
ATOM   1493  O    PHE  387     -8.629 -30.420  -7.388  1.00  0.00
ATOM   1494  N    GLN  388     -9.802 -31.148  -9.100  1.00  0.00
ATOM   1495  HN   GLN  388    -10.454 -30.946  -9.798  1.00  0.00
ATOM   1496  CA   GLN  388     -9.212 -32.511  -9.011  1.00  0.00
ATOM   1497  HA   GLN  388     -9.612 -33.142  -9.787  1.00  0.00
ATOM   1498  CB   GLN  388     -7.721 -32.308  -9.230  1.00  0.00
ATOM   1499  HB1  GLN  388     -7.174 -33.101  -8.745  1.00  0.00
ATOM   1500  HB2  GLN  388     -7.421 -31.356  -8.817  1.00  0.00
ATOM   1501  CG   GLN  388     -7.428 -32.331 -10.728  1.00  0.00
ATOM   1502  HG1  GLN  388     -6.592 -31.685 -10.941  1.00  0.00
ATOM   1503  HG2  GLN  388     -8.299 -31.986 -11.270  1.00  0.00
ATOM   1504  CD   GLN  388     -7.091 -33.757 -11.158  1.00  0.00
```

Figure 9-27

| | | | | | | | | |
|---|---|---|---|---|---|---|---|---|
| ATOM | 1505 | OE1 | GLN | 388 | -7.969 | -34.583 | -11.304 | 1.00 0.00 |
| ATOM | 1506 | NE2 | GLN | 388 | -5.847 | -34.083 | -11.368 | 1.00 0.00 |
| ATOM | 1507 | HE21 | GLN | 388 | -5.139 | -33.416 | -11.252 | 1.00 0.00 |
| ATOM | 1508 | HE22 | GLN | 388 | -5.620 | -34.996 | -11.641 | 1.00 0.00 |
| ATOM | 1509 | C | GLN | 388 | -9.488 | -33.122 | -7.634 | 1.00 0.00 |
| ATOM | 1510 | O | GLN | 388 | -9.519 | -32.428 | -6.637 | 1.00 0.00 |
| ATOM | 1511 | N | PRO | 389 | -9.684 | -34.411 | -7.633 | 1.00 0.00 |
| ATOM | 1512 | CA | PRO | 389 | -9.963 | -35.142 | -6.374 | 1.00 0.00 |
| ATOM | 1513 | HA | PRO | 389 | -10.763 | -34.670 | -5.829 | 1.00 0.00 |
| ATOM | 1514 | CB | PRO | 389 | -10.400 | -36.523 | -6.850 | 1.00 0.00 |
| ATOM | 1515 | HB1 | PRO | 389 | -11.473 | -36.573 | -6.929 | 1.00 0.00 |
| ATOM | 1516 | HB2 | PRO | 389 | -10.033 | -37.286 | -6.173 | 1.00 0.00 |
| ATOM | 1517 | CG | PRO | 389 | -9.777 | -36.682 | -8.203 | 1.00 0.00 |
| ATOM | 1518 | HG1 | PRO | 389 | -10.406 | -37.292 | -8.830 | 1.00 0.00 |
| ATOM | 1519 | HG2 | PRO | 389 | -8.797 | -37.133 | -8.108 | 1.00 0.00 |
| ATOM | 1520 | CD | PRO | 389 | -9.656 | -35.299 | -8.797 | 1.00 0.00 |
| ATOM | 1521 | HD1 | PRO | 389 | -10.492 | -35.090 | -9.444 | 1.00 0.00 |
| ATOM | 1522 | HD2 | PRO | 389 | -8.721 | -35.197 | -9.334 | 1.00 0.00 |
| ATOM | 1523 | C | PRO | 389 | -8.700 | -35.237 | -5.510 | 1.00 0.00 |
| ATOM | 1524 | O | PRO | 389 | -7.603 | -34.971 | -5.962 | 1.00 0.00 |
| ATOM | 1525 | N | PHE | 390 | -8.849 | -35.618 | -4.269 | 1.00 0.00 |
| ATOM | 1526 | HN | PHE | 390 | -9.742 | -35.829 | -3.926 | 1.00 0.00 |
| ATOM | 1527 | CA | PHE | 390 | -7.662 | -35.732 | -3.374 | 1.00 0.00 |
| ATOM | 1528 | HA | PHE | 390 | -7.000 | -34.893 | -3.516 | 1.00 0.00 |
| ATOM | 1529 | CB | PHE | 390 | -8.231 | -35.715 | -1.956 | 1.00 0.00 |
| ATOM | 1530 | HB1 | PHE | 390 | -7.479 | -36.057 | -1.261 | 1.00 0.00 |
| ATOM | 1531 | HB2 | PHE | 390 | -9.092 | -36.366 | -1.906 | 1.00 0.00 |
| ATOM | 1532 | CG | PHE | 390 | -8.643 | -34.308 | -1.599 | 1.00 0.00 |
| ATOM | 1533 | CD1 | PHE | 390 | -9.651 | -33.668 | -2.328 | 1.00 0.00 |
| ATOM | 1534 | HD1 | PHE | 390 | -10.135 | -34.181 | -3.145 | 1.00 0.00 |
| ATOM | 1535 | CD2 | PHE | 390 | -8.015 | -33.643 | -0.539 | 1.00 0.00 |
| ATOM | 1536 | HD2 | PHE | 390 | -7.237 | -34.137 | 0.023 | 1.00 0.00 |
| ATOM | 1537 | CE1 | PHE | 390 | -10.032 | -32.364 | -1.999 | 1.00 0.00 |
| ATOM | 1538 | HE1 | PHE | 390 | -10.811 | -31.871 | -2.563 | 1.00 0.00 |
| ATOM | 1539 | CE2 | PHE | 390 | -8.396 | -32.337 | -0.209 | 1.00 0.00 |
| ATOM | 1540 | HE2 | PHE | 390 | -7.911 | -31.824 | 0.608 | 1.00 0.00 |
| ATOM | 1541 | CZ | PHE | 390 | -9.404 | -31.698 | -0.939 | 1.00 0.00 |
| ATOM | 1542 | HZ | PHE | 390 | -9.698 | -30.690 | -0.686 | 1.00 0.00 |
| ATOM | 1543 | C | PHE | 390 | -6.927 | -37.047 | -3.641 | 1.00 0.00 |
| ATOM | 1544 | O | PHE | 390 | -7.530 | -38.053 | -3.956 | 1.00 0.00 |
| ATOM | 1545 | N | VAL | 391 | -5.630 | -37.044 | -3.520 | 1.00 0.00 |
| ATOM | 1546 | HN | VAL | 391 | -5.164 | -36.221 | -3.265 | 1.00 0.00 |
| ATOM | 1547 | CA | VAL | 391 | -4.854 | -38.293 | -3.768 | 1.00 0.00 |
| ATOM | 1548 | HA | VAL | 391 | -5.509 | -39.091 | -4.059 | 1.00 0.00 |
| ATOM | 1549 | CB | VAL | 391 | -3.906 | -37.953 | -4.916 | 1.00 0.00 |
| ATOM | 1550 | HB | VAL | 391 | -3.087 | -37.372 | -4.536 | 1.00 0.00 |
| ATOM | 1551 | CG1 | VAL | 391 | -3.366 | -39.242 | -5.540 | 1.00 0.00 |
| ATOM | 1552 | HG11 | VAL | 391 | -2.431 | -39.035 | -6.039 | 1.00 0.00 |
| ATOM | 1553 | HG12 | VAL | 391 | -4.079 | -39.623 | -6.256 | 1.00 0.00 |
| ATOM | 1554 | HG13 | VAL | 391 | -3.205 | -39.977 | -4.768 | 1.00 0.00 |
| ATOM | 1555 | CG2 | VAL | 391 | -4.657 | -37.150 | -5.984 | 1.00 0.00 |
| ATOM | 1556 | HG21 | VAL | 391 | -4.038 | -37.054 | -6.864 | 1.00 0.00 |
| ATOM | 1557 | HG22 | VAL | 391 | -4.891 | -36.169 | -5.599 | 1.00 0.00 |
| ATOM | 1558 | HG23 | VAL | 391 | -5.572 | -37.663 | -6.242 | 1.00 0.00 |
| ATOM | 1559 | C | VAL | 391 | -4.065 | -38.678 | -2.513 | 1.00 0.00 |
| ATOM | 1560 | O | VAL | 391 | -3.835 | -37.865 | -1.640 | 1.00 0.00 |
| ATOM | 1561 | N | ARG | 392 | -3.652 | -39.909 | -2.417 | 1.00 0.00 |
| ATOM | 1562 | HN | ARG | 392 | -3.848 | -40.546 | -3.132 | 1.00 0.00 |

Figure 9-28

```
ATOM   1563  CA   ARG  392    -2.879 -40.348  -1.221  1.00  0.00
ATOM   1564  HA   ARG  392    -2.887 -39.583  -0.463  1.00  0.00
ATOM   1565  CB   ARG  392    -3.604 -41.593  -0.717  1.00  0.00
ATOM   1566  HB1  ARG  392    -3.021 -42.470  -0.954  1.00  0.00
ATOM   1567  HB2  ARG  392    -4.572 -41.664  -1.193  1.00  0.00
ATOM   1568  CG   ARG  392    -3.786 -41.500   0.799  1.00  0.00
ATOM   1569  HG1  ARG  392    -4.713 -41.974   1.079  1.00  0.00
ATOM   1570  HG2  ARG  392    -3.808 -40.460   1.095  1.00  0.00
ATOM   1571  CD   ARG  392    -2.622 -42.207   1.499  1.00  0.00
ATOM   1572  HD1  ARG  392    -1.703 -42.047   0.958  1.00  0.00
ATOM   1573  HD2  ARG  392    -2.827 -43.266   1.592  1.00  0.00
ATOM   1574  NE   ARG  392    -2.540 -41.573   2.843  1.00  0.00
ATOM   1575  HE   ARG  392    -3.192 -40.889   3.103  1.00  0.00
ATOM   1576  CZ   ARG  392    -1.600 -41.929   3.676  1.00  0.00
ATOM   1577  NH1  ARG  392    -0.495 -41.238   3.746  1.00  0.00
ATOM   1578  HH11 ARG  392    -0.368 -40.437   3.161  1.00  0.00
ATOM   1579  HH12 ARG  392     0.226 -41.511   4.384  1.00  0.00
ATOM   1580  NH2  ARG  392    -1.765 -42.974   4.439  1.00  0.00
ATOM   1581  HH21 ARG  392    -2.611 -43.504   4.386  1.00  0.00
ATOM   1582  HH22 ARG  392    -1.044 -43.246   5.077  1.00  0.00
ATOM   1583  C    ARG  392    -1.444 -40.690  -1.624  1.00  0.00
ATOM   1584  O    ARG  392    -0.772 -41.465  -0.973  1.00  0.00
ATOM   1585  N    GLY  393    -0.972 -40.121  -2.698  1.00  0.00
ATOM   1586  HN   GLY  393    -1.534 -39.504  -3.211  1.00  0.00
ATOM   1587  CA   GLY  393     0.417 -40.410  -3.146  1.00  0.00
ATOM   1588  HA1  GLY  393     0.391 -40.941  -4.084  1.00  0.00
ATOM   1589  HA2  GLY  393     0.917 -41.015  -2.401  1.00  0.00
ATOM   1590  C    GLY  393     1.175 -39.096  -3.330  1.00  0.00
ATOM   1591  O    GLY  393     0.825 -38.082  -2.759  1.00  0.00
ATOM   1592  N    ASP  394     2.209 -39.102  -4.123  1.00  0.00
ATOM   1593  HN   ASP  394     2.477 -39.930  -4.575  1.00  0.00
ATOM   1594  CA   ASP  394     2.987 -37.848  -4.341  1.00  0.00
ATOM   1595  HA   ASP  394     2.342 -36.988  -4.274  1.00  0.00
ATOM   1596  CB   ASP  394     4.014 -37.820  -3.210  1.00  0.00
ATOM   1597  HB1  ASP  394     3.505 -37.734  -2.261  1.00  0.00
ATOM   1598  HB2  ASP  394     4.675 -36.975  -3.344  1.00  0.00
ATOM   1599  CG   ASP  394     4.830 -39.114  -3.231  1.00  0.00
ATOM   1600  OD1  ASP  394     4.932 -39.709  -4.291  1.00  0.00
ATOM   1601  OD2  ASP  394     5.339 -39.488  -2.187  1.00  0.00
ATOM   1602  C    ASP  394     3.686 -37.890  -5.701  1.00  0.00
ATOM   1603  O    ASP  394     4.895 -37.830  -5.790  1.00  0.00
ATOM   1604  N    SER  395     2.934 -37.992  -6.762  1.00  0.00
ATOM   1605  HN   SER  395     1.960 -38.040  -6.670  1.00  0.00
ATOM   1606  CA   SER  395     3.559 -38.038  -8.114  1.00  0.00
ATOM   1607  HA   SER  395     4.540 -38.476  -8.059  1.00  0.00
ATOM   1608  CB   SER  395     2.638 -38.930  -8.944  1.00  0.00
ATOM   1609  HB1  SER  395     1.840 -38.330  -9.367  1.00  0.00
ATOM   1610  HB2  SER  395     2.215 -39.693  -8.317  1.00  0.00
ATOM   1611  OG   SER  395     3.390 -39.544  -9.985  1.00  0.00
ATOM   1612  HG   SER  395     3.371 -40.493  -9.846  1.00  0.00
ATOM   1613  C    SER  395     3.636 -36.631  -8.721  1.00  0.00
ATOM   1614  O    SER  395     4.650 -36.234  -9.258  1.00  0.00
ATOM   1615  N    ALA  396     2.575 -35.873  -8.637  1.00  0.00
ATOM   1616  HN   ALA  396     1.765 -36.206  -8.198  1.00  0.00
ATOM   1617  CA   ALA  396     2.602 -34.495  -9.214  1.00  0.00
ATOM   1618  HA   ALA  396     3.616 -34.191  -9.410  1.00  0.00
ATOM   1619  CB   ALA  396     1.831 -34.605 -10.527  1.00  0.00
ATOM   1620  HB1  ALA  396     1.110 -35.406 -10.455  1.00  0.00
```

Figure 9-29

| ATOM | 1621 | HB2 | ALA | 396 | 2.520 | -34.814 | -11.332 | 1.00 | 0.00 |
| ATOM | 1622 | HB3 | ALA | 396 | 1.318 | -33.675 | -10.723 | 1.00 | 0.00 |
| ATOM | 1623 | C | ALA | 396 | 1.920 | -33.496 | -8.271 | 1.00 | 0.00 |
| ATOM | 1624 | O | ALA | 396 | 0.821 | -33.043 | -8.520 | 1.00 | 0.00 |
| ATOM | 1625 | N | ARG | 397 | 2.565 | -33.155 | -7.188 | 1.00 | 0.00 |
| ATOM | 1626 | HN | ARG | 397 | 3.437 | -33.546 | -7.002 | 1.00 | 0.00 |
| ATOM | 1627 | CA | ARG | 397 | 1.959 | -32.184 | -6.225 | 1.00 | 0.00 |
| ATOM | 1628 | HA | ARG | 397 | 0.893 | -32.327 | -6.178 | 1.00 | 0.00 |
| ATOM | 1629 | CB | ARG | 397 | 2.591 | -32.522 | -4.855 | 1.00 | 0.00 |
| ATOM | 1630 | HB1 | ARG | 397 | 2.685 | -33.594 | -4.763 | 1.00 | 0.00 |
| ATOM | 1631 | HB2 | ARG | 397 | 1.947 | -32.154 | -4.068 | 1.00 | 0.00 |
| ATOM | 1632 | CG | ARG | 397 | 3.989 | -31.875 | -4.710 | 1.00 | 0.00 |
| ATOM | 1633 | HG1 | ARG | 397 | 4.191 | -31.699 | -3.665 | 1.00 | 0.00 |
| ATOM | 1634 | HG2 | ARG | 397 | 4.020 | -30.938 | -5.237 | 1.00 | 0.00 |
| ATOM | 1635 | CD | ARG | 397 | 5.060 | -32.815 | -5.276 | 1.00 | 0.00 |
| ATOM | 1636 | HD1 | ARG | 397 | 4.957 | -32.906 | -6.341 | 1.00 | 0.00 |
| ATOM | 1637 | HD2 | ARG | 397 | 4.995 | -33.787 | -4.803 | 1.00 | 0.00 |
| ATOM | 1638 | NE | ARG | 397 | 6.356 | -32.162 | -4.948 | 1.00 | 0.00 |
| ATOM | 1639 | HE | ARG | 397 | 6.451 | -31.190 | -5.035 | 1.00 | 0.00 |
| ATOM | 1640 | CZ | ARG | 397 | 7.368 | -32.882 | -4.552 | 1.00 | 0.00 |
| ATOM | 1641 | NH1 | ARG | 397 | 7.865 | -32.705 | -3.359 | 1.00 | 0.00 |
| ATOM | 1642 | HH11 | ARG | 397 | 7.469 | -32.018 | -2.750 | 1.00 | 0.00 |
| ATOM | 1643 | HH12 | ARG | 397 | 8.641 | -33.257 | -3.054 | 1.00 | 0.00 |
| ATOM | 1644 | NH2 | ARG | 397 | 7.886 | -33.778 | -5.348 | 1.00 | 0.00 |
| ATOM | 1645 | HH21 | ARG | 397 | 7.506 | -33.913 | -6.264 | 1.00 | 0.00 |
| ATOM | 1646 | HH22 | ARG | 397 | 8.661 | -34.331 | -5.042 | 1.00 | 0.00 |
| ATOM | 1647 | C | ARG | 397 | 2.280 | -30.740 | -6.648 | 1.00 | 0.00 |
| ATOM | 1648 | O | ARG | 397 | 2.227 | -29.823 | -5.852 | 1.00 | 0.00 |
| ATOM | 1649 | N | THR | 398 | 2.616 | -30.536 | -7.894 | 1.00 | 0.00 |
| ATOM | 1650 | HN | THR | 398 | 2.655 | -31.289 | -8.519 | 1.00 | 0.00 |
| ATOM | 1651 | CA | THR | 398 | 2.940 | -29.155 | -8.370 | 1.00 | 0.00 |
| ATOM | 1652 | HA | THR | 398 | 2.548 | -28.419 | -7.688 | 1.00 | 0.00 |
| ATOM | 1653 | CB | THR | 398 | 4.468 | -29.086 | -8.394 | 1.00 | 0.00 |
| ATOM | 1654 | HB | THR | 398 | 4.843 | -29.689 | -9.206 | 1.00 | 0.00 |
| ATOM | 1655 | OG1 | THR | 398 | 4.983 | -29.574 | -7.162 | 1.00 | 0.00 |
| ATOM | 1656 | HG1 | THR | 398 | 5.045 | -28.835 | -6.553 | 1.00 | 0.00 |
| ATOM | 1657 | CG2 | THR | 398 | 4.912 | -27.636 | -8.597 | 1.00 | 0.00 |
| ATOM | 1658 | HG21 | THR | 398 | 5.976 | -27.558 | -8.425 | 1.00 | 0.00 |
| ATOM | 1659 | HG22 | THR | 398 | 4.388 | -26.998 | -7.901 | 1.00 | 0.00 |
| ATOM | 1660 | HG23 | THR | 398 | 4.688 | -27.329 | -9.607 | 1.00 | 0.00 |
| ATOM | 1661 | C | THR | 398 | 2.371 | -28.942 | -9.776 | 1.00 | 0.00 |
| ATOM | 1662 | O | THR | 398 | 2.785 | -29.577 | -10.725 | 1.00 | 0.00 |
| ATOM | 1663 | N | ILE | 399 | 1.429 | -28.053 | -9.916 | 1.00 | 0.00 |
| ATOM | 1664 | HN | ILE | 399 | 1.111 | -27.547 | -9.139 | 1.00 | 0.00 |
| ATOM | 1665 | CA | ILE | 399 | 0.836 | -27.803 | -11.261 | 1.00 | 0.00 |
| ATOM | 1666 | HA | ILE | 399 | 0.863 | -28.701 | -11.855 | 1.00 | 0.00 |
| ATOM | 1667 | CB | ILE | 399 | -0.610 | -27.409 | -10.982 | 1.00 | 0.00 |
| ATOM | 1668 | HB | ILE | 399 | -1.118 | -28.229 | -10.494 | 1.00 | 0.00 |
| ATOM | 1669 | CG1 | ILE | 399 | -1.311 | -27.086 | -12.302 | 1.00 | 0.00 |
| ATOM | 1670 | HG11 | ILE | 399 | -0.828 | -26.242 | -12.769 | 1.00 | 0.00 |
| ATOM | 1671 | HG12 | ILE | 399 | -2.348 | -26.848 | -12.109 | 1.00 | 0.00 |
| ATOM | 1672 | CG2 | ILE | 399 | -0.638 | -26.179 | -10.074 | 1.00 | 0.00 |
| ATOM | 1673 | HG21 | ILE | 399 | 0.184 | -25.526 | -10.327 | 1.00 | 0.00 |
| ATOM | 1674 | HG22 | ILE | 399 | -0.547 | -26.490 | -9.044 | 1.00 | 0.00 |
| ATOM | 1675 | HG23 | ILE | 399 | -1.571 | -25.653 | -10.210 | 1.00 | 0.00 |
| ATOM | 1676 | CD1 | ILE | 399 | -1.228 | -28.298 | -13.232 | 1.00 | 0.00 |
| ATOM | 1677 | HD11 | ILE | 399 | -0.588 | -28.066 | -14.070 | 1.00 | 0.00 |
| ATOM | 1678 | HD12 | ILE | 399 | -2.216 | -28.545 | -13.592 | 1.00 | 0.00 |

Figure 9-30

| | | | | | | | | |
|---|---|---|---|---|---|---|---|---|
| ATOM | 1679 | HD13 | ILE | 399 | -0.821 | -29.141 | -12.691 | 1.00 0.00 |
| ATOM | 1680 | C | ILE | 399 | 1.577 | -26.667 | -11.975 | 1.00 0.00 |
| ATOM | 1681 | O | ILE | 399 | 2.082 | -25.754 | -11.353 | 1.00 0.00 |
| ATOM | 1682 | N | SER | 400 | 1.642 | -26.717 | -13.279 | 1.00 0.00 |
| ATOM | 1683 | HN | SER | 400 | 1.225 | -27.462 | -13.762 | 1.00 0.00 |
| ATOM | 1684 | CA | SER | 400 | 2.349 | -25.642 | -14.036 | 1.00 0.00 |
| ATOM | 1685 | HA | SER | 400 | 3.207 | -25.294 | -13.486 | 1.00 0.00 |
| ATOM | 1686 | CB | SER | 400 | 2.794 | -26.302 | -15.336 | 1.00 0.00 |
| ATOM | 1687 | HB1 | SER | 400 | 1.979 | -26.896 | -15.734 | 1.00 0.00 |
| ATOM | 1688 | HB2 | SER | 400 | 3.639 | -26.939 | -15.148 | 1.00 0.00 |
| ATOM | 1689 | OG | SER | 400 | 3.165 | -25.297 | -16.271 | 1.00 0.00 |
| ATOM | 1690 | HG | SER | 400 | 3.899 | -24.802 | -15.900 | 1.00 0.00 |
| ATOM | 1691 | C | SER | 400 | 1.392 | -24.484 | -14.329 | 1.00 0.00 |
| ATOM | 1692 | O | SER | 400 | 1.765 | -23.329 | -14.281 | 1.00 0.00 |
| ATOM | 1693 | N | GLY | 401 | 0.160 | -24.787 | -14.635 | 1.00 0.00 |
| ATOM | 1694 | HN | GLY | 401 | -0.119 | -25.726 | -14.668 | 1.00 0.00 |
| ATOM | 1695 | CA | GLY | 401 | -0.824 | -23.708 | -14.931 | 1.00 0.00 |
| ATOM | 1696 | HA1 | GLY | 401 | -0.650 | -23.323 | -15.923 | 1.00 0.00 |
| ATOM | 1697 | HA2 | GLY | 401 | -0.713 | -22.911 | -14.208 | 1.00 0.00 |
| ATOM | 1698 | C | GLY | 401 | -2.239 | -24.279 | -14.852 | 1.00 0.00 |
| ATOM | 1699 | O | GLY | 401 | -2.758 | -24.519 | -13.780 | 1.00 0.00 |
| ATOM | 1700 | N | THR | 402 | -2.869 | -24.496 | -15.990 | 1.00 0.00 |
| ATOM | 1701 | HN | THR | 402 | -2.418 | -24.291 | -16.836 | 1.00 0.00 |
| ATOM | 1702 | CA | THR | 402 | -4.270 | -25.058 | -16.013 | 1.00 0.00 |
| ATOM | 1703 | HA | THR | 402 | -4.473 | -25.495 | -16.977 | 1.00 0.00 |
| ATOM | 1704 | CB | THR | 402 | -4.299 | -26.153 | -14.937 | 1.00 0.00 |
| ATOM | 1705 | HB | THR | 402 | -4.560 | -25.717 | -13.986 | 1.00 0.00 |
| ATOM | 1706 | OG1 | THR | 402 | -3.016 | -26.758 | -14.848 | 1.00 0.00 |
| ATOM | 1707 | HG1 | THR | 402 | -2.770 | -27.063 | -15.725 | 1.00 0.00 |
| ATOM | 1708 | CG2 | THR | 402 | -5.338 | -27.211 | -15.310 | 1.00 0.00 |
| ATOM | 1709 | HG21 | THR | 402 | -5.995 | -26.819 | -16.072 | 1.00 0.00 |
| ATOM | 1710 | HG22 | THR | 402 | -5.916 | -27.471 | -14.436 | 1.00 0.00 |
| ATOM | 1711 | HG23 | THR | 402 | -4.836 | -28.091 | -15.685 | 1.00 0.00 |
| ATOM | 1712 | C | THR | 402 | -5.310 | -23.962 | -15.706 | 1.00 0.00 |
| ATOM | 1713 | O | THR | 402 | -6.382 | -23.942 | -16.277 | 1.00 0.00 |
| ATOM | 1714 | N | GLY | 403 | -5.006 | -23.053 | -14.814 | 1.00 0.00 |
| ATOM | 1715 | HN | GLY | 403 | -4.144 | -23.078 | -14.364 | 1.00 0.00 |
| ATOM | 1716 | CA | GLY | 403 | -5.982 | -21.975 | -14.486 | 1.00 0.00 |
| ATOM | 1717 | HA1 | GLY | 403 | -6.136 | -21.940 | -13.419 | 1.00 0.00 |
| ATOM | 1718 | HA2 | GLY | 403 | -6.922 | -22.179 | -14.981 | 1.00 0.00 |
| ATOM | 1719 | C | GLY | 403 | -5.434 | -20.628 | -14.962 | 1.00 0.00 |
| ATOM | 1720 | O | GLY | 403 | -4.258 | -20.486 | -15.232 | 1.00 0.00 |
| ATOM | 1721 | N | LEU | 404 | -6.277 | -19.636 | -15.066 | 1.00 0.00 |
| ATOM | 1722 | HN | LEU | 404 | -7.222 | -19.771 | -14.842 | 1.00 0.00 |
| ATOM | 1723 | CA | LEU | 404 | -5.803 | -18.297 | -15.525 | 1.00 0.00 |
| ATOM | 1724 | HA | LEU | 404 | -4.728 | -18.282 | -15.598 | 1.00 0.00 |
| ATOM | 1725 | CB | LEU | 404 | -6.423 | -18.114 | -16.909 | 1.00 0.00 |
| ATOM | 1726 | HB1 | LEU | 404 | -7.493 | -18.015 | -16.813 | 1.00 0.00 |
| ATOM | 1727 | HB2 | LEU | 404 | -6.194 | -18.974 | -17.522 | 1.00 0.00 |
| ATOM | 1728 | CG | LEU | 404 | -5.854 | -16.856 | -17.562 | 1.00 0.00 |
| ATOM | 1729 | HG | LEU | 404 | -5.121 | -16.409 | -16.905 | 1.00 0.00 |
| ATOM | 1730 | CD1 | LEU | 404 | -5.191 | -17.226 | -18.889 | 1.00 0.00 |
| ATOM | 1731 | HD11 | LEU | 404 | -5.227 | -16.381 | -19.559 | 1.00 0.00 |
| ATOM | 1732 | HD12 | LEU | 404 | -5.714 | -18.060 | -19.333 | 1.00 0.00 |
| ATOM | 1733 | HD13 | LEU | 404 | -4.161 | -17.502 | -18.711 | 1.00 0.00 |
| ATOM | 1734 | CD2 | LEU | 404 | -6.989 | -15.861 | -17.819 | 1.00 0.00 |
| ATOM | 1735 | HD21 | LEU | 404 | -7.663 | -15.858 | -16.975 | 1.00 0.00 |
| ATOM | 1736 | HD22 | LEU | 404 | -7.528 | -16.152 | -18.708 | 1.00 0.00 |

Figure 9-31

| ATOM | 1737 | HD23 | LEU | 404 | -6.577 | -14.872 | -17.955 | 1.00 | 0.00 |
| ATOM | 1738 | C | LEU | 404 | -6.293 | -17.204 | -14.570 | 1.00 | 0.00 |
| ATOM | 1739 | O | LEU | 404 | -6.743 | -16.157 | -14.989 | 1.00 | 0.00 |
| ATOM | 1740 | N | GLY | 405 | -6.207 | -17.440 | -13.289 | 1.00 | 0.00 |
| ATOM | 1741 | HN | GLY | 405 | -5.840 | -18.291 | -12.972 | 1.00 | 0.00 |
| ATOM | 1742 | CA | GLY | 405 | -6.668 | -16.415 | -12.309 | 1.00 | 0.00 |
| ATOM | 1743 | HA1 | GLY | 405 | -7.171 | -16.902 | -11.489 | 1.00 | 0.00 |
| ATOM | 1744 | HA2 | GLY | 405 | -7.350 | -15.732 | -12.797 | 1.00 | 0.00 |
| ATOM | 1745 | C | GLY | 405 | -5.465 | -15.640 | -11.773 | 1.00 | 0.00 |
| ATOM | 1746 | O | GLY | 405 | -4.354 | -16.132 | -11.756 | 1.00 | 0.00 |
| ATOM | 1747 | N | LEU | 406 | -5.675 | -14.430 | -11.331 | 1.00 | 0.00 |
| ATOM | 1748 | HN | LEU | 406 | -6.579 | -14.051 | -11.350 | 1.00 | 0.00 |
| ATOM | 1749 | CA | LEU | 406 | -4.540 | -13.624 | -10.796 | 1.00 | 0.00 |
| ATOM | 1750 | HA | LEU | 406 | -3.599 | -14.042 | -11.115 | 1.00 | 0.00 |
| ATOM | 1751 | CB | LEU | 406 | -4.723 | -12.230 | -11.394 | 1.00 | 0.00 |
| ATOM | 1752 | HB1 | LEU | 406 | -5.618 | -11.781 | -10.992 | 1.00 | 0.00 |
| ATOM | 1753 | HB2 | LEU | 406 | -4.810 | -12.308 | -12.469 | 1.00 | 0.00 |
| ATOM | 1754 | CG | LEU | 406 | -3.515 | -11.363 | -11.040 | 1.00 | 0.00 |
| ATOM | 1755 | HG | LEU | 406 | -3.350 | -11.396 | -9.972 | 1.00 | 0.00 |
| ATOM | 1756 | CD1 | LEU | 406 | -2.276 | -11.892 | -11.762 | 1.00 | 0.00 |
| ATOM | 1757 | HD11 | LEU | 406 | -2.532 | -12.787 | -12.309 | 1.00 | 0.00 |
| ATOM | 1758 | HD12 | LEU | 406 | -1.508 | -12.120 | -11.038 | 1.00 | 0.00 |
| ATOM | 1759 | HD13 | LEU | 406 | -1.912 | -11.142 | -12.449 | 1.00 | 0.00 |
| ATOM | 1760 | CD2 | LEU | 406 | -3.779 | -9.919 | -11.473 | 1.00 | 0.00 |
| ATOM | 1761 | HD21 | LEU | 406 | -4.819 | -9.808 | -11.744 | 1.00 | 0.00 |
| ATOM | 1762 | HD22 | LEU | 406 | -3.159 | -9.680 | -12.324 | 1.00 | 0.00 |
| ATOM | 1763 | HD23 | LEU | 406 | -3.546 | -9.250 | -10.658 | 1.00 | 0.00 |
| ATOM | 1764 | C | LEU | 406 | -4.610 | -13.568 | -9.269 | 1.00 | 0.00 |
| ATOM | 1765 | O | LEU | 406 | -3.618 | -13.356 | -8.600 | 1.00 | 0.00 |
| ATOM | 1766 | N | ALA | 407 | -5.776 | -13.754 | -8.711 | 1.00 | 0.00 |
| ATOM | 1767 | HN | ALA | 407 | -6.565 | -13.922 | -9.268 | 1.00 | 0.00 |
| ATOM | 1768 | CA | ALA | 407 | -5.907 | -13.711 | -7.227 | 1.00 | 0.00 |
| ATOM | 1769 | HA | ALA | 407 | -5.529 | -12.778 | -6.841 | 1.00 | 0.00 |
| ATOM | 1770 | CB | ALA | 407 | -7.407 | -13.819 | -6.957 | 1.00 | 0.00 |
| ATOM | 1771 | HB1 | ALA | 407 | -7.950 | -13.303 | -7.734 | 1.00 | 0.00 |
| ATOM | 1772 | HB2 | ALA | 407 | -7.634 | -13.370 | -6.001 | 1.00 | 0.00 |
| ATOM | 1773 | HB3 | ALA | 407 | -7.696 | -14.859 | -6.945 | 1.00 | 0.00 |
| ATOM | 1774 | C | ALA | 407 | -5.164 | -14.892 | -6.599 | 1.00 | 0.00 |
| ATOM | 1775 | O | ALA | 407 | -4.260 | -15.451 | -7.186 | 1.00 | 0.00 |
| ATOM | 1776 | N | ILE | 408 | -5.536 | -15.277 | -5.410 | 1.00 | 0.00 |
| ATOM | 1777 | HN | ILE | 408 | -6.264 | -14.809 | -4.950 | 1.00 | 0.00 |
| ATOM | 1778 | CA | ILE | 408 | -4.846 | -16.424 | -4.749 | 1.00 | 0.00 |
| ATOM | 1779 | HA | ILE | 408 | -4.449 | -17.099 | -5.489 | 1.00 | 0.00 |
| ATOM | 1780 | CB | ILE | 408 | -3.702 | -15.786 | -3.963 | 1.00 | 0.00 |
| ATOM | 1781 | HB | ILE | 408 | -4.107 | -15.125 | -3.211 | 1.00 | 0.00 |
| ATOM | 1782 | CG1 | ILE | 408 | -2.814 | -14.987 | -4.926 | 1.00 | 0.00 |
| ATOM | 1783 | HG11 | ILE | 408 | -3.323 | -14.079 | -5.213 | 1.00 | 0.00 |
| ATOM | 1784 | HG12 | ILE | 408 | -2.615 | -15.581 | -5.807 | 1.00 | 0.00 |
| ATOM | 1785 | CG2 | ILE | 408 | -2.871 | -16.878 | -3.289 | 1.00 | 0.00 |
| ATOM | 1786 | HG21 | ILE | 408 | -3.465 | -17.366 | -2.531 | 1.00 | 0.00 |
| ATOM | 1787 | HG22 | ILE | 408 | -1.999 | -16.435 | -2.832 | 1.00 | 0.00 |
| ATOM | 1788 | HG23 | ILE | 408 | -2.562 | -17.603 | -4.027 | 1.00 | 0.00 |
| ATOM | 1789 | CD1 | ILE | 408 | -1.492 | -14.632 | -4.242 | 1.00 | 0.00 |
| ATOM | 1790 | HD11 | ILE | 408 | -1.686 | -14.295 | -3.234 | 1.00 | 0.00 |
| ATOM | 1791 | HD12 | ILE | 408 | -1.000 | -13.845 | -4.795 | 1.00 | 0.00 |
| ATOM | 1792 | HD13 | ILE | 408 | -0.855 | -15.504 | -4.214 | 1.00 | 0.00 |
| ATOM | 1793 | C | ILE | 408 | -5.810 | -17.167 | -3.811 | 1.00 | 0.00 |
| ATOM | 1794 | O | ILE | 408 | -5.404 | -18.000 | -3.026 | 1.00 | 0.00 |

Figure 9-32

```
ATOM   1795  N    VAL   409      -7.084  -16.874   -3.893  1.00  0.00
ATOM   1796  HN   VAL   409      -7.390  -16.204   -4.535  1.00  0.00
ATOM   1797  CA   VAL   409      -8.074  -17.563   -3.007  1.00  0.00
ATOM   1798  HA   VAL   409      -8.087  -17.116   -2.030  1.00  0.00
ATOM   1799  CB   VAL   409      -9.420  -17.359   -3.689  1.00  0.00
ATOM   1800  HB   VAL   409      -9.601  -16.301   -3.819  1.00  0.00
ATOM   1801  CG1  VAL   409      -9.407  -18.047   -5.056  1.00  0.00
ATOM   1802  HG11 VAL   409     -10.343  -17.865   -5.560  1.00  0.00
ATOM   1803  HG12 VAL   409      -9.272  -19.110   -4.921  1.00  0.00
ATOM   1804  HG13 VAL   409      -8.595  -17.653   -5.650  1.00  0.00
ATOM   1805  CG2  VAL   409     -10.524  -17.968   -2.821  1.00  0.00
ATOM   1806  HG21 VAL   409     -11.237  -18.478   -3.451  1.00  0.00
ATOM   1807  HG22 VAL   409     -11.025  -17.184   -2.272  1.00  0.00
ATOM   1808  HG23 VAL   409     -10.089  -18.672   -2.127  1.00  0.00
ATOM   1809  C    VAL   409      -7.748  -19.050   -2.907  1.00  0.00
ATOM   1810  O    VAL   409      -7.971  -19.678   -1.891  1.00  0.00
ATOM   1811  N    GLN   410      -7.231  -19.623   -3.953  1.00  0.00
ATOM   1812  HN   GLN   410      -7.067  -19.111   -4.764  1.00  0.00
ATOM   1813  CA   GLN   410      -6.894  -21.053   -3.917  1.00  0.00
ATOM   1814  HA   GLN   410      -7.776  -21.646   -3.746  1.00  0.00
ATOM   1815  CB   GLN   410      -6.332  -21.339   -5.299  1.00  0.00
ATOM   1816  HB1  GLN   410      -5.342  -20.919   -5.382  1.00  0.00
ATOM   1817  HB2  GLN   410      -6.976  -20.900   -6.049  1.00  0.00
ATOM   1818  CG   GLN   410      -6.265  -22.833   -5.502  1.00  0.00
ATOM   1819  HG1  GLN   410      -7.256  -23.208   -5.688  1.00  0.00
ATOM   1820  HG2  GLN   410      -5.865  -23.291   -4.611  1.00  0.00
ATOM   1821  CD   GLN   410      -5.366  -23.153   -6.695  1.00  0.00
ATOM   1822  OE1  GLN   410      -5.058  -22.286   -7.489  1.00  0.00
ATOM   1823  NE2  GLN   410      -4.926  -24.370   -6.856  1.00  0.00
ATOM   1824  HE21 GLN   410      -5.173  -25.068   -6.214  1.00  0.00
ATOM   1825  HE22 GLN   410      -4.352  -24.587   -7.620  1.00  0.00
ATOM   1826  C    GLN   410      -5.842  -21.319   -2.839  1.00  0.00
ATOM   1827  O    GLN   410      -6.082  -22.030   -1.892  1.00  0.00
ATOM   1828  N    ARG   411      -4.681  -20.743   -2.981  1.00  0.00
ATOM   1829  HN   ARG   411      -4.516  -20.171   -3.757  1.00  0.00
ATOM   1830  CA   ARG   411      -3.599  -20.956   -1.968  1.00  0.00
ATOM   1831  HA   ARG   411      -3.200  -21.954   -2.047  1.00  0.00
ATOM   1832  CB   ARG   411      -2.520  -19.933   -2.325  1.00  0.00
ATOM   1833  HB1  ARG   411      -2.379  -19.255   -1.498  1.00  0.00
ATOM   1834  HB2  ARG   411      -2.828  -19.376   -3.199  1.00  0.00
ATOM   1835  CG   ARG   411      -1.204  -20.657   -2.618  1.00  0.00
ATOM   1836  HG1  ARG   411      -0.906  -21.229   -1.753  1.00  0.00
ATOM   1837  HG2  ARG   411      -0.438  -19.931   -2.851  1.00  0.00
ATOM   1838  CD   ARG   411      -1.391  -21.601   -3.808  1.00  0.00
ATOM   1839  HD1  ARG   411      -1.192  -21.084   -4.734  1.00  0.00
ATOM   1840  HD2  ARG   411      -2.394  -22.009   -3.809  1.00  0.00
ATOM   1841  NE   ARG   411      -0.389  -22.681   -3.602  1.00  0.00
ATOM   1842  HE   ARG   411      -0.088  -22.905   -2.696  1.00  0.00
ATOM   1843  CZ   ARG   411       0.090  -23.331   -4.627  1.00  0.00
ATOM   1844  NH1  ARG   411       0.863  -22.722   -5.484  1.00  0.00
ATOM   1845  HH11 ARG   411       1.089  -21.756   -5.355  1.00  0.00
ATOM   1846  HH12 ARG   411       1.231  -23.220   -6.269  1.00  0.00
ATOM   1847  NH2  ARG   411      -0.205  -24.591   -4.795  1.00  0.00
ATOM   1848  HH21 ARG   411      -0.797  -25.058   -4.139  1.00  0.00
ATOM   1849  HH22 ARG   411       0.163  -25.089   -5.581  1.00  0.00
ATOM   1850  C    ARG   411      -4.123  -20.712   -0.551  1.00  0.00
ATOM   1851  O    ARG   411      -3.608  -21.253    0.401  1.00  0.00
ATOM   1852  N    ILE   412      -5.129  -19.899   -0.396  1.00  0.00
```

Figure 9-33

| | | | | | | | | |
|---|---|---|---|---|---|---|---|---|
| ATOM | 1853 | HN | ILE | 412 | -5.532 | -19.457 | -1.173 | 1.00 | 0.00 |
| ATOM | 1854 | CA | ILE | 412 | -5.660 | -19.646 | 0.977 | 1.00 | 0.00 |
| ATOM | 1855 | HA | ILE | 412 | -4.882 | -19.249 | 1.614 | 1.00 | 0.00 |
| ATOM | 1856 | CB | ILE | 412 | -6.781 | -18.599 | 0.789 | 1.00 | 0.00 |
| ATOM | 1857 | HB | ILE | 412 | -7.202 | -18.698 | -0.200 | 1.00 | 0.00 |
| ATOM | 1858 | CG1 | ILE | 412 | -6.191 | -17.193 | 0.956 | 1.00 | 0.00 |
| ATOM | 1859 | HG11 | ILE | 412 | -5.260 | -17.256 | 1.495 | 1.00 | 0.00 |
| ATOM | 1860 | HG12 | ILE | 412 | -6.886 | -16.577 | 1.510 | 1.00 | 0.00 |
| ATOM | 1861 | CG2 | ILE | 412 | -7.884 | -18.802 | 1.836 | 1.00 | 0.00 |
| ATOM | 1862 | HG21 | ILE | 412 | -7.458 | -19.236 | 2.727 | 1.00 | 0.00 |
| ATOM | 1863 | HG22 | ILE | 412 | -8.641 | -19.463 | 1.439 | 1.00 | 0.00 |
| ATOM | 1864 | HG23 | ILE | 412 | -8.330 | -17.849 | 2.077 | 1.00 | 0.00 |
| ATOM | 1865 | CD1 | ILE | 412 | -5.941 | -16.566 | -0.418 | 1.00 | 0.00 |
| ATOM | 1866 | HD11 | ILE | 412 | -5.340 | -17.235 | -1.017 | 1.00 | 0.00 |
| ATOM | 1867 | HD12 | ILE | 412 | -5.424 | -15.626 | -0.297 | 1.00 | 0.00 |
| ATOM | 1868 | HD13 | ILE | 412 | -6.882 | -16.392 | -0.907 | 1.00 | 0.00 |
| ATOM | 1869 | C | ILE | 412 | -6.194 | -20.964 | 1.558 | 1.00 | 0.00 |
| ATOM | 1870 | O | ILE | 412 | -5.738 | -21.429 | 2.583 | 1.00 | 0.00 |
| ATOM | 1871 | N | VAL | 413 | -7.147 | -21.570 | 0.909 | 1.00 | 0.00 |
| ATOM | 1872 | HN | VAL | 413 | -7.501 | -21.185 | 0.081 | 1.00 | 0.00 |
| ATOM | 1873 | CA | VAL | 413 | -7.697 | -22.852 | 1.430 | 1.00 | 0.00 |
| ATOM | 1874 | HA | VAL | 413 | -8.019 | -22.741 | 2.451 | 1.00 | 0.00 |
| ATOM | 1875 | CB | VAL | 413 | -8.883 | -23.175 | 0.532 | 1.00 | 0.00 |
| ATOM | 1876 | HB | VAL | 413 | -8.552 | -23.220 | -0.496 | 1.00 | 0.00 |
| ATOM | 1877 | CG1 | VAL | 413 | -9.467 | -24.524 | 0.938 | 1.00 | 0.00 |
| ATOM | 1878 | HG11 | VAL | 413 | -8.751 | -25.059 | 1.544 | 1.00 | 0.00 |
| ATOM | 1879 | HG12 | VAL | 413 | -9.691 | -25.102 | 0.054 | 1.00 | 0.00 |
| ATOM | 1880 | HG13 | VAL | 413 | -10.369 | -24.367 | 1.503 | 1.00 | 0.00 |
| ATOM | 1881 | CG2 | VAL | 413 | -9.949 | -22.086 | 0.683 | 1.00 | 0.00 |
| ATOM | 1882 | HG21 | VAL | 413 | -9.872 | -21.638 | 1.663 | 1.00 | 0.00 |
| ATOM | 1883 | HG22 | VAL | 413 | -10.929 | -22.522 | 0.562 | 1.00 | 0.00 |
| ATOM | 1884 | HG23 | VAL | 413 | -9.798 | -21.327 | -0.072 | 1.00 | 0.00 |
| ATOM | 1885 | C | VAL | 413 | -6.635 | -23.941 | 1.319 | 1.00 | 0.00 |
| ATOM | 1886 | O | VAL | 413 | -6.669 | -24.936 | 2.016 | 1.00 | 0.00 |
| ATOM | 1887 | N | ASP | 414 | -5.692 | -23.757 | 0.443 | 1.00 | 0.00 |
| ATOM | 1888 | HN | ASP | 414 | -5.683 | -22.944 | -0.097 | 1.00 | 0.00 |
| ATOM | 1889 | CA | ASP | 414 | -4.620 | -24.771 | 0.274 | 1.00 | 0.00 |
| ATOM | 1890 | HA | ASP | 414 | -5.029 | -25.766 | 0.307 | 1.00 | 0.00 |
| ATOM | 1891 | CB | ASP | 414 | -4.019 | -24.491 | -1.102 | 1.00 | 0.00 |
| ATOM | 1892 | HB1 | ASP | 414 | -3.293 | -23.697 | -1.023 | 1.00 | 0.00 |
| ATOM | 1893 | HB2 | ASP | 414 | -4.804 | -24.195 | -1.783 | 1.00 | 0.00 |
| ATOM | 1894 | CG | ASP | 414 | -3.336 | -25.754 | -1.629 | 1.00 | 0.00 |
| ATOM | 1895 | OD1 | ASP | 414 | -3.928 | -26.421 | -2.461 | 1.00 | 0.00 |
| ATOM | 1896 | OD2 | ASP | 414 | -2.231 | -26.032 | -1.192 | 1.00 | 0.00 |
| ATOM | 1897 | C | ASP | 414 | -3.577 | -24.578 | 1.365 | 1.00 | 0.00 |
| ATOM | 1898 | O | ASP | 414 | -2.804 | -25.463 | 1.672 | 1.00 | 0.00 |
| ATOM | 1899 | N | ASN | 415 | -3.557 | -23.417 | 1.956 | 1.00 | 0.00 |
| ATOM | 1900 | HN | ASN | 415 | -4.211 | -22.740 | 1.712 | 1.00 | 0.00 |
| ATOM | 1901 | CA | ASN | 415 | -2.574 | -23.142 | 3.032 | 1.00 | 0.00 |
| ATOM | 1902 | HA | ASN | 415 | -1.688 | -23.696 | 2.865 | 1.00 | 0.00 |
| ATOM | 1903 | CB | ASN | 415 | -2.292 | -21.643 | 2.949 | 1.00 | 0.00 |
| ATOM | 1904 | HB1 | ASN | 415 | -1.784 | -21.322 | 3.844 | 1.00 | 0.00 |
| ATOM | 1905 | HB2 | ASN | 415 | -3.226 | -21.108 | 2.852 | 1.00 | 0.00 |
| ATOM | 1906 | CG | ASN | 415 | -1.408 | -21.356 | 1.732 | 1.00 | 0.00 |
| ATOM | 1907 | OD1 | ASN | 415 | -1.366 | -22.136 | 0.801 | 1.00 | 0.00 |
| ATOM | 1908 | ND2 | ASN | 415 | -0.695 | -20.264 | 1.700 | 1.00 | 0.00 |
| ATOM | 1909 | HD21 | ASN | 415 | -0.726 | -19.636 | 2.451 | 1.00 | 0.00 |
| ATOM | 1910 | HD22 | ASN | 415 | -0.129 | -20.071 | 0.923 | 1.00 | 0.00 |

Figure 9-34

| | | | | | | | | |
|---|---|---|---|---|---|---|---|---|
| ATOM | 1911 | C | ASN | 415 | -3.179 | -23.514 | 4.372 | 1.00 0.00 |
| ATOM | 1912 | O | ASN | 415 | -2.555 | -23.409 | 5.409 | 1.00 0.00 |
| ATOM | 1913 | N | HIS | 416 | -4.396 | -23.943 | 4.350 | 1.00 0.00 |
| ATOM | 1914 | HN | HIS | 416 | -4.865 | -24.013 | 3.501 | 1.00 0.00 |
| ATOM | 1915 | CA | HIS | 416 | -5.078 | -24.333 | 5.596 | 1.00 0.00 |
| ATOM | 1916 | HA | HIS | 416 | -4.474 | -24.097 | 6.450 | 1.00 0.00 |
| ATOM | 1917 | CB | HIS | 416 | -6.368 | -23.518 | 5.613 | 1.00 0.00 |
| ATOM | 1918 | HB1 | HIS | 416 | -7.096 | -24.007 | 6.242 | 1.00 0.00 |
| ATOM | 1919 | HB2 | HIS | 416 | -6.756 | -23.435 | 4.608 | 1.00 0.00 |
| ATOM | 1920 | CG | HIS | 416 | -6.079 | -22.150 | 6.154 | 1.00 0.00 |
| ATOM | 1921 | ND1 | HIS | 416 | -6.232 | -21.003 | 5.389 | 1.00 0.00 |
| ATOM | 1922 | HD1 | HIS | 416 | -6.547 | -20.961 | 4.462 | 1.00 0.00 |
| ATOM | 1923 | CD2 | HIS | 416 | -5.634 | -21.728 | 7.379 | 1.00 0.00 |
| ATOM | 1924 | HD2 | HIS | 416 | -5.409 | -22.373 | 8.215 | 1.00 0.00 |
| ATOM | 1925 | CE1 | HIS | 416 | -5.883 | -19.957 | 6.160 | 1.00 0.00 |
| ATOM | 1926 | HE1 | HIS | 416 | -5.893 | -18.929 | 5.829 | 1.00 0.00 |
| ATOM | 1927 | NE2 | HIS | 416 | -5.512 | -20.346 | 7.380 | 1.00 0.00 |
| ATOM | 1928 | C | HIS | 416 | -5.379 | -25.819 | 5.536 | 1.00 0.00 |
| ATOM | 1929 | O | HIS | 416 | -5.546 | -26.472 | 6.543 | 1.00 0.00 |
| ATOM | 1930 | N | ASN | 417 | -5.458 | -26.353 | 4.341 | 1.00 0.00 |
| ATOM | 1931 | HN | ASN | 417 | -5.356 | -25.782 | 3.542 | 1.00 0.00 |
| ATOM | 1932 | CA | ASN | 417 | -5.749 | -27.806 | 4.179 | 1.00 0.00 |
| ATOM | 1933 | HA | ASN | 417 | -5.612 | -28.100 | 3.149 | 1.00 0.00 |
| ATOM | 1934 | CB | ASN | 417 | -4.739 | -28.541 | 5.070 | 1.00 0.00 |
| ATOM | 1935 | HB1 | ASN | 417 | -4.760 | -29.595 | 4.837 | 1.00 0.00 |
| ATOM | 1936 | HB2 | ASN | 417 | -4.998 | -28.399 | 6.108 | 1.00 0.00 |
| ATOM | 1937 | CG | ASN | 417 | -3.332 | -27.997 | 4.812 | 1.00 0.00 |
| ATOM | 1938 | OD1 | ASN | 417 | -3.118 | -26.802 | 4.823 | 1.00 0.00 |
| ATOM | 1939 | ND2 | ASN | 417 | -2.356 | -28.833 | 4.579 | 1.00 0.00 |
| ATOM | 1940 | HD21 | ASN | 417 | -2.528 | -29.798 | 4.572 | 1.00 0.00 |
| ATOM | 1941 | HD22 | ASN | 417 | -1.451 | -28.495 | 4.410 | 1.00 0.00 |
| ATOM | 1942 | C | ASN | 417 | -7.174 | -28.091 | 4.624 | 1.00 0.00 |
| ATOM | 1943 | O | ASN | 417 | -7.594 | -29.227 | 4.712 | 1.00 0.00 |
| ATOM | 1944 | N | GLY | 418 | -7.928 | -27.065 | 4.907 | 1.00 0.00 |
| ATOM | 1945 | HN | GLY | 418 | -7.571 | -26.149 | 4.822 | 1.00 0.00 |
| ATOM | 1946 | CA | GLY | 418 | -9.327 | -27.281 | 5.345 | 1.00 0.00 |
| ATOM | 1947 | HA1 | GLY | 418 | -9.755 | -26.350 | 5.665 | 1.00 0.00 |
| ATOM | 1948 | HA2 | GLY | 418 | -9.346 | -27.991 | 6.162 | 1.00 0.00 |
| ATOM | 1949 | C | GLY | 418 | -10.121 | -27.828 | 4.170 | 1.00 0.00 |
| ATOM | 1950 | O | GLY | 418 | -10.197 | -29.023 | 3.968 | 1.00 0.00 |
| ATOM | 1951 | N | MET | 419 | -10.693 | -26.960 | 3.375 | 1.00 0.00 |
| ATOM | 1952 | HN | MET | 419 | -10.585 | -25.999 | 3.544 | 1.00 0.00 |
| ATOM | 1953 | CA | MET | 419 | -11.490 | -27.434 | 2.196 | 1.00 0.00 |
| ATOM | 1954 | HA | MET | 419 | -10.869 | -28.003 | 1.528 | 1.00 0.00 |
| ATOM | 1955 | CB | MET | 419 | -12.591 | -28.327 | 2.765 | 1.00 0.00 |
| ATOM | 1956 | HB1 | MET | 419 | -13.353 | -27.715 | 3.216 | 1.00 0.00 |
| ATOM | 1957 | HB2 | MET | 419 | -12.181 | -28.991 | 3.500 | 1.00 0.00 |
| ATOM | 1958 | CG | MET | 419 | -13.209 | -29.132 | 1.629 | 1.00 0.00 |
| ATOM | 1959 | HG1 | MET | 419 | -12.444 | -29.726 | 1.156 | 1.00 0.00 |
| ATOM | 1960 | HG2 | MET | 419 | -13.636 | -28.453 | 0.906 | 1.00 0.00 |
| ATOM | 1961 | SD | MET | 419 | -14.507 | -30.216 | 2.278 | 1.00 0.00 |
| ATOM | 1962 | CE | MET | 419 | -13.630 | -30.763 | 3.760 | 1.00 0.00 |
| ATOM | 1963 | HE1 | MET | 419 | -13.812 | -30.060 | 4.563 | 1.00 0.00 |
| ATOM | 1964 | HE2 | MET | 419 | -12.574 | -30.806 | 3.557 | 1.00 0.00 |
| ATOM | 1965 | HE3 | MET | 419 | -13.981 | -31.744 | 4.046 | 1.00 0.00 |
| ATOM | 1966 | C | MET | 419 | -12.132 | -26.265 | 1.456 | 1.00 0.00 |
| ATOM | 1967 | O | MET | 419 | -12.229 | -25.164 | 1.958 | 1.00 0.00 |
| ATOM | 1968 | N | LEU | 420 | -12.568 | -26.508 | 0.258 | 1.00 0.00 |

Figure 9-35

| | | | | | | | | |
|---|---|---|---|---|---|---|---|---|
| ATOM | 1969 | HN | LEU | 420 | -12.474 | -27.408 | -0.119 | 1.00 0.00 |
| ATOM | 1970 | CA | LEU | 420 | -13.212 | -25.441 | -0.546 | 1.00 0.00 |
| ATOM | 1971 | HA | LEU | 420 | -13.697 | -24.725 | 0.101 | 1.00 0.00 |
| ATOM | 1972 | CB | LEU | 420 | -12.076 | -24.774 | -1.328 | 1.00 0.00 |
| ATOM | 1973 | HB1 | LEU | 420 | -11.675 | -25.473 | -2.048 | 1.00 0.00 |
| ATOM | 1974 | HB2 | LEU | 420 | -11.297 | -24.473 | -0.644 | 1.00 0.00 |
| ATOM | 1975 | CG | LEU | 420 | -12.615 | -23.545 | -2.062 | 1.00 0.00 |
| ATOM | 1976 | HG | LEU | 420 | -13.333 | -23.857 | -2.807 | 1.00 0.00 |
| ATOM | 1977 | CD1 | LEU | 420 | -13.294 | -22.610 | -1.062 | 1.00 0.00 |
| ATOM | 1978 | HD11 | LEU | 420 | -14.358 | -22.606 | -1.239 | 1.00 0.00 |
| ATOM | 1979 | HD12 | LEU | 420 | -12.904 | -21.610 | -1.183 | 1.00 0.00 |
| ATOM | 1980 | HD13 | LEU | 420 | -13.097 | -22.954 | -0.057 | 1.00 0.00 |
| ATOM | 1981 | CD2 | LEU | 420 | -11.458 | -22.806 | -2.742 | 1.00 0.00 |
| ATOM | 1982 | HD21 | LEU | 420 | -10.614 | -22.761 | -2.069 | 1.00 0.00 |
| ATOM | 1983 | HD22 | LEU | 420 | -11.771 | -21.804 | -2.995 | 1.00 0.00 |
| ATOM | 1984 | HD23 | LEU | 420 | -11.174 | -23.333 | -3.641 | 1.00 0.00 |
| ATOM | 1985 | C | LEU | 420 | -14.219 | -26.092 | -1.496 | 1.00 0.00 |
| ATOM | 1986 | O | LEU | 420 | -13.950 | -26.280 | -2.666 | 1.00 0.00 |
| ATOM | 1987 | N | GLU | 421 | -15.377 | -26.439 | -1.002 | 1.00 0.00 |
| ATOM | 1988 | HN | GLU | 421 | -15.576 | -26.276 | -0.055 | 1.00 0.00 |
| ATOM | 1989 | CA | GLU | 421 | -16.399 | -27.083 | -1.883 | 1.00 0.00 |
| ATOM | 1990 | HA | GLU | 421 | -15.925 | -27.523 | -2.743 | 1.00 0.00 |
| ATOM | 1991 | CB | GLU | 421 | -17.022 | -28.180 | -1.023 | 1.00 0.00 |
| ATOM | 1992 | HB1 | GLU | 421 | -17.835 | -27.768 | -0.446 | 1.00 0.00 |
| ATOM | 1993 | HB2 | GLU | 421 | -16.274 | -28.584 | -0.355 | 1.00 0.00 |
| ATOM | 1994 | CG | GLU | 421 | -17.555 | -29.293 | -1.925 | 1.00 0.00 |
| ATOM | 1995 | HG1 | GLU | 421 | -17.887 | -28.870 | -2.861 | 1.00 0.00 |
| ATOM | 1996 | HG2 | GLU | 421 | -18.385 | -29.786 | -1.438 | 1.00 0.00 |
| ATOM | 1997 | CD | GLU | 421 | -16.443 | -30.309 | -2.194 | 1.00 0.00 |
| ATOM | 1998 | OE1 | GLU | 421 | -15.767 | -30.681 | -1.249 | 1.00 0.00 |
| ATOM | 1999 | OE2 | GLU | 421 | -16.286 | -30.696 | -3.340 | 1.00 0.00 |
| ATOM | 2000 | C | GLU | 421 | -17.470 | -26.084 | -2.320 | 1.00 0.00 |
| ATOM | 2001 | O | GLU | 421 | -18.404 | -25.802 | -1.596 | 1.00 0.00 |
| ATOM | 2002 | N | LEU | 422 | -17.344 | -25.551 | -3.502 | 1.00 0.00 |
| ATOM | 2003 | HN | LEU | 422 | -16.582 | -25.792 | -4.069 | 1.00 0.00 |
| ATOM | 2004 | CA | LEU | 422 | -18.355 | -24.572 | -3.992 | 1.00 0.00 |
| ATOM | 2005 | HA | LEU | 422 | -18.923 | -24.168 | -3.169 | 1.00 0.00 |
| ATOM | 2006 | CB | LEU | 422 | -17.547 | -23.468 | -4.671 | 1.00 0.00 |
| ATOM | 2007 | HB1 | LEU | 422 | -16.963 | -22.941 | -3.931 | 1.00 0.00 |
| ATOM | 2008 | HB2 | LEU | 422 | -18.221 | -22.776 | -5.158 | 1.00 0.00 |
| ATOM | 2009 | CG | LEU | 422 | -16.613 | -24.087 | -5.709 | 1.00 0.00 |
| ATOM | 2010 | HG | LEU | 422 | -16.947 | -25.089 | -5.941 | 1.00 0.00 |
| ATOM | 2011 | CD1 | LEU | 422 | -16.629 | -23.239 | -6.982 | 1.00 0.00 |
| ATOM | 2012 | HD11 | LEU | 422 | -17.651 | -23.034 | -7.265 | 1.00 0.00 |
| ATOM | 2013 | HD12 | LEU | 422 | -16.137 | -23.776 | -7.779 | 1.00 0.00 |
| ATOM | 2014 | HD13 | LEU | 422 | -16.112 | -22.308 | -6.803 | 1.00 0.00 |
| ATOM | 2015 | CD2 | LEU | 422 | -15.189 | -24.138 | -5.146 | 1.00 0.00 |
| ATOM | 2016 | HD21 | LEU | 422 | -15.197 | -23.807 | -4.118 | 1.00 0.00 |
| ATOM | 2017 | HD22 | LEU | 422 | -14.549 | -23.492 | -5.728 | 1.00 0.00 |
| ATOM | 2018 | HD23 | LEU | 422 | -14.819 | -25.152 | -5.195 | 1.00 0.00 |
| ATOM | 2019 | C | LEU | 422 | -19.280 | -25.265 | -4.997 | 1.00 0.00 |
| ATOM | 2020 | O | LEU | 422 | -18.979 | -26.334 | -5.489 | 1.00 0.00 |
| ATOM | 2021 | N | GLY | 423 | -20.400 | -24.676 | -5.312 | 1.00 0.00 |
| ATOM | 2022 | HN | GLY | 423 | -20.634 | -23.812 | -4.911 | 1.00 0.00 |
| ATOM | 2023 | CA | GLY | 423 | -21.320 | -25.327 | -6.286 | 1.00 0.00 |
| ATOM | 2024 | HA1 | GLY | 423 | -21.608 | -26.295 | -5.909 | 1.00 0.00 |
| ATOM | 2025 | HA2 | GLY | 423 | -20.816 | -25.452 | -7.229 | 1.00 0.00 |
| ATOM | 2026 | C | GLY | 423 | -22.577 | -24.474 | -6.481 | 1.00 0.00 |

Figure 9-36

| ATOM | 2027 | O | GLY | 423 | -22.664 | -23.354 | -6.001 | 1.00 | 0.00 |
|------|------|------|-----|-----|---------|---------|--------|------|------|
| ATOM | 2028 | N | THR | 424 | -23.542 | -25.010 | -7.199 | 1.00 | 0.00 |
| ATOM | 2029 | HN | THR | 424 | -23.418 | -25.908 | -7.571 | 1.00 | 0.00 |
| ATOM | 2030 | CA | THR | 424 | -24.828 | -24.280 | -7.463 | 1.00 | 0.00 |
| ATOM | 2031 | HA | THR | 424 | -24.960 | -23.465 | -6.777 | 1.00 | 0.00 |
| ATOM | 2032 | CB | THR | 424 | -24.711 | -23.749 | -8.894 | 1.00 | 0.00 |
| ATOM | 2033 | HB | THR | 424 | -24.261 | -24.498 | -9.515 | 1.00 | 0.00 |
| ATOM | 2034 | OG1 | THR | 424 | -23.904 | -22.579 | -8.900 | 1.00 | 0.00 |
| ATOM | 2035 | HG1 | THR | 424 | -24.132 | -22.057 | -8.128 | 1.00 | 0.00 |
| ATOM | 2036 | CG2 | THR | 424 | -26.108 | -23.413 | -9.434 | 1.00 | 0.00 |
| ATOM | 2037 | HG21 | THR | 424 | -26.696 | -22.954 | -8.653 | 1.00 | 0.00 |
| ATOM | 2038 | HG22 | THR | 424 | -26.595 | -24.318 | -9.764 | 1.00 | 0.00 |
| ATOM | 2039 | HG23 | THR | 424 | -26.019 | -22.729 | -10.265 | 1.00 | 0.00 |
| ATOM | 2040 | C | THR | 424 | -25.990 | -25.274 | -7.356 | 1.00 | 0.00 |
| ATOM | 2041 | O | THR | 424 | -25.796 | -26.470 | -7.429 | 1.00 | 0.00 |
| ATOM | 2042 | N | SER | 425 | -27.190 | -24.800 | -7.186 | 1.00 | 0.00 |
| ATOM | 2043 | HN | SER | 425 | -27.335 | -23.832 | -7.129 | 1.00 | 0.00 |
| ATOM | 2044 | CA | SER | 425 | -28.344 | -25.741 | -7.078 | 1.00 | 0.00 |
| ATOM | 2045 | HA | SER | 425 | -28.030 | -26.748 | -7.300 | 1.00 | 0.00 |
| ATOM | 2046 | CB | SER | 425 | -28.796 | -25.647 | -5.625 | 1.00 | 0.00 |
| ATOM | 2047 | HB1 | SER | 425 | -29.857 | -25.861 | -5.564 | 1.00 | 0.00 |
| ATOM | 2048 | HB2 | SER | 425 | -28.612 | -24.655 | -5.253 | 1.00 | 0.00 |
| ATOM | 2049 | OG | SER | 425 | -28.065 | -26.584 | -4.843 | 1.00 | 0.00 |
| ATOM | 2050 | HG | SER | 425 | -28.594 | -27.381 | -4.763 | 1.00 | 0.00 |
| ATOM | 2051 | C | SER | 425 | -29.469 | -25.315 | -8.019 | 1.00 | 0.00 |
| ATOM | 2052 | O | SER | 425 | -29.408 | -24.277 | -8.646 | 1.00 | 0.00 |
| ATOM | 2053 | N | GLU | 426 | -30.497 | -26.113 | -8.126 | 1.00 | 0.00 |
| ATOM | 2054 | HN | GLU | 426 | -30.523 | -26.948 | -7.614 | 1.00 | 0.00 |
| ATOM | 2055 | CA | GLU | 426 | -31.631 | -25.756 | -9.027 | 1.00 | 0.00 |
| ATOM | 2056 | HA | GLU | 426 | -31.292 | -25.669 | -10.046 | 1.00 | 0.00 |
| ATOM | 2057 | CB | GLU | 426 | -32.615 | -26.916 | -8.897 | 1.00 | 0.00 |
| ATOM | 2058 | HB1 | GLU | 426 | -32.148 | -27.827 | -9.239 | 1.00 | 0.00 |
| ATOM | 2059 | HB2 | GLU | 426 | -33.492 | -26.713 | -9.496 | 1.00 | 0.00 |
| ATOM | 2060 | CG | GLU | 426 | -33.022 | -27.073 | -7.433 | 1.00 | 0.00 |
| ATOM | 2061 | HG1 | GLU | 426 | -33.109 | -26.098 | -6.977 | 1.00 | 0.00 |
| ATOM | 2062 | HG2 | GLU | 426 | -32.271 | -27.650 | -6.910 | 1.00 | 0.00 |
| ATOM | 2063 | CD | GLU | 426 | -34.368 | -27.792 | -7.351 | 1.00 | 0.00 |
| ATOM | 2064 | OE1 | GLU | 426 | -35.178 | -27.399 | -6.526 | 1.00 | 0.00 |
| ATOM | 2065 | OE2 | GLU | 426 | -34.568 | -28.723 | -8.113 | 1.00 | 0.00 |
| ATOM | 2066 | C | GLU | 426 | -32.276 | -24.450 | -8.559 | 1.00 | 0.00 |
| ATOM | 2067 | O | GLU | 426 | -33.066 | -23.848 | -9.260 | 1.00 | 0.00 |
| ATOM | 2068 | N | ARG | 427 | -31.945 | -24.009 | -7.374 | 1.00 | 0.00 |
| ATOM | 2069 | HN | ARG | 427 | -31.310 | -24.514 | -6.825 | 1.00 | 0.00 |
| ATOM | 2070 | CA | ARG | 427 | -32.534 | -22.741 | -6.852 | 1.00 | 0.00 |
| ATOM | 2071 | HA | ARG | 427 | -33.608 | -22.766 | -6.924 | 1.00 | 0.00 |
| ATOM | 2072 | CB | ARG | 427 | -32.108 | -22.682 | -5.381 | 1.00 | 0.00 |
| ATOM | 2073 | HB1 | ARG | 427 | -32.623 | -21.869 | -4.890 | 1.00 | 0.00 |
| ATOM | 2074 | HB2 | ARG | 427 | -31.041 | -22.518 | -5.323 | 1.00 | 0.00 |
| ATOM | 2075 | CG | ARG | 427 | -32.461 | -24.000 | -4.686 | 1.00 | 0.00 |
| ATOM | 2076 | HG1 | ARG | 427 | -32.650 | -24.760 | -5.428 | 1.00 | 0.00 |
| ATOM | 2077 | HG2 | ARG | 427 | -33.345 | -23.861 | -4.079 | 1.00 | 0.00 |
| ATOM | 2078 | CD | ARG | 427 | -31.291 | -24.437 | -3.796 | 1.00 | 0.00 |
| ATOM | 2079 | HD1 | ARG | 427 | -31.325 | -23.923 | -2.849 | 1.00 | 0.00 |
| ATOM | 2080 | HD2 | ARG | 427 | -30.349 | -24.247 | -4.295 | 1.00 | 0.00 |
| ATOM | 2081 | NE | ARG | 427 | -31.488 | -25.898 | -3.591 | 1.00 | 0.00 |
| ATOM | 2082 | HE | ARG | 427 | -31.389 | -26.516 | -4.345 | 1.00 | 0.00 |
| ATOM | 2083 | CZ | ARG | 427 | -31.790 | -26.358 | -2.407 | 1.00 | 0.00 |
| ATOM | 2084 | NH1 | ARG | 427 | -31.119 | -25.960 | -1.361 | 1.00 | 0.00 |

Figure 9-37

```
ATOM   2085  HH11 ARG   427     -30.373 -25.304  -1.467  1.00  0.00
ATOM   2086  HH12 ARG   427     -31.351 -26.311  -0.454  1.00  0.00
ATOM   2087  NH2  ARG   427     -32.765 -27.214  -2.270  1.00  0.00
ATOM   2088  HH21 ARG   427     -33.280 -27.519  -3.071  1.00  0.00
ATOM   2089  HH22 ARG   427     -32.996 -27.566  -1.363  1.00  0.00
ATOM   2090  C    ARG   427     -31.969 -21.538  -7.617  1.00  0.00
ATOM   2091  O    ARG   427     -32.350 -20.409  -7.384  1.00  0.00
ATOM   2092  N    GLY   428     -31.063 -21.771  -8.527  1.00  0.00
ATOM   2093  HN   GLY   428     -30.762 -22.685  -8.698  1.00  0.00
ATOM   2094  CA   GLY   428     -30.479 -20.641  -9.299  1.00  0.00
ATOM   2095  HA1  GLY   428     -31.155 -19.801  -9.282  1.00  0.00
ATOM   2096  HA2  GLY   428     -30.307 -20.950 -10.322  1.00  0.00
ATOM   2097  C    GLY   428     -29.160 -20.240  -8.653  1.00  0.00
ATOM   2098  O    GLY   428     -28.792 -19.083  -8.626  1.00  0.00
ATOM   2099  N    GLY   429     -28.443 -21.195  -8.131  1.00  0.00
ATOM   2100  HN   GLY   429     -28.762 -22.121  -8.169  1.00  0.00
ATOM   2101  CA   GLY   429     -27.144 -20.886  -7.480  1.00  0.00
ATOM   2102  HA1  GLY   429     -27.070 -19.824  -7.315  1.00  0.00
ATOM   2103  HA2  GLY   429     -26.333 -21.213  -8.115  1.00  0.00
ATOM   2104  C    GLY   429     -27.073 -21.608  -6.138  1.00  0.00
ATOM   2105  O    GLY   429     -28.045 -22.169  -5.673  1.00  0.00
ATOM   2106  N    LEU   430     -25.933 -21.608  -5.511  1.00  0.00
ATOM   2107  HN   LEU   430     -25.157 -21.152  -5.899  1.00  0.00
ATOM   2108  CA   LEU   430     -25.814 -22.297  -4.197  1.00  0.00
ATOM   2109  HA   LEU   430     -26.780 -22.390  -3.746  1.00  0.00
ATOM   2110  CB   LEU   430     -25.253 -23.682  -4.504  1.00  0.00
ATOM   2111  HB1  LEU   430     -24.371 -23.582  -5.082  1.00  0.00
ATOM   2112  HB2  LEU   430     -25.984 -24.253  -5.058  1.00  0.00
ATOM   2113  CG   LEU   430     -24.918 -24.410  -3.205  1.00  0.00
ATOM   2114  HG   LEU   430     -24.938 -23.710  -2.382  1.00  0.00
ATOM   2115  CD1  LEU   430     -25.944 -25.516  -2.963  1.00  0.00
ATOM   2116  HD11 LEU   430     -26.741 -25.431  -3.687  1.00  0.00
ATOM   2117  HD12 LEU   430     -26.350 -25.419  -1.968  1.00  0.00
ATOM   2118  HD13 LEU   430     -25.466 -26.478  -3.066  1.00  0.00
ATOM   2119  CD2  LEU   430     -23.519 -25.029  -3.322  1.00  0.00
ATOM   2120  HD21 LEU   430     -22.791 -24.357  -2.892  1.00  0.00
ATOM   2121  HD22 LEU   430     -23.285 -25.194  -4.364  1.00  0.00
ATOM   2122  HD23 LEU   430     -23.496 -25.971  -2.794  1.00  0.00
ATOM   2123  C    LEU   430     -24.873 -21.510  -3.282  1.00  0.00
ATOM   2124  O    LEU   430     -25.255 -20.507  -2.703  1.00  0.00
ATOM   2125  N    SER   431     -23.642 -21.936  -3.145  1.00  0.00
ATOM   2126  HN   SER   431     -23.323 -22.725  -3.646  1.00  0.00
ATOM   2127  CA   SER   431     -22.716 -21.178  -2.253  1.00  0.00
ATOM   2128  HA   SER   431     -22.741 -20.129  -2.491  1.00  0.00
ATOM   2129  CB   SER   431     -23.268 -21.401  -0.850  1.00  0.00
ATOM   2130  HB1  SER   431     -24.318 -21.133  -0.830  1.00  0.00
ATOM   2131  HB2  SER   431     -22.731 -20.790  -0.148  1.00  0.00
ATOM   2132  OG   SER   431     -23.109 -22.771  -0.496  1.00  0.00
ATOM   2133  HG   SER   431     -23.944 -23.084  -0.140  1.00  0.00
ATOM   2134  C    SER   431     -21.285 -21.712  -2.351  1.00  0.00
ATOM   2135  O    SER   431     -21.001 -22.647  -3.071  1.00  0.00
ATOM   2136  N    ILE   432     -20.387 -21.112  -1.619  1.00  0.00
ATOM   2137  HN   ILE   432     -20.647 -20.361  -1.055  1.00  0.00
ATOM   2138  CA   ILE   432     -18.970 -21.558  -1.641  1.00  0.00
ATOM   2139  HA   ILE   432     -18.840 -22.368  -2.332  1.00  0.00
ATOM   2140  CB   ILE   432     -18.172 -20.335  -2.094  1.00  0.00
ATOM   2141  HB   ILE   432     -18.526 -20.014  -3.064  1.00  0.00
ATOM   2142  CG1  ILE   432     -16.684 -20.698  -2.185  1.00  0.00
```

Figure 9-38

```
ATOM   2143 HG11 ILE   432     -16.560 -21.755  -2.010  1.00  0.00
ATOM   2144 HG12 ILE   432     -16.132 -20.142  -1.440  1.00  0.00
ATOM   2145  CG2 ILE   432     -18.358 -19.203  -1.083  1.00  0.00
ATOM   2146 HG21 ILE   432     -18.610 -18.292  -1.605  1.00  0.00
ATOM   2147 HG22 ILE   432     -17.443 -19.060  -0.530  1.00  0.00
ATOM   2148 HG23 ILE   432     -19.154 -19.458  -0.401  1.00  0.00
ATOM   2149  CD1 ILE   432     -16.157 -20.349  -3.579  1.00  0.00
ATOM   2150 HD11 ILE   432     -16.304 -19.296  -3.767  1.00  0.00
ATOM   2151 HD12 ILE   432     -16.690 -20.925  -4.321  1.00  0.00
ATOM   2152 HD13 ILE   432     -15.103 -20.580  -3.633  1.00  0.00
ATOM   2153  C    ILE   432     -18.565 -21.979  -0.224  1.00  0.00
ATOM   2154  O    ILE   432     -18.445 -21.158   0.666  1.00  0.00
ATOM   2155  N    ARG   433     -18.361 -23.249  -0.004  1.00  0.00
ATOM   2156  HN   ARG   433     -18.465 -23.895  -0.731  1.00  0.00
ATOM   2157  CA   ARG   433     -17.967 -23.714   1.359  1.00  0.00
ATOM   2158  HA   ARG   433     -18.402 -23.078   2.109  1.00  0.00
ATOM   2159  CB   ARG   433     -18.545 -25.121   1.477  1.00  0.00
ATOM   2160  HB1  ARG   433     -18.442 -25.469   2.493  1.00  0.00
ATOM   2161  HB2  ARG   433     -18.012 -25.787   0.813  1.00  0.00
ATOM   2162  CG   ARG   433     -20.025 -25.097   1.098  1.00  0.00
ATOM   2163  HG1  ARG   433     -20.147 -25.491   0.101  1.00  0.00
ATOM   2164  HG2  ARG   433     -20.386 -24.080   1.130  1.00  0.00
ATOM   2165  CD   ARG   433     -20.820 -25.955   2.084  1.00  0.00
ATOM   2166  HD1  ARG   433     -21.730 -25.453   2.370  1.00  0.00
ATOM   2167  HD2  ARG   433     -20.219 -26.179   2.957  1.00  0.00
ATOM   2168  NE   ARG   433     -21.139 -27.201   1.336  1.00  0.00
ATOM   2169  HE   ARG   433     -21.436 -27.149   0.403  1.00  0.00
ATOM   2170  CZ   ARG   433     -21.023 -28.362   1.921  1.00  0.00
ATOM   2171  NH1  ARG   433     -21.857 -28.702   2.865  1.00  0.00
ATOM   2172 HH11  ARG   433     -22.583 -28.073   3.141  1.00  0.00
ATOM   2173 HH12  ARG   433     -21.769 -29.592   3.313  1.00  0.00
ATOM   2174  NH2  ARG   433     -20.074 -29.182   1.563  1.00  0.00
ATOM   2175 HH21  ARG   433     -19.433 -28.921   0.840  1.00  0.00
ATOM   2176 HH22  ARG   433     -19.986 -30.072   2.011  1.00  0.00
ATOM   2177  C    ARG   433     -16.448 -23.749   1.509  1.00  0.00
ATOM   2178  O    ARG   433     -15.729 -24.130   0.607  1.00  0.00
ATOM   2179  N    ALA   434     -15.958 -23.353   2.648  1.00  0.00
ATOM   2180  HN   ALA   434     -16.562 -23.048   3.360  1.00  0.00
ATOM   2181  CA   ALA   434     -14.488 -23.357   2.878  1.00  0.00
ATOM   2182  HA   ALA   434     -13.990 -23.966   2.140  1.00  0.00
ATOM   2183  CB   ALA   434     -14.069 -21.899   2.735  1.00  0.00
ATOM   2184  HB1  ALA   434     -13.875 -21.680   1.696  1.00  0.00
ATOM   2185  HB2  ALA   434     -13.176 -21.723   3.314  1.00  0.00
ATOM   2186  HB3  ALA   434     -14.864 -21.260   3.095  1.00  0.00
ATOM   2187  C    ALA   434     -14.203 -23.866   4.290  1.00  0.00
ATOM   2188  O    ALA   434     -14.496 -23.205   5.263  1.00  0.00
ATOM   2189  N    TRP   435     -13.629 -25.030   4.420  1.00  0.00
ATOM   2190  HN   TRP   435     -13.398 -25.559   3.624  1.00  0.00
ATOM   2191  CA   TRP   435     -13.340 -25.556   5.792  1.00  0.00
ATOM   2192  HA   TRP   435     -14.076 -25.189   6.487  1.00  0.00
ATOM   2193  CB   TRP   435     -13.458 -27.069   5.689  1.00  0.00
ATOM   2194  HB1  TRP   435     -13.162 -27.514   6.628  1.00  0.00
ATOM   2195  HB2  TRP   435     -12.813 -27.426   4.909  1.00  0.00
ATOM   2196  CG   TRP   435     -14.863 -27.444   5.390  1.00  0.00
ATOM   2197  CD1  TRP   435     -15.460 -27.318   4.187  1.00  0.00
ATOM   2198  HD1  TRP   435     -14.998 -26.929   3.292  1.00  0.00
ATOM   2199  CD2  TRP   435     -15.860 -28.004   6.289  1.00  0.00
ATOM   2200  NE1  TRP   435     -16.757 -27.772   4.285  1.00  0.00
```

Figure 9-39

```
ATOM   2201  HE1  TRP  435  -17.398 -27.794   3.554  1.00  0.00
ATOM   2202  CE2  TRP  435  -17.054 -28.204   5.566  1.00  0.00
ATOM   2203  CE3  TRP  435  -15.840 -28.356   7.652  1.00  0.00
ATOM   2204  HE3  TRP  435  -14.939 -28.214   8.230  1.00  0.00
ATOM   2205  CZ2  TRP  435  -18.194 -28.734   6.169  1.00  0.00
ATOM   2206  HZ2  TRP  435  -19.095 -28.875   5.595  1.00  0.00
ATOM   2207  CZ3  TRP  435  -16.987 -28.890   8.265  1.00  0.00
ATOM   2208  HZ3  TRP  435  -16.963 -29.157   9.312  1.00  0.00
ATOM   2209  CH2  TRP  435  -18.162 -29.078   7.523  1.00  0.00
ATOM   2210  HH2  TRP  435  -19.041 -29.489   7.997  1.00  0.00
ATOM   2211  C    TRP  435  -11.940 -25.195   6.282  1.00  0.00
ATOM   2212  O    TRP  435  -11.083 -24.744   5.542  1.00  0.00
ATOM   2213  N    LEU  436  -11.737 -25.419   7.548  1.00  0.00
ATOM   2214  HN   LEU  436  -12.458 -25.797   8.069  1.00  0.00
ATOM   2215  CA   LEU  436  -10.444 -25.139   8.224  1.00  0.00
ATOM   2216  HA   LEU  436   -9.620 -25.204   7.529  1.00  0.00
ATOM   2217  CB   LEU  436  -10.571 -23.720   8.798  1.00  0.00
ATOM   2218  HB1  LEU  436   -9.694 -23.493   9.385  1.00  0.00
ATOM   2219  HB2  LEU  436  -11.447 -23.667   9.428  1.00  0.00
ATOM   2220  CG   LEU  436  -10.699 -22.697   7.661  1.00  0.00
ATOM   2221  HG   LEU  436  -11.404 -23.054   6.930  1.00  0.00
ATOM   2222  CD1  LEU  436  -11.192 -21.365   8.228  1.00  0.00
ATOM   2223  HD11 LEU  436  -10.904 -20.563   7.565  1.00  0.00
ATOM   2224  HD12 LEU  436  -10.753 -21.203   9.202  1.00  0.00
ATOM   2225  HD13 LEU  436  -12.268 -21.388   8.318  1.00  0.00
ATOM   2226  CD2  LEU  436   -9.333 -22.491   7.000  1.00  0.00
ATOM   2227  HD21 LEU  436   -9.313 -21.530   6.505  1.00  0.00
ATOM   2228  HD22 LEU  436   -9.162 -23.272   6.274  1.00  0.00
ATOM   2229  HD23 LEU  436   -8.560 -22.523   7.753  1.00  0.00
ATOM   2230  C    LEU  436  -10.301 -26.172   9.357  1.00  0.00
ATOM   2231  O    LEU  436  -11.253 -26.441  10.062  1.00  0.00
ATOM   2232  N    PRO  437   -9.134 -26.713   9.498  1.00  0.00
ATOM   2233  CA   PRO  437   -8.900 -27.724  10.560  1.00  0.00
ATOM   2234  HA   PRO  437   -9.654 -28.490  10.514  1.00  0.00
ATOM   2235  CB   PRO  437   -7.543 -28.312  10.200  1.00  0.00
ATOM   2236  HB1  PRO  437   -7.664 -29.199   9.601  1.00  0.00
ATOM   2237  HB2  PRO  437   -6.980 -28.536  11.099  1.00  0.00
ATOM   2238  CG   PRO  437   -6.855 -27.243   9.402  1.00  0.00
ATOM   2239  HG1  PRO  437   -6.206 -27.690   8.667  1.00  0.00
ATOM   2240  HG2  PRO  437   -6.282 -26.602  10.062  1.00  0.00
ATOM   2241  CD   PRO  437   -7.936 -26.442   8.709  1.00  0.00
ATOM   2242  HD1  PRO  437   -8.072 -26.784   7.697  1.00  0.00
ATOM   2243  HD2  PRO  437   -7.697 -25.386   8.729  1.00  0.00
ATOM   2244  C    PRO  437   -8.873 -27.099  11.961  1.00  0.00
ATOM   2245  O    PRO  437   -8.336 -26.030  12.173  1.00  0.00
ATOM   2246  N    VAL  438   -9.454 -27.782  12.920  1.00  0.00
ATOM   2247  HN   VAL  438   -9.875 -28.643  12.714  1.00  0.00
ATOM   2248  CA   VAL  438   -9.483 -27.262  14.320  1.00  0.00
ATOM   2249  HA   VAL  438   -9.172 -26.237  14.349  1.00  0.00
ATOM   2250  CB   VAL  438  -10.947 -27.380  14.746  1.00  0.00
ATOM   2251  HB   VAL  438  -11.341 -28.318  14.397  1.00  0.00
ATOM   2252  CG1  VAL  438  -11.052 -27.321  16.274  1.00  0.00
ATOM   2253  HG11 VAL  438  -10.164 -26.860  16.679  1.00  0.00
ATOM   2254  HG12 VAL  438  -11.147 -28.323  16.666  1.00  0.00
ATOM   2255  HG13 VAL  438  -11.920 -26.741  16.553  1.00  0.00
ATOM   2256  CG2  VAL  438  -11.752 -26.230  14.135  1.00  0.00
ATOM   2257  HG21 VAL  438  -11.323 -25.958  13.182  1.00  0.00
ATOM   2258  HG22 VAL  438  -11.726 -25.378  14.799  1.00  0.00
```

Figure 9-40

```
ATOM   2259  HG23 VAL  438   -12.777 -26.543  13.993  1.00  0.00
ATOM   2260  C    VAL  438    -8.588 -28.130  15.221  1.00  0.00
ATOM   2261  O    VAL  438    -9.074 -28.965  15.959  1.00  0.00
ATOM   2262  N    PRO  439    -7.305 -27.898  15.128  1.00  0.00
ATOM   2263  CA   PRO  439    -6.330 -28.665  15.941  1.00  0.00
ATOM   2264  HA   PRO  439    -6.499 -29.722  15.851  1.00  0.00
ATOM   2265  CB   PRO  439    -4.985 -28.291  15.338  1.00  0.00
ATOM   2266  HB1  PRO  439    -4.697 -29.007  14.585  1.00  0.00
ATOM   2267  HB2  PRO  439    -4.230 -28.229  16.112  1.00  0.00
ATOM   2268  CG   PRO  439    -5.209 -26.949  14.711  1.00  0.00
ATOM   2269  HG1  PRO  439    -4.567 -26.828  13.859  1.00  0.00
ATOM   2270  HG2  PRO  439    -5.018 -26.168  15.438  1.00  0.00
ATOM   2271  CD   PRO  439    -6.654 -26.906  14.273  1.00  0.00
ATOM   2272  HD1  PRO  439    -6.747 -27.188  13.237  1.00  0.00
ATOM   2273  HD2  PRO  439    -7.071 -25.920  14.443  1.00  0.00
ATOM   2274  C    PRO  439    -6.401 -28.223  17.399  1.00  0.00
ATOM   2275  O    PRO  439    -5.647 -27.378  17.837  1.00  0.00
ATOM   2276  N    VAL  440    -7.294 -28.785  18.156  1.00  0.00
ATOM   2277  HN   VAL  440    -7.895 -29.458  17.789  1.00  0.00
ATOM   2278  CA   VAL  440    -7.403 -28.388  19.576  1.00  0.00
ATOM   2279  HA   VAL  440    -6.470 -27.981  19.919  1.00  0.00
ATOM   2280  CB   VAL  440    -8.480 -27.280  19.558  1.00  0.00
ATOM   2281  HB   VAL  440    -8.837 -27.160  18.545  1.00  0.00
ATOM   2282  CG1  VAL  440    -9.665 -27.640  20.466  1.00  0.00
ATOM   2283  HG11 VAL  440    -9.953 -28.666  20.289  1.00  0.00
ATOM   2284  HG12 VAL  440   -10.498 -26.990  20.245  1.00  0.00
ATOM   2285  HG13 VAL  440    -9.377 -27.520  21.498  1.00  0.00
ATOM   2286  CG2  VAL  440    -7.855 -25.967  20.031  1.00  0.00
ATOM   2287  HG21 VAL  440    -8.591 -25.179  19.979  1.00  0.00
ATOM   2288  HG22 VAL  440    -7.016 -25.719  19.396  1.00  0.00
ATOM   2289  HG23 VAL  440    -7.516 -26.076  21.050  1.00  0.00
ATOM   2290  C    VAL  440    -7.811 -29.595  20.445  1.00  0.00
ATOM   2291  O    VAL  440    -8.379 -30.557  19.966  1.00  0.00
ATOM   2292  N    THR  441    -7.522 -29.542  21.718  1.00  0.00
ATOM   2293  HN   THR  441    -7.063 -28.757  22.083  1.00  0.00
ATOM   2294  CA   THR  441    -7.888 -30.674  22.618  1.00  0.00
ATOM   2295  HA   THR  441    -7.633 -31.616  22.165  1.00  0.00
ATOM   2296  CB   THR  441    -7.057 -30.459  23.879  1.00  0.00
ATOM   2297  HB   THR  441    -7.410 -31.114  24.657  1.00  0.00
ATOM   2298  OG1  THR  441    -7.182 -29.107  24.301  1.00  0.00
ATOM   2299  HG1  THR  441    -8.089 -28.966  24.581  1.00  0.00
ATOM   2300  CG2  THR  441    -5.590 -30.770  23.583  1.00  0.00
ATOM   2301  HG21 THR  441    -5.063 -30.938  24.511  1.00  0.00
ATOM   2302  HG22 THR  441    -5.143 -29.938  23.060  1.00  0.00
ATOM   2303  HG23 THR  441    -5.527 -31.657  22.969  1.00  0.00
ATOM   2304  C    THR  441    -9.383 -30.621  22.943  1.00  0.00
ATOM   2305  O    THR  441    -9.896 -29.611  23.382  1.00  0.00
ATOM   2306  N    ARG  442   -10.086 -31.700  22.734  1.00  0.00
ATOM   2307  HN   ARG  442    -9.655 -32.507  22.384  1.00  0.00
ATOM   2308  CA   ARG  442   -11.549 -31.705  23.033  1.00  0.00
ATOM   2309  HA   ARG  442   -11.770 -31.034  23.847  1.00  0.00
ATOM   2310  CB   ARG  442   -12.214 -31.208  21.750  1.00  0.00
ATOM   2311  HB1  ARG  442   -11.904 -31.824  20.921  1.00  0.00
ATOM   2312  HB2  ARG  442   -11.920 -30.184  21.567  1.00  0.00
ATOM   2313  CG   ARG  442   -13.735 -31.284  21.898  1.00  0.00
ATOM   2314  HG1  ARG  442   -14.007 -32.218  22.364  1.00  0.00
ATOM   2315  HG2  ARG  442   -14.194 -31.221  20.921  1.00  0.00
ATOM   2316  CD   ARG  442   -14.219 -30.123  22.770  1.00  0.00
```

Figure 9-41

| | | | | | | | | |
|---|---|---|---|---|---|---|---|---|
| ATOM | 2317 | HD1 | ARG | 442 | -13.415 | -29.429 | 22.951 | 1.00 | 0.00 |
| ATOM | 2318 | HD2 | ARG | 442 | -14.614 | -30.497 | 23.706 | 1.00 | 0.00 |
| ATOM | 2319 | NE | ARG | 442 | -15.291 | -29.463 | 21.977 | 1.00 | 0.00 |
| ATOM | 2320 | HE | ARG | 442 | -15.377 | -29.648 | 21.017 | 1.00 | 0.00 |
| ATOM | 2321 | CZ | ARG | 442 | -16.117 | -28.636 | 22.560 | 1.00 | 0.00 |
| ATOM | 2322 | NH1 | ARG | 442 | -16.567 | -28.898 | 23.756 | 1.00 | 0.00 |
| ATOM | 2323 | HH11 | ARG | 442 | -16.280 | -29.732 | 24.227 | 1.00 | 0.00 |
| ATOM | 2324 | HH12 | ARG | 442 | -17.202 | -28.265 | 24.202 | 1.00 | 0.00 |
| ATOM | 2325 | NH2 | ARG | 442 | -16.490 | -27.546 | 21.948 | 1.00 | 0.00 |
| ATOM | 2326 | HH21 | ARG | 442 | -16.144 | -27.343 | 21.032 | 1.00 | 0.00 |
| ATOM | 2327 | HH22 | ARG | 442 | -17.124 | -26.914 | 22.394 | 1.00 | 0.00 |
| ATOM | 2328 | C | ARG | 442 | -12.018 | -33.123 | 23.368 | 1.00 | 0.00 |
| ATOM | 2329 | O | ARG | 442 | -12.080 | -33.511 | 24.518 | 1.00 | 0.00 |
| ATOM | 2330 | N | ALA | 443 | -12.349 | -33.901 | 22.374 | 1.00 | 0.00 |
| ATOM | 2331 | HN | ALA | 443 | -12.293 | -33.572 | 21.453 | 1.00 | 0.00 |
| ATOM | 2332 | CA | ALA | 443 | -12.813 | -35.291 | 22.644 | 1.00 | 0.00 |
| ATOM | 2333 | HA | ALA | 443 | -13.255 | -35.720 | 21.761 | 1.00 | 0.00 |
| ATOM | 2334 | CB | ALA | 443 | -11.548 | -36.059 | 23.024 | 1.00 | 0.00 |
| ATOM | 2335 | HB1 | ALA | 443 | -11.175 | -35.692 | 23.968 | 1.00 | 0.00 |
| ATOM | 2336 | HB2 | ALA | 443 | -10.797 | -35.916 | 22.260 | 1.00 | 0.00 |
| ATOM | 2337 | HB3 | ALA | 443 | -11.777 | -37.111 | 23.111 | 1.00 | 0.00 |
| ATOM | 2338 | C | ALA | 443 | -13.814 | -35.291 | 23.804 | 1.00 | 0.00 |
| ATOM | 2339 | O | ALA | 443 | -14.425 | -34.284 | 24.106 | 1.00 | 0.00 |
| ATOM | 2340 | N | GLN | 444 | -13.987 | -36.410 | 24.455 | 1.00 | 0.00 |
| ATOM | 2341 | HN | GLN | 444 | -13.486 | -37.211 | 24.195 | 1.00 | 0.00 |
| ATOM | 2342 | CA | GLN | 444 | -14.951 | -36.470 | 25.595 | 1.00 | 0.00 |
| ATOM | 2343 | HA | GLN | 444 | -15.180 | -37.494 | 25.842 | 1.00 | 0.00 |
| ATOM | 2344 | CB | GLN | 444 | -14.225 | -35.800 | 26.762 | 1.00 | 0.00 |
| ATOM | 2345 | HB1 | GLN | 444 | -14.547 | -34.774 | 26.846 | 1.00 | 0.00 |
| ATOM | 2346 | HB2 | GLN | 444 | -13.159 | -35.830 | 26.587 | 1.00 | 0.00 |
| ATOM | 2347 | CG | GLN | 444 | -14.551 | -36.541 | 28.060 | 1.00 | 0.00 |
| ATOM | 2348 | HG1 | GLN | 444 | -14.803 | -37.566 | 27.836 | 1.00 | 0.00 |
| ATOM | 2349 | HG2 | GLN | 444 | -15.389 | -36.061 | 28.548 | 1.00 | 0.00 |
| ATOM | 2350 | CD | GLN | 444 | -13.334 | -36.508 | 28.988 | 1.00 | 0.00 |
| ATOM | 2351 | OE1 | GLN | 444 | -12.945 | -37.521 | 29.534 | 1.00 | 0.00 |
| ATOM | 2352 | NE2 | GLN | 444 | -12.713 | -35.377 | 29.191 | 1.00 | 0.00 |
| ATOM | 2353 | HE21 | GLN | 444 | -13.026 | -34.560 | 28.750 | 1.00 | 0.00 |
| ATOM | 2354 | HE22 | GLN | 444 | -11.934 | -35.346 | 29.785 | 1.00 | 0.00 |
| ATOM | 2355 | C | GLN | 444 | -16.231 | -35.703 | 25.244 | 1.00 | 0.00 |
| ATOM | 2356 | O | GLN | 444 | -16.345 | -34.520 | 25.493 | 1.00 | 0.00 |
| ATOM | 2357 | N | GLY | 445 | -17.192 | -36.369 | 24.664 | 1.00 | 0.00 |
| ATOM | 2358 | HN | GLY | 445 | -17.078 | -37.322 | 24.470 | 1.00 | 0.00 |
| ATOM | 2359 | CA | GLY | 445 | -18.463 | -35.680 | 24.296 | 1.00 | 0.00 |
| ATOM | 2360 | HA1 | GLY | 445 | -18.345 | -34.615 | 24.421 | 1.00 | 0.00 |
| ATOM | 2361 | HA2 | GLY | 445 | -19.262 | -36.033 | 24.936 | 1.00 | 0.00 |
| ATOM | 2362 | C | GLY | 445 | -18.805 | -35.983 | 22.834 | 1.00 | 0.00 |
| ATOM | 2363 | O | GLY | 445 | -19.793 | -35.512 | 22.308 | 1.00 | 0.00 |
| ATOM | 2364 | N | THR | 446 | -17.995 | -36.767 | 22.173 | 1.00 | 0.00 |
| ATOM | 2365 | HN | THR | 446 | -17.203 | -37.137 | 22.614 | 1.00 | 0.00 |
| ATOM | 2366 | CA | THR | 446 | -18.276 | -37.098 | 20.748 | 1.00 | 0.00 |
| ATOM | 2367 | HA | THR | 446 | -19.164 | -36.601 | 20.413 | 1.00 | 0.00 |
| ATOM | 2368 | CB | THR | 446 | -17.072 | -36.578 | 19.974 | 1.00 | 0.00 |
| ATOM | 2369 | HB | THR | 446 | -16.936 | -37.175 | 19.093 | 1.00 | 0.00 |
| ATOM | 2370 | OG1 | THR | 446 | -15.909 | -36.663 | 20.795 | 1.00 | 0.00 |
| ATOM | 2371 | HG1 | THR | 446 | -15.473 | -35.808 | 20.788 | 1.00 | 0.00 |
| ATOM | 2372 | CG2 | THR | 446 | -17.316 | -35.122 | 19.563 | 1.00 | 0.00 |
| ATOM | 2373 | HG21 | THR | 446 | -17.131 | -35.011 | 18.504 | 1.00 | 0.00 |
| ATOM | 2374 | HG22 | THR | 446 | -16.651 | -34.474 | 20.115 | 1.00 | 0.00 |

Figure 9-42

| | | | | | | | | |
|---|---|---|---|---|---|---|---|---|
| ATOM | 2375 | HG23 | THR | 446 | -18.340 | -34.853 | 19.779 | 1.00 0.00 |
| ATOM | 2376 | C | THR | 446 | -18.414 | -38.614 | 20.572 | 1.00 0.00 |
| ATOM | 2377 | O | THR | 446 | -18.095 | -39.383 | 21.458 | 1.00 0.00 |
| ATOM | 2378 | N | THR | 447 | -18.885 | -39.046 | 19.436 | 1.00 0.00 |
| ATOM | 2379 | HN | THR | 447 | -19.134 | -38.408 | 18.735 | 1.00 0.00 |
| ATOM | 2380 | CA | THR | 447 | -19.045 | -40.510 | 19.200 | 1.00 0.00 |
| ATOM | 2381 | HA | THR | 447 | -18.125 | -41.030 | 19.413 | 1.00 0.00 |
| ATOM | 2382 | CB | THR | 447 | -20.137 | -40.952 | 20.178 | 1.00 0.00 |
| ATOM | 2383 | HB | THR | 447 | -19.851 | -40.686 | 21.182 | 1.00 0.00 |
| ATOM | 2384 | OG1 | THR | 447 | -20.310 | -42.361 | 20.091 | 1.00 0.00 |
| ATOM | 2385 | HG1 | THR | 447 | -21.014 | -42.612 | 20.694 | 1.00 0.00 |
| ATOM | 2386 | CG2 | THR | 447 | -21.452 | -40.253 | 19.827 | 1.00 0.00 |
| ATOM | 2387 | HG21 | THR | 447 | -21.280 | -39.538 | 19.036 | 1.00 0.00 |
| ATOM | 2388 | HG22 | THR | 447 | -21.832 | -39.741 | 20.699 | 1.00 0.00 |
| ATOM | 2389 | HG23 | THR | 447 | -22.173 | -40.987 | 19.498 | 1.00 0.00 |
| ATOM | 2390 | C | THR | 447 | -19.481 | -40.762 | 17.753 | 1.00 0.00 |
| ATOM | 2391 | O | THR | 447 | -20.509 | -41.357 | 17.499 | 1.00 0.00 |
| ATOM | 2392 | N | LYS | 448 | -18.706 | -40.312 | 16.803 | 1.00 0.00 |
| ATOM | 2393 | HN | LYS | 448 | -17.881 | -39.834 | 17.030 | 1.00 0.00 |
| ATOM | 2394 | CA | LYS | 448 | -19.077 | -40.525 | 15.373 | 1.00 0.00 |
| ATOM | 2395 | HA | LYS | 448 | -19.662 | -41.422 | 15.265 | 1.00 0.00 |
| ATOM | 2396 | CB | LYS | 448 | -19.918 | -39.304 | 15.004 | 1.00 0.00 |
| ATOM | 2397 | HB1 | LYS | 448 | -20.855 | -39.336 | 15.539 | 1.00 0.00 |
| ATOM | 2398 | HB2 | LYS | 448 | -20.109 | -39.307 | 13.939 | 1.00 0.00 |
| ATOM | 2399 | CG | LYS | 448 | -19.158 | -38.032 | 15.385 | 1.00 0.00 |
| ATOM | 2400 | HG1 | LYS | 448 | -18.335 | -37.888 | 14.702 | 1.00 0.00 |
| ATOM | 2401 | HG2 | LYS | 448 | -18.779 | -38.129 | 16.392 | 1.00 0.00 |
| ATOM | 2402 | CD | LYS | 448 | -20.098 | -36.828 | 15.307 | 1.00 0.00 |
| ATOM | 2403 | HD1 | LYS | 448 | -20.917 | -36.964 | 15.996 | 1.00 0.00 |
| ATOM | 2404 | HD2 | LYS | 448 | -20.483 | -36.736 | 14.301 | 1.00 0.00 |
| ATOM | 2405 | CE | LYS | 448 | -19.328 | -35.558 | 15.678 | 1.00 0.00 |
| ATOM | 2406 | HE1 | LYS | 448 | -18.864 | -35.668 | 16.644 | 1.00 0.00 |
| ATOM | 2407 | HE2 | LYS | 448 | -19.991 | -34.701 | 15.669 | 1.00 0.00 |
| ATOM | 2408 | NZ | LYS | 448 | -18.286 | -35.422 | 14.624 | 1.00 0.00 |
| ATOM | 2409 | HZ1 | LYS | 448 | -18.706 | -35.616 | 13.693 | 1.00 0.00 |
| ATOM | 2410 | HZ2 | LYS | 448 | -17.518 | -36.102 | 14.807 | 1.00 0.00 |
| ATOM | 2411 | HZ3 | LYS | 448 | -17.905 | -34.457 | 14.635 | 1.00 0.00 |
| ATOM | 2412 | C | LYS | 448 | -17.819 | -40.594 | 14.498 | 1.00 0.00 |
| ATOM | 2413 | O | LYS | 448 | -17.080 | -39.636 | 14.379 | 1.00 0.00 |
| ATOM | 2414 | N | GLU | 449 | -17.572 | -41.720 | 13.883 | 1.00 0.00 |
| ATOM | 2415 | HN | GLU | 449 | -18.181 | -42.480 | 13.991 | 1.00 0.00 |
| ATOM | 2416 | CA | GLU | 449 | -16.363 | -41.850 | 13.015 | 1.00 0.00 |
| ATOM | 2417 | HA | GLU | 449 | -16.310 | -42.838 | 12.589 | 1.00 0.00 |
| ATOM | 2418 | CB | GLU | 449 | -16.558 | -40.814 | 11.908 | 1.00 0.00 |
| ATOM | 2419 | HB1 | GLU | 449 | -16.511 | -39.822 | 12.330 | 1.00 0.00 |
| ATOM | 2420 | HB2 | GLU | 449 | -17.523 | -40.962 | 11.442 | 1.00 0.00 |
| ATOM | 2421 | CG | GLU | 449 | -15.455 | -40.970 | 10.858 | 1.00 0.00 |
| ATOM | 2422 | HG1 | GLU | 449 | -15.800 | -41.618 | 10.066 | 1.00 0.00 |
| ATOM | 2423 | HG2 | GLU | 449 | -14.577 | -41.400 | 11.320 | 1.00 0.00 |
| ATOM | 2424 | CD | GLU | 449 | -15.108 | -39.598 | 10.276 | 1.00 0.00 |
| ATOM | 2425 | OE1 | GLU | 449 | -14.107 | -39.037 | 10.690 | 1.00 0.00 |
| ATOM | 2426 | OE2 | GLU | 449 | -15.848 | -39.132 | 9.426 | 1.00 0.00 |
| ATOM | 2427 | C | GLU | 449 | -15.094 | -41.546 | 13.820 | 1.00 0.00 |
| ATOM | 2428 | O | GLU | 449 | -14.857 | -40.425 | 14.223 | 1.00 0.00 |
| ATOM | 2429 | N | GLY | 450 | -14.278 | -42.538 | 14.055 | 1.00 0.00 |
| ATOM | 2430 | HN | GLY | 450 | -14.487 | -43.435 | 13.720 | 1.00 0.00 |
| ATOM | 2431 | CA | GLY | 450 | -13.027 | -42.306 | 14.833 | 1.00 0.00 |
| ATOM | 2432 | HA1 | GLY | 450 | -13.137 | -41.418 | 15.435 | 1.00 0.00 |

Figure 9-43

| | | | | | | | | |
|---|---|---|---|---|---|---|---|---|
| ATOM | 2433 | HA2 | GLY | 450 | -12.198 | -42.179 | 14.150 | 1.00 | 0.00 |
| ATOM | 2434 | C | GLY | 450 | -12.761 | -43.506 | 15.744 | 1.00 | 0.00 |
| ATOM | 2435 | OT1 | GLY | 450 | -11.704 | -43.540 | 16.352 | 1.00 | 0.00 |
| ATOM | 2436 | OT2 | GLY | 450 | -13.619 | -44.371 | 15.818 | 1.00 | 0.00 |
| ATOM | 2437 | O3G | ANP | 451 | -13.242 | -21.284 | -18.267 | 1.00 | 14.20 |
| ATOM | 2438 | HO3 | ANP | 451 | -13.780 | -21.257 | -19.060 | 0.00 | 0.00 |
| ATOM | 2439 | PG | ANP | 451 | -11.809 | -21.889 | -18.680 | 1.00 | 12.47 |
| ATOM | 2440 | O1G | ANP | 451 | -11.656 | -21.610 | -20.125 | 1.00 | 14.96 |
| ATOM | 2441 | O2G | ANP | 451 | -11.838 | -23.309 | -18.266 | 1.00 | 10.96 |
| ATOM | 2442 | N1B | ANP | 451 | -10.691 | -21.081 | -17.833 | 0.00 | 0.00 |
| ATOM | 2443 | HN1 | ANP | 451 | -11.140 | -20.544 | -17.119 | 0.00 | 0.00 |
| ATOM | 2444 | PB | ANP | 451 | -9.666 | -22.129 | -17.150 | 1.00 | 11.61 |
| ATOM | 2445 | O1B | ANP | 451 | -9.521 | -23.334 | -17.998 | 1.00 | 14.01 |
| ATOM | 2446 | O2B | ANP | 451 | -8.423 | -21.437 | -16.743 | 1.00 | 15.08 |
| ATOM | 2447 | O3A | ANP | 451 | -10.353 | -22.630 | -15.787 | 1.00 | 13.84 |
| ATOM | 2448 | PA | ANP | 451 | -9.971 | -23.830 | -14.790 | 1.00 | 14.01 |
| ATOM | 2449 | O1A | ANP | 451 | -9.031 | -24.733 | -15.489 | 1.00 | 15.21 |
| ATOM | 2450 | O2A | ANP | 451 | -9.598 | -23.242 | -13.484 | 1.00 | 13.60 |
| ATOM | 2451 | O5' | ANP | 451 | -11.376 | -24.597 | -14.617 | 1.00 | 16.63 |
| ATOM | 2452 | C5' | ANP | 451 | -12.269 | -24.229 | -13.565 | 1.00 | 15.02 |
| ATOM | 2453 | H5' | ANP | 451 | -12.378 | -25.064 | -12.879 | 0.00 | 0.00 |
| ATOM | 2454 | H5'' | ANP | 451 | -11.849 | -23.382 | -13.029 | 0.00 | 0.00 |
| ATOM | 2455 | C4' | ANP | 451 | -13.643 | -23.844 | -14.100 | 1.00 | 16.64 |
| ATOM | 2456 | H4' | ANP | 451 | -13.983 | -24.611 | -14.799 | 0.00 | 0.00 |
| ATOM | 2457 | O4' | ANP | 451 | -14.594 | -23.737 | -13.018 | 1.00 | 16.01 |
| ATOM | 2458 | C1' | ANP | 451 | -15.104 | -22.383 | -12.935 | 1.00 | 17.25 |
| ATOM | 2459 | H1' | ANP | 451 | -16.191 | -22.405 | -12.997 | 0.00 | 0.00 |
| ATOM | 2460 | N9 | ANP | 451 | -14.706 | -21.757 | -11.658 | 1.00 | 16.89 |
| ATOM | 2461 | C4 | ANP | 451 | -15.424 | -20.825 | -10.937 | 1.00 | 14.99 |
| ATOM | 2462 | N3 | ANP | 451 | -16.614 | -20.303 | -11.272 | 1.00 | 14.98 |
| ATOM | 2463 | C2 | ANP | 451 | -17.035 | -19.427 | -10.358 | 1.00 | 15.41 |
| ATOM | 2464 | H2 | ANP | 451 | -17.996 | -18.949 | -10.549 | 0.00 | 0.00 |
| ATOM | 2465 | N1 | ANP | 451 | -16.402 | -19.070 | -9.229 | 1.00 | 15.41 |
| ATOM | 2466 | C6 | ANP | 451 | -15.207 | -19.615 | -8.920 | 1.00 | 15.56 |
| ATOM | 2467 | N6 | ANP | 451 | -14.594 | -19.253 | -7.794 | 1.00 | 11.16 |
| ATOM | 2468 | H61 | ANP | 451 | -13.699 | -19.657 | -7.554 | 1.00 | 0.00 |
| ATOM | 2469 | H62 | ANP | 451 | -15.027 | -18.581 | -7.176 | 1.00 | 0.00 |
| ATOM | 2470 | C5 | ANP | 451 | -14.675 | -20.544 | -9.815 | 1.00 | 15.66 |
| ATOM | 2471 | N7 | ANP | 451 | -13.487 | -21.290 | -9.819 | 1.00 | 17.45 |
| ATOM | 2472 | C8 | ANP | 451 | -13.599 | -21.952 | -10.916 | 1.00 | 15.92 |
| ATOM | 2473 | H8 | ANP | 451 | -12.822 | -22.645 | -11.238 | 0.00 | 0.00 |
| ATOM | 2474 | C2' | ANP | 451 | -14.550 | -21.599 | -14.111 | 1.00 | 18.24 |
| ATOM | 2475 | H2' | ANP | 451 | -14.017 | -20.720 | -13.743 | 0.00 | 0.00 |
| ATOM | 2476 | O2' | ANP | 451 | -15.600 | -21.189 | -14.993 | 1.00 | 16.32 |
| ATOM | 2477 | H2'' | ANP | 451 | -15.588 | -21.783 | -15.747 | 0.00 | 0.00 |
| ATOM | 2478 | C3' | ANP | 451 | -13.587 | -22.501 | -14.816 | 1.00 | 18.07 |
| ATOM | 2479 | H3' | ANP | 451 | -12.578 | -22.084 | -14.733 | 0.00 | 0.00 |
| ATOM | 2480 | O3' | ANP | 451 | -13.939 | -22.646 | -16.198 | 1.00 | 21.99 |
| ATOM | 2481 | H3'' | ANP | 451 | -13.701 | -23.539 | -16.460 | 0.00 | 0.00 |

END

SEQUENCE LISTING

```
<160> NUMBER OF SEQ ID NOS: 20

<210> SEQ ID NO 1
<211> LENGTH: 1353
<212> TYPE: DNA
<213> ORGANISM: Escherichia coli
<220> FEATURE:
<221> NAME/KEY: CDS
<222> LOCATION: (1)..(1353)

<400> SEQUENCE: 1 atg agg cga ttg cgc ttc tcg cca cga agt tca ttt gcc cgt acg tta      48
Met Arg Arg Leu Arg Phe Ser Pro Arg Ser Ser Phe Ala Arg Thr Leu
  1               5                  10                  15 ttg ctc atc gtc acc ttg ctg ttc gcc agc ctg gtg acg act tat ctg      96
Leu Leu Ile Val Thr Leu Leu Phe Ala Ser Leu Val Thr Thr Tyr Leu
             20                  25                  30 gtg gtg ctg aac ttc gcg att ttg ccg agc ctc cag cag ttt aat aaa     144
```

```
                Val Val Leu Asn Phe Ala Ile Leu Pro Ser Leu Gln Gln Phe Asn Lys
                             35                  40                  45 gtc ctc gcg tac gaa gtg cgt atg ttg atg acc gac aaa ctg caa ctg              192
Val Leu Ala Tyr Glu Val Arg Met Leu Met Thr Asp Lys Leu Gln Leu
 50                  55                  60 gag gac ggc acg cag ttg gtt gtg cct ccc gct ttc cgt cgg gag atc              240
Glu Asp Gly Thr Gln Leu Val Val Pro Pro Ala Phe Arg Arg Glu Ile
 65                  70                  75                  80 tac cgt gag ctg ggg atc tct ctc tac tcc aac gag gct gcc gaa gag              288
Tyr Arg Glu Leu Gly Ile Ser Leu Tyr Ser Asn Glu Ala Ala Glu Glu
                 85                  90                  95 gca ggt ctg cgt tgg gcg caa cac tat gaa ttc tta agc cat cag atg              336
Ala Gly Leu Arg Trp Ala Gln His Tyr Glu Phe Leu Ser His Gln Met
                100                 105                 110 gcg cag caa ctg ggc ggc ccg acg gaa gtg cgc gtt gag gtc aac aaa              384
Ala Gln Gln Leu Gly Gly Pro Thr Glu Val Arg Val Glu Val Asn Lys
                115                 120                 125 agt tcg cct gtc gtc tgg ctg aaa acc tgg ctg tcg ccc aat atc tgg              432
Ser Ser Pro Val Val Trp Leu Lys Thr Trp Leu Ser Pro Asn Ile Trp
        130                 135                 140 gta cgc gtg ccg ctg acc gaa att cat cag ggc gat ttc tct ccg ctg              480
Val Arg Val Pro Leu Thr Glu Ile His Gln Gly Asp Phe Ser Pro Leu
145                 150                 155                 160 ttc cgc tat acg ctg gcg att atg cta ttg gcg ata ggc ggg gcg tgg              528
Phe Arg Tyr Thr Leu Ala Ile Met Leu Leu Ala Ile Gly Gly Ala Trp
                165                 170                 175 ctg ttt att cgt atc cag aac cga ccg ttg gtc gat ctc gaa cac gca              576
Leu Phe Ile Arg Ile Gln Asn Arg Pro Leu Val Asp Leu Glu His Ala
                180                 185                 190 gcc ttg cag gtt ggt aaa ggg att att ccg ccg ctg cgt gag tat              624
Ala Leu Gln Val Gly Lys Gly Ile Ile Pro Pro Leu Arg Glu Tyr
                195                 200                 205 ggc gct tcg gag gtg cgt tcc gtt acc cgt gcc ttt aac cat atg gcg              672
Gly Ala Ser Glu Val Arg Ser Val Thr Arg Ala Phe Asn His Met Ala
210                 215                 220 gct ggt gtt aag caa ctg gcg gat gac cgc acg ctg ctg atg gcg ggg              720
Ala Gly Val Lys Gln Leu Ala Asp Asp Arg Thr Leu Leu Met Ala Gly
225                 230                 235                 240 gta agt cac gac ttg cgc acg ccg ctg acg cgt att cgc ctg gcg act              768
Val Ser His Asp Leu Arg Thr Pro Leu Thr Arg Ile Arg Leu Ala Thr
                245                 250                 255 gag atg atg agc gag cag gat ggc tat ctg gca gaa tcg atc aat aaa              816
Glu Met Met Ser Glu Gln Asp Gly Tyr Leu Ala Glu Ser Ile Asn Lys
                260                 265                 270 gat atc gaa gag tgc aac gcc atc att gag cag ttt atc gac tac ctg              864
Asp Ile Glu Glu Cys Asn Ala Ile Ile Glu Gln Phe Ile Asp Tyr Leu
                275                 280                 285 cgc acc ggg cag gag atg ccg atg gaa atg gcg gat ctt aat gca gta              912
Arg Thr Gly Gln Glu Met Pro Met Glu Met Ala Asp Leu Asn Ala Val
290                 295                 300 ctc ggt gag gtg att gct gcc gaa agt ggc tat gag cgg gaa att gaa              960
Leu Gly Glu Val Ile Ala Ala Glu Ser Gly Tyr Glu Arg Glu Ile Glu
305                 310                 315                 320 acc gcg ctt tac ccc ggc agc att gaa gtg aaa atg cac ccg ctg tcg             1008
Thr Ala Leu Tyr Pro Gly Ser Ile Glu Val Lys Met His Pro Leu Ser
                325                 330                 335 atc aaa cgc gcg gtg gcg aat atg gtg gtc aac gcc gcc cgt tat ggc             1056
Ile Lys Arg Ala Val Ala Asn Met Val Val Asn Ala Ala Arg Tyr Gly
                340                 345                 350
```

```
aat ggc tgg atc aaa gtc agc agc gga acg gag ccg aat cgc gcc tgg      1104
Asn Gly Trp Ile Lys Val Ser Ser Gly Thr Glu Pro Asn Arg Ala Trp
        355                 360                 365 ttc cag gtg gaa gat gac ggt ccg gga att gcg ccg gaa caa cgt aag      1152
Phe Gln Val Glu Asp Asp Gly Pro Gly Ile Ala Pro Glu Gln Arg Lys
370                 375                 380 cac ctg ttc cag ccg ttt gtc cgc ggc gac agt gcg cgc acc att agc      1200
His Leu Phe Gln Pro Phe Val Arg Gly Asp Ser Ala Arg Thr Ile Ser
385                 390                 395                 400 ggc acg gga tta ggg ctg gca att gtg cag cgt atc gtg gat aac cat      1248
Gly Thr Gly Leu Gly Leu Ala Ile Val Gln Arg Ile Val Asp Asn His
                405                 410                 415 aac ggg atg ctg gag ctt ggc acc agc gag cgg ggc ggg ctt tcc att      1296
Asn Gly Met Leu Glu Leu Gly Thr Ser Glu Arg Gly Gly Leu Ser Ile
            420                 425                 430 cgc gcc tgg ctg cca gtg ccg gta acg cgg gcg cag ggc acg aca aaa      1344
Arg Ala Trp Leu Pro Val Pro Val Thr Arg Ala Gln Gly Thr Thr Lys
        435                 440                 445 gaa ggg taa                                                          1353
Glu Gly
    450

<210> SEQ ID NO 2
<211> LENGTH: 450
<212> TYPE: PRT
<213> ORGANISM: Escherichia coli

<400> SEQUENCE: 2

Met Arg Arg Leu Arg Phe Ser Pro Arg Ser Phe Ala Arg Thr Leu
 1               5                  10                  15

Leu Leu Ile Val Thr Leu Leu Phe Ala Ser Leu Val Thr Thr Tyr Leu
                20                  25                  30

Val Val Leu Asn Phe Ala Ile Leu Pro Ser Leu Gln Gln Phe Asn Lys
            35                  40                  45

Val Leu Ala Tyr Glu Val Arg Met Leu Met Thr Asp Lys Leu Gln Leu
        50                  55                  60

Glu Asp Gly Thr Gln Leu Val Val Pro Pro Ala Phe Arg Arg Glu Ile
65                  70                  75                  80

Tyr Arg Glu Leu Gly Ile Ser Leu Tyr Ser Asn Glu Ala Ala Glu Glu
                85                  90                  95

Ala Gly Leu Arg Trp Ala Gln His Tyr Glu Phe Leu Ser His Gln Met
            100                 105                 110

Ala Gln Gln Leu Gly Gly Pro Thr Glu Val Arg Val Glu Val Asn Lys
        115                 120                 125

Ser Ser Pro Val Val Trp Leu Lys Thr Trp Leu Ser Pro Asn Ile Trp
    130                 135                 140

Val Arg Val Pro Leu Thr Glu Ile His Gln Gly Asp Phe Ser Pro Leu
145                 150                 155                 160

Phe Arg Tyr Thr Leu Ala Ile Met Leu Leu Ala Ile Gly Gly Ala Trp
                165                 170                 175

Leu Phe Ile Arg Ile Gln Asn Arg Pro Leu Val Asp Leu Glu His Ala
            180                 185                 190

Ala Leu Gln Val Gly Lys Gly Ile Ile Pro Pro Leu Arg Glu Tyr
        195                 200                 205

Gly Ala Ser Glu Val Arg Ser Val Thr Arg Ala Phe Asn His Met Ala
    210                 215                 220

Ala Gly Val Lys Gln Leu Ala Asp Asp Arg Thr Leu Leu Met Ala Gly
```

```
                    225                 230                 235                 240
            Val Ser His Asp Leu Arg Thr Pro Leu Thr Arg Ile Arg Leu Ala Thr
                            245                 250                 255
            Glu Met Met Ser Glu Gln Asp Gly Tyr Leu Ala Glu Ser Ile Asn Lys
                            260                 265                 270
            Asp Ile Glu Glu Cys Asn Ala Ile Ile Glu Gln Phe Ile Asp Tyr Leu
                        275                 280                 285
            Arg Thr Gly Gln Glu Met Pro Met Glu Met Ala Asp Leu Asn Ala Val
                    290                 295                 300
            Leu Gly Glu Val Ile Ala Ala Glu Ser Gly Tyr Glu Arg Glu Ile Glu
            305                 310                 315                 320
            Thr Ala Leu Tyr Pro Gly Ser Ile Glu Val Lys Met His Pro Leu Ser
                            325                 330                 335
            Ile Lys Arg Ala Val Ala Asn Met Val Val Asn Ala Ala Arg Tyr Gly
                            340                 345                 350
            Asn Gly Trp Ile Lys Val Ser Ser Gly Thr Glu Pro Asn Arg Ala Trp
                        355                 360                 365
            Phe Gln Val Glu Asp Asp Gly Pro Gly Ile Ala Pro Glu Gln Arg Lys
                    370                 375                 380
            His Leu Phe Gln Pro Phe Val Arg Gly Asp Ser Ala Arg Thr Ile Ser
            385                 390                 395                 400
            Gly Thr Gly Leu Gly Leu Ala Ile Val Gln Arg Ile Val Asp Asn His
                            405                 410                 415
            Asn Gly Met Leu Glu Leu Gly Thr Ser Glu Arg Gly Leu Ser Ile
                            420                 425                 430
            Arg Ala Trp Leu Pro Val Pro Val Thr Arg Ala Gln Gly Thr Thr Lys
                        435                 440                 445
            Glu Gly
                450

<210> SEQ ID NO 3
<211> LENGTH: 813
<212> TYPE: DNA
<213> ORGANISM: Escherichia coli
<220> FEATURE:
<221> NAME/KEY: CDS
<222> LOCATION: (1)..(813)

<400> SEQUENCE: 3 cgt atc cag aac cga ccg ttg gtc gat ctc gaa cac gca gcc ttg cag      48
Arg Ile Gln Asn Arg Pro Leu Val Asp Leu Glu His Ala Ala Leu Gln
  1               5                  10                  15 gtt ggt aaa ggg att att ccg ccg ccg ctg cgt gag tat ggc gct tcg      96
Val Gly Lys Gly Ile Ile Pro Pro Pro Leu Arg Glu Tyr Gly Ala Ser
             20                  25                  30 gag gtg cgt tcc gtt acc cgt gcc ttt aac cat atg gcg gct ggt gtt     144
Glu Val Arg Ser Val Thr Arg Ala Phe Asn His Met Ala Ala Gly Val
         35                  40                  45 aag caa ctg gcg gat gac cgc acg ctg ctg atg gcg ggg gta agt cac     192
Lys Gln Leu Ala Asp Asp Arg Thr Leu Leu Met Ala Gly Val Ser His
     50                  55                  60 gac ttg cgc acg ccg ctg acg cgt att cgc ctg gcg act gag atg atg     240
Asp Leu Arg Thr Pro Leu Thr Arg Ile Arg Leu Ala Thr Glu Met Met
 65                  70                  75                  80 agc gag cag gat ggc tat ctg gca gaa tcg atc aat aaa gat atc gaa     288
Ser Glu Gln Asp Gly Tyr Leu Ala Glu Ser Ile Asn Lys Asp Ile Glu
                 85                  90                  95
```

```
gag tgc aac gcc atc att gag cag ttt atc gac tac ctg cgc acc ggg    336
Glu Cys Asn Ala Ile Ile Glu Gln Phe Ile Asp Tyr Leu Arg Thr Gly
            100                 105                 110 cag gag atg ccg atg gaa atg gcg gat ctt aat gca gta ctc ggt gag    384
Gln Glu Met Pro Met Glu Met Ala Asp Leu Asn Ala Val Leu Gly Glu
        115                 120                 125 gtg att gct gcc gaa agt ggc tat gag cgg gaa att gaa acc gcg ctt    432
Val Ile Ala Ala Glu Ser Gly Tyr Glu Arg Glu Ile Glu Thr Ala Leu
130                 135                 140 tac ccc ggc agc att gaa gtg aaa atg cac ccg ctg tcg atc aaa cgc    480
Tyr Pro Gly Ser Ile Glu Val Lys Met His Pro Leu Ser Ile Lys Arg
145                 150                 155                 160 gcg gtg gcg aat atg gtg gtc aac gcc gcc cgt tat ggc aat ggc tgg    528
Ala Val Ala Asn Met Val Val Asn Ala Ala Arg Tyr Gly Asn Gly Trp
                165                 170                 175 atc aaa gtc agc agc gga acg gag ccg aat cgc gcc tgg ttc cag gtg    576
Ile Lys Val Ser Ser Gly Thr Glu Pro Asn Arg Ala Trp Phe Gln Val
            180                 185                 190 gaa gat gac ggt ccg gga att gcg ccg gaa caa cgt aag cac ctg ttc    624
Glu Asp Asp Gly Pro Gly Ile Ala Pro Glu Gln Arg Lys His Leu Phe
        195                 200                 205 cag ccg ttt gtc cgc ggc gac agt gcg cgc acc att agc ggc acg gga    672
Gln Pro Phe Val Arg Gly Asp Ser Ala Arg Thr Ile Ser Gly Thr Gly
    210                 215                 220 tta ggg ctg gca att gtg cag cgt atc gtg gat aac cat aac ggg atg    720
Leu Gly Leu Ala Ile Val Gln Arg Ile Val Asp Asn His Asn Gly Met
225                 230                 235                 240 ctg gag ctt ggc acc agc gag cgg ggc ggg ctt tcc att cgc gcc tgg    768
Leu Glu Leu Gly Thr Ser Glu Arg Gly Gly Leu Ser Ile Arg Ala Trp
                245                 250                 255 ctg cca gtg ccg gta acg cgg gcg cag ggc acg aca aaa gaa ggg        813
Leu Pro Val Pro Val Thr Arg Ala Gln Gly Thr Thr Lys Glu Gly
            260                 265                 270

<210> SEQ ID NO 4
<211> LENGTH: 271
<212> TYPE: PRT
<213> ORGANISM: Escherichia coli

<400> SEQUENCE: 4

Arg Ile Gln Asn Arg Pro Leu Val Asp Leu Glu His Ala Ala Leu Gln
 1               5                  10                  15

Val Gly Lys Gly Ile Ile Pro Pro Leu Arg Glu Tyr Gly Ala Ser
            20                  25                  30

Glu Val Arg Ser Val Thr Arg Ala Phe Asn His Met Ala Ala Gly Val
         35                  40                  45

Lys Gln Leu Ala Asp Asp Arg Thr Leu Leu Met Ala Gly Val Ser His
     50                  55                  60

Asp Leu Arg Thr Pro Leu Thr Arg Ile Arg Leu Ala Thr Glu Met Met
 65                  70                  75                  80

Ser Glu Gln Asp Gly Tyr Leu Ala Glu Ser Ile Asn Lys Asp Ile Glu
                 85                  90                  95

Glu Cys Asn Ala Ile Ile Glu Gln Phe Ile Asp Tyr Leu Arg Thr Gly
            100                 105                 110

Gln Glu Met Pro Met Glu Met Ala Asp Leu Asn Ala Val Leu Gly Glu
        115                 120                 125

Val Ile Ala Ala Glu Ser Gly Tyr Glu Arg Glu Ile Glu Thr Ala Leu
130                 135                 140
```

```
Tyr Pro Gly Ser Ile Glu Val Lys Met His Pro Leu Ser Ile Lys Arg
145                 150                 155                 160

Ala Val Ala Asn Met Val Val Asn Ala Ala Arg Tyr Gly Asn Gly Trp
            165                 170                 175

Ile Lys Val Ser Ser Gly Thr Glu Pro Asn Arg Ala Trp Phe Gln Val
            180                 185                 190

Glu Asp Asp Gly Pro Gly Ile Ala Pro Glu Gln Arg Lys His Leu Phe
            195                 200                 205

Gln Pro Phe Val Arg Gly Asp Ser Ala Arg Thr Ile Ser Gly Thr Gly
210                 215                 220

Leu Gly Leu Ala Ile Val Gln Arg Ile Val Asp Asn His Asn Gly Met
225                 230                 235                 240

Leu Glu Leu Gly Thr Ser Glu Arg Gly Leu Ser Ile Arg Ala Trp
            245                 250                 255

Leu Pro Val Pro Val Thr Arg Ala Gln Gly Thr Thr Lys Glu Gly
            260                 265                 270

<210> SEQ ID NO 5
<211> LENGTH: 813
<212> TYPE: DNA
<213> ORGANISM: Escherichia coli
<220> FEATURE:
<221> NAME/KEY: CDS
<222> LOCATION: (1)..(813)

<400> SEQUENCE: 5 cgt atc cag aac cga ccg ttg gtc gat ctc gaa cac gca gcc ttg cag       48
Arg Ile Gln Asn Arg Pro Leu Val Asp Leu Glu His Ala Ala Leu Gln
1               5                   10                  15 gtt ggt aaa ggg att att ccg ccg ctg cgt gag tat ggc gct tcg           96
Val Gly Lys Gly Ile Ile Pro Pro Pro Leu Arg Glu Tyr Gly Ala Ser
            20                  25                  30 gag gtg cgt tcc gtt acc cgt gcc ttt aac cat atg gcg gct ggt gtt      144
Glu Val Arg Ser Val Thr Arg Ala Phe Asn His Met Ala Ala Gly Val
        35                  40                  45 aag caa ctg gcg gat gac cgc acg ctg ctg atg gcg ggg gta agt gtc      192
Lys Gln Leu Ala Asp Asp Arg Thr Leu Leu Met Ala Gly Val Ser Val
    50                  55                  60 gac ttg cgc acg ccg ctg acg cgt att cgc ctg gcg act gag atg atg      240
Asp Leu Arg Thr Pro Leu Thr Arg Ile Arg Leu Ala Thr Glu Met Met
65                  70                  75                  80 agc gag cag gat ggc tat ctg gca gaa tcg atc aat aaa gat atc gaa      288
Ser Glu Gln Asp Gly Tyr Leu Ala Glu Ser Ile Asn Lys Asp Ile Glu
                85                  90                  95 gag tgc aac gcc atc att gag cag ttt atc gac tac ctg cgc acc ggg      336
Glu Cys Asn Ala Ile Ile Glu Gln Phe Ile Asp Tyr Leu Arg Thr Gly
            100                 105                 110 cag gag atg ccg atg gaa atg gcg gat ctt aat gca gta ctc ggt gag      384
Gln Glu Met Pro Met Glu Met Ala Asp Leu Asn Ala Val Leu Gly Glu
        115                 120                 125 gtg att gct gcc gaa agt ggc tat gag cgg gaa att gaa acc gcg ctt      432
Val Ile Ala Ala Glu Ser Gly Tyr Glu Arg Glu Ile Glu Thr Ala Leu
    130                 135                 140 tac ccc ggc agc att gaa gtg aaa atg cac ccg ctg tcg atc aaa cgc      480
Tyr Pro Gly Ser Ile Glu Val Lys Met His Pro Leu Ser Ile Lys Arg
145                 150                 155                 160 gcg gtg gcg aat atg gtg gtc aac gcc gcc cgt tat ggc aat ggc tgg      528
Ala Val Ala Asn Met Val Val Asn Ala Ala Arg Tyr Gly Asn Gly Trp
                165                 170                 175
```

```
atc aaa gtc agc agc gga acg gag ccg aat cgc gcc tgg ttc cag gtg    576
Ile Lys Val Ser Ser Gly Thr Glu Pro Asn Arg Ala Trp Phe Gln Val
            180                 185                 190 gaa gat gac ggt ccg gga att gcg ccg gaa caa cgt aag cac ctg ttc    624
Glu Asp Asp Gly Pro Gly Ile Ala Pro Glu Gln Arg Lys His Leu Phe
        195                 200                 205 cag ccg ttt gtc cgc ggc gac agt gcg cgc acc att agc ggc acg gga    672
Gln Pro Phe Val Arg Gly Asp Ser Ala Arg Thr Ile Ser Gly Thr Gly
    210                 215                 220 tta ggg ctg gca att gtg cag cgt atc gtg gat aac cat aac ggg atg    720
Leu Gly Leu Ala Ile Val Gln Arg Ile Val Asp Asn His Asn Gly Met
225                 230                 235                 240 ctg gag ctt ggc acc agc gag cgg ggc ggg ctt tcc att cgc gcc tgg    768
Leu Glu Leu Gly Thr Ser Glu Arg Gly Gly Leu Ser Ile Arg Ala Trp
                245                 250                 255 ctg cca gtg ccg gta acg cgg gcg cag ggc acg aca aaa gaa ggg        813
Leu Pro Val Pro Val Thr Arg Ala Gln Gly Thr Thr Lys Glu Gly
            260                 265                 270

<210> SEQ ID NO 6
<211> LENGTH: 271
<212> TYPE: PRT
<213> ORGANISM: Escherichia coli

<400> SEQUENCE: 6

Arg Ile Gln Asn Arg Pro Leu Val Asp Leu Glu His Ala Ala Leu Gln
 1               5                  10                  15

Val Gly Lys Gly Ile Ile Pro Pro Leu Arg Glu Tyr Gly Ala Ser
            20                  25                  30

Glu Val Arg Ser Val Thr Arg Ala Phe Asn His Met Ala Ala Gly Val
        35                  40                  45

Lys Gln Leu Ala Asp Asp Arg Thr Leu Leu Met Ala Gly Val Ser Val
    50                  55                  60

Asp Leu Arg Thr Pro Leu Thr Arg Ile Arg Leu Ala Thr Glu Met Met
65                  70                  75                  80

Ser Glu Gln Asp Gly Tyr Leu Ala Glu Ser Ile Asn Lys Asp Ile Glu
                85                  90                  95

Glu Cys Asn Ala Ile Ile Glu Gln Phe Ile Asp Tyr Leu Arg Thr Gly
            100                 105                 110

Gln Glu Met Pro Met Glu Met Ala Asp Leu Asn Ala Val Leu Gly Glu
        115                 120                 125

Val Ile Ala Ala Glu Ser Gly Tyr Glu Arg Glu Ile Glu Thr Ala Leu
    130                 135                 140

Tyr Pro Gly Ser Ile Glu Val Lys Met His Pro Leu Ser Ile Lys Arg
145                 150                 155                 160

Ala Val Ala Asn Met Val Val Asn Ala Ala Arg Tyr Gly Asn Gly Trp
                165                 170                 175

Ile Lys Val Ser Ser Gly Thr Glu Pro Asn Arg Ala Trp Phe Gln Val
            180                 185                 190

Glu Asp Asp Gly Pro Gly Ile Ala Pro Glu Gln Arg Lys His Leu Phe
        195                 200                 205

Gln Pro Phe Val Arg Gly Asp Ser Ala Arg Thr Ile Ser Gly Thr Gly
    210                 215                 220

Leu Gly Leu Ala Ile Val Gln Arg Ile Val Asp Asn His Asn Gly Met
225                 230                 235                 240

Leu Glu Leu Gly Thr Ser Glu Arg Gly Gly Leu Ser Ile Arg Ala Trp
                245                 250                 255
```

```
Leu Pro Val Pro Val Thr Arg Ala Gln Gly Thr Thr Lys Glu Gly
            260                 265                 270

<210> SEQ ID NO 7
<211> LENGTH: 684
<212> TYPE: DNA
<213> ORGANISM: Escherichia coli
<220> FEATURE:
<221> NAME/KEY: CDS
<222> LOCATION: (1)..(684)

<400> SEQUENCE: 7 atg gcg gct ggt gtt aag caa ctg gcg gat gac cgc acg ctg ctg atg        48
Met Ala Ala Gly Val Lys Gln Leu Ala Asp Asp Arg Thr Leu Leu Met
 1               5                  10                  15 gcg ggg gta agt cac gac ttg cgc acg ccg ctg acg cgt att cgc ctg        96
Ala Gly Val Ser His Asp Leu Arg Thr Pro Leu Thr Arg Ile Arg Leu
             20                  25                  30 gcg act gag atg atg agc gag cag gat ggc tat ctg gca gaa tcg atc       144
Ala Thr Glu Met Met Ser Glu Gln Asp Gly Tyr Leu Ala Glu Ser Ile
         35                  40                  45 aat aaa gat atc gaa gag tgc aac gcc atc att gag cag ttt atc gac       192
Asn Lys Asp Ile Glu Glu Cys Asn Ala Ile Ile Glu Gln Phe Ile Asp
     50                  55                  60 tac ctg cgc acc ggg cag gag atg ccg atg gaa atg gcg gat ctt aat       240
Tyr Leu Arg Thr Gly Gln Glu Met Pro Met Glu Met Ala Asp Leu Asn
 65                  70                  75                  80 gca gta ctc ggt gag gtg att gct gcc gaa agt ggc tat gag cgg gaa       288
Ala Val Leu Gly Glu Val Ile Ala Ala Glu Ser Gly Tyr Glu Arg Glu
                 85                  90                  95 att gaa acc gcg ctt tac ccc ggc agc att gaa gtg aaa atg cac ccg       336
Ile Glu Thr Ala Leu Tyr Pro Gly Ser Ile Glu Val Lys Met His Pro
            100                 105                 110 ctg tcg atc aaa cgc gcg gtg gcg aat atg gtg gtc aac gcc gcc cgt       384
Leu Ser Ile Lys Arg Ala Val Ala Asn Met Val Val Asn Ala Ala Arg
        115                 120                 125 tat ggc aat ggc tgg atc aaa gtc agc agc gga acg gag ccg aat cgc       432
Tyr Gly Asn Gly Trp Ile Lys Val Ser Ser Gly Thr Glu Pro Asn Arg
    130                 135                 140 gcc tgg ttc cag gtg gaa gat gac ggt ccg gga att gcg ccg gaa caa       480
Ala Trp Phe Gln Val Glu Asp Asp Gly Pro Gly Ile Ala Pro Glu Gln
145                 150                 155                 160 cgt aag cac ctg ttc cag ccg ttt gtc cgc ggc gac agt gcg cgc acc       528
Arg Lys His Leu Phe Gln Pro Phe Val Arg Gly Asp Ser Ala Arg Thr
                165                 170                 175 att agc ggc acg gga tta ggg ctg gca att gtg cag cgt atc gtg gat       576
Ile Ser Gly Thr Gly Leu Gly Leu Ala Ile Val Gln Arg Ile Val Asp
            180                 185                 190 aac cat aac ggg atg ctg gag ctt ggc acc agc gag cgg ggc ggg ctt       624
Asn His Asn Gly Met Leu Glu Leu Gly Thr Ser Glu Arg Gly Gly Leu
        195                 200                 205 tcc att cgc gcc tgg ctg cca gtg ccg gta acg cgg gcg cag ggc acg       672
Ser Ile Arg Ala Trp Leu Pro Val Pro Val Thr Arg Ala Gln Gly Thr
    210                 215                 220 aca aaa gaa ggg                                                       684
Thr Lys Glu Gly
225

<210> SEQ ID NO 8
<211> LENGTH: 228
```

-continued

```
<212> TYPE: PRT
<213> ORGANISM: Escherichia coli

<400> SEQUENCE: 8

Met Ala Ala Gly Val Lys Gln Leu Ala Asp Asp Arg Thr Leu Leu Met
 1               5                  10                  15

Ala Gly Val Ser His Asp Leu Arg Thr Pro Leu Thr Arg Ile Arg Leu
             20                  25                  30

Ala Thr Glu Met Met Ser Glu Gln Asp Gly Tyr Leu Ala Glu Ser Ile
         35                  40                  45

Asn Lys Asp Ile Glu Glu Cys Asn Ala Ile Ile Glu Gln Phe Ile Asp
     50                  55                  60

Tyr Leu Arg Thr Gly Gln Glu Met Pro Met Glu Met Ala Asp Leu Asn
 65                  70                  75                  80

Ala Val Leu Gly Glu Val Ile Ala Ala Glu Ser Gly Tyr Glu Arg Glu
                 85                  90                  95

Ile Glu Thr Ala Leu Tyr Pro Gly Ser Ile Glu Val Lys Met His Pro
            100                 105                 110

Leu Ser Ile Lys Arg Ala Val Ala Asn Met Val Val Asn Ala Ala Arg
        115                 120                 125

Tyr Gly Asn Gly Trp Ile Lys Val Ser Ser Gly Thr Glu Pro Asn Arg
    130                 135                 140

Ala Trp Phe Gln Val Glu Asp Asp Gly Pro Gly Ile Ala Pro Glu Gln
145                 150                 155                 160

Arg Lys His Leu Phe Gln Pro Phe Val Arg Gly Asp Ser Ala Arg Thr
                165                 170                 175

Ile Ser Gly Thr Gly Leu Gly Leu Ala Ile Val Gln Arg Ile Val Asp
            180                 185                 190

Asn His Asn Gly Met Leu Glu Leu Gly Thr Ser Glu Arg Gly Gly Leu
        195                 200                 205

Ser Ile Arg Ala Trp Leu Pro Val Pro Val Thr Arg Ala Gln Gly Thr
    210                 215                 220

Thr Lys Glu Gly
225

<210> SEQ ID NO 9
<211> LENGTH: 525
<212> TYPE: DNA
<213> ORGANISM: Escherichia coli
<220> FEATURE:
<221> NAME/KEY: CDS
<222> LOCATION: (1)..(525)

<400> SEQUENCE: 9 atg gcg gct ggt gtt aag caa ctg gcg gat gac cgc acg ctg ctg atg      48
Met Ala Ala Gly Val Lys Gln Leu Ala Asp Asp Arg Thr Leu Leu Met
 1               5                  10                  15 gcg ggg gta agt cac gac ttg cgc acg ccg ctg acg cgt att cgc ctg      96
Ala Gly Val Ser His Asp Leu Arg Thr Pro Leu Thr Arg Ile Arg Leu
             20                  25                  30 gcg act gag atg atg agc gag cag gat ggc tat ctg gca gaa tcg atc     144
Ala Thr Glu Met Met Ser Glu Gln Asp Gly Tyr Leu Ala Glu Ser Ile
         35                  40                  45 aat aaa gat atc gaa gag tgc aac gcc atc att gag cag ttt atc gac     192
Asn Lys Asp Ile Glu Glu Cys Asn Ala Ile Ile Glu Gln Phe Ile Asp
     50                  55                  60 tac ctg cgc acc ggg cag gag atg ccg atg gaa atg gcg gat ctt aat     240
Tyr Leu Arg Thr Gly Gln Glu Met Pro Met Glu Met Ala Asp Leu Asn
```

```
                65                  70                  75                  80
gca gta ctc ggt gag gtg att gct gcc gaa agt ggc tat gag cgg gaa        288
Ala Val Leu Gly Glu Val Ile Ala Ala Glu Ser Gly Tyr Glu Arg Glu
                85                  90                  95 att gaa acc gcg ctt tac ccc ggc agc att gaa gtg aaa atg cac ccg        336
Ile Glu Thr Ala Leu Tyr Pro Gly Ser Ile Glu Val Lys Met His Pro
            100                 105                 110 ctg tcg atc aaa cgc gcg gtg gcg aat atg gtg gtc aac gcc gcc cgt        384
Leu Ser Ile Lys Arg Ala Val Ala Asn Met Val Val Asn Ala Ala Arg
        115                 120                 125 tat ggc aat ggc tgg atc aaa gtc agc agc gga acg gag ccg aat cgc        432
Tyr Gly Asn Gly Trp Ile Lys Val Ser Ser Gly Thr Glu Pro Asn Arg
    130                 135                 140 gcc tgg ttc cag gtg gaa gat gac ggt ccg gga att gcg ccg gaa caa        480
Ala Trp Phe Gln Val Glu Asp Asp Gly Pro Gly Ile Ala Pro Glu Gln
145                 150                 155                 160 cgt aag cac ctg ttc cag ccg ttt gtc cgc ggc gac agt gcg cgc            525
Arg Lys His Leu Phe Gln Pro Phe Val Arg Gly Asp Ser Ala Arg
                165                 170                 175

<210> SEQ ID NO 10
<211> LENGTH: 175
<212> TYPE: PRT
<213> ORGANISM: Escherichia coli

<400> SEQUENCE: 10

Met Ala Ala Gly Val Lys Gln Leu Ala Asp Asp Arg Thr Leu Leu Met
1               5                   10                  15

Ala Gly Val Ser His Asp Leu Arg Thr Pro Leu Thr Arg Ile Arg Leu
            20                  25                  30

Ala Thr Glu Met Met Ser Glu Gln Asp Gly Tyr Leu Ala Glu Ser Ile
        35                  40                  45

Asn Lys Asp Ile Glu Glu Cys Asn Ala Ile Ile Glu Gln Phe Ile Asp
    50                  55                  60

Tyr Leu Arg Thr Gly Gln Glu Met Pro Met Glu Met Ala Asp Leu Asn
65                  70                  75                  80

Ala Val Leu Gly Glu Val Ile Ala Ala Glu Ser Gly Tyr Glu Arg Glu
                85                  90                  95

Ile Glu Thr Ala Leu Tyr Pro Gly Ser Ile Glu Val Lys Met His Pro
            100                 105                 110

Leu Ser Ile Lys Arg Ala Val Ala Asn Met Val Val Asn Ala Ala Arg
        115                 120                 125

Tyr Gly Asn Gly Trp Ile Lys Val Ser Ser Gly Thr Glu Pro Asn Arg
    130                 135                 140

Ala Trp Phe Gln Val Glu Asp Asp Gly Pro Gly Ile Ala Pro Glu Gln
145                 150                 155                 160

Arg Lys His Leu Phe Gln Pro Phe Val Arg Gly Asp Ser Ala Arg
                165                 170                 175

<210> SEQ ID NO 11
<211> LENGTH: 201
<212> TYPE: DNA
<213> ORGANISM: Escherichia coli
<220> FEATURE:
<221> NAME/KEY: CDS
<222> LOCATION: (1)..(201)

<400> SEQUENCE: 11 atg gcg gct ggt gtt aag caa ctg gcg gat gac cgc acg ctg ctg atg        48
```

```
Met Ala Ala Gly Val Lys Gln Leu Ala Asp Asp Arg Thr Leu Leu Met
  1               5                  10                  15 gcg ggg gta agt cac gac ttg cgc acg ccg ctg acg cgt att cgc ctg      96
Ala Gly Val Ser His Asp Leu Arg Thr Pro Leu Thr Arg Ile Arg Leu
                 20                  25                  30 gcg act gag atg atg agc gag cag gat ggc tat ctg gca gaa tcg atc     144
Ala Thr Glu Met Met Ser Glu Gln Asp Gly Tyr Leu Ala Glu Ser Ile
         35                  40                  45 aat aaa gat atc gaa gag tgc aac gcc atc att gag cag ttt atc gac     192
Asn Lys Asp Ile Glu Glu Cys Asn Ala Ile Ile Glu Gln Phe Ile Asp
     50                  55                  60 tac ctg cgc                                                          201
Tyr Leu Arg
 65
```

<210> SEQ ID NO 12
<211> LENGTH: 67
<212> TYPE: PRT
<213> ORGANISM: Escherichia coli

<400> SEQUENCE: 12

```
Met Ala Ala Gly Val Lys Gln Leu Ala Asp Asp Arg Thr Leu Leu Met
  1               5                  10                  15

Ala Gly Val Ser His Asp Leu Arg Thr Pro Leu Thr Arg Ile Arg Leu
                 20                  25                  30

Ala Thr Glu Met Met Ser Glu Gln Asp Gly Tyr Leu Ala Glu Ser Ile
         35                  40                  45

Asn Lys Asp Ile Glu Glu Cys Asn Ala Ile Ile Glu Gln Phe Ile Asp
     50                  55                  60

Tyr Leu Arg
 65
```

<210> SEQ ID NO 13
<211> LENGTH: 483
<212> TYPE: DNA
<213> ORGANISM: Escherichia coli
<220> FEATURE:
<221> NAME/KEY: CDS
<222> LOCATION: (1)..(483)

<400> SEQUENCE: 13

```
acc ggg cag gag atg ccg atg gaa atg gcg gat ctt aat gca gta ctc      48
Thr Gly Gln Glu Met Pro Met Glu Met Ala Asp Leu Asn Ala Val Leu
  1               5                  10                  15 ggt gag gtg att gct gcc gaa agt ggc tat gag cgg gaa att gaa acc      96
Gly Glu Val Ile Ala Ala Glu Ser Gly Tyr Glu Arg Glu Ile Glu Thr
                 20                  25                  30 gcg ctt tac ccc ggc agc att gaa gtg aaa atg cac ccg ctg tcg atc     144
Ala Leu Tyr Pro Gly Ser Ile Glu Val Lys Met His Pro Leu Ser Ile
         35                  40                  45 aaa cgc gcg gtg gcg aat atg gtg gtc aac gcc gcc cgt tat ggc aat     192
Lys Arg Ala Val Ala Asn Met Val Val Asn Ala Ala Arg Tyr Gly Asn
     50                  55                  60 ggc tgg atc aaa gtc agc agc gga acg gag ccg aat cgc gcc tgg ttc     240
Gly Trp Ile Lys Val Ser Ser Gly Thr Glu Pro Asn Arg Ala Trp Phe
 65                  70                  75                  80 cag gtg gaa gat gac ggt ccg gga att gcg ccg gaa caa cgt aag cac     288
Gln Val Glu Asp Asp Gly Pro Gly Ile Ala Pro Glu Gln Arg Lys His
                 85                  90                  95 ctg ttc cag ccg ttt gtc cgc ggc gac agt gcg cgc acc att agc ggc     336
Leu Phe Gln Pro Phe Val Arg Gly Asp Ser Ala Arg Thr Ile Ser Gly
```

```
                  100                 105                 110
acg  gga  tta  ggg  ctg  gca  att  gtg  cag  cgt  atc  gtg  gat  aac  cat  aac        384
Thr  Gly  Leu  Gly  Leu  Ala  Ile  Val  Gln  Arg  Ile  Val  Asp  Asn  His  Asn
               115                      120                      125 ggg  atg  ctg  gag  ctt  ggc  acc  agc  gag  cgg  ggc  ggg  ctt  tcc  att  cgc        432
Gly  Met  Leu  Glu  Leu  Gly  Thr  Ser  Glu  Arg  Gly  Gly  Leu  Ser  Ile  Arg
130                      135                      140 gcc  tgg  ctg  cca  gtg  ccg  gta  acg  cgg  gcg  cag  ggc  acg  aca  aaa  gaa        480
Ala  Trp  Leu  Pro  Val  Pro  Val  Thr  Arg  Ala  Gln  Gly  Thr  Thr  Lys  Glu
145                      150                      155                      160 ggg                                                                                    483
Gly
```

<210> SEQ ID NO 14
<211> LENGTH: 161
<212> TYPE: PRT
<213> ORGANISM: Escherichia coli

<400> SEQUENCE: 14

```
Thr  Gly  Gln  Glu  Met  Pro  Met  Glu  Met  Ala  Asp  Leu  Asn  Ala  Val  Leu
 1                  5                       10                      15

Gly  Glu  Val  Ile  Ala  Ala  Glu  Ser  Gly  Tyr  Glu  Arg  Glu  Ile  Glu  Thr
                20                      25                      30

Ala  Leu  Tyr  Pro  Gly  Ser  Ile  Glu  Val  Lys  Met  His  Pro  Leu  Ser  Ile
            35                      40                      45

Lys  Arg  Ala  Val  Ala  Asn  Met  Val  Val  Asn  Ala  Ala  Arg  Tyr  Gly  Asn
        50                      55                      60

Gly  Trp  Ile  Lys  Val  Ser  Ser  Gly  Thr  Glu  Pro  Asn  Arg  Ala  Trp  Phe
65                      70                      75                      80

Gln  Val  Glu  Asp  Asp  Gly  Pro  Gly  Ile  Ala  Pro  Glu  Gln  Arg  Lys  His
                85                      90                      95

Leu  Phe  Gln  Pro  Phe  Val  Arg  Gly  Asp  Ser  Ala  Arg  Thr  Ile  Ser  Gly
                100                     105                     110

Thr  Gly  Leu  Gly  Leu  Ala  Ile  Val  Gln  Arg  Ile  Val  Asp  Asn  His  Asn
            115                     120                     125

Gly  Met  Leu  Glu  Leu  Gly  Thr  Ser  Glu  Arg  Gly  Gly  Leu  Ser  Ile  Arg
130                     135                     140

Ala  Trp  Leu  Pro  Val  Pro  Val  Thr  Arg  Ala  Gln  Gly  Thr  Thr  Lys  Glu
145                     150                     155                     160

Gly
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Linker

<400> SEQUENCE: 15
tatgcaccat caccatcacc a                                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Linker
<220> FEATURE:
<223> OTHER INFORMATION: Reverse complementary strand of Seq ID No. 15.

-continued

```
<400> SEQUENCE: 16
tatggtgatg gtgatggtgc a                                              21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
agtgcgcgct gaattagcgg                                                20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
tacctgcgct aagggcagga g                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer 7109

<400> SEQUENCE: 19
cgcatatgac cgggcaggag                                                20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer 4163

<400> SEQUENCE: 20
tcggatcccg ttatttac                                                  18
```

METHODS OF IDENTIFYING INHIBITORS OF SENSOR HISTIDINE KINASES THROUGH RATIONAL DRUG DESIGN

GOVERNMENTAL SUPPORT

The research leading to the present invention was supported, at least in part, by a grant from the National Institutes of Health, Grant No. GM19043. Accordingly, the Government may have certain rights in the invention.

FIELD OF THE INVENTION

The present relates to N-terminal truncated transmembrane sensor histidine kinases that retain their ability to be autophosphorylated and/or their related histidine kinase activity. The N-terminal truncated transmembrane sensor histidine kinases are used for obtaining detailed three-dimensional structural data of the catalytic portion of the protein. In addition, methodology for related structure based rational drug design using the three-dimensional data are disclosed. Nucleotide and amino acid sequences of the N-terminal truncated transmembrane sensor histidine kinases are also provided.

BACKGROUND OF THE INVENTION

Bacterial are particularly susceptible to acute environmental changes which require rapid adaptation for survival. These environmental changes include nutritional deficiencies, exposure to a chemical toxin, and changes in osmolarity. In order to cope with such environmental stresses, bacteria have developed a sophisticated signaling system which enables the cell to respond swiftly to any given environmental alteration. The most common signaling system in bacteria is the histidyl-aspartyl (His-Asp) phosphorelay signal transduction system. Recently His-Asp phosphorelay systems also have been identified in eukaryotic cells [Egger et al., Genes to Cells, 2:167–184 (1997); Appleyby et al., cell, 86:845–848 (1996); Inouye, Cell, 85:13–14 (1996); Parkinson and Kofoid, Ann. Rev. Gen., 26:71–112 (1992); Stock et al., Microbiol. Rev., 53:450–490 (1989)].

There are two key participants in the His-Asp phosphorelay signal transduction system: (1) a sensor histidine kinase, which is generally a transmembrane protein; and (2) a response regulator which mediates changes in gene expression and/or cellular locomotion. The sensor histidine kinase responds to a particular environmental parameter by activating the response regulator. The activated response regulator then serves as a mediator of the signal to effect the cellular response to the environmental parameter. Thus, for each particular type of environmental challenge, a corresponding bacterial sensor histidine kinase exists that initiates the appropriate cellular response. Recently 23–28 open reading frames were identified in the *Escherichia coli* genome as encoding putative sensory kinases, whereas 32 open reading frames were identified as encoding putative response regulators [Mizuno, DNA Research, 4:161–168 (1997)].

The transmembrane sensor histidine kinase (TSHK) of the His-Asp phosphorelay signal transduction system contains a specific histidine that is autophosphorylated using ATP as the co-substrate. The TSHK can then transfer the phosphoryl group to a specific aspartyl residue of the response regulator. This phosphoryl transfer activates the response regulator and thereby mediates the signal. Unlike the analogous eukaryotic signal transduction pathways that employ either tyrosine (e.g., STATs) or threonine and/or serine (e.g., Smads) and in which the flow of the phosphoryl group is irreversible, the His-Asp pathway is based on a reversible phosphoryl transfer between histidine and aspartic acid residues.

Bacterial infections remain among the most common and deadly causes of human disease. For example, evidence of a virulent strain of *E. coli* in ground beef resulted in a recall of approximately $15 million worth of that food product. Such virulent strains can cause severe diarrhea, a condition which kills a million more people (3 million) each year worldwide than malaria. [D. Leff, BIOWORLD TODAY, 9:1,3 (1998)].

Although, there was initial optimism in the middle of this century that diseases caused by bacteria would be quickly eradicated, it has become evident that the so-called "miracle drugs" are not sufficient to accomplish this task. Indeed, antibiotic resistant pathogenic strains of bacteria have become common-place, and bacterial resistance to the new variations of these drugs appears to be outpacing the ability of scientists to develop effective chemical analogs of the existing drugs (See, Stuart B. Levy, The Challenge of Antibiotic Resistance, in Scientific American, 46–53 (March, 1998)). Therefore, new approaches to drug development are necessary to combat the ever-increasing number of antibiotic-resistance pathogens.

Classical penicillin-type antibiotics effect a single class of proteins known as autolysins. Thus, the development of new drugs which effect an alternative bacterial target protein would be desirable. Such a target protein ideally would be indispensable for bacterial survival. A protein involved in the His-Asp pathway such as a sensor histidine kinase would thus be a prime candidate for such drug development.

Therefore, there is a need to develop methods for identifying drugs that interfere with transmembrane sensor histidine kinase activity. Unfortunately, such identification has heretofore relied on serendipity and/or systematic screening of large numbers of natural and synthetic compounds. One superior method for drug screening relies on structure based rational drug design. In such cases, a three dimensional structure of the protein or peptide is determined and potential agonists and/or antagonists are designed with the aid of computer modeling [Bugg et al., Scientific American, December 92–98 (1993); West et al., TIPS, 16:67–74 (1995); Dunbrack et al., Folding & Design, 2:27–42 (1997)]. Unfortunately, with the notable exception of certain sensors involved in chemotaxis, bacterial sensors tend to be transmembrane proteins having multiple domains and have heretofor not been amenable to three-dimensional structural analysis. This is due to the intrinsic difficulty in preparing high quality TSHK crystals required for X-ray crystallographic analysis and the fact that the multidomain TSHK is too large for NMR three-dimensional analysis. Therefore, there is essentially no detailed structural information for TSHKs.

Therefore, there is a need for obtaining a form of the transmembrane sensor histidine kinase that is amenable for NMR analysis and/or X-ray crystallographic analysis. In addition, there is a need for determining the three-dimensional structure of such a TSHK form. Furthermore, there is a need for developing procedures of structure based rational drug design using such three-dimensional information. Finally, there is a need to employ such procedures to develop new anti-bacterial drugs.

The citation of any reference herein should not be construed as an admission that such reference is available as "Prior Art" to the instant application.

SUMMARY OF THE INVENTION

The present invention provides detailed three-dimensional structural information for transmembrane sensor histidine kinase (TSHK), proteins that play a crucial role in the signal transduction pathways of prokaryotes. The present invention further provides methods of using this structural information in the rational design of drugs for use in treatment and/or prevention of bacterial infections.

One aspect of the present invention includes a nucleic acid encoding an N-terminal truncated transmembrane sensor histidine kinase ($N_t$TSHK) that comprises an amino acid sequence that is substantially homologous to that of SEQ ID NO:12, and contains a histidine that can be phosphorylated by a protein histidine kinase. In a preferred embodiment of this type, the protein histidine kinase is a transmembrane sensor histidine kinase (TSHK). In another embodiment, the protein histidine kinase is a fragment of the TSHK having protein histidine kinase activity.

In a particular embodiment of this aspect of the invention the nucleic acid encodes a $N_t$TSHK that comprises the amino acid sequence of SEQ ID NO:12. In a related embodiment of this type the nucleic acid encodes a $N_t$TSHK that comprises the amino acid sequence of SEQ ID NO:12 with a conservative amino acid substitution. In a preferred embodiment of this type the nucleic acid encodes a $N_t$TSHK that consists of the amino acid sequence of SEQ ID NO:12 with a conservative amino acid substitution. In a related embodiment, the nucleic acid encodes a $N_t$TSHK that consists of an amino acid sequence of SEQ ID NO:12. In a preferred embodiment the nucleic acid encoding the $N_t$TSHK comprises the coding sequence of SEQ ID NO:11.

A related aspect of the present invention includes a nucleic acid encoding an N-terminal truncated transmembrane sensor histidine kinase that comprises an amino acid sequence that is substantially homologous to that of SEQ ID NO:10 and contains a histidine that can be phosphorylated by a protein histidine kinase. In a preferred embodiment of this type, the protein histidine kinase is a transmembrane sensor histidine kinase. In another embodiment, the protein histidine kinase is a fragment of a TSHK that has protein histidine kinase activity.

One embodiment of this aspect of the invention is a nucleic acid that encodes an $N_t$TSHK that comprises the amino acid sequence of SEQ ID NO:10. In a related embodiment of this type, the nucleic acid encodes an $N_t$TSHK that comprises the amino acid of SEQ ID NO:10 with a conservative amino acid substitution. In a preferred embodiment of this type the nucleic acid encodes a $N_t$TSHK that consists of the amino acid sequence of SEQ ID NO:10 with a conservative amino acid substitution. In a particular embodiment of this type, the nucleic acid encodes a $N_t$TSHK that consists of the amino acid sequence of SEQ ID NO:10. In a preferred embodiment, the nucleic acid encoding the $N_t$TSHK comprises the coding sequence of SEQ ID NO:9.

Another related aspect of the present invention includes a nucleic acid encoding an N-terminal truncated transmembrane sensor histidine kinase that comprises an amino acid sequence that is substantially homologous to that of SEQ ID NO:8, and contains a histidine that can phosphorylated by a protein histidine kinase. In a preferred embodiment of this type, the protein histidine kinase is a transmembrane sensor histidine kinase. In another embodiment, the protein histidine kinase is a fragment of a TSHK that has protein histidine kinase activity.

In another embodiment of this aspect of the invention is a nucleic acid that encodes a $N_t$TSHK that comprises the amino acid sequence of SEQ ID NO:8. In a related embodiment of this type, the nucleic acid encodes an $N_t$TSHK that comprises the amino acid sequence of SEQ ID NO:8 with a conservative amino acid substitution. In a preferred embodiment of this type the nucleic acid encodes a $N_t$TSHK that consists of the amino acid sequence of SEQ ID NO:8. In a related embodiment of this type the nucleic acid encodes a $N_t$TSHK that consists of the amino acid sequence of SEQ ID NO:8 with a conservative amino acid substitution. In a preferred embodiment, the nucleic acid encodes a $N_t$TSHK comprising the coding sequence of SEQ ID NO:7.

Yet another related aspect of the present invention includes a nucleic acid encoding a N-terminal truncated transmembrane sensor histidine kinase that comprises an amino acid sequence that is substantially homologous to that SEQ ID NO:4, and contains a histidine that can be phosphorylated by a protein histidine kinase. In a preferred embodiment of this type the protein histidine kinase is a transmembrane sensor histidine kinase. In another embodiment, the protein histidine kinase is a fragment of a TSHK that has protein histidine kinase activity.

In another embodiment of this aspect of the invention, the nucleic acid encodes a $N_t$TSHK that comprises the amino acid sequence of SEQ ID NO:4. In a related embodiment of this type the nucleic acid encodes a $N_t$TSHK that comprises the amino acid sequence of SEQ ID NO:4 with a conservative amino acid substitution. In a preferred embodiment of this type the nucleic acid encodes a $N_t$TSHK that consists of the amino acid sequence of SEQ ID NO:4. In a related embodiment the nucleic acid encodes a $N_t$TSHK that consists of the amino acid sequence of SEQ ID NO:4 with a conservative amino acid substitution. In a preferred embodiment, the nucleic acid encodes a $N_t$TSHK comprising the coding sequence of SEQ ID NO:3.

Another aspect of the invention provides a nucleic acid encoding an N-terminal truncated transmembrane sensor histidine kinase that comprises an amino acid sequence that is substantially homologous to SEQ ID NO:14, wherein the $N_t$TSHK is capable of phosphorylating the corresponding TSHK. In a preferred embodiment of this type the $N_t$TSHK lacks the autophosphorylatable histidine of the TSHK.

In a particular embodiment of this aspect of the invention, the nucleic acid encodes a $N_t$TSHK that comprises the amino acid sequence of SEQ ID NO:14. In a related embodiment of this type, the nucleic acid encodes a $N_t$TSHK which comprises the amino acid sequence of SEQ ID NO:14 with a conservative amino acid substitution. In a preferred embodiment of this type the nucleic acid encodes a $N_t$TSHK that consists of the amino acid sequence of SEQ ID NO:14. In a related embodiment, the nucleic acid encodes a $N_t$TSHK that consists of the amino acid sequence of SEQ ID NO:14 with a conservative amino acid substitution. In a preferred embodiment, the nucleic acid encoding the $N_t$TSHK comprises the coding sequence of SEQ ID NO:13.

A related aspect of the present invention includes a nucleic acid including an N-terminal truncated transmembrane sensor histidine kinase that comprises an amino acid sequence that is substantially homologous to that of SEQ ID NO:6, wherein the $N_t$TSHK is capable of phosphorylating the corresponding TSHK. In a preferred embodiment of this type the $N_t$TSHK lacks the autophosphorylatable histidine of the TSHK. In a particular embodiment of this aspect of the invention, the nucleic acid encodes a $N_t$TSHK that comprises the amino acid sequence of SEQ ID NO:6. In a related embodiment of this type, the nucleic acid encodes a $N_t$TSHK that comprises the amino acid sequence of SEQ ID NO:6 with a conservative amino acid substitution. In a preferred embodiment, the nucleic acid encodes a N$_t$TSHK which consists of the amino acid sequence of SEQ ID NO:6. In another such embodiment, the nucleic acid encodes a N$_t$TSHK which consists of the amino acid sequence of SEQ ID NO:6 with a conservative amino acid substitution. In a preferred embodiment, the nucleic acid encoding the N$_t$TSHK comprises the coding sequence of SEQ ID NO:5.

The present invention also provides a nucleic acid encoding a N$_t$TSHK that further comprises a heterologous nucleotide sequence. In one such embodiment, the nucleic acid encodes a N$_t$TSHK that comprises an amino acid sequence that is substantially homologous to that of SEQ ID NO:12 and a heterologous nucleotide sequence. In another such embodiment the nucleic acid encodes the amino acid sequence of SEQ ID NO:12 with a conservative substitution and a heterologous nucleotide sequence. In a preferred embodiment of this type the nucleic acid encodes the amino acid sequence of SEQ ID NO:12 with a heterologous nucleotide sequence. In a more preferred embodiment of this type, the nucleic acid comprises the nucleotide sequence of SEQ ID NO:11 with a heterologous nucleotide sequence.

The present invention also provides a nucleic acid that encodes a $N_t$TSHK that comprises an amino acid sequenced that is substantially homologous to that of SEQ ID NO:10, and a heterologous nucleotide sequence. In another such embodiment, the nucleic acid encodes a $N_t$TSHK having the amino acid sequence of SEQ ID NO:10 with a conservative substitution and a heterologous nucleotide sequence. In a preferred embodiment of this type, the nucleic acid encodes a $N_t$TSHK having the amino acid sequence of SEQ ID NO:10 and a heterologous nucleotide sequence. In a more preferred embodiment of this type, the nucleic acid comprises the nucleotide sequence of SEQ ID NO:9 with a heterologous nucleotide sequence.

The present invention further provides a nucleic acid that encodes a $N_t$TSHK that comprises an amino acid sequence that is substantially homologous to that of SEQ ID NO:8, and a heterologous nucleotide sequence. Another embodiment of this type the nucleic acid encodes a $N_t$TSHK having the amino acid sequence of SEQ ID NO:8 with a conservative substitution, and a heterologous nucleotide sequence. In a preferred embodiment of this type, the nucleic acid encodes a $N_t$TSHK having the amino acid sequence of SEQ ID NO:8 and a heterologous nucleotide sequence. In a more preferred embodiment of this type, the nucleic acid comprises the nucleotide sequence of SEQ ID NO:7 with a heterologous nucleotide sequence.

The present invention also provides a nucleic acid that encodes a $N_t$TSHK that comprises a nucleic acid sequence that is substantially homologous to that of SEQ ID NO:4, and a heterologous nucleotide sequence. In another embodiment of this type the nucleic acid encodes a $N_t$TSHK having the amino acid sequence of SEQ ID NO:4 with a conservative substitution, and a heterologous nucleotide sequence. In a preferred embodiment of this type the nucleic acid encodes a $N_t$TSHK having the amino acid sequence of SEQ ID NO:4 and a heterologous nucleotide sequence. In a more preferred embodiment of this type, the nucleic acid comprises the nucleotide sequence of SEQ ID NO:3 with a heterologous nucleotide sequence.

The present invention further provides a nucleic acid encoding an N-terminal truncated transmembrane sensor histidine kinase ($N_t$TSHK) fragment that is capable of phosphorylating a transmembrane sensor histidine kinase (TSHK) but lacks the autophosphorylatable histidine of the TSHK, comprising a catalytic core that has a single globular fold that contains four glycines analagous to G375, G403, G405, and G429 of SEQ ID NO:2. In a preferred embodiment of this type, the single globular fold further contains two asparagines analogous to N343 and N347 of SEQ ID NO:2. In a more preferred embodiment the single fold comprises a α/β sandwich fold with one layer consisting of a five stranded β-sheet and the other layer comprising three helices wherein the two layers enclose an extensive hydrophobic core, augmented by a small anti-parallel β-sheet which seals the sandwich at one end.

In one such particular embodiment the nucleic acid encodes an $N_t$TSHK that contains amino acids 380 to 417 of SEQ ID NO:2. In another such embodiment the nucleic acid encodes an $N_t$TSHK that contains amino acids 380 to 417 of SEQ ID NO:2 with a conservative amino acid substitution. In yet another such particular embodiment the nucleic acid encodes an $N_t$TSHK that contains amino acids 366 to 425 of SEQ ID NO:2. In still another such embodiment the nucleic acid encodes an $N_t$TSHK that contains amino acids 366 to 425 of SEQ ID NO:2 with a conservative amino acid substitution. In yet another such particular embodiment the nucleic acid encodes an $N_t$TSHK that contains amino acids 334 to 437 of SEQ ID NO:2. In still another such embodiment the nucleic acid encodes an $N_t$TSHK that contains amino acids 334 to 437 of SEQ ID NO:2 with a conservative amino acid substitution.

Additionally, the present invention also provides a nucleic acid that encodes a $N_t$TSHK that comprises an amino acid sequence that is substantially homologous to that of SEQ ID NO:14, and a heterologous nucleotide sequence. In another embodiment of this type, the nucleic acid encodes a $N_t$T-SHK having the amino acid sequence of SEQ ID NO:14 with a conservative substitution, and a heterologous nucleotide sequence. In a preferred embodiment of this type of nucleic acid encodes a $N_t$TSHK having a the amino acid sequence of SEQ ID NO:14 and a heterologous nucleotide sequence. In a more preferred embodiment of this type, the nucleic acid comprises the nucleotide sequence of SEQ ID NO:13 with a heterologous nucleotide sequence.

The present invention also provides a nucleic acid that encodes a $N_t$TSHK that comprises an amino acid sequence that is substantially homologous to that of SEQ ID NO:6, and a heterologous nucleotide sequence. In another embodiment of this type, the nucleic acid encodes a $N_t$TSHK having the amino acid sequence of SEQ ID NO:6 with a conservative substitution, and a heterologous nucleotide sequence. In a preferred embodiment of this type, the nucleic acid encodes a $N_t$TSHK having the amino acid sequence of SEQ ID NO:6 and a heterologous nucleotide sequence. In a more preferred embodiment of this type, the nucleic acid comprises the nucleotide sequence of SEQ ID NO:5 with a heterologous nucleotide sequence.

The present invention further provides all of the nucleic acids of the present invention in isolated form, and/or operatively linked to an expression control sequence. Similarly, any of the nucleic acids of the present invention operatively linked to an expression control sequence can be used to transform or transfect a unicellular host.

The present invention also provides methods of expressing a $N_t$TSHK of the present invention that is contained in the unicellular host. One such method comprises culturing the unicellular host in an appropriate cell culture medium under conditions that provide for the expression of the $N_t$TSHK by the cell. In addition, the present invention includes methods that further comprise the step of purifying the N$_t$TSHK. The purified form of the N$_t$TSHK is also includes as part of the present invention.

In addition, the N-terminal truncated transmembrane sensor histidine kinase are part of the present invention. Thus, the present invention provides a N$_t$TSHK comprising an amino acid sequence substantially homologous to that of SEQ ID NO:12 which contains a histidine that can be phosphorylated by a protein histidine kinase. In one such embodiment, the protein histidine kinase is a transmembrane sensor histidine kinase. In another such embodiment, the protein histidine kinase is a fragment of the TSHK having protein histidine kinase activity. In one particular embodiment of this type, the $N_t$TSHK comprises the amino acid sequence of SEQ ID NO:12 with a conservative amino acid substitution. In another embodiment the $N_t$TSHK comprises the amino acid sequence of SEQ ID NO:12. In still another embodiment of this type the $N_t$TSHK consists of the amino acid sequence of SEQ ID NO:12 with a conservative amino acid substitution. In a more preferred embodiment of this type the $N_t$TSHK consists of the amino acid sequence of SEQ ID NO:12.

In a related aspect, the present invention provides a $N_t$TSHK that comprises an amino acid sequence substantially homologous to that of SEQ ID NO:10, which contains a histidine that can be phosphorylated by a protein histidine kinase. In one such embodiment, the protein histidine kinase is a TSHK. In another such embodiment the protein histidine kinase is a fragment of the TSHK having protein histidine kinase activity.

In a particular embodiment of this aspect of the invention, the $N_t$TSHK comprises the amino acid sequence of SEQ ID NO:10 with a conservative amino acid substitution. In another embodiment the $N_t$TSHK comprises the amino acid sequence of SEQ ID NO:10. In still another embodiment of this type, the $N_t$TSHK consists of the amino acid sequence of SEQ type the NTSHK consists of the amino acid sequence of SEQ ID NO:10.

In another related aspect of the present invention, the $N_t$TSHK comprises an amino acid sequence substantially homologous to that of SEQ ID NO:8, and contains a histidine that can be phosphorylated by a protein histidine kinase. In one such embodiment, the protein histidine kinase is a TSHK. In another such embodiment, the protein histidine kinase is a fragment of the TSHK, having protein histidine kinase activity.

In a particular embodiment of this type, the $N_t$TSHK comprises the amino acid sequence of SEQ ID NO:8 with a conservative amino acid substitution. In another embodiment the $N_t$TSHK comprises the amino acid sequence of SEQ ID NO:8. In still another embodiment of this type the $N_t$TSHK consists of the amino acid sequence of SEQ ID NO:8 with a conservative amino acid substitution. In a preferred embodiment of this type the $N_t$TSHK consists of the amino acid sequence of SEQ ID NO:8.

In another related aspect, the present invention provides a $N_t$TSHK comprising an amino acid sequence substantially homologous to that of SEQ ID NO:4, and contains a histidine that can be phosphorylated by a protein histidine kinase. In one such embodiment, the protein histidine kinase is a TSHK. In another such embodiment the protein histidine kinase is a fragment of a TSHK, having protein histidine kinase activity.

In one particular embodiment of this aspect of the invention, the $N_t$TSHK comprises the amino acid sequence of SEQ ID NO:4 with a conservative amino acid substitution. In another embodiment, the $N_t$TSHK comprises the amino acid sequence of SEQ ID NO:4. In still another embodiment of this type the $N_t$TSHK consists of the amino acid sequence of SEQ ID NO:4 with a conservative amino acid substitution. In a preferred embodiment of this type the $N_t$TSHK consists of the amino acid sequence of SEQ ID NO:4.

Another aspect of the present invention provides a $N_t$TSHK that comprises an amino acid sequence that is substantially homologous to SEQ ID NO:14, wherein the $N_t$TSHK is capable of phosphorylating a TSHK. In a preferred embodiment of this type, the $N_t$TSHK lacks the autophosphorylatable histidine of the TSHK. In a particular embodiment of this type, the $N_t$TSHK comprises the amino acid sequence of SEQ ID NO:14 with a conservative amino acid substitution. In another such embodiment the $N_t$TSHK comprises the amino acid sequence of SEQ ID NO:14. In still another embodiment of this type, the $N_t$TSHK consists of the amino acid sequence of SEQ ID NO:14. In a preferred embodiment of this type, the $N_t$TSHK consists of the amino acid sequence of SEQ ID NO:14.

The present invention also provides a $N_t$TSHK that comprises an amino acid sequence that is substantially homologous to SEQ ID NO:6, wherein the $N_t$TSHK is capable of phosphorylating a TSHK. In a preferred embodiment of this type, the $N_t$TSHK lacks the autophosphorylatable histidine of the TSHK.

In a particular embodiment of this type, the $N_t$TSHK comprises the amino acid sequence of SEQ ID NO:6 with a conservative amino acid substitution. In another such embodiment, the $N_t$TSHK comprises the amino acid sequence of SEQ ID NO:6. In a related embodiment of this type, the $N_t$TSHK consists of the amino acid sequence of SEQ ID NO:6 with a conservative amino acid substitution. In a preferred embodiment of this type, the $N_t$TSHK consists of the amino acid sequence of SEQ ID NO:6.

The present invention further provides an N-terminal truncated transmembrane sensor histidine kinase ($N_t$SHK) fragment that is capable of phosphorylating a transmembrane sensor histidine kinase (TSHK) but lacks the autophosphorylatable histidine of the TSHK, comprising a catalytic core that has a single globular fold that contains four glycines analagous to G375, G403, G405, and G429 of SEQ ID NO:2. In a preferred embodiment of this type, the single globular fold further contains two asparagines analogous to N343 and N347 of SEQ ID NO:2. In a more preferred embodiment the single fold comprises an $\alpha/\beta$ sandwich fold with one layer consisting of a five stranded $\beta$-sheet and the other layer comprising three helices wherein the two layers enclose an extensive hydrophobic core, augmented by a small anti-parallel $\beta$-sheet which seals the sandwich at one end.

In one such particular embodiment the $N_t$TSHK contains amino acids 380 to 417 of SEQ ID NO:2. In another such embodiment the $N_t$TSHK contains amino acids 380 to 417 of SEQ ID NO:2 with a conservative amino acid substitution. In yet another such particular embodiment the $N_t$TSHK contains amino acids 366 to 425 of SEQ ID NO:2 with a conservative amino acid substitution. In yet another such particular embodiment the $N_t$TSHK contains amino acids 334 to 437 of SEQ ID NO:2. In still another such embodiment the $N_t$TSHK contains amino acids 334 to 437 of SEQ ID NO:2 with a conservative amino acid substitution.

The present invention allso provides fusion proteins/peptides and chimeric proteins/peptides comprising the $N_t$TSHKs of the present invention. All of the isolated $N_t$TSHKs of the present invention, and all of the recombinant $N_t$T-

SHKs of the present invention may be parts of these fusion and chimeric proteins/peptides. In one such embodiment, a fusion protein comprises a $N_t$TSHK of the present invention and the green fluorescent protein. In another such embodiment, the fusion protein comprises a $N_t$TSHK of the present invention together with a FLAGG tag. In a preferred embodiment of the present invention, the fusion protein comprises SEQ ID NO:12 containing six histidines (H6) at its N-terminus.

The present invention further provides methods of using an $N_t$TSHK in a drug screening assay. Any of the $N_t$TSHKs, and/or fusion proteins/peptides of the present invention may be used in such methods. One such method comprises selecting a potential drug by performing structure based rational drug design with the determined three-dimensional structure of a $N_t$TSHK. The selecting is preferably performed in conjunction with computer modeling. In a preferred embodiment the $N_t$TSHK used in the three-dimensional structural analysis has the amino acid sequence of SEQ ID NO:14. In another preferred embodiment the $N_t$TSHK used in the three-dimensional structural analysis has the amino acid sequence of SEQ ID NO:12.

The selected potential drug can then be contacted with a polypeptide that comprises a $N_t$TSHK. The binding of the selected potential drug with the polypeptide is detected, and a potential drug is selected as a drug if it binds to the polypeptide. In one preferred embodiment, the $N_t$TSHK has the amino acid sequence of SEQ ID NO:14. In another preferred embodiment, the $N_t$TSHK has the amino acid sequence of SEQ ID NO:12.

The polypeptide comprising the $N_t$TSHK can also be labeled. In another such embodiment, the polypeptide comprising the $N_t$TSHK can be bound to a solid support.

In an alternative embodiment, a potential drug can be identified using the three-dimensional structure determined for an NtTSHK and then the potential drug can be contacted with a polypeptide comprising the $N_t$TSHK in the presence of a protein histidine kinase, under conditions in which in the absence of a potential drug the protein histidine kinase phosphorylates the $N_t$TSHK. The phosphorylation state of the $N_t$TSHK is then determined. A drug is selected when a change in the phosphorylation state of the $N_t$TSHK is determined in the presence of the potential drug relative to in its absence. When the change in phosphorylation state of the $N_t$TSHK is determined to be increased in the presence of the potential drug relative to in its absence, the potential drug is selected as an agonist of the corresponding TSHK. Alternatively, when the change in the phosphorylation state of the $N_t$TSHK determined in the presence of the potential drug is determined to be decreased, relative to in its absence, the potential drug is selected as an inhibitor of the corresponding TSHK.

In one particular embodiment of this type, the polypeptide comprises a $N_t$TSHK having the amino acid sequence of SEQ ID NO:4. In another such embodiment, the polypeptide comprises a $N_t$TSHK having the amino acid sequence of SEQ ID NO:8. In still another such embodiment, the polypeptide comprises a $N_t$TSHK having the amino acid sequence of SEQ ID NO:10. In a preferred embodiment of this type, the polypeptide comprises a $N_t$TSHK having the amino acid sequence of SEQ ID NO:12.

In still another embodiment, a potential drug can be identified using the three-dimensional structure determined for an $N_t$TSHK of the present invention and then the potential drug can be contacted with a polypeptide comprising a $N_t$TSHK in the presence of a protein histidine kinase substrate, wherein in the absence of the potential drug, the protein histidine kinase substrate is phosphorylated by the $N_t$TSHK. The phosphorylation state of the protein histidine kinase substrate is then determined, wherein a drug is selected when a change in the phosphorylation state of the protein histidine kinase substrate is determined in the presence of the potential drug relative to in its absence. When the change in phosphorylation state of the protein histidine kinase substrate determined in the presence of the potential drug, relative to in its absence increases, the potential drug is selected as a stimulator of the TSHK. When the change in phosphorylation state of the protein histidine kinase substrate decreases in the presence of the potential drug, relative to in its absence, the potential drug is selected as an inhibitor of the TSHK. In one embodiment of this type, the polypeptide comprises a $N_t$TSHK that has the amino acid sequence of SEQ ID NO:14. In a preferred embodiment of this type the polypeptide comprises $N_t$TSHK that has the amino acid sequence of SEQ ID NO:6.

The present invention further provides assays for testing potential drugs that are selected/identified by the three-dimensional structural analysis of an $N_t$TSHK of the present invention, for the ability of the potential drug to modulate the signal transduction mediated by the TSHK and its corresponding response regulator. For example, a cell can be constructed to contain a reporter gene (such as a gene encoding green fluorescent protein, or β-galactosidase) under the transcriptional control of the TSHK. The TSHK can be activated and thereby stimulate the transcription of the reporter gene. The potential drug can be added and the change in the amount of transcription of the reporter gene. The potential drug can be added and the change in the amount of transcription of the reporter gene can be determined. A potential drug causing an increase in transcription is selected as an agonist of the TSHK, whereas a potential drug causing a decrease is selected as an antagonist of the TSHK.

Controls can be performed to confirm that the potential drug is acting on the TSHK directly. In one such control, a cell is constructed to be lacking a functional TSHK. In this case, the response regulator is activated artificially. The transcription of the reporter gene is monitored in such cells in the presence or absence of the selected drug. A selected drug is identified as acting directly on the TSHK when it has no effect on the transcription of the reporter gene in a cell lacking functional TSHK.

As anyone having skill in the art of drug development would readily understand, the potential drugs selected by the above methodologies can be refined by re-testing in appropriate drug assays, including those disclosed herein. Chemical analogues of such potential drugs can be obtained (either through chemical synthesis or drug libraries) and be analogously tested. Therefore methods comprising successive iterations of the steps of the individual drug assays, as exemplified herein, using either repetitive or different binding studies, phosphorylation studies, or transcription activation studies or other such studies are envisioned in the present invention. In addition, potential drugs may be identified first by rapid throughput drug screening, as described below, prior to performing computer modeling on a potential drug using the three-dimensional structure of an $N_t$TSHK.

Any of the drug assays of the present invention can further comprise a step of contacting the potential drug and the $N_t$TSHK, wherein a binding complex forms between the potential drug and the $N_t$TSHK. The three-dimensional structure of the binding complex can then be determined by NMR. A drug can then be selected by performing structure based rational drug design with the three-dimensional structure determined for the binding complex. The selection is preferably performed in conjunction with computer modeling. Such a drug can be further tested as described above.

The present invention further comprises all of the potential, selected, and putative drugs as well as the drugs identified by methods of the present invention.

The present invention further provides specific antibodies that react with an $N_t$TSHK of the present invention but does not cross react with the corresponding TSHK. The antibodies are raised against the $N_t$TSHK of the present invention. Such antibodies include but are not limited to polyclonal, monoclonal, chimeric, single chain, fab fragments and a fab expression library. These antibodies may also be labeled. Also included is an immortal cell line that produces a monoclonal antibody that reacts with a $N_t$TSHK of the present invention but not its corresponding TSHK.

Accordingly, it is principal object of the present invention to provide detailed structural information regarding the catalytic site of a transmembrane sensor histidine kinase (TSHK).

It is a further object of the present invention to provide structural characteristics and properties of N-terminal truncated TSHKs ($N_t$TSHKs) which are amenable for detailed NMR structural analysis and which (1) retain their ability to be autophosphorylated, and/or (2) transfer a phosphoryl group from the autophosphorylated phosphoryl histidine to an aspartyl group of their corresponding response regulators and/or (3) function as a protein histidine kinase.

It is further object of the present invention to provide methodologies for exploiting such structural information in order to develop potential anti-bacterial drugs through structure based rational drug design.

It is a further object of the present invention to provide structural characteristics and properties of $N_t$TSHKs which can be used to form X-ray quality crystals and which (1) retain their ability to be autophosphorylated, and/or (2) transfer a phosphoryl group from the autophosphorylated phosphoryl histidine to an aspartyl group of their corresponding response regulators and/or (3) function as a protein histidine kinase.

It is a further object of the present invention to provide nucleic acid and amino acid sequences for the $N_t$TSHKs of the present invention.

It is a further object of the present invention to provide a method of producing the $N_t$TSHKs of the present invention, including by proteolysis and through recombinant technology.

It is a further object of the present invention to provide a method of selecting an appropriate $N_t$TSHK for use in structure based rational drug design of TSHK inhibitors.

It is a further object of the present invention to provide a method of screening drug libraries for agents that interfere with TSHK-response regulator activity by interfering with the binding of the TSHK to the response regulator.

It is a further object of the present invention to provide a method of screening drug libraries for agents that interfere with TSHK autophosphorylation by interfering with the binding of the interaction of sub-domain A and sub-domain B of the TSHK.

It is a further object of the present invention to provide an antibody specific for an $N_t$TSHK of the present invention that binds to the $N_t$TSHK fragment but does not bind to the corresponding full-length TSHK.

It is further object of the present invention to provide drugs obtained by the methodology of the present invention for treating and/or preventing bacterial inflammations and infections.

These and other aspects of the present invention will be better appreciated by reference to the following drawings and Detailed Description.

BRIEF DESCRIPTION OF THE DRAWINGS

FIG. 1A shows the serial deletions of EnvZ(C) proteins. The N- and C-terminal amino acid residue numbers of each EnvZ(C) fragment are shown above ends of the bar. Solid bars represent the EnvZ sequence. The transmembrane regions, TM1 and TM2, are indicated by shaded boxes. The open bars at the left hand side of the bars indicate the six-histidine residues [Met-(His) 6] at the N-terminal end. Conserved motifs among all of the histidine kinases, H243, N347, F387, two glycine-rich regions G1 (residues 373–377 of SEQ ID NO:2) and G2 (residues 403–405 of SEQ ID NO:2) are shown on the top of the full-length EnvZ. The activities of autophosphorylation and phosphorylation by EnvZ(C)H1 of each protein are indicated by + or − (no activity) or ND (not determined). FIGS. 1B and 1C show the purified EnvZ(C) fragments (3 µg each) which were incubated with 0.2 µCi of [γ-$^{32}$P]ATP in a 20-µl reaction mixture consisting of 50 mM Tris-HCl (pH 8.0), 50 mM KCl, 5 mM CACl$_2$, 5% glycerol, and 1 mM PMSF (buffer A) for 10 minutes at room temperature. The autophosphorylation reaction was stopped by adding 5×SDS gel loading buffer. The reaction mixture was subjected to SDS-PAGE using a 16% Tricine gel (Novex), followed by Coomassie brilliant blue staining in FIG. 1B and autoradiography in FIG. 1C. Lane 1, protein molecular weight markers; lane 2, H6-EnvZ(C)wt; lane 3, H6-EnvZ(C)H1; lane 4, H6-EnvZ(C)ΔL; lane 5, H6-EnvZ(C)ΔG2; lane 6, H6-EnvZ(C)(223–289 of SEQ ID NO:2); lane 7, EnvZ(C) (223–289 of SEQ ID NO:2, [SEQ ID NO:12]and lane 8, EnvZ(C)(290–450 of SEQ ID NO: 2, [SEQ ID NO:14].

FIG. 2A shows the results of the kinase assay using the EnvZ(C) fragments. The purified protein H6-EnvZ(C)ΔL [0.13 µM in the upper panel with H6-EnvZ (C)ΔG2 or 0.26 µM in the lower panel with H6-EnvZ(C) (223–289)]was autophosphorylated with 0.2 µCi of [γ-$^{32}$P] ATP at room temperature for 15 min as a control (lane 1). For trans-autophosphorylation of H6-EnvZ(C)ΔG2 [or H6-EnvZ(C)(223–289)] by H6-EnvZ(C)H1, equimolar concentrations of each protein (1.3 µM each) were mixed and incubated with 0.2 µCi of [γ-$^{32}$P]ATP for 15 minutes (lane 2) and 25 minutes (lane 7) at room temperature. For the phosphotransfer reaction to OmpR, H6-EnvZ(C)ΔG2 [or H6-EnvZ(C)(223–289)] and H6-EnvZ(C)H1 were mixed and the mixture was first incubated for 15 minutes (lane 2). After incubation, OmpR was added to the mixture. The molar ratio of H6-EnvZ(C)H1 and OmpR was 1:1:1 (1.3 µM each). The phosphotransfer reaction was stopped by adding 5×SDS gel loading buffer at 15 seconds (lane 3), 1 minute (lane 4), 5 minutes (lane 5), and 10 minutes (lane 6). The samples were then subjected to SDS-PAGE analysis followed by autoradiography. The position of each protein is indicated by an arrow. FIG. 2B shows the results of the phosphatase assay of the EnvZ(C) fragments. The phosphorylated OmpR in 2.6 µM of total OmpR protein [Pan et al., Proc. Natl. Acad. Sci. USA, 90:9939–9943 (1993)] was incubated at room temperature with the following proteins; 2.6 µM of BSA, H-6EnvZ(C)H1, H6-EnvZ(C) wt, H6-EnvZ (C)ΔL, H6-EnvZ(C)ΔG2, H6-EnvZ(C)(223–289 of SEQ ID NO:2) and EnvZ(C)(290–450, SEQ ID NO:14) as indicated at the right hand side. The reaction was carried out in the presence of 1 mM ADP. The reaction times are indicated at the bottom of the figures. The reaction was stopped by adding 5×SDS gel loading buffer and analyzed by SDS-PAGE, followed by autoradiography.

FIG. 4 shows the analysis of the dimerization of EnvZ (C)(223–289) and its interaction with OmpR.

FIG. 6 shows the sequence comparison of the EnvZ catalytic domain, sub-domain B with other members of the histidine kinase family.

FIG. 8 shows the atomic coordinates determined by NMR of sub-domain A [EnvZ(C)(223–289), SEQ ID NO:12].

FIG. 9 shows the atomic coordinates determined by NMR of sub-domain B [EnvZ(C)(290–450), SEQ ID NO:14].

DETAILED DESCRIPTION OF THE INVENTION

The present invention provides detailed structural information regarding a transmembrane sensor histidine kinase (TSHK), a protein that plays a crucial role in signal transduction pathways of prokaryotes. More particularly, the present invention provides structural information regarding the cytoplasmic kinase domain of EnvZ, a transmembrane osmosensor of *Escherichia coli*. This cytoplasmic kinase domain is shown to contain two distinct functional sub-domains; sub-domains A [EnvZ(C)(223–289 of SEQ ID NO:12) containing 67 residues (SEQ ID NO:12)] and sub-domain B [EnvZ(C)(290–450 of SEQ ID NO:12) containing 161 residues (SEQ ID NO:14)], each of which are a N$_t$T-SHK of the present invention.

The three-dimensional structures of the two subdomains, determined by NMR spectroscopy, are also provided. Sub-domain A, SEQ ID NO:12 is shown, herein, to have a high helical content and to contain the autophosphorylation site, H243 of SEQ ID NO:2, i.e., the autophosphorylatable substrate site. Consistently sub-domain A is also shown to contain the recognition site for OmpR, the cognate response regulator of EnvZ, which is phosphorylated by the TSHK following the autophosphorylation.

Figure 5:
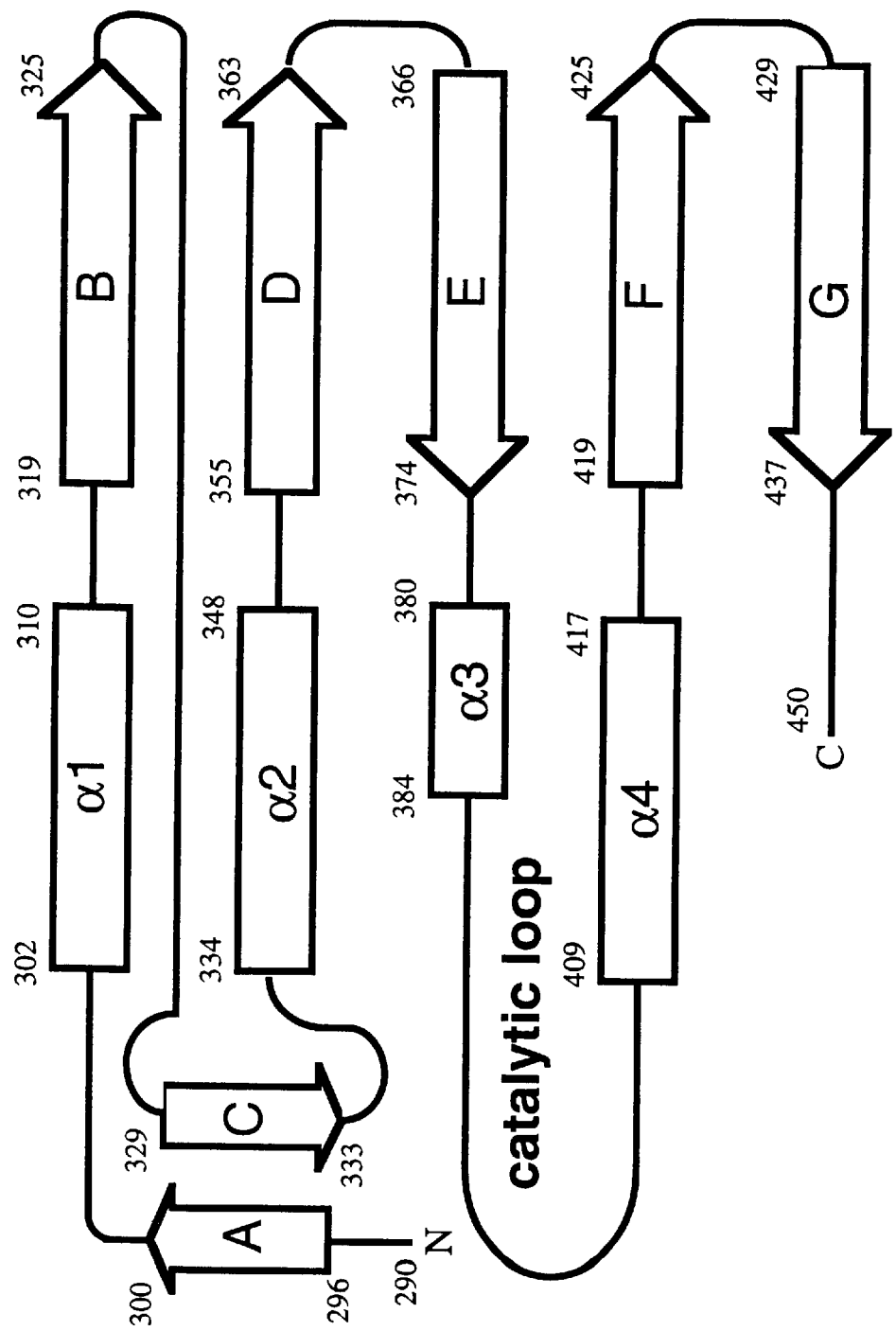
FIG. 5 depicts a the secondary structure of the N$_t$TSHK, sub-domain B [EnvZ(C)(290–450) containing 161 residues (SEQ ID NO:14)].

Sub-domain B is shown to contain the catalytic kinase activity. The overall fold of this histidine kinase catalytic domain differs significantly from the known structures of protein serine/threonine and tyrosine kinases. The envZ histidine kinase domain comprises a single globular fold of 161 residues that has all the functionalities of a protein kinase. A striking feature in this fold is the presence of a long polypeptide segment that extends away from the rest of the molecule (See Example 2, FIG. 5). This segment consists of a short $\alpha$-helix $\alpha$3 (380–384 of SEQ ID NO:2) followed by a long loop (385–409 of SEQ ID NO:2) that appears to be a random coil that is highly mobile in solution relative to the overall tumbling motion of the molecule. This characteristic loop, together with helix $\alpha$3, provides a nucleotide binding site where the phosphorylation catalysis takes place, and is thereby referred to as "catalytic loop" (FIG. 5). The disclosed structure of *E. coli* EnvZ histidine kinase catalytic domain of the present invention provides a vital foundation for rational design of effective antibiotics specifically blocking the histidine kinases *E. coli* as well as in other microbial species.

The present invention further discloses that whereas sub-domain A of SEQ ID NO:12 forms a stable dimer, sub-domain B of SEQ ID NO:14 exists as a monomer. The present invention also discloses that when the individual sub-domains A of SEQ ID NO:12 and B of SEQ ID NO:14 are mixed together, the kinase activity of sub-domain B of SEQ ID NO:14 acts to phosphorylate sub-domain A SEQ ID NO:2 His which correspond to His243 of SEQ ID NO:2 in the presence of ATP. The phosphorylated sub-domain A is then capable to transfer its phosphoryl group to OmpR.

By providing a two-sub-domain structure of the cytoplasmic histidine kinase domain of a TSHK, the present invention further provides insight into the structural arrangement of the TSHK, and its corresponding transphosphorylation mechanism. The structural information provided by the present invention further allows new means for designing drug screens for agents that interfere with the signal transduction function of this important bacterial pathway. Thus, by identifying the specific structural sub-domains involved in both the autophosphorylation of TSHK, and in the subsequent phosphoryl transfer between TSHK and OmpR, the present invention allows specific protein sites to be targeted in novel drug assays. The present invention, therefore, provides new methodologies for identifying potential drugs, which can be used for treating bacterial infections.

The present invention is partially based on the need to identify new classes of anti-bacterial drugs which are necessary to replace standard antibiotics, due to the increasing number of antibiotic-resistant bacterial strains. These drugs would ideally target enzyme systems required for bacterial survival, such as the proteins involved in the His-Asp phosphorelay signal transduction system, and more particularly a transmembrane sensor histidine kinase.

Structure based rational drug design is the most efficient method of such drug development. However, to date, little information is known regarding the structure of the catalytic domains(s) of TSHKs. Proteolytic digestions, as described below, allow initial insight into the structural analysis. However, obtaining detailed structural information requires an extensive NMR or X-ray crystallographic analysis. In the former case, TSHK exists as a dimer having a molecular weight which is beyond the present capabilities of NMR analysis. In the latter case, transmembrane proteins such as a TSHK are particularly difficult to crystallize, and therefore not surprisingly, it has not been possible to grow TSHK crystals of X-ray crystallographic quality.

The present invention overcomes the difficulties described above, by providing N-terminal truncated TSHK fragments ($N_t$TSHKs) that retain the structure of the individual sub-domains of the catalytic sites of a TSHK. Such $N_t$TSHKs are amenable to NMR structural analysis, and in addition, can be used to grow X-ray quality crystals. By determining and then exploiting the detailed structural information of these sub-domains (exemplified by NMR analysis below) the present invention provides novel methods for developing new anti-bacterial drugs through structure based rational drug design.

In addition the present invention provides spatial coordinates for sub-domain A (FIG. 8) and sub-domain B (FIG. 9). Furthermore, the coordinates (data set) of FIG. 8 and FIG. 9 in a computer readable form are also part of the present invention. In addition, methods of these coordinates (including such computer readable forms) in the in the drug assays disclosed below, are fully contemplated by the present invention. More particularly, such coordinates can be used to identify potential ligands or drugs which will bind to a $N_t$TSHK of the present invention.

Therefore, if appearing herein, the following terms shall have the definitions set out below As used herein the term "transmembrane sensor histidine kinase", "transmembrane sensor kinase", "TSHK", "transmembrane histidine kinase sensor" and any variants not specifically listed, may be used herein interchangeably, and as used throughout the present Application and claims refer to proteinaceous material including single or multiple proteins (including dimers and the like). Accordingly, proteins displaying substantially equivalent activity are likewise contemplated. In addition, these terms are intended to include within their scope proteins specifically recited herein as well as all substantially homologous analogs and allelic variations. A TSHK minimally contains a putative periplasmic receptor domain, a transmembrane domain, and a cytoplasmic histidine kinase domain. One example of a TSHK is *E. coli* EnvZ, a transmembrane osmosensor having an amino acid sequence of SEQ ID NO:2.

Unless otherwise stated, the use of the term "TSHK" indicates a full-length transmembrane histidine kinase sensor as opposed to an "N-terminal truncated TSHK fragment" which is defined below.

As used herein an "N-terminal truncated TSHK fragment," an "N-terminal fragment of a TSHK", "$N_t$TSHK" and any analogous variants not specifically listed, may be used herein interchangeably, and as used throughout the present application and claims and refer to a TSHK fragment that minimally contains at least a portion of a TSHK cytoplasmic domain, but is missing at least a portion of the N-terminal transmembrane domain of the TSHK. Preferably all of the N-terminal transmembrane domain(s) of the TSHK are deleted. Examples of N-terminal truncated TSHK fragments include peptides having SEQ ID NOs:2, 4, 6, 8, 10, 12 and 14. As disclosed herein, these fragments can be produced by a number of means including by proteolytic digestion of a TSHK, chemical synthesis and more preferably by recombinant DNA techniques.

Accordingly as used herein an "isolated nucleic acid encoding an N-terminal truncated TSHK fragment" is meant to include a purified nucleic acid, as well as a recombinant nucleic acid.

A "polypeptide" comprising an "N-terminal truncated TSHK fragment" as used herein can be the "$N_t$TSHK" alone, or a larger chimeric or fusion peptide/protein which contains a "$N_t$TSHK".

As used herein, and unless otherwise specified, the terms "agent", "potential drug", "test compound" and the like are used interchangeably, and refer to chemicals which potentially have a use as an inhibitor or activator of a TSHK, or preferably as a drug in the treatment or prevention of a disease caused by bacteria. Therefore, such "agents", "potential drugs", and "test compounds" may be used, as described herein, in drug assays and drug screens and the like.

General Techniques for Constructing Nucleic Acids
That Express N-terminal Truncated Fragments of
Transmembrane Sensor Histidine Kinases
($N_t$TSHKs)

In accordance with the present invention there may be employed conventional molecular biology, microbiology, and recombinant DNA techniques within the skill of the art. Such techniques are explained fully in the literature. See, e.g. Sambrook, Fritsch & Maniatis, *Molecular Cloning: A Laboratory Manual,* Second Edition (1989) Cold Spring Harbor Laboratory Press, Cold Spring Harbor, New York (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]*Animal Cell Culture* [R. I. Freshney, ed (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA—DNA, DNA—RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

IN a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promotoer sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)]. Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

Two DNA sequences are "substantially homologous" when at least about 60% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. Likewise, two polypeptide sequences are "substantially homologous" when at least about 60% (preferably at least about 80%, and most preferably at least about 90 or 95%) of the amino acids are either identical or contain conservative changes, as defined herein, over the defined length of the polypeptide sequences, e.g., preferably without gaps.

The term "corresponding to" is used herein to refer similar or homologous sequences, whether the exact position is identical or different from the molecule to which the similarity or homology is measured. Thus, the term "corresponding to " refers to the sequence similarity, and not the numbering of the amino acid residues or nucleotide bases.

As used herein, an amino acid residue in a N$_t$TSHK is said to be "analogous" to an amino acid residue of a TSHK amino acid sequence, when the amino acid residue in the N$_t$TSHK is contained in a domain that corresponds to a domain of the TSHK, and the amino acid residue of the N$_t$TSHK and the analogous amino acid of the TSHK play the essentially the same role in the three diminsional configuration of their respective domains.

A gene encoding a TSHK, whether genomic DNA or cDNA, can be isolated from any source, particularly from a prokaryotic cell. Methods for obtaining the TSHK gene are well known in the art, as exemplified above [see, e.g., Sambrook et al., 1989, supra].

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins or peptides. Thus the heterologous nucleotide sequence can encode peptides and/or proteins which contains regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed (the H6 sequence described in Examples 1, below). In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing genes encoding analogs and derivatives of the N$_t$TSHK of the present invention, including modified N$_t$TSHKs, that have the same or homologous functional activity as the individual N$_t$TSHKs, and homologs thereof. The production and use of derivatives and analogs related to the N$_t$TSHKs are within the scope of the present invention.

As exemplified below any of a number of cells (preferably prokaryotic cells) can be used to express wild-type TSHK, mutant TSHK and/or N-terminal truncated TSHK fragments. E. coli B BL21-DE3 (f-ompTrBmB) was used in Example 1, below. Once expressed the TSHK or N$_t$TSHK can be purified by standard methodology, see, e.g., Park et al., [J. Bacteriol., 179:4382–4390 (1997)]. Similarly the construction of plasmids containing nucleotide sequences encoding a TSHK or an N$_t$TSHK can be performed by standard methodology [Park et al., J. Bacteriol., 179:4382–4390 (1997)]. For example, pET11a-EnvZ(C) ΔL, which contains the EnvZ sequence encoding residues Met223 to Gly450 of SEQ ID NO:2, was constructed by the digestion of pET11a-EnvZ(C) with a restriction enzyme, NdeI, followed by self-ligation in Example 1. In this case a linker

5'TATGCACCATCACCATCACCA3'(SEQ ID NO:15)

3'ACGTGGTAGTGGTAGTGGTAT5'(SEQ ID NO:16)

was inserted at an NdeI site of pET11a-EnvZ(C) ΔL, generating pPH006 which encodes H6-EnvZ(C) ΔL. Confirmation of the nucleotide sequence by sequencing can be performed using Sequenase (USB).

As further exemplified below, a restriction fragment obtained from the construct, pPH006, can be used for site-directed mutagenesis, e.g., to create a stop codon at either Thr397, or Thr290 of SEQ ID NO:2, using 5'AGTGCGCGCTGAATTAGCGG3'(SEQ ID NO:17) and 5'TACCTGCGCTAAGGGCAGGAG3'(SEQ ID NO:18) oligomers, respectively; or to change a particular amino acid residue. In the former case, nucleotide fragments containing the stop codons can then be subcloned back into the construct, pPH006. In the latter procedure, PCR can be used as described in Example 1, in the construction of plasmid pET11a-EnvZ(C)(290–450) containing the EnvZ sequence from Thr290 to Gly450 of SEQ ID NO:2. In this case PCR was carried out with primer 7109 (5'CGCATATGACCGGGCAGGAG3',SEQ ID NO:19 ) that contained an NdeI site to substitute Arg289 (CGC) with Met (ATG), and primer 4163 (5'TCGGATCCCGTTATTTAC3', SEQ ID NO:20) containing a BamHI site downstream of Gly450 codon. pET11a-EnvZ(C)ΔL was used as the template. The 507-bp PCR fragment thus obtained was digested with NdeI and BamHI and subcloned into the pET11a-EnvZ (C) ΔL vector cut with NdeI and BamHI. The sequence of PCR product can be confirmed by DNA sequencing [Park et al., J. Bacteriol, 179:4382–4390 (1997)].

In another such embodiment, the highly conserved HIS243 of E. Coli EnvZ can be replaced by a leucine or a valine (as described in Example 1, below).

Due to the degeneracy of nucleotide coding sequences, other DNA sequences which encode substantially the same amino acid sequence as a nucleic acid encoding an N$_t$TSHK of the present invention may be used in the practice of the present invention. These include but are not limited to allelic genes, homologous genes from other species, which are altered by the substitution of different codons that encode the same amino acid residue within the sequence, thus producing a silent change. Likewise, the $N_t$TSHKs of the invention include, but are not limited to, those containing, as a primary amino acid sequence, analogous portions of the amino acid sequences of a TSHK including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. the positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained;

(e) Ile for Leu or for Val or vice versa as roughly equivalent hydrophobic amino acids; and (f) Phe for Tyr or vice versa as roughly equivalent aromatic amino acids.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

All of the $N_t$TSHKs of the present invention can be modified by being placed in a fusion or chimeric peptide or protein, or labeled e.g., to have an N-terminal FLAG-tag, or H6 tag as described in detail below. In a particular embodiment the $N_t$TSHK can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The genes encoding $N_t$TSHKs and analogs thereof can be produced by various methods known in the art. The manipulations which result in their production can occur at the gene or protein level [Sambrook et al., 1989, supra]. The nucleotide sequence can be cleaved at appropriate sites with restriction endonuclease(s), followed by further enzymatic modification if desired, isolated, and ligated in vitro. In the production of the gene encoding a derivative or analog of an $N_t$TSHK care should be taken to ensure that the modified gene remains within the same translational reading frame as the TSHK gene, uninterrupted by translational stop signals, in the gene region where the desired activity is encoded.

Additionally, the $N_t$TSHK-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson et al., *J. Biol. Chem.* 253:6551 (1978); Zoller and Smith, *DNA,* 3:479–488 (984); Oliphant et al., *Gene,* 44:177 (1986); Hutchinson et al., *Proc. Natl. Acad. Sci. U.S.A.,* 83:710 (1986)], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplifcation,* H. Erlich, ed., Stockton Press, Chapter 6, pp. 61–70].

The identified and isolated gene can then be inserted into an appropriate cloning vector. A large number of vector-hose systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini (as exemplified in Example 1, below); these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E., coli* and *Saccharomyces cerevisiae* by linking sequences from an *E. coli* plasmid with sequences form the yeast 2$\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of N-terminal Truncated TSHK Fragments

The nucleotide sequence coding for an $N_t$TSHK or analogs therefore, including a chimeric protein, thereof, can be inserted into an appropriate expression vector, i.e., a vector which contains the necessary elements for the transcription and translation of the inserted protein-coding sequence, as exemplified below. Such elements are termed herein a "promoter." Thus, the nucleic acid encoding an $N_t$TSHK or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector.

Potential host-vector systems include but are not limited to prokaryotic cell systems such as bacteria transformed with bacteriophage, DNA, plasmid DNA as exemplified below, or cosmid DNA; inset cell systems infected with virus (e.g., baculovirus); microorganisms such as yeast containing yeast vectors. The expression elements of vectors vary in their strengths and specificities. Depending on the host-vector systems utilized, any one of a number of suitable transcription and translation elements may be used.

A recombinant $N_rTSHK$ of the invention, may be expressed chromosomally, after integration of the coding sequence by recombination. In this regard, any of a number of amplification systems may be used to achieve high levels of stable gene expression [See Sambrook et al., 1989, supra].

The cell into which the recombinant vector comprising the nucleic acid encoding the $N_rTSHK$ is cultured in an appropriate cell culture medium under conditions that provide for expression of the protein or peptide by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of an $N_t$TSHK may be controlled by any promoter/enhancer element known in the art, but these regulatory elements must be functional in the host selected for expression.

Expression vectors containing a nucleic acid encoding an $N_t$TSHK of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding the $N_t$TSHK is inserted within the "selection marker" gene sequence of the vector, recombinants containing the insert can be identified by the absence of the selection maker gene function. In the fourth approach, recombinant expression vectors can be identified by assaying for the activity, biochemical, or immunological characteristics of the gene product expressed by the recombinant, provided that the expressed protein assumes a functionally active conformation, e.g. protein histidine kinase activity or ability to be a substrate for a protein histidine kinase.

A wide variety of host/expression vector combinations may be employed in expressing the DNA sequences of this invention which are well known in the field.

Once a particular recombinant DNA molecule is identified and isolated, several methods known in the art may be used to propagate it. Once a suitable host system and growth conditions are established, recombinant expression vectors can be propagated and prepared in quantity. Vectors are introduced into the desired host cells by methods known in the art, e.g., transfection, electrophoration, microinjection, transduction, cell fusion, DEAE dextran, calcium phosphate, precipitation, lipofection (lysosome fusion), use of a gene gun, or a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

Synthetic Polypeptides

The term "polypeptide" is used in its broadest sense to refer to a compound of two or more subunit amino acids, amino acid analogs, or peptidomimetics. The subunits are linked by peptide bonds. The $N_t$TSHKs of the present invention may be chemically synthesized.

In addition, potential drugs or agents that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting neutralization, coupling and wash protocols of the original solid phase procedure of Merrifield [*J. Am. Chem. Soc.,* 85:2149–2154 (1963)], or the base-labile $N^\alpha$-amino protected 9-fluorenylmethoxycarbonyl (Fmoc) amino acids first described by Carpino and Han [*J. Org. Chem.* 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young [Solid Phase Synthesis, Second Edition, Pierce Chemical Co., Rockford, Ill. (1984)] and Fields and Noble [*Int. J. Pept. Protein Res.* 35:161–214 (1990)], or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, β-helices, α turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or seuqences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, *Life Sciences*, 31:189–199 (1982); Hruby et al., *Biochem. J.* 268:249–262 (1990)]; the present invention provides a method to produce a constrained peptide that incorporates random sequences at all other positions.

Constrained and cyclic peptides

A constrained, cyclic or rigidized petide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cystein to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson [*Biophys. Biochem. Res. Commun.*, 94:1128–1132 (1980)]. A peptide in which the peptide sequence comprises at least two amino acids capable of crosslinking may be treated, e.g., by oxidation of cysteine residues to form a disulfide or addition of a meal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, in The Peptides: Analysis, Synthesis, Biology, Vol. 3, Gross and Meienhofer, eds., Academic Press: New York, pp. 137–167 (1981); Ponsanti et al., *Tetrahedron*, 46:8255–8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints

The following non-classical amino acids may be incorporated in the peptide in order to introduce particular conformational motifs: 1,2,3,4-tetrahydroisoquinoline-3-carboxylate [Kazmierski et al., *J. Am. Chem. Soc.*, 113:2275–2283 (1991)]; (2S,3S)-methyl-phenylalanine, (2S,3R)-methyl-phenylalanine, (2R,3S)-methyl-phenylananine and (2R,3R)-methyl-phenylalanine (Kazmierski and Hruby, *Tetrahedron Lett.* (1991)]; 2-ainotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al., *J. Takeda Res. Labs,* 43:53–76 (1989)]; β-carboline (D and L) [Kazmierski, Ph.D. Thesis, University of Arizona (1988)]; HIC (histidine isoquinoline carboxylic acid) [Zechel et al., *Int. J. Pep. Protein Res.,* 43 (1991)]; and HIC (histidine cyclic urea) (Dharanipragada).

The following amino acid analogs and peptidomimetics may be incorporated into a peptide to induce or favor specific secondary structures: LL-Acp-(LL-3-amino-2-propenidone-6-carboxylic acid), a β-turn inducing dipeptide analog [Kemp et al., *J. Org. Chem.* 50:5834–5838 (1985)]; β-sheet inducing analogs [Kemp et al., *Tetrahedron Lett.* 29:5081–5082 (1988); β-turn including analogs [Kemp et al., *Tetrahedron Lett.,* 29:5057–5060 (1988)]; -helix inducing analogs [Kemp et al., *Tetrahedron Lett.,* 29:4935–4938 (1988)]; γ-turn inducing analogs [Kemp et al., *J. Org. Chem.* 54:109:115 (1989)]; and analogs provided by the following references: Nagai and Sato, *Tetrahedron Lett.,* 26:647;14 650 (1985); DiMaio et al., *J. Chem. Soc. Perkin Trans.* p. 1687 (1989); also a Gly-Ala turn analog [Kahn et al., *Tetrahedron Lett.,* 30:2317 (1989)]; amide bond isotere [Jones et al., *Tetrahedron Lett.,* 29:3853–3856 (1988)] tretazol [Zabrocki et al., *J. Am. Chem. Soc.* 110:5875–5880 (1988)]; DTC [Samanen et al., *Int. J. Protein Pep. Res.,* 35:501:509 (1990)]; and analogs taught in Olson et al., *J. Am. Chem. Sci.,* 112:323–333 (1990) and Garvey et al., *J. Org. Chem.,* 56:436 (1990). Conformationally restricted mimetics of beta turns and beta bulges, and peptides containing them, are described in U.S. Pat. No. 5,440,013, issued Aug. 8, 1995 to Kahn.

Nuclear Magnetic Resonance Analysis of the Catalytic Core Domain of EnvZ

The catalytic core domain of EnvZ assumes α/β sandwich fold: one layer consists of a five-stranded β- sheet (strand B, residues 319–323; D, 356–363; E, 366–373; F, 419–425; G, 429–436) and the other layer comprises three helices (α1, 301–311; α2, 334–343; α4, 410–414) in a topology. The two layers encode an extensive hydrophobic core, augmented b a small anti-parallel β-sheet (strand A, 297–299; C, 330–332) which seals the sandwich at one end. The hydrophobic core consists of the following residues: L301, L305, I309 in helix α1; I319, T321, L323 in strand B; V330, M332 in strand C; I337, V341 in helix α2; I356, V358 in strand D; A367, F369, V371 in strand E; V409, V413 in helix α4; L420 in strand F; I432, A434; L436 in strand G. The sequence conservation of these structurally critical residues are indicative that the histidine kinase domain of other proteins adapt the α/β sandwich fold observed in EnvZ.

The overall fold of the histidine kinase catalytic domain differs significantly from the known structures of protein serine/threonine and tyrosine kinases. The EnvZ histidine kinase domain comprises a single globular fold of 161 residues that has all the functionalities of a protein kinase. Indeed, the present invention provides the identification of this unique and characteristic globular fold of histidine kinases.

A striking feature in this fold is the presence of a long polypeptide segment that extends away from the rest of the molecule (See Example 2, FIG. 5). This segment consists of a short α-helix α3 (380–384) followed by a long loop (385–409) that appears to be a random coil that is highly mobile in solution relative to the overall tumbling motion of the molecule. This characteristic loop, together with helix α3, provides a nucleotide binding site where the phosphorylation catalysis takes place, and is thereby referred to as "catalytic loop" (FIG. 5).

When the corresponding structure was determined in the presence of a nonhydrolysable analog of ATP (AMPPNP) and $Mg^{2+}$ a number of intermolecular NOE interactions between the protein and the adenosine moiety of AMPPNP can be identified. The AMPPNP molecule is mainly surrounded by part of the catalytic loop and helix α3, and also contacts with strand F and helix α4. The AMPPNP adenine is placed in a pocket made of conserved residues such as N343, V346, N347, I378, F387, and I408. In addition to those residues, highly conserved are residues (V345, A348, I356, V371, D373, G375, P376, G377, F390, G401, G403, L404, G405, L406, A407, V409, G418, G429, L438) that also cluster around the AMPPNP binding site. The degree of conservation is even greater than that of the hydrophobic core of the α/β sandwich fold, suggesting that the nucleotide binding site is the most important part of the molecule and that members of the histidine kinase family are a similar nucleotide binding site made of a long loop and a short α-helix. Most remarkably, four glycines (G375, G403, G405, G429) and two asparagines (N343 and N347) in the catalytic core are absolutely conserved and strategically located in the structure, indicating their structural and functional significance. Importantly, the glycine-rich regions, G1 (D373–G377) and G2 (G401–G405), are essential for the kinase activity. G403 and G405, located within G2, are in close spatial proximity to the triphosphate chain of AMP-PNP. G375 in G1 and G429 allow a sharp kink between strand E and helix α3 and between strands F and G, respectively, adjacent to the AMPPNP binding site. N343 and N347 in helix α2 camp the adenine ring of AMPPNP in the binding pocket.

The triphosphate chain and part of the ribose ring are surface exposed, with the terminal phosphate group most accessible to solvent, consistent with its potential to transfer the γ-phosphate to H243 in domain A. It is apparent that the residues in the catalytic loop are the candidates for being active participants in catalysis. For example, R383 and/or K384 could be involved in direct interaction with the triphosphate chain by electrostatic attraction, and E381 might be involved in $Mg^{2+}$ coordination and charge compensation upon binding to domain A.

Protein-Structure Based Design of Agonists and Antagonists of TSHKs and $N_tTSHKs$ Once the three-dimensional structure of an $N_tTSHK$ is determined, a potential drug or agent (antagonist or agonist) can be examined through the use of computer modeling using a docking program such as GRAM, DOCK, or AUTODOCK [Dumbrack et al., 1997, supra]. This procedure can include computer fitting of potential agents to the $N_tTSHK$ to ascertain how well the shape and the chemical structure of the potential ligand will complement or interfere with the dimerization of sub-domain A, or the interaction between sub-domain A and sub-domain B [Bugg et al., Scientific American, Dec.:92–98 (1993); West et al., TIPS, 16:67–74 (1995)]. Computer programs can also be employed to estimate the attraction, repulsion, and steric hindrance of the agent to the dimer-dimer binding site, for example. Generally the tighter the fit (e.g., the lower the steric hindrance, and/or the greater the attractive force) the more potent the potential drug will be since these properties are consistent with a tighter binding constraint. Furthermore, the more specificity in the design of a potential drug the more likely that the drug will not interfere with related mammalian proteins (particularly mammalian transmembrane sensor histidine kinases). This will minimize potential side-effects due to unwanted interactions with other proteins.

Initially a potential drug could be obtained by screening a random peptide library produced by recombinant bacteriophage for example, [Scott and Smith, Science, 249:386–390 (1990); Cwirla et al., Proc. Natl. Acad. Sci., 87:6378–6382 (1990); Devlin et al., Science, 249:404–406 (1990)] or a chemical library. An agent selected in this manner could be then be systematically modified by computer modeling programs until one or more promising potential drugs are identified. Such analysis has been shown to be effective in the development of HIV protease inhibitors [Lam et al., Science 263:380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1:109–128 (1993)].

Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structural analysis disclosed herein and cmputer modeling, a large number of these compounds can be rapidly screened on the computer monitor screen, and a few likely candidates can be determined without the laborious synthesis of untold numbers of compounds.

Once a potential drug (agonist or antagonist) is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential drug may be synthesized de novo. As mentioned above, the de novo synthesis of one or even a relatively small group of specific compounds is reasonable in the art of drug design.

The potential drug can then be tested in any standard binding assay (including in high throughput binding assays) for its ability to bind to a TSHK or fragment thereof, including a $N_tTSHK$. Alternatively the potential drug can be tested for: (1) its ability to modulate (either inhibit or stimulate) the histidine kinase activity of a TSHK or $N_tT$-SHK; (2) its ability to effect (either positively or negatively) the autophosphorylation of the TSHK or $N_tTSHK$; or (3) its ability to effect the phosphoryl transfer from the TSHK or $N_tTSHK$ to its corresponding response regulator. When a suitable potential drug is identified, a second NMR structural analysis can optionally be performed on the binding complex formed between the $N_tTSHK$ and the potential drug. Computer programs that can be used to aid in solving the three-dimensional structure of the $N_tTSHKs$ and binding complexes thereof include QUANTA, CHARMM, INSIGHT, SYBYL, MACROMODE, and ICM, MOLMOL, RASMOL, AND GRASP [Kraulis, J. Appl. Crystallogr. 24:946–950 (1991)]. Most if not all of these programs and others as well can be also obtained from the World Wide Web through the internet.

Using the approach described herein and equipped with the structural analysis disclosed herein, the three-dimensional structures of other transmembrane sensor histidine kinases can also be readily obtained and analyzed. Such analysis will, in turn, allow corresponding drug screening methodology to be performed using the three-dimensional structures of such related TSHK proteins and $N_tTSHKs$.

For all of the drug screening assays described herein further refinements to the structure of the drug will generally be necessary and can be made by the successive iterations of any and/or all of the steps provided by the particular drug screening assay, including further structural analysis by NMR, for example.

Phage libraries for Drug Screening

Phage libraries have been constructed which when infected into host *E. coli* produce random peptide sequences of approximately 10 to 15 amino acids [Parmley and Smith, Gene 73:305–318 (1988), Scott and Smith, Science 249:386–249 (1990)]. Specifically, the phage library can be mixed in low dilution with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and laced in washing solutions to block any remaining absorbent sites. The filters can then be placed in a solution containing, for example, a radioactive $N_t$TSHK (e.g., preferably an $N_t$TSHK having an amino acid sequence comprising SEQ ID NO:14 or SEQ ID NO:12). After a specified incubation period, the filters can be thoroughly washed and developed for autoradiography. Plaques containing the phage that bind to the radioactive $N_t$TSHK can then be identified. These phages can be further cloned and then retested for their ability to bind to the $N_t$TSHK as before. Once the phage has been purified, the binding sequence contained within the phage can be determined by standard DNA sequencing techniques. Once the DNA sequence is known, synthetic peptides can be generated which are encoded by these sequences.

These peptides can be tested, for example, for their ability to e.g., (1) interfere with the dimerization of sub-domain A and/or (2) interfere with phosphorylation of the autophosphorylatable histidine of a TSHK or an $N_t$TSHK and/or (3) interfere with the kinase activity of a TSHK or an $N_t$TSHK; and/or (4) interfere with the phosphoryl transfer of a histidyl phosphate to an aspartyl residue of a response regulator or fragment thereof (e.g., OmpR).

The effective peptide(s) can be synthesized in large quantities for use in in vivo models and eventually in humans to aid in the fight against diseases caused by bacteria. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine,* 10:175–178 (1990)].

Assays for Drug Screening Assays

The drug screening assays of the present invention may use any of a number of means for determining the interaction between an agent or drug and a TSHK or an $N_t$TSHK.

In one such assay, a drug can be specifically designed to bind to a $N_t$TSHK of the present invention through NMR based methodology. [Shuker et al., pi Science 274:1531–1534 (1996) hereby incorporated by reference herein in its entirety.] In one such embodiment, a library of low molecular weight compounds is screened to identify a binding partner for the $N_t$TSHK. Any such chemical library can be used including those discussed herein.

The assay begins with contacting a compound with a $^{15}$N-labeled $N_t$TSHK. Binding of the compound with the $N_t$TSHK can be determined by monitoring the $^{15}$N- or $^{1}$H-amide chemical shift changes in two dimensional $^{15}$H-heteronuclear single-quantum correlation ($^{15}$N-HSQC) spectra upon the addition of the compound to the $^{15}$N-labeled $N_t$TSHK. Since these spectra can be rapidly obtained, it is feasible to screen a large number of compounds [Shuker et al., *Science* 274:1531–1534 (1996)]. A compound is identified as a potential ligand if it binds to the $N_t$TSHK. In a further embodiment, the potential ligand can then be used as a model structure, and analogs to the compound can be obtained (e.g., from the vast chemical libraries commercially available, or alternatively through de novo synthesis). The analogs are then screened for their ability to bind the $N_t$TSHK to obtain a ligand. An analog of the potential ligand is chosen as a ligand when it binds to the $N_t$TSHK with a higher binding affinity than the potential ligand. In a preferred embodiment of this type the analogs are screened by monitoring the $^{15}$N- or $^{1}$H-amide chemical shift changes in two dimensional $^{15}$N-heteronuclear single-quantum correlation ($^{15}$N-HSQC) spectra upon the addition of the analog to the $^{15}$N-labeled $N_t$TSHK as described above.

In another further embodiment, compounds are screened for binding to two nearby sites on an $N_t$TSHK. In this case, a compound that binds a first site of the $N_t$TSHK does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by NMR spectroscopy or X-ray crystallography. On the basis of this structural information, a linked compound is synthesized in which the ligand for the first site and the ligand for the second site are linked. In a preferred embodiment of this type the two ligands are covalently linked. This linked compound is tested to determine if it has a higher binding affinity for the $N_t$TSHK than either of the two individual ligands. A linked compound is selected as a ligand when it has a higher binding affinity for the $N_t$TSHK than either of the two ligand. In a preferred embodiment the affinity of the linked compound with the $N_t$TSHK is determined monitoring the $^{15}$N- or $^{1}$H-amide chemical shift changes in two dimensional $^{15}$N-heteronuclear single-quantum correlation ($^{15}$N-HSQC) spectra upon the addition of the linked compound to the $^{15}$N-labeled $N_t$TSHK as described above.

Any of the $N_t$TSHKs of the invention may be used in this NMR drug screening procedure. In addition, a larger linked compound can be constructed in an analogous manner, e.g., linking three ligands which bind to three nearby sites on the $N_t$TSHK to form a multilinked compound that has an even higher affinity for the $N_t$TSHK than linked compound.

In another assay, a TSHK or $N_t$TSHK is placed on or coated onto a solid support. Methods for placing the peptides or proteins on the solid support are well known in the art and include such things as linking biotin to the protein and linking avidin to the solid support. An agent is allowed to equilibrate with the TSHK or $N_t$TSHK to test for binding. Generally, the solid support is washed and agents that are retained are selected as potential drugs. In a particular embodiment of this type, the $N_t$TSHK comprises the amino acid sequence of SEQ ID NO:12. In another embodiment, the $N_t$TSHK comprises the amino acid sequence of SEQ ID NO:14.

The agent may be labeled. For example, in one embodiment radiolabeled agents are used to measure the binding of the agent. In another embodiment the agents have fluorescent markers. In yet another embodiment, a Biocore chip (Pharmacia) coated with the TSHK or the N$_t$TSHK is used and the change in surface conductivity can be measured.

In yet another embodiment, the affect of a prospective drug (a test compound or agent) on a TSHK or N$_t$TSHK is assayed in a living cell that contains or can be induced to contain a TSHK or N$_t$TSHK, and OmpR. This cell also contains or can be constructed to contain a reporter gene, such as the heterologuous gene for lucerifase, green fluorescent protein, chloramphenicol acetyl transferase or β-galactosidase, operably linked to a promoter that is activated through the histidyl-aspartyl (His-Asp) phosphorelay signal transduction system. The prospective drug is tested under conditions in which the TSHK or N$_t$TSHK has been activated. In one such embodiment, the expression of the TSHK, or N$_t$TSHK is constitutive. The amount (and/or activity) of reporter produced in the absence and presence of prospective drug is determined and compared. Prospective drugs which reduce the amount (and/or activity) of reporter produced are candidate antagonists of the N-terminal interaction, whereas prospective drugs which increase the amount (and/or activity) of reporter produced are candidate agonists.

Cells that naturally encode a TSHK may be used, or alternatively a cell that is transfected with a plasmid encoding the TSHK or an N$_t$TSHK can be used. The cells can also be modified to contain one or more reporter genes, a heterologous gene encoding a reporter such as lucerifase, green fluorescent protein or derivative thereof, chloramphenicol acetyl transferase, β-galactosidase, etc. Such reporter genes can be operably linked to promoters comprising a binding site for a transcription factor under the control of the His-Asp phosphorelay pathway. Assays for detecting the reporter genes products are readily available in the literature. For example, lucerifacse assays can be performed according to the manufacturer's protocol (Promega), and β-galactosidase assays can be performed as described by Ausubel et al. [in *Current Protocols in Molecular Biology*, J. Wiley & Sons, Inc. (1994)]. The preparation of such plasmid containing reporter genes is now routine in the art, and many appropriate plasmids are now commercially available which can be readily modified for such assays. The transmembrane sensor histidine kinase may also be activated by an antibody. Alternatively, a permantively activated N$_t$TSHK can be constitutively expressed.

Labels

Suitable labels include enzymes, fluorophores (e.g., fluorescein isothiocyanate (FITC), phycoerythrin (PE), Texas red (TR), rhodamine, free or chelated lanthanide series salts, especially $EU^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogensae, urease, these and others have been discussed in detail by Eva Engvall in Enzyme Immunoassay ELISA and EMIT in *Methods in Enzymology*, 70:419–439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

The kinase activity of a TSHK or fragment thereof can be determined by many appropriate means including with the aid of an antibody against phospho-histidine or $^{32}P$. Thus the autophosphorylation of the TSHK histidine, and the phosphotransfer to OmpR, and Phospho-OmpR phosphatase activity can be readily determined [Yang, et al., *Proc. Natl. Acad. Sci. USA*, 88, 11057–11061 (1991); and Park et al., *J. Bacteriol.*, 179:4382–4390 (1997), each of which are hereby incorporated by reference in their entireties herein].

General Protein Purification Procedures

The purification of the N-terminal truncated TSHK fragments of the present invention can be performed by any conventional method. One such method employs linking a small peptide to the N$_t$TSHK. The small peptide can be FLAG or H6 for example. In Example 1, below N$_t$TSHKs are prepared containing H6, and are purified using Ni-NTA resin. Similarly an N$_t$TSHK can be constructed as a fusion protein containing a fusion partner which is a protein that binds with specificity to a particular affinity resin. Such a fusion partner can be joined in-frame to the N$_t$TSHK. Preferably the fusion protein also contains a cleavage site for a specific protease, e.g., thrombin or Factor Xa, which is placed at the juncture of the fusion partner and the N$_t$TSHK. After the fusion protein is bound to the affinity resin, and purified, the protease is added to release the N$_t$TSHK from the fusion partner and resin.

Alternatively, classical means of purifying a TSHK or N$_t$TSHK can be performed. Thus, initial steps for purifying the N$_t$TSHKs of the present invention can include salting in or salting out, such as in ammonium sulfate fractionations; solvent exclusion fractionatins, e.g., an ethanol precipitation; detergent extractions to free membrane bound proteins using such detergents as TRITON X-100, TWEEN-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl[2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer, affinity-binding, using, e.g. immuno-binding, using an anitbody to an $N_t$TSHK bound to an activated support. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Materials to perform all of these techniques are available from a variety of sources such as Sigma Chemical Company in St. Louis, Mo.

Antibodies to the N-terminal Truncated TSHK Fragments

According to the present invention, the N-terminal truncated TSHK fragment as produced by a recombinant source, or through chemical synthesis, or through the modification of a TSHK isolated from natural sources; and derivatives or analogs thereof, including fusion proteins, may be used as an immunogen to generate antibodies that specifically recognize the $N_t$TSHKs and not TSHK itself. Such antibodies include but are not limited to polyclonal, monocolonal, chimeric, single chain, Fab fragments, and a Fab expression library. The antibodies of the invention may be cross reactive, that is, they may recognize the $N_t$TSHKs derived from a different natural TSHK. Polyclonalanitbodies have greater likelihood of cross reactivity. Alternatively, an antibody of the invention may be specific for a single form of an $N_t$TSHK, such as the $N_t$TSHK having an amino acid sequence of SEQ ID NO:12 or SEQ ID NO:14.

Various procedures known in the art may be used for the production of polyclonal antibodies to the $N_t$TSHK or derivative or analog thereof. For the production of anitbody, various host animals can be immunized by injection with the $N_t$TSHK, or a derivative (e.g., or fusion protein) thereof, including but not limited to rabbits, mice, rats, sheep, goats, etc. In one embodiment, the $N_t$TSHK can be conjugated to an immunogenic carrier, e.g., bovine serum albumin (BSA) or keyhold limpet hemocyanin (KLH). Various adjuvants may be used to increase the immunological response, depending on the host species, including but not limited to Freund's (complete and incomplete), mineral gels such as aluminum hydroxide, safe active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monocolonal antibodies directed toward the $N_t$TSHK of the present invention, or analog, or derivatives thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today,* 4:72 (1983); Cote et al., *Proc. Natl. Acad. Sci. U.S.A.,* 80:2026–2030 (1983)], and the EBV-hybridoma technique to produce human monoclonal antibodies [Cole et al., in *Monoclonal Antibodies and Cancer Therapy,* Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604–608 (1984); Takeda et al., *Nature,* 314:452–454 (1985)] by splicing the genes from a mouse antibody molecule specific for an $N_t$TSHK together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce $N_t$TSHK-specific single chain antibodies. An additional embodiment of the invention utilizes the techniques described for the construction of Fab expression libraries [Huse et al., *Science,* 246:1275–1281 (1989)] to allow rapid and easy identification of monoclonal Fab fragments with the desired specificity for an $N_t$TSHK, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in suit immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the $N_t$TSHK and not TSHK, one may assay generated hybridomas for a product which binds to the $N_t$TSHK containing such epitope and choose those which do not cross-react with TSHK. For selection of an antibody specific to the fragment from a particular source, one can select on the basis of positive binding with the $N_t$TSHK expressed by or isolated from that specific source.

The foregoing antibodies can be used in methods known in the art relating to the localization and activity of the $N_t$TSHK, e.g., for Western blotting, imaging the fragment in situ, measuring levels thereof in appropriate physiological samples, etc. using any of the detection techniques mentioned herein or known in the art.

In a specific embodiment, antibodies that agonize or antagonize the activity of $N_t$TSHK can be generated. Such antibodies can be tested using the assays described infra for identifying agents or potential drugs.

The present invention may be better understood by reference to the following non-limiting Examples, which are provided as exemplary of the invention. The following examples are presented in order to move fully illustrate the preferred embodiments of the invention. They should in no way be construed, however, as limiting the broad scope of the invention.

EXAMPLES

Example 1
TWO-DOMAIN RECONSTITUTION OF A FUNCTIONAL PROTEIN HISTIDINE KINASE
Introduction
*Escherichia coli* possess a large number of transmembrane sensors for cellular adaption to various environmental stresses. With the notable exception of certain sensors that are involved in chemotaxis, most bacterial sensors are transmembrane histidine kinase sensors that contain a cytoplasmic signaling domain having histidine kinase activity. Such transmembrane sensor histidine kinases are part of a histidyl-aspartyl (His-Asp) phosphorelay signal transduction pathway, which recently has been reported also to exist in eukaryotic cells [Egger et al., *Genes to Cells*, 2:167–184 (1997); Appelby et al., *Cell*, 86:845–848 (1996); Inouye, *Cell.*, 85:13–14 (1996); Parkinson and Kofoid, *Ann, Rev. Gen.*, 26:71–112 (1992); Stock et al., *Microbiol. Rev.*, 53:45–490 (1989)].

Autophosphorylation of sensor histidine kinases, which is an obligatory step for the phosphorylation their corresponding response regulators, occurs through a bimolecular transphosphorylation reaction. This has been surmised on the basis of complementation experiments with two defective mutants of EnvZ, a transmembrane osmosensor of *E. coli* and Taz1, a hybrid sensor between Tar and EnvZ [Yang et al., *Proc. Natl. Acad. Sci. USA*, 88:11057–11061 (1991) and Yang et al., *J. Mol. Biol.*, 231:335–342 (1993)]. Tar is a chemosensor for aspartate which may be able to transduce a signal within a single cytoplasmic domain [Gardina et al., *Science*, 274:425–426 (1996) and Tatsuno et al., *Science*, 274:423–425 (1996)]. In the case of Taz1, asymmetric binding of its ligand, aspartate, at the interphase of two Taz1 receptor domains in a dimer has been shown to modulate the function of the cytoplasmic signaling domain in the dimer [Yang et al., *J. Mol. Biol.* 232:493–498 (1993); Milburn et al., *Science*, 254:1342–1347 (1991) and Jin et al., *J. Mol. Biol.*, 232:484–492 (1993)]. Autophosphorylation of other histidine kinases also has been shown to occur by a transphosphorylation reaction [Uhl et al., *EMBO J.*, 15:1028–1036 (1996); Pan et al., *Proc. Natl. Acad. Sci. USA*, 90:9939–9943 (1993); Ninfa et al., *J. Bacteriol*, 175:7024–7032 (1993); Swanson et al., *Mol. Microbiol*, 8:435–441 (1993); Swanson et al., *Biochem.*, 32:7623–7629 (1993) and Surette et al., *J. Biol. Chem.*, 271:939–945 (1996)].

EnvZ, a transmembrance histidine kinase osmosensor of *E. coli* interacts with the response regulator, OmpR. OmpR functions as a transcription factor for the outer membrane porin genes, ompC and ompF [Aiba et al., *J. Biol. Chem.*, 64:8563–8567 (1989) and Delgado et al., *Mol. Microbiol.*, 10:1037–1047 (1993)]. EnvZ consists of the periplasmic putative receptor domain from residue 48 to 162, which is anchored in the cytoplasmic membrane with two transmembrane domains (TM1, residue 16 to 47; and TM2, residue 163 to 179) [Forst et al., *J. Biol. Chem.*, 262:16433–16438 (1987)]. The second membrane segment is connected to the cytoplasmic signaling domain (residue 180 to 450), which is the portion of the EnvZ polypeptide that contains the histidine kinase activity. This domain undergoes autophosphorylation at His243 with ATP [Roberts et al., *J. Biol. Chem.*, 269:8728–8733 (1994)]. the phosphate group is subsequently transferred to Asp55 of OmpR.

The EnvZ signaling domain performs dual enzymatic functions, one as a kinase for OmpR and the other as a phosphatase for phosphorylated OmpR. The ratio of kinase and phosphatase activities is believed to control the level of phosphorylated OmpR [Igo et al., *Gen. And Dev.*, 3:1725–1734 (1989); Tokishita et al., *J. Biochem.*, 108:488–493 (1990) and Park et al., *J. Bacteriol.*, 179:4382–4390 (1997]. However, the precise regulatory mechanism for controlling the functional activity of EnvZ is yet to be elucidated.

As presented herein, the cytoplasmic signaling domain of EnvZ can be further divided into two distinct sub-domains, sub-domain A (67 residues) and sub-domain B (161 residues). These subdomains complement their respective abilities to phosphorylate OmpR. Furthermore, the two-domain structure of the histidine kinase disclosed herein provides crucial information in the determination of the structural arrangement of the transmembrane histidine kinase sensors that are involved in the unique His-Asp pathway.

Materials and Methods

Strains and Plasmids: *E. coli* B BL21-DE3 (F-ompTrBmB) was used for the expression and purification of wild-type and mutant EnvZ(C) proteins [Park et al., *J. Bacteriol.*, 179:4382–4390 (1997)]. Construction of plasmid pET11a-EnvZ(C) was described as elsewhere [Park et al., *J. Bactriol.*, 179:4382–4390 (1997)]. pET11a-EnvZ(C) ΔL which contains the EnvZ sequence encoding residues Met223 to Gly450 was constructed by the digestion of pET11a-EnvZ(C) with NdeI followed by self-ligation. A linker, $^{5'}$TATGCACCATCACCATCACCA$^{3'}$ (SEQ ID NO: 15)

$^{3'}$ACGTGGTAGTGGTAGTGGTAT$^{5'}$ (SEQ ID NO: 16)

was inserted at the NdeI site of pET11a-EnvZ(C) ΔL, generating pPH006 which encodes H6-EnvZ(C) ΔL. The construct was confirmed by DNA sequencing (Sequenase, USB). The 1.4-kb XbaI—EcoRI fragment from pPH006 was used for site-directed mutagenesis to create a stop codon at either Thr397, or Thr290. For this purpose, $^{5'}$AGTGCGCGCTGAATTAGCGG$^{3'}$ (SEQ ID NO: 17), and $^{5'}$TACCTGCGCTAAGGGCAGGAC$^{3'}$ (SEQ ID NO: 18)

oligomers were used, respectively. After confirming the mutations by DNA sequencing, the 1.4-kb XbaI-EcoRl fragments containing the mutations were subcloned back into pPH006. Thus the plasmid designated pPH007 for Thr398 (ACC)→(TGA) which encodes H6-EnvZ(C)ΔG2, and pPH009 for Thr290 (ACC)→(TAA) which encodes H6-EnvZ(C)(223–289), respectively. pET11a-EnvZ(C) (223–289) was obtained by digestion of pPH009 with NdeI followed by self-ligation. For the construction of plasmid pET11a-EnvZ(C)(290–450) containing the EnvZ sequence from Thr290 to Gly450, PCR was carried out with primer 7109 (5'CGCATATGACCGGGCAGGAG3', SEQ ID NO: 19) that contained an NdeI site to substitute Arg289 (CGC) with Met (ATG), and primer 4163 (5'TCGGATCCCGTTATTTAC3', SEQ ID NO: 20) containing a BamHI site downstream of Gly450 codon. pET11a-EnvZ(C)ΔL was used as the template. The 507-bp PCR fragment thus obtained was digested with NdeI and BamHI and subcloned into the pET11a-EnvZ(C) ΔL vector cut with NdeI and BamHI. The sequence of PCR product was confirmed by DNA sequencing as previously described [Part et al., *J. Bacteriol*, 179:4382–4390 (1997)].

Biochemical Assays of EnvZ and EnvZ(C) Constructs: Autophosphorylation, phosphotransfer to OmpR, an Phospho-OmpR phosphatase activity were determined essentially in the same way as was carried out previously [Yang, et al., *Proc. Natl. Acad. Sci. USA*, 88,11057–11061 (1991) and Part et al., *J. Bacteriol.*, 179:4382–4390 (1997), each of which are hereby incorporated by reference in their entireties herein]. The phosphorylated OmpR was prepared as follows. The membrane fraction containing EnvZ-T247R (Kinase+/Phosphatase) was first phosphorylated with 50 µCi [γ-$^{32}$P]ATP in 200 µl of buffer A for 20 minutes at room temperature. The reaction mixture was centrifuged at 393, 000×g for 14 minutes at 4° C. using a Beckman TL100 ultracentrifuge.

The membrane pellet was washed five times with 200 µl of buffer A, sonicated, and then re-suspended in the same buffer. Purified OmpR protein was incubated with the membrane fraction containing phosphorylated EnvZ-T247R for 20 minutes at room temperature in order to allow phosphotransfer to OmpR. After incubation, the reaction mixture was centrifuged at 393,000×g for 14 minutes at 4° C. to remove the membrane containing EnvZ-T247R. The supernatant containing phospho-OmpR was then applied onto a G-50 gel filtration column in order to remove residual [γ-$^{32}$P]ATP and inorganic phosphate [$^{32}$Pi]. Each fraction was analyzed by thin-layer chromatography to confirm that the phospho-OmpR preparation was not contaminated with [γ-$^{32}$P]ATP or inorganic phosphate [$^{32}$Pi]. The fractions containing only phospho-OmpR were pooled and total OmpR protein, concentration was measured by the Bio-Rad protein concentration assay. During the preparation, protein solutions were kept on ice.

Binding Assay on Ni-NTA Resin: Purified proteins, EnvZ (C)(223–289) plus either H6-EnvZ(C)wt or H6-EnvZ(C) (223–289) were mixed in 20 µl of buffer I [50 mM sodium-phosphate buffer (pH7.8), 0.3 M NaCl, 5% glycerol] at room temperature for 30 minutes, and 10 µl of Ni-NTA resin (50% v/v) was added to the protein mixture followed by a 30 minute incubation on ice. After washing three times with buffer II [50 mM sodium-phosphate buffer (pH 6.0), 0.3 M NaCl, 5% glycerol] using ultrafree-MC centrifugal filters (Millipore Corp.), proteins bound to Ni-NTA resin were eluted with 0.2 M imidazole/buffer II. The binding experiments between OmpR and either H6-EnvZ(C)wt or H6-EnvZ(C)(223–289) were carried out as described previously [Hidaka et al., *FEBS LET.*, 400:238–242 (1997), hereby incorporated by reference in its entirely herein]. The proteins eluted with 0.2 M imidazole/buffer II in each binding assay were subjected to 20% SDS-PAGE followed by silver staining [Sambrook et al., *Molecular Cloning: A Laboratory Manual*, 18.56–18.57 (1989)].

Circular Dichroism Spectral Analysis: The CD spectrum was obtained using a Aviv Model 62DS spectropolarimeter at 25° C. Far-UV CD spectra (200 nm–250 nm) of EnvZ (C)(223–289) and Env(C)(290–450) in sodium phosphate buffer [50 mM sodium phosphate (pH 7.4), 0.3 M KCl, and 1 mM PMSF] was measured in a cuvette with a 1-cm path length. Protein concentrations of EnvZ(C)(223–289) and Env(C)(289–450) were 0.338 mg/ml and 0.118 mg/ml, respectively. These values were determined by Absorbance readings at 280 nm and calculated based on protein molar extinction coefficients which are 2680 for EnvZ(C) (223–289) and 20910 for EnvZ(C)(290–450) [Gill et al., *Analytical Biochem.*, 182:319–326 (1989)].

Analytical Size Exclusion Chromatography and Light Scattering: Gel filtration chromatography of the purified EnvZ(C)(223–289) or EnvZ(C)(290–450) protein was accomplished by HPLC (model 110B, Beckman) using a TSK-GEL column (TosoHaas). Protein samples and standard marker proteins were loaded in an equal volume (0.2 ml) to the column pre-equilibrated with buffer [20 mM Tris-HCl (pH 8.0), 350 mM ammonium acetate, 200 mM NaCl, 2 mM DTT, 10% glycerol, 100 mM sodium azide, and 1 mM PMSF] at a flow rate of 0.5 ml/min. The absorbance of the fractions were monitored at 280 nm, and fractions at each peak were pooled. The void volume of the column was determined using blue dextran 2000. For light scattering experiment, EnvZ(C)(223–289) (6.5 mg/l) and EnvZ(C) (290–450) (4.5 mg/l) proteins were analyzed with a DanaPro-901 dynamic light scattering instrument, and the molecular weights of each protein were determined by using the AutoPro software.

Results

Figure 1A:
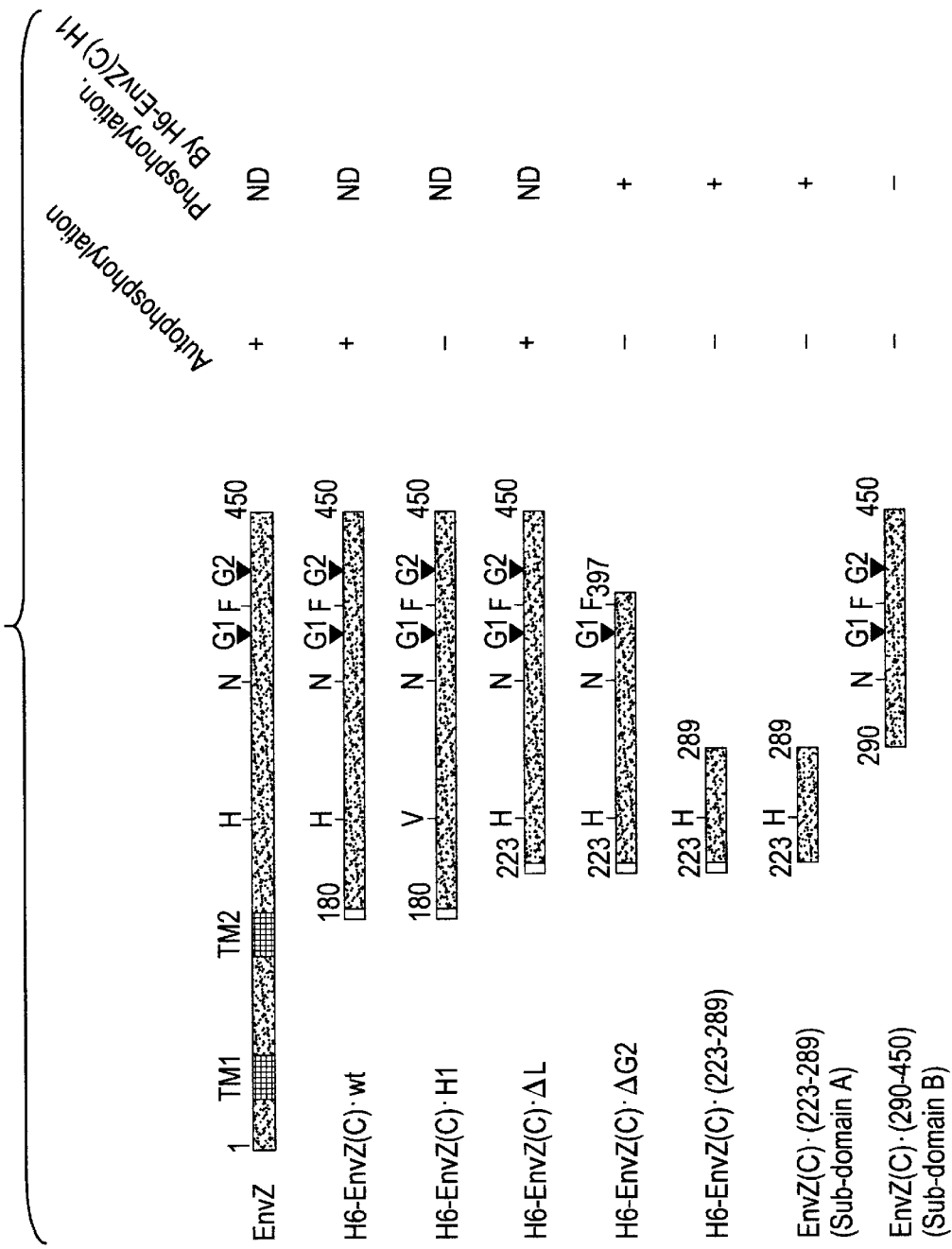
FIGS. 1A–1C shows the purification and autophosphorylation of various EnvZ(C) fragments.

The kinase activity of the cytoplasmic domain of EnvZ was initially analyzed (residue 180 to 450). This domain retained the kinase activity even when it was detached from TM2 (FIG. 1A). The cytoplasmic domain was further truncated by deleting the so-called linker region between residue 180 to 222, resulting in EnvZ(C)ΔL(FIG. 1A). This truncated domain still retained both the kinase and phosphatase activities of the holoprotein (FIG. 1C, lane 3 and FIG. 2B, respectively) [Part et al., *J. Bacteriol.* 179:4382–4390 (1997)]. The resulting 228-residue EnvZ fragment has been shown to contain all of the features that are highly conserved in the histidine kinases [Egger et al., *Genes to Cells*, 2:167–184 (1997); Appleby et al., *Cell*, 86:845–848 (1996); Inouye et al., *Cell*, 85:13–14 (1996); Parkinson et al., *Ann. Rev. Gen.*, 26:71–112 (1992); and stock et al., *Microbiol. Rev.*, 53:450–490 (1989)], His243 (autophosphorylation site), Asn347, Phe387, and the two Gly-rich boxes, G1 (DXGXG; 373 TO 377) and G2 (GXG; 403 TO 405) (See FIG. 1A).

Figure 1B:
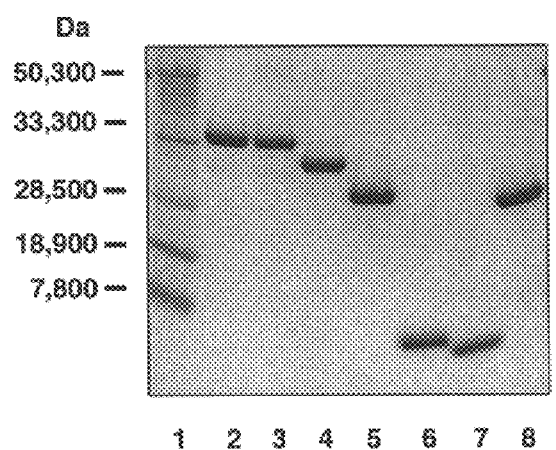
Figure 2A:
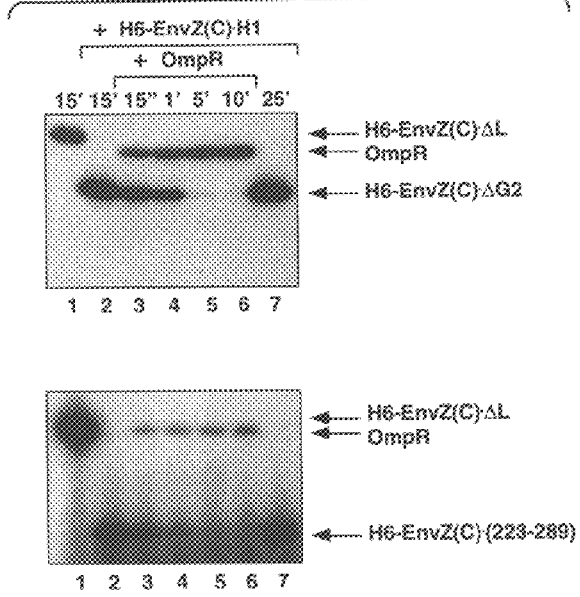
FIGS. 2A–2B shows the enzymatic assay of various EnvZ(C) fragments.
Figure 2B:
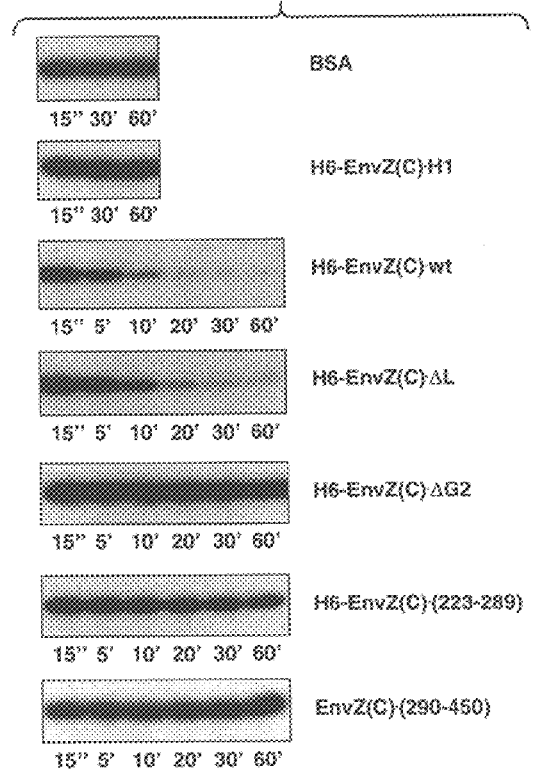

In order to further dissect structural domains of H6-EnvZ (C)ΔL [6 histindine residues were tagged at the N-terminal end of EnvZ(C)ΔL], the smallest kinase, a limited tryptic digestion was carried out. The mass spectrometer analysis of the tryptic fragments revealed that there are two major cleavage sites, one at Arg289 and the other at Arg397. The latter site is located between the G1 and G2 boxes. Thus, two N-terminal fragments, one from residue 223 to 397 [H6-EnvZ(C)ΔG2] and the other from residue 223 to 289 [H6-EnvZ(C)(223–289) or EnvZ(C)(223–289)] were generated (See FIGS. 1A and 1B). As evident from the enzymatic assays, it was determined that not only H6-EnvZ(C)ΔG2 but also H6-EnvZ(C)(223–289), which consists of only 67 residues, were transphosphorylated by H6-EnvZ(C)H1 (FIG. 2A; lanes 2 and 7). H6-EnvZ(C)H1, an EnvZ truncated fragment in which the autophosphorylation site of His 243 is replaced with Val, is known to transphosphorylate EnvZ fragments deficient in kinase activity, even through it is obviously unable to phosphorylate itself [Yang et al., *Proc. Natl. Acad. Sci. USA*, 88:11057–11061 (1991) and Yang et al., *J. Mol. Biol.*, 231:335–342 (1993)]. Furthermore, such N-terminal fragments of H6-EnvZ(C)H1 were able to phosphorylate OmpR (FIG. 2A, lanes 3 to 6). Interestingly these fragments no longer possess the corresponding phosphatase activity (FIG. 2B). A further attempt to obtain a shorter fragment having kinase activity, such as the fragment from Met223 to Lys272, proved unsuccessful.

Figure 1C:
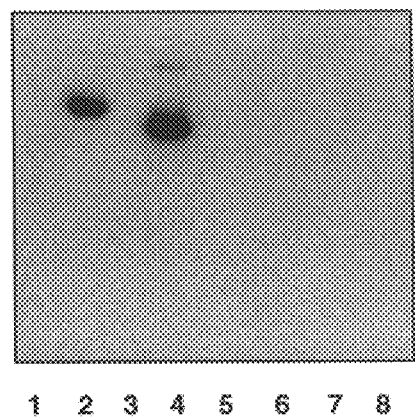
Figure 3A:
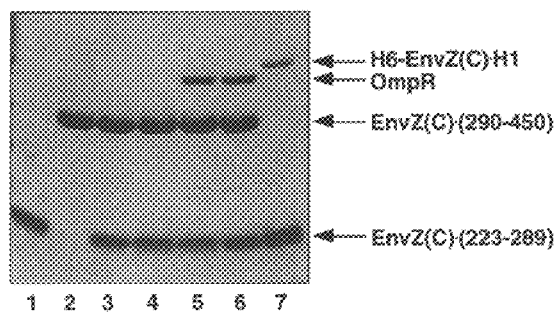
FIG. 3A–3B shows the recovery of kinase activity by complementation between EnvZ(C)(223–289) and EnvZ(C) (290–450). EnvZ(C)(223–289) (lane 1) or EnvZ(C) (290–450) (lane 2) ($1.2 \times 10^{-5}$M) was incubated with 0.5 $\mu$Ci of [$\gamma$-$^{32}$P]ATP for 20 minutes. For trans-autophosphorylation of EnvZ(C)(223–289)($1.2 \times 10^{-5}$M) by EnvZ(C)(290–450) ($1.2 \times 10^{-5}$M), two proteins were incubated with 0.5 $\mu$Ci of [$\gamma$-$^{32}$P]ATP for 5 minutes (lane 3) and 20 minutes (lane 4). For the phosphotransfer reaction to OmpR, EnvZ(C) (223–289, SEQ ID NO:12) ($1.2 \times 10^{-5}$M) was first trans-autophosphorylated by EnvZ(C)(290–450, SEQ ID NO:14) ($1.2 \times 10^{-5}$M) with 0.5 $\mu$Ci of [$\gamma$-$^{32}$P]ATP for 5 minutes (lane 3), then OmpR ($2.4 \times 10^{-5}$M) was added into the trans-autophosphorylation mixture and the mixture was incubated for another 15 seconds (lane 5) and 15 minutes (lane 6). Lane 7 shows trans-autophosphorylation of EnvZ(C) (223–289) ($1.2 \times 10^{-5}$M) by H6-EnvZ(C)H1 ($2.4 \times 10^{-6}$M) with 0.5 $\mu$Ci of [$\gamma$-$^{32}$P]ATP for 5 minutes. All reactions were conducted at room temperature in 20 $\mu$l of buffer A and stopped by adding 5×SDS gel loading buffer. Samples were then subjected to SDS-PAGE using a 16% Tricine gel (Novex), followed by staining with Coomassie brilliant blue FIG. 3A and autoradiography FIG. 3B.
Figure 3B:
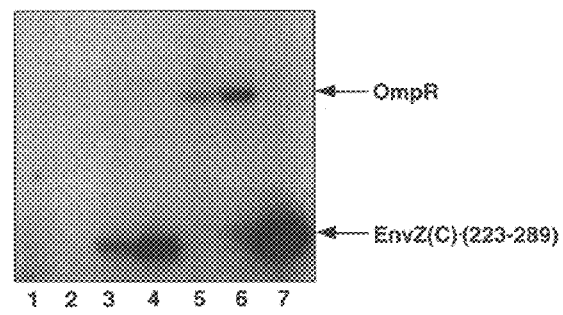

These results indicate that EnvZ(C)ΔL can be divided into two sub-domains, A and B, severed at Arg 289: EnvZ(C) (223–289), subdomain A, and EnvZ(C)(290–450), subdomain B. Both sub-domains can be expressed as stable soluble proteins (FIG. 1B, lanes 7 and 8, respectively). Although sub-domain B had neither autophosphorylation activity (FIG. 1C, lane 8) nor phosphatase activity (FIG. 2B), it was able to phosphorylate sub-domain A when sub-domains A and B were mixed in the presence of ATP (FIGS. 3A and 3B, lanes 3 and 4). Furthermore, when the response regulator, OmpR, was added to the mixture, it was phosphorylated in a time-dependent manner (FIGS. 3A and 3B, lanes 5 and 6). In comparison with the transphosphorylation of sub-domain A with H6-EnvZ(C)H1 (FIGS. 3A and 3B, lane 7), the phosphorylation activity was approximately 5% with sub-domain B.

Figure 4A:
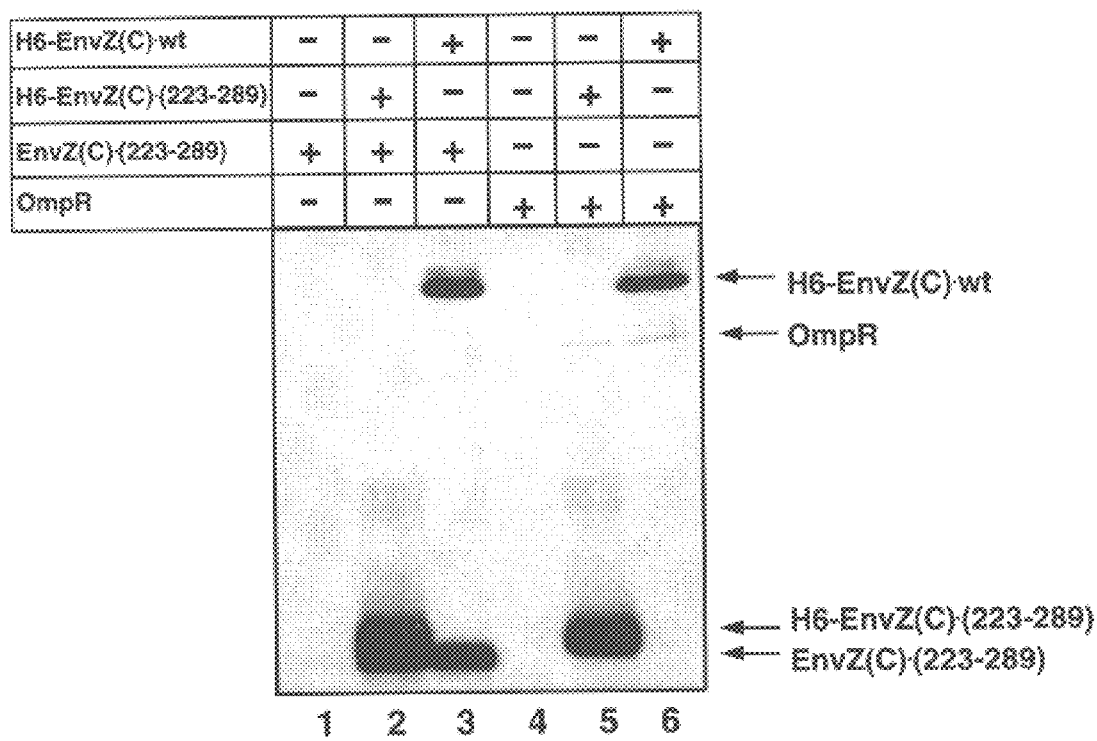
In FIG. 4A the purified proteins were mixed at room temperature for 30 minutes (lanes 1, 2 and 3) or 60 minutes (lanes 4, 5 and 6) in 20 $\mu$l of buffer I [50 mM Na-Phosphate (pH 9.0), 0.3 M NaCl, and 5% glycerol], 10 $\mu$l of Ni-NTA resin (50% v/v, Qiagen) equilibrated with buffer I was added, followed by further incubation for 30 minutes on ice. After washing three times with buffer II [50 mM Na-phosphate (pH 6.0), 0.3 M NaCl, and 5% glycerol], proteins bound to Ni-NTA resin were eluted by 0.2 M imidazole in buffer II. Proteins thus eluted were subjected to 20% SDS-PAGE and the gel was stained by silver staining. Lane 1, EnvZ(C)(223–289, SEQ ID NO:12) ($2.5 \times 10^{-5}$M); lane 2, H6-EnvZ(C) (223–289 of SEQ ID NO:2) and EnvZ(C)(223–289, SEQ ID NO:12) ($2.5 \times 10^{-5}$M each); lane 3, H6-EnvZ(C)wt and EnvZ(C) (223–289, SEQ ID NO:12) ($2.5 \times 10^{-5}$M each); lane 4, OmpR ($6.1 \times 10^{-6}$M); lane 5, OmpR ($6.1 \times 10^{-6}$M) and H6-EnvZ(C)(223–289) ($2.5 \times 10^{-5}$M); and lane 6, OmpR ($6.1 \times 10^{-6}$M) and H6-EnvZ(C)wt($2.5 \times 10^{-5}$M).

Circular dichroism analysis of sub-domain A showed a high α-helical content (55%), while sub-domain B had both α-helix (29%) and β-sheet (26%). Sub-domain A was found to be a dimer by Ni-NTA resin chromatography [Hidaka et al., FEBS Lett. 400:238–242 (1997)]. Sub-domain A binds to the resin only when it contains a His-tag, i.e., [H6-EnvZ (C)(223–289)] (compare lane 1 and lane 2 in FIG. 4A). Sub-domain A also binds to H6-EnvZ(C)wt (lane 3) as anticipated from FIG. 2A. Since it has been demonstrated that EnvZ(C) is a dimeric protein [Roberts et al., *J. Biol. Chem.*, 269:8728–8733 (1994) and Hidaka et al., *FEBS Lett.*, 400:238–242 (1997)], the present results indicate that the region required for the dimer formation resides in the 67-residue of sub-domain A. This domain further contains the region required for OmpR interaction, since the response regulator, OmpR, was trapped on the resin only in the presence of His-tagged sub-domain A (compare land 4 and 5 in FIG. 4A). Note that the amount of OmpR bound to the resin in lane 5 is comparable to that found with H6-EnvZ (C)wt shown in lane 6. Consistent with this finding, when purified phosphorylated sub-domain A was mixed with OmpR, the phosphoryl group could be efficiently transferred to OmpR in the absence of sub-domain B.

Figure 4B:
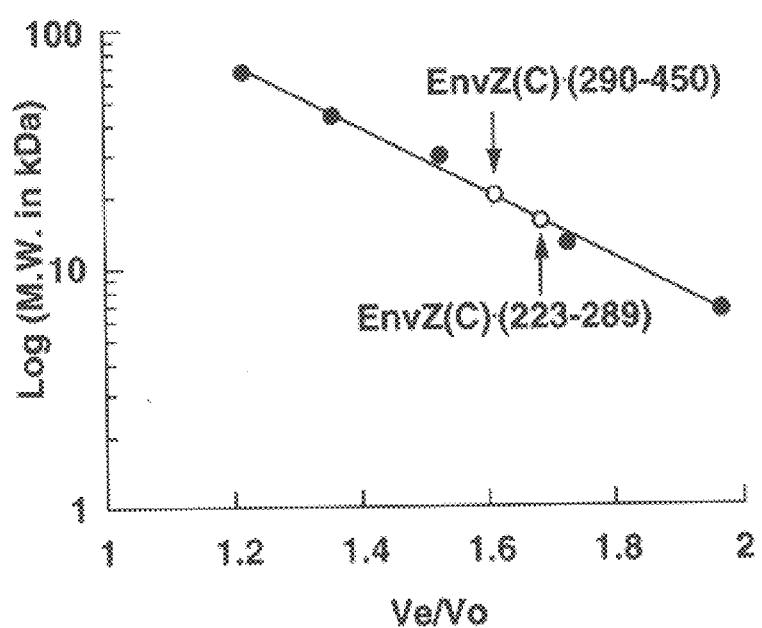
FIG. 4B shows the gel filtration profiles of EnvZ(C)(223–289) and EnvZ(C)(290–450). The migrations of EnvZ(C)(223–289, SEQ ID NO:12) and EnvZ(C)(290–450 SEQ ID NO:14) were analyzed by using a TSK-GEL column (TosoHaas) equipped with HPLC system (model 110B, Beckman). The standard proteins are indicated as closed circles; bovine serum albumin (66,000 Da), ovalbumin (43,000 Da), carbonic anhydrase (29,000 Da), cytochrome C (12,400 Da) and CspA (7,400 Da). The proteins of EnvZ(C)(233–289, SEQ ID NO:12) and EnvZ(C)(290–450, SEQ ID NO:14) are indicated by open circles and arrows. The Y-axis represents the molecular weight (Da) in a log scale. The X-axis represents the ratio of the elution volume of sample (Ve) to the void volume (Vo).

The conclusion that sub-domain A forms a dimer was further confirmed by size exclusion chromatography. The molecular weight of sub-domain A was determined to be about 19.9 kDa by gel filtration (FIG. 4B). In addition, light scattering data showed it to be about 20 kDa. These results are fully consistent with sub-domain A (calculated molecular weight, 7.6 kDa) being a dimer in solution. In direct contrast, the molecular weight of sub-domain B (calculated molecular weight, 17.6 kDa) was determined to be 21.6 kDa (FIG. 4b) and 26.5 kDa by gel filtration and light scattering respectively, indicating that sub-domain B exists as a monomer in solution.

Discussion

Identification of the dimerization of domain together with the fact that autophosphorylation occurs via transphosphorylation between two kinase molecules indicates that signal transduction by histidine kinases is carried out through obligatory bimolecular transphosphorylation reaction within the dimer. The two EnvZ signaling domains in the dimer apparently assemble symmetrically in such a way as to allow the autophosphorylation domain (sub-domain A) of one monomer to interact with the catalytic domain (sub-domain B) of the other monomer. Thus, sub-domain A serves as the substrate for sub-domain B kinase activity.

Despite having a number of similarities, transmembrane signal transduction by histindine kinases cannot be carried out through a single cytoplasmic signaling domain, [Utsumi et al., *Science*, 245:1246–1249 (1989) and Baumgartner et al., *J. Bacteriol.*, 176:1157–1163 (1994)], as is apparently true for methyl accepting chemotaxis receptors (MCPs) [Gardina et al., *Science*, 274:425–426 (1996) and Tatsuno et al., *Science*, 274:423–425 (1996)].

Previously it has been suggested that the kinase activity of the transmembrane sensor histidine kinase is independent of ligand concentration, whereas the corresponding phosphatase activity is inhibited by an increase in the ligand concentration [Jin et al., *J. Mol. Biol.*, 232:484–492 (1993)]. An explanation for this phenomena within the context of the results disclosed herein, may be that such high ligand concentrations stimulate the interaction of sub-domain A with sub-domain B to directly inhibit the phosphatase activity, or alternatively, to inhibit the binding of phospho-OmpR to the sub-domain A:B complex. Indeed, as disclosed herein, the phosphatase activity appears to be very sensitive to the structural arrangement of the signaling domain, since the phosphatase activity could not be detected in the complementation experiment with sub-domains A and B.

Example 2

A NOVEL PROTEIN KINASE FOLD IN *ESCHERICHIA COLI* OSMOSENSOR ENVZ

Introduction

The His-Asp phosphorelay signal transduction system (so-called two-component system) plays a major role in cellular adaptation to growth conditions and environmental changes in prokaryotes [Egger et al., *Genes to Cells*, 2:167–184 (1997); Wurgler-Murphy and Saito, *Trends. in Biochem. Sci.*, 22:172–176 (1997)]. In this system, protein histidine kinases function as sensors or as signal transducers. There are 100 examples of His-Asp phosphorelay or two-component systems in bacteria, and 17 such systems have been biochemically characterized in *E. coli* [Egger et al., *Genes to Cells*, 2:167–184 (1997)]. In the gram-negative bacterium *Salmonella typhimurium*, the PhoP/PhoQ two-component system appears to be essential for virulence in host organisms [Soncini and Groisman, *J. Bacteriol.*, 178:6796–6801 (1996)]. Since all two-component systems contain a conserved histidine kinase domain and the His-Asp phosphorelay system has never been found in mammalian cells, histidine kinases are excellent targets for antimicrobial action [Dziejman and Mekalanos, in *Two-Component Signal Transduction*, Eds. J. A. Hock and T. J. Silhavy, ASM Press, Washington, D.C., pp. 25–52 (1995)].

In spite of their importance in cellular functions and as a possible target for antibiotics, the three-dimensional structure of protein histidine kinases has remained unknown. *E. coli* osmosensor EnvZ is a transmembrane receptor of which cytoplasmic signalling domain is a histidine kinase. As disclosed above (Example 1) this domain can be dissected into two functional subdomains A and B; subdomain A (67 residues) contains the essential histidine residue for autophosphorylation and transphosphorylation, and subdomain B (161 residues) contains all the other highly conserved residues. In the presence of ATP, subdomain B exhibits kinase activity to phosphorylate subdomain A. The phosphoryl group is subsequently transferred to OmpR, the response regulator for EnvZ. As disclosed herein, using heteronuclear multidimensional NMR spectroscopy the solution structure of subdomain B, the catalytic domain of EnvZ is determined. The structure reveals a novel protein kinase fold distinct from the previously known protein kinase fold found in eukaryotic protein serine/theonine and tyrosine kinases.

Methods

NMR Spectroscopy and Structure Calculations: NMR spectra were recorded at 23° C. using Varian Unity Plus 500 and unity 600 spectrometers, each equipped with a pulsed-field gradient triple resonance probe as analyzed as described in Bagby et al., [*Cell* 82:857–867 (1995)] hereby incorporated by reference in its entirely. Sequential resonance assignments of backbone $^1H$, $^{15}N$, and $^{13}C$ atoms were made using a combination of triple resonance experiments similar to those previously described [Bagby et al., *Biochemistry*, 33:2409–2421 (1994a)], except with enhanced sensitivity [Muhandiram and Kay, *J. Magn. Reson.*, 103: 203–216 (1994)] and minimal $H_2O$ saturation [Kay et al., *J. Magn. Reson.*, 109:129–133 (1994)]. Side chain $^1H$ and $^{13}C$ assignments were made using HCCH-TOCSY [Bax et al., *J. Magn. Reson.*, 87:620–627 (1990)] experiments with mixing times of 8 ms and 16 ms.in solution and were not included in structure calculations. Nuclear Overhauser effect (NOE) cross peaks in two-dimensional $^1H$—$^1H$ NOE spectroscopy (NOESY), three-dimensional $^{15}N$-edited NOESY-HSQC [Zhang et al., *J. Biomol, NMR*, 4:845–858 (1994)] and three-dimensional simultaneous acquisition $^{15}N/^{13}C$-edited NOE [Pascal et al., *J. Magn. Reson.*, 103:197–201 (1994)] spectra were obtained with 100 ms NOE mixing times. Standard pseudo-atom distance corrections [Wüthrich et al., *J. Mol. Biol.*, 169:949–961 (1983)] were incorporated to account for center averaging. An additional 0.5 Å was added to the upper limits for distances involving methyl groups [Wagner et al., *J. Mol. Biol.*, 196:611–639 (1987); Clore et al., *Biochemistry*, 26:8012–8023 (1987)].

The structures can be calculated using a simulated annealing protocol [Nilges et al., In *computational Aspects of the Study of Biological Macromolecules by Nuclear Magnetic Resonance Spectroscopy*, J. C. Hoch, F. M. Poulsen, and C. Redfield, eds., New York: Plenum Press, pp. 451–455 (1991] within X-PLOR [Brünger, X-PLOR Manual, Version 3.1, New Haven, Conn.: Department of Molecular Biophysics and Biochemistry, Yale University (1993] using the previously described strategy [Bagby et al., *Structure*, 2:107–122 (1994b)]. Structural coordinates are reported in FIG. 8 and FIGS. 9. Interhelical anges were calculated using an in-house program written by K. Yap. Accessible surface areas were calculated using the program Naccess, available from Prof. J. Thornton, University College, London.

Results

The catalytic core domain of EnvZ (FIG. 5) assumes an α/βsandwich fold: one layer consists of a five-stranded β-sheet (strand B, residues 319–323; D, 356–363; E, 366–373; F, 419–425; G, 429–436) and the other layer comprises three helices (α1, 301–311; α2, 334–343; α4, 410–414) in a topology shown in FIG. 5. The two layers enclose an extensive hydrophobic core, augmented by a small anti-parallel β-sheet (strand A, 297–299; C, 330–332) which seals the sandwich at one end. The hydrophobic core consists of the following residues: L301, L305, I309 in helix α1; I319, T321, L323 in strand B; V330, M332 in strand C; I337, V341 in helix α2; I356, V358 in strand D; A367, F369, V371 in strand E; V409, V413 in helix α4; L420 in strand F; I432, A434, L436 in strand G. The sequence conservation of these structurally critical residues (FIG. 6) suggest that the histidine kinase domain of other proteins adapts the α/β sandwich fold observed in EnvZ.

The overall fold of the histindine kinase catalytic domain differs significantly from the known structures of protein serine/theonine and tyrosine kinases [Taylor and Radzio-Andzelm, In *Protein Kinases*, Ed. J. R. Woodgett, 1–29 (1994)]. The EnvZ histidine kinase domain comprises a single globular fold of 161 residues that has all the functionalities of a protein kinase. In contrast, the catalytic core of serine/threonine and tyrosine kinases consists of two lobes: a smaller lobe of approximately 90 residues primarily responsible for ATP binding and a larger lobe of about 170 residues responsible for catalysis and substrate/inhibitor binding. The histidine kinase fold is unrelated to the serine/threonine and tyrosine kinase fold, and is also distinct from the folds found in other bacterial kinases such as pyruvate and adenylate kinases [Mattevi et al., *Structure*, 3:729–741 (1995); Berry et al., *Protein: Struct. Function, and Genetics*, 19:183–198 (1994] and in the sugar phosphotransferase system [Liao et al., *Structure*, 4:861–872 (1996); Garrett et al., *Biochemistry*, 36:2517–2530 (1997); Herzberg and Klevit, *Curr. Opin. Struct. Biol.*, 4:814–822 (1994)]. Finally, a search of folds in the Protein Data Bank using the SARF algorithm [Alexandrov et al., *J. Mol. Biol.*, 225:5–9 (1992)] indicates that the histidine kinase fold is uniquely novel. A striking feature in this fold is the presence of a long polypeptide segment that extends away from the rest of the molecule (FIG. 5). This segment consists of a short α-helix α3 (380–384) followed by a long loop (385–409). Almost no medium- or long-range NOEs were detected for the residues in this loop, and the chemical shifts and backbone coupling constants ($^3J_{NH, H\alpha}$) are nearly consistent with those in a random coil. Furthermore, $^{1-15}N$ heteronuclear NOE measurements showed significantly small NOE values for the residues in this loop, suggesting that this region is highly mobile in solution relative to the overall tumbling motion of the molecule. This characteristic loop, together with helix α3, provides a nucleotide binding site where the phosphorylation catalysis takes place, and is thereby referred to as 'catalytic loop'.

As for other kinases, the catalytic reaction of histidine kinase requires the presence of ATP and $Mg^{2+}$ [Stock et al., In *Two-Component Signal Transduction*, Eds. J. A. Hock and T. J. Silhavy, ASM Press, Washington, D.C., pp. 25–52 (1995]. The present structure was determined in the presence of 3 mM AMPPNP, a nonhydrolysable analog of ATP, and 3 mM $Mg^{2+}$. Combined use of isotopically $^{13}C/^{15}N$ labelled or unlabelled AMPPNP with $^{15}N/^{13}C$ labelled protein enabled us to identify a number of intermolecular NOE interactions between the protein and the adenosine moiety of AMPPNP. The AMPPNP molecule is mainly surrounded by part of the catalytic loop and helix α3, and also contacts with strand F and helix α4. The AMPPNP adenine is placed in a pocket made of conserved residues such as N343, V346, N347, I378, F387, and I408. In addition to those residues, highly conserved are residues (V345, A348, I356, V371, D373, G375, P376, G377, F390, G401, G403, L404, G405, L406, A407, V409, G418, G429, L438) that also cluster around the AMPPNP binding site. The degree of conservation is even greater than that of the hydrophobic core of the α/β sandwich fold, suggesting that the nucleotide binding site is the most important part of the molecule and that members of the histidine kinase family share a similar nucleotide binding site made of a long loop and a short α-helix. Most remarkably, four glycines (G375, G403, G405, G429) and two asparagines (N343 and N347) in the catalytic core are absolutely conserved and strategically located in the structure, indicating their structural and functional significance. In fact, the glycine-rich regions, G1 (D373–G377) and G2 (G401–G405), are essential for the kinase activity. G403 and G405, located within G2, are inclose spatial proximity to the triphosphate chain of AMPPNP. G375 in G1 and G429 allow a sharp kink between strand E and helix α3 and between strands F and G, respectively, adjacent to the AMPPNP binding site. N343 and N347 in helix α2 clamp the adenine ring of AMPPNP in the binding pocket. Interestingly, the mutation of N347 to aspartate results in a kinase−/phosphatase+phenotype [Dutta and Inouye, *J. Biol. Chem.*, 271:1424–1429 (1996)], suggesting that conformational change at the adenine binding pocket has an impact on the bifunctional activity of EnvZ.

The triphosphate chain and part of the ribose ring are surface exposed, with the terminal phosphate group most accessible to solvent, consistent with its potential to transfer the γ-phosphate to H243 in domain A. High deviation of the catalytic loop in the NMR-derived structure, due to high mobility, precludes close examination of the residues that could be involved in the catalysis. It is, however, apparent that the residues in the catalytic loop are the most probable candidates for active participants in catalysis. For example, R383 and/or K384 might be involved in direct interaction with the triphosphate chain by electrostatic attraction, and E381 might be involved in $Mg^{2+}$ coordination and charge compensation upon binding to domain A. Known structures of numerous ATP-binding proteins suggest that $Mg^{2+}$ plays a role in stabilizing the phosphate chain by bridging the β- and γ-phosphates of ATP.

Figure 7:
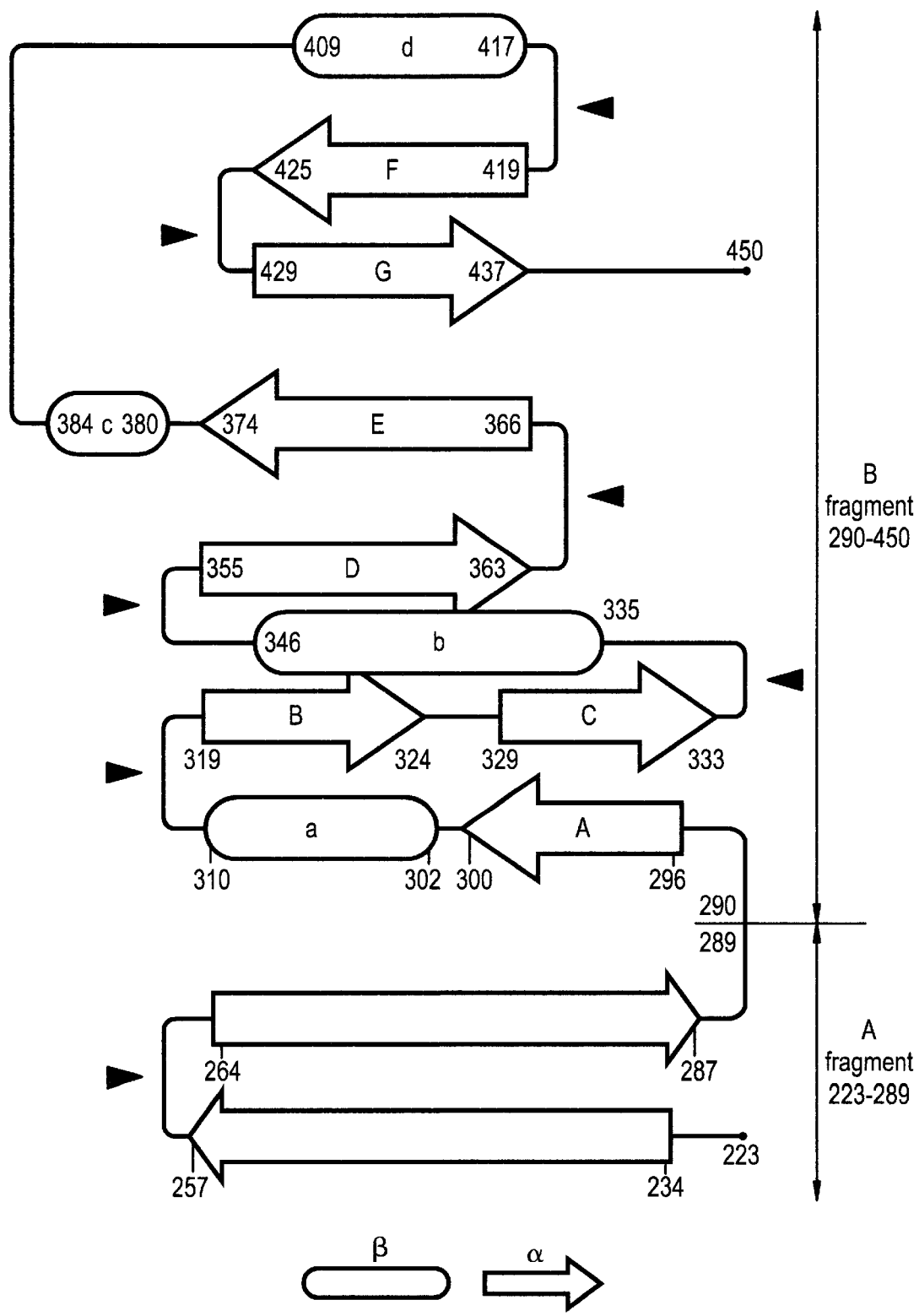
FIG. 7 depicts the secondary structure of the N$_t$TSHK, containing both sub-domain A and sub-domain B (SEQ ID NO:8). The arrowheads indicate regions in which the protein can be fragmented while still maintaining the structural integrity of its structural domains.

315 gene and protein sequences have been identified as members of the histidine kinase family by a BLAST search [Altschul et al., *J. Mol. Boil.*, 215:403–410 (1990)]. SLN1, an osmosensor in yeast [Ota and Varshavsky, *Science*, 262:566–569 (1993)], shares all the secondary structural elements found in EnvZ, and contains a significantly long insertion (120 residues) between strands D and E in the EnvZ structure. DokA, a histindine kinase in *Dictyostelium* [Alex et al., *Proc. Natl. Acad. Sci. USA*, 93:3416–3421 (1996)], contains two insertions different from the one in SLN1: 19 residues between helix α4 and strand F and 49 residues between strands F and G. ETR1, an ethylene-sensing histidine kinase in *Arabidopsis* [Chang et al., *Science*, 262:539–544 (1993)], also contains similar insertions as DokA, in addition to an insertion (16 residues) between strands D and E. These results suggest that additional structural elements (possibly domains) have been added to the catalytic core of eukaryotic members of the histidine kinase family, presumably owing to additional signal transduction functions. It is also interesting to note that members of the histidine kinase family have diverged significantly throughout evolution, whereas members of the serine/theonine kinase family retained a relatively high sequence conservation (~30% identity, with no significant insertion or deletion, between human and a gram-negative bacterium, *Myxococcus xanthus* [Munoz-Dorado et al., *J. Cell. Biochem.*, 51:29–33 (1993)]. FIG. 7 shows that the two functional features of the catalytic domain, i.e., the autophosphorylatable histidine and the catalytic kinase domain can be contained by $N_tTSHKs$ with overlapping sequences, e.g., the domain comprising the autophosphorylatable histidine can consisting of amino acids 223 to 340 of SEQ ID NO: 2 and the kinase domain can consisting of amino acids 330 to 450 of SEQ ID NO: 2.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference herein in their entireties.

What is claimed is:

1. A method of using the three-dimensional structure of an N-terminal truncated transmembrane sensor histidine kinase (N$_t$TSHK) in a drug screening assay comprising:
   (a) selecting a potential drug by performing rational drug design with the three-dimensional structure determined from one or more sets of atomic coordinates in FIG. 8 and FIG. 9; wherein said selecting is performed in conjunction with computer modeling;
   (b) contacting the potential drug with a first polypeptide comprising a first N$_t$TSHK; and
   (c) detecting the binding of the potential drug with said first polypeptide; wherein a potential drug is selected as a drug if the potential drug binds to said first polypeptide.

2. The method of claim 1 wherein said first polypeptide comprises the N$_t$TSHK having the amino acid sequence of SEQ ID NO: 12 or SEQ ID NO: 12 having a conservative amino acid substitution.

3. The method of claim 1 wherein said first polypeptide comprises the N$_t$TSHK having the amino acid sequence of SEQ ID NO: 14 or SEQ ID NO: 14 having a conservative amino acid substitution.

4. The method of claim 1 wherein said first polypeptide is labeled.

5. The method of claim 1 wherein said first polypeptide is bound to a solid support.

6. The method of claim 1 further comprising:
   (d) contacting the potential drug with an N$_t$TSHK for NMR analysis; wherein a binding complex forms between the potential drug and said N$_t$TSHK for NMR analysis; wherein said N$_t$TSHK for NMR analysis comprises an amino acid sequence selected from the group consisting of SEQ ID NO: 12, SEQ ID NO: 12 having a conservative amino acid substitution, SEQ ID NO: 14, and SEQ ID NO: 14 having a conservative amino acid substitution;
   (e) determining the three-dimensional structure of the binding complex by NMR;
   (f) selecting a candidate drug by performing structure based rotional drug design with the three-dimensional structure determined for the binding complex; wherein said selecting is performed in conjunction with computer modeling;

(g) contacting the candidate drug with a second polypeptide comprising a second $N_t$TSHK; and (h) detecting the binding of the candidate drug with said second polypeptide; wherein a candidate drug is selected as a drug if the candidate drug binds to said second polypeptide; wherein said first $N_t$TSHK and said second $N_t$TSHK can be but are not necessarily the same; and wherein said first polypeptide and said second polypeptide can be but are not necessarily the same.

7. The method of claim 6 wherein said second $N_t$TSHK comprises the amino acid sequence of SEQ ID NO: 12 or SEQ ID NO: 12 having a conservative amino acid substitution.

8. The method of claim 6 wherein said second $N_t$TSHK comprises the amino acid sequence of SEQ ID NO: 14 or SEQ ID NO: 14 having a conservative amino acid substitution.

9. The method of claim 6 wherein said second polypeptide is labeled.

10. The method of claim 6 wherein said second polypeptide is bound to a solid support.

11. A method of using the three-dimensional structure of an N-terminal truncated transmembrane sensor histidine kinase ($N_t$TSHK) in a drug screening assay comprising:

(a) selecting a potential drug by performing structure based rational drug design with the three-dimensional structure defined by the set of atomic coordinates in FIG. 8; wherein said selecting is performed in conjunction with computer modeling;

(b) contacting the potential drug with a first polypeptide comprising a first $N_t$TSHK in the presence of a protein histidine kinase; wherein in the absence of the potential drug the protein histidine kinase phosphorylates said first $N_t$TSHK; and (c) determining the amount of phosphorylation of said first $N_t$TSHK; wherein a drug is selected when a decrease in amount of phosphorylation of said first $N_t$TSHK is determined in the presence of the potential drug relative to in its absence.

12. The method of claim 11 and wherein said $N_t$TSHK is incapable of phosphorylating a transmembrane sensor histidine kinase (TSHK) but contains a histidine that can be phosphorylated by the TSHK.

13. The method of claim 12 wherein said first $N_t$TSHK comprises the amino acid sequence of SEQ ID NO: 12 or SEQ ID NO: 12 having a conservative amino acid substitution.

14. The method of claim 11 further comprising:

(d) contacting the potential drug with an $N_t$TSHK for NMR analysis; wherein a binding complex forms between the potential drug and said $N_t$TSHK for NMR analysis; wherein said $N_t$TSHK for NMR analysis comprises an amino acid sequence selected from the group consisting of SEQ ID NO: 12 and SEQ ID NO: 12 having a conservative amino acid substitution;

(e) determining the three-dimensional structure of the binding complex by NMR; and (f) selecting a candidate drug by performing structural based rational drug design with the three-dimensional structure determined for the binding complex; wherein said selecting is performed in conjunction with computer modeling;

(g) contacting the candidate drug with a second polypeptide comprising a second $N_t$TSHK in the presence of a protein histidine kinase; wherein in the absence of the candidate drug the protein histidine kinase phosphorylates said second $N_t$TSHK; and (h) determining the amount of phosphorylation of said second $N_t$TSHK; wherein a drug is selected when a decrease in the amount of phosphorylation of said second $N_t$TSHK is determined in the presence of the candidate drug relative to in its absence; wherein said first $N_t$TSHK and said second $N_t$TSHK can be but are not necessarily the same; and wherein said first polypeptide and said second polypeptide can be but are not necessarily the same.

15. A method of using the three-dimensional structure of an N-terminal truncated transmembrane sensor histidine kinase ($N_t$TSHK) in a drug screening assay comprising:

(a) selecting a potential drug by performing structural based rotational drug design with the three-dimensional structure determined defined by the set of atomic coordinates in FIG. 9; wherein said selecting is performed in conjunction with computer modeling;

(b) contacting the potential drug with a first polypeptide comprising a first $N_t$TSHK in the presence of a protein histidine substrate; wherein in the absence of the potential drug the protein histidine kinase substrate is phosphorylated by said first $N_t$TSHK; and (c) determining the amount of phosphorylation of the protein histidine kinase substrate; wherein a drug is selected when a decrease in the amount of phosphorylation of the protein histidine kinase substrate is determined in the presence of the potential drug relative to in its absence.

16. The method of claim 15 wherein said $N_t$TSHK is capable of phosphorylating a transmembrane sensor histidine kinase (TSHK) but lacks the autophosphorylatable histidine.

17. The method of claim 16 wherein said first $N_t$TSHK has amino acid sequence of SEQ ID NO: 14 or SEQ ID NO: 14 having a conservative amino acid substitution.

18. The method of claim 15 further comprising:

(d) contacting the potential drug with an $N_t$TSHK for NMR analysis; wherein a binding complex forms between the potential drug and said $N_t$TSHK for NMR analysis; wherein said $N_t$TSHK for NMR analysis comprises an amino acid sequence selected from the group consisting of SEQ ID NO: 14 and SEQ ID NO: 14 having a conservative amino acid substitution;

(e) determining the three-dimensional structure of the binding complex by NMR; and (f) selecting a candidate drug by performing structural based rational drug design with the three-dimensional structure determined for the binding complex; wherein said selecting is performed in conjunction with computer modeling;

(g) contacting the candidate drug with a second polypeptide comprising a second $N_t$TSHK in the presence of a protein histidine kinase substrate; wherein in the absence of the candidate drug the protein histidine kinase substrate is phosphorylated by said second $N_t$SHK; and (h) determining the amount of phosphorylation of the protein histidine kinase substrate; wherein a drug is selected when a decrease in the amount of phosphorylation of the protein histidine kinase substrate is determined in the presence of the candidate drug relative to in its absence; wherein said first $N_t$TSHK and said second $N_t$TSHK can be but are not necessarily the same; and wherein said first polypeptide and said second polypeptide can be but are not necessarily the same.

* * * * *